United States Patent
Chen et al.

(10) Patent No.: US 8,138,208 B2
(45) Date of Patent: Mar. 20, 2012

(54) AMINOTETRAHYDROINDAZOLOACETIC ACIDS

(75) Inventors: Li Chen, Shanghai (CN); Fariborz Firooznia, Florham Park, NJ (US); Paul Gillespie, Westfield, NJ (US); Yun He, Shanghai (CN); Tai-An Lin, Pequannock, NJ (US); Sung-Sau So, Nutley, NJ (US); HongYing Yun, Shanghai (CN); Zhenshan Zhang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 241 days.

(21) Appl. No.: 12/497,807

(22) Filed: Jul. 6, 2009

(65) Prior Publication Data
US 2010/0016369 A1    Jan. 21, 2010

Related U.S. Application Data

(60) Provisional application No. 61/080,706, filed on Jul. 15, 2008.

(51) Int. Cl.
*A61K 31/4439* (2006.01)
*A61K 31/416* (2006.01)
*C07D 231/54* (2006.01)
*C07D 401/02* (2006.01)

(52) U.S. Cl. ............ 514/338; 514/406; 546/275.7; 548/360.1

(58) Field of Classification Search ............ None
See application file for complete search history.

(56) References Cited

U.S. PATENT DOCUMENTS

| | | |
|---|---|---|
| 3,899,529 A | 8/1975 | Witzel |
| 4,868,331 A | 9/1989 | Niewöhner et al. |
| 4,921,998 A | 5/1990 | Niewöhner et al. |
| 2006/0154965 A1 | 7/2006 | Harris et al. |

FOREIGN PATENT DOCUMENTS

| | | |
|---|---|---|
| DE | 4411856 | 1/1994 |
| EP | 0 253 257 | 1/1988 |
| EP | 0 405 602 | 1/1991 |
| WO | WO 92/01675 | 2/1992 |
| WO | WO 00/16798 | 3/2000 |
| WO | WO 2005/040114 | 5/2005 |
| WO | WO 2005/054232 | 6/2005 |
| WO | WO 2006/034418 | 3/2006 |
| WO | WO 2006/091674 | 8/2006 |

OTHER PUBLICATIONS

U.S. Appl. No. 12/497,807, filed Jul. 6, 2009, Chen et al.
U.S. Appl. No. 12/540,804, filed Aug. 13, 2009, Blanc et al.
U.S. Appl. No. 12/540,839, filed Aug. 13, 2009, Firooznia et al.
U.S. Appl. No. 12/540,780, filed Aug. 13, 2009, Blanc et al.
U.S. Appl. No. 61/222,235, filed Jul. 1, 2009, Firooznia et al.
U.S. Appl. No. 61/222,182, filed Jul. 1, 2009, Chen et al.
U.S. Appl. No. 61/222,262, filed Jul. 1, 2009, Firooznia et al.
Anderson et al., J. Am. Chem. Soc., 128, pp. 10694-10695 (2006).
Walsh, D.A., J. Medicinal Chem., 21, pp. 582-585 (1978).
Feixas et al., Bioorganic & Medicinal Chemistry Letter, 11, pp. 2687-2690 (2001).
Molteni et al., Synthesis , pp. 1669-1674 (2002).
Leeds et al., Synth. Comm., 18, pp. 777-782 (1988).
Fuji et al., Am. Chem. Soc., 118, pp. 2521-2522 (1996).
Wagner et al., Agnew. Chem. Internat. Edit., 9, pp. 50-54 (1970).
Ho et al., J. Org. Chem., 65, pp. 6743-6748 (2000).
Lee et al., Bioorg. Med. Chem. Lett., 15, pp. 2998-3001 (2005).
Staas et al., Bioorg. Med. Chem., 14, pp. 6900-6916 (2006).
Cherney et al., J. Med. Chem., 46, pp. 1811-1823 (2003).
Sugimoto et al., Eur. J. Pharmacol., 524, pp. 30-37 (2005).

*Primary Examiner* — Kamal Saeed
(74) *Attorney, Agent, or Firm* — George W. Johnston; Dennis P. Tramaloni; Brian C. Remy

(57) ABSTRACT

The invention is concerned with the compounds of formula I:

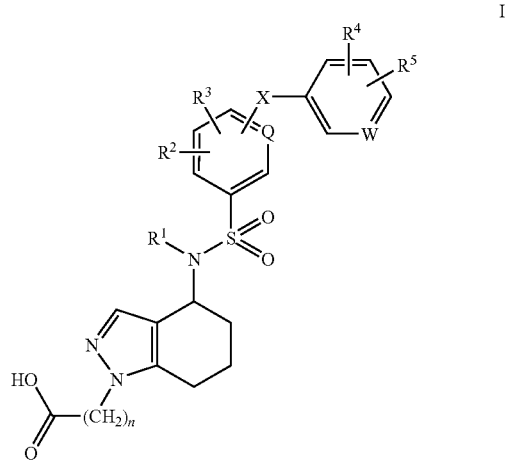

and pharmaceutically acceptable salts and esters thereof, wherein Q, W, X, $R^1$-$R^5$ and n are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

28 Claims, No Drawings

AMINOTETRAHYDROINDAZOLOACETIC ACIDS

PRIORITY TO RELATED APPLICATIONS

This application claims the benefit of U.S. Provisional Application No. 61/080,706, filed Jul. 15, 2008, which is hereby incorporated by reference in its entirety.

BACKGROUND OF THE INVENTION

The present invention relates to novel aminotetrahydroindazoloacetic acids, their manufacture, pharmaceutical compositions containing them and their use as CRTH2 antagonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention is concerned with the compounds of formula I:

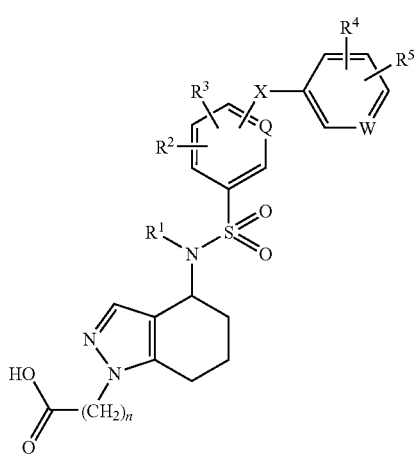

and pharmaceutically acceptable salts and esters thereof, wherein Q, W, X, $R^1$-$R^5$ and n are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen moieties (i.e, trifluoromethyl, difluoromethyl, fluoromethyl, chloromethyl, etc.). Similarly, the term "lower cycloalkyl substituted by lower alkyl" refers to the fact that one or more hydrogen atoms of a lower cycloalkyl (as defined below) is replaced by one or more lower alkyls (i.e, 1-methyl-cyclopropyl, 1-ethyl-cyclopropyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "heteroatom" refers to nitrogen, oxygen, or sulfur.

The term "lower heterocycloalkyl" refers to a saturated or partly unsaturated non-aromatic ring moiety having 3 to 7 ring atoms bonded together to form a ring structure wherein one, two or three of the ring atoms is a heteroatom while the remaining ring atoms are carbon atoms. Examples of lower heterocycloalkyls include piperidinyl, piperazinyl, pyrrolidinyl and tetrahydropyran-4-yl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower cycloalkoxy" refers to the moiety —O—R, wherein R is a lower cycloalkyl as defined previously. Examples of lower cycloalkoxy moieties include cyclopropoxy, cyclobutoxy, cyclopentoxy, and cyclohexoxy.

The term "lower heterocycloalkyloxy" refers to the moiety R—O—, wherein R is a lower heterocycloalkyl as defined above. An example of a lower heterocycloalkyloxy is tetrahydropyran-4-yloxy.

The term "lower alkanoyl" refers to the moiety —C(O)—R, wherein R is lower alkyl as defined previously. An example of a lower alkanoyl is acetyl.

The term "lower alkylsulfanyl" refers to the moiety —S—R, wherein R is lower alkyl as defined previously. Examples of lower alkylsulfanyls include methylsulfanyl and ethylsulfanyl.

The term "lower cycloalkylsulfanyl" refers to the moiety —S—R, wherein R is lower cycloalkyl as defined previously. Examples of lower cycloalkylsulfanyls include cyclopropylsulfanyl, cyclobutylsulfanyl and cyclopentylsulfanyl.

The term "lower alkylsulfinyl" refers to the moiety —S(O)—R, wherein R is lower alkyl as defined previously. Examples of lower alkylsulfinyls include methylsulfinyl and ethylsulfinyl.

The term "lower cycloalkylsulfinyl" refers to the moiety —S(O)—R, wherein R is lower cycloalkyl as defined previously. Examples of lower cycloalkylsulfinyls include cyclopropylsulfinyl, cyclobutylsulfinyl and cyclopentylsulfinyl.

The term "lower alkylsulfonyl" refers to the moiety —S(O)$_2$—R, wherein R is lower alkyl as defined previously. Examples of lower alkylsulfonyls include methylsulfonyl and ethylsulfonyl.

The term "lower cycloalkylsulfonyl" refers to the moiety —S(O)$_2$—R, wherein R is lower cycloalkyl as defined previously. Examples of lower cycloalkylsulfonyls include cyclopropylsulfonyl, cyclobutylsulfonyl and cyclopentylsulfonyl.

The term "lower alkylamino" refers to the moiety —N(H)(R), wherein R is lower alkyl as defined previously. An example of a lower alkylamino is methylamino.

The term "lower dialkylamino" refers to the moiety —N(R)(R'), wherein R and R' are lower alkyl as defined previously. An example of a lower dialkylamino is dimethylamino.

The term "carbamoyl" refers to the moiety —C(O)—NH$_2$.

The term "lower alkylaminocarbonyl" refers to the moiety —C(O)—N(H)(R), wherein R is lower alkyl as defined previously. An example of a lower alkylaminocarbonyl is methylaminocarbonyl.

The term "lower dialkylaminocarbonyl" refers to the moiety —C(O)—N(R)(R'), wherein R and R' are lower alkyl as defined previously. An example of a lower dialkylaminocarbonyl is dimethylaminocarbonyl.

The term "lower alkylcarbonylamino" refers to the moiety —N(H)—C(O)—R, wherein R is lower alkyl as defined previously. An example of a lower alkylcarbonylamino is methylcarbonylamino.

The term "lower trialkylsilyl" refers to the moiety —Si(R)(R')(R") wherein R, R' and R" are lower alkyl as defined previously. An example of a lower trialkylsilyl is trimethylsilyl.

The term "halogen" refers to a moiety of fluoro, chloro, bromo or iodo.

Unless otherwise indicated, the term "hydrogen" or "hydro" refers to the moiety of a hydrogen atom (—H) and not H$_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R— and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

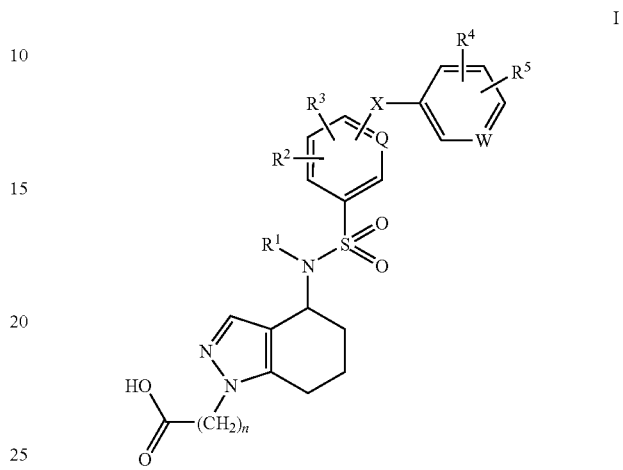

and pharmaceutically acceptable salts and esters thereof, wherein:

X is a direct bond, oxygen, or —S(O)$_2$—; and X is bonded to the ring containing Q by substitution of a hydrogen atom of a ring carbon atom;

Q and W, independently of each other, are carbon or nitrogen with the proviso that when Q or W is nitrogen, the nitrogen is unsubstituted;

$R^1$ is hydrogen or methyl;

$R^2$ and $R^3$ are bonded to the ring containing Q by substitution of a hydrogen atom of a ring carbon atom; and $R^2$ and $R^3$, independently of each other, are selected from the group consisting of:
  (1) hydrogen;
  (2) halogen;
  (3) lower alkyl optionally substituted by halogen; and
  (4) lower cycloalkyl optionally substituted by lower alkyl;

$R^4$ and $R^5$ are bonded to the ring containing W by substitution of a hydrogen atom of a ring carbon atom; and $R^4$ and $R^5$, independently of each other, are selected from the group consisting of:
  (1) hydrogen;
  (2) hydroxyl;
  (3) halogen;
  (4) nitro;
  (5) cyano;
  (6) lower alkyl optionally substituted by halogen;
  (7) lower alkoxy optionally substituted by halogen;
  (8) lower cycloalkoxy;
  (9) lower heterocycloalkyloxy;
  (10) lower alkanoyl;
  (11) carbamoyl, lower alkylaminocarbonyl, or lower dialkylaminocarbonyl;
  (12) lower alkylcarbonylamino;
  (13) lower alkylsulfanyl or lower cycloalkylsulfanyl
  (14) lower alkylsulfinyl or lower cycloalkylsulfinyl;
  (15) lower alkylsulfonyl or lower cycloalkylsulfonyl; and
  (16) trimethylsilyl; and n is 1 or 2.

Unless indicated otherwise, the term "Q and W, independently of each other, are carbon or nitrogen" (or similar references to Q or W in relation to carbon or nitrogen) indicates that: (1) when Q or W is carbon as depicted in formula I, the carbon is either unsubstituted by being bonded to a hydrogen (C—H) or substituted by being bonded to another moiety as indicated in formula I (for example, W may be bonded to $R^4$ or $R^5$; and Q may be bonded to $R^2$, $R^3$, or X (if X is oxygen or —$S(O)_2$—) or to the ring containing W (if X is a direct bond); and (2) when Q or W is nitrogen, the nitrogen is not bonded to either a hydrogen or $R^2$, $R^3$, $R^4$, $R^5$ or X.

Unless indicated otherwise, the term "X is bonded to the ring containing Q by substitution of a hydrogen atom of a ring carbon atom" refers to the fact that: (1) when X is oxygen or —$S(O)_2$—, the oxygen or —$S(O)_2$— is bonded to one of the ring carbon atoms (of the aromatic ring in formula I containing Q) in place of a hydrogen atom that would otherwise be bonded to that carbon atom absent being substituted by X; and (2) when X is a direct bond, the ring containing W is bonded to one of the ring carbon atoms (of the aromatic ring in formula I containing Q) in place of a hydrogen atom that would otherwise be bonded to that carbon atom absent being substituted by the ring containing W.

Similarly, unless indicated otherwise, the term "$R^2$ and $R^3$ are bonded to the ring containing Q by substitution of a hydrogen atom of a ring carbon atom" refers to the fact that $R^2$ and $R^3$ as depicted in formula I (independently of each other) are bonded to one of the ring carbon atoms (of the aromatic ring in formula I containing Q) in place of a hydrogen atom that would otherwise be bonded to that carbon atom absent being substituted by $R^2$ or $R^3$; with the understanding that $R^2$ and $R^3$ are not simultaneously bonded to the same carbon atom.

Likewise, unless indicated otherwise, the term "$R^4$ and $R^5$ are bonded to the ring containing W by substitution of a hydrogen atom of a ring carbon atom" refers to the fact that $R^4$ and $R^5$ as depicted in formula I (independently of each other) are bonded to one of the ring carbon atoms (of the aromatic ring in formula I containing W) in place of a hydrogen atom that would otherwise be bonded to that carbon atom absent being substituted by $R^4$ or $R^5$; with the understanding that $R^4$ and $R^5$ are not simultaneously bonded to the same carbon atom.

Unless indicated otherwise, the genus of formula I and any subgenera thereof encompass all possible stereoisomers (i.e., (R)-enantiomers and (S)-enantiomers) as well as racemic and scalemic mixtures thereof. In one embodiment of the invention, the compounds of formula I are (R)-enantiomers or pharmaceutically acceptable salts or esters thereof as depicted in the following subgeneric structural formula IA for the (R)-enantiomers of formula I:

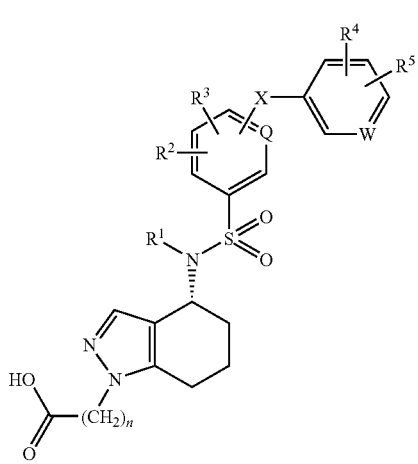

IA wherein Q, W, X, $R^1$-$R^5$ and n are as defined previously.

In another embodiment, the compounds of formula I are (S)-enantiomers or pharmaceutically acceptable salts or esters thereof as depicted in the following subgeneric structural formula IB for the (S)-enantiomers of formula I:

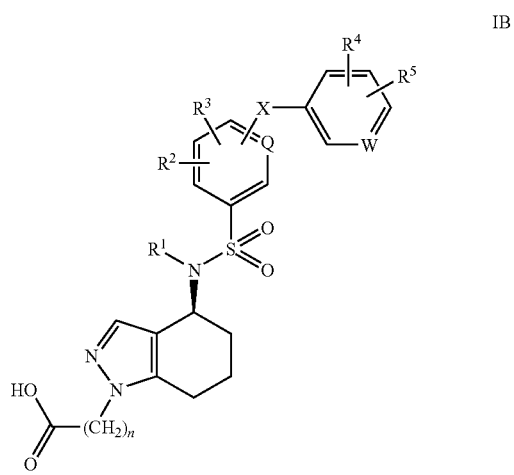

IB wherein Q, W, X, $R^1$-$R^5$ and n are as defined previously.

In another embodiment the present invention is directed to a composition comprising a mixture (racemic or otherwise) of the (R)-enantiomers and (S)-enantiomers of a compound of formula I.

In one embodiment the present invention is directed to the compounds of formula I or pharmaceutically acceptable salts or esters thereof wherein Q and W are carbon.

In another embodiment the present invention is directed to the compounds of formula I or pharmaceutically acceptable salts or esters thereof wherein Q is nitrogen and W is carbon.

In another embodiment the present invention is directed to the compounds of formula I or pharmaceutically acceptable salts or esters thereof wherein W is nitrogen and Q is carbon.

In another embodiment the present invention is directed to the compounds of formula I or pharmaceutically acceptable salts or esters thereof wherein Q and W are nitrogen.

In one embodiment the present invention is directed to the compounds of formula I or pharmaceutically acceptable salts or esters thereof wherein X is a direct bond.

In one embodiment the present invention is directed to the compounds of formula I or pharmaceutically acceptable salts or esters thereof wherein X is oxygen.

In one embodiment the present invention is directed to the compounds of formula I or pharmaceutically acceptable salts or esters thereof wherein X is —$S(O)_2$—.

In one embodiment the present invention is directed to the compounds of formula I or pharmaceutically acceptable salts or esters thereof wherein $R^1$ is hydrogen.

In another embodiment the present invention is directed to the compounds of formula I or pharmaceutically acceptable salts or esters thereof wherein $R^1$ is methyl.

In another embodiment the present invention is directed to the compounds of formula I or pharmaceutically acceptable salts or esters thereof wherein $R^2$ and $R^3$, independently of each other, are selected from the group consisting of:
(1) hydrogen;
(2) halogen; and
(3) lower alkyl optionally substituted by halogen.

In another embodiment the present invention is directed to the compounds of formula I or pharmaceutically acceptable salts or esters thereof wherein $R^2$ and $R^3$, independently of each other, are selected from the group consisting of:
(1) hydrogen;
(2) bromo;
(3) chloro;
(4) fluoro;
(5) methyl;
(6) isopropyl;
(7) trifluoromethyl; and
(8) 1-methylcyclopropyl.

In another embodiment the present invention is directed to the compounds of formula I or pharmaceutically acceptable salts or esters thereof wherein $R^4$ and $R^5$, independently of each other, are selected from the group consisting of:
(1) hydrogen;
(2) hydroxyl;
(3) fluoro or chloro;
(4) cyano;
(5) methyl, ethyl, propyl, isopropyl, butyl, sec-butyl, or tert-butyl;
(6) difluoromethyl or trifluoromethyl;
(7) methoxy, ethoxy, isopropoxy or trifluoromethoxy;
(8) methylcarbonylamino;
(9) carbamoyl;
(10) acetyl;
(11) nitro;
(12) trimethylsilyl;
(13) methylsulfinyl or ethylsulfinyl; and
(14) methylsulfonyl or ethylsulfonyl.

In another embodiment the present invention is directed to the compounds of formula I or pharmaceutically acceptable salts or esters thereof wherein $R^4$ and $R^5$, independently of each other, are selected from the group consisting of:
(1) hydrogen;
(2) halogen;
(3) cyano;
(4) lower alkyl optionally substituted by halogen;
(5) lower alkoxy optionally substituted by halogen; and
(6) lower alkylsulfonyl or lower cycloalkylsulfonyl.

In another embodiment the present invention is directed to the compounds of formula I or pharmaceutically acceptable salts or esters thereof wherein:
X is oxygen;
$R^2$ and $R^3$, independently of each other, are selected from the group consisting of:
(1) hydrogen;
(2) bromo;
(3) chloro;
(4) fluoro;
(5) methyl;
(6) isopropyl;
(7) trifluoromethyl; and
(8) 1-methylcyclopropyl; and
$R^4$ and $R^5$, independently of each other, are selected from the group consisting of:
(1) hydrogen;
(2) fluoro or chloro;
(3) cyano;
(4) methyl, ethyl, propyl, isopropyl, butyl, sec-butyl, or tert-butyl;
(5) methoxy, ethoxy, isopropoxy or trifluoromethoxy; and
(6) methylsulfonyl or ethylsulfonyl;
wherein Q, W, $R^1$ and n are as defined previously.

In another embodiment the present invention is directed to the compounds of formula I or pharmaceutically acceptable salts or esters thereof wherein:
X is $-S(O)_2-$;
Q is carbon;
$R^2$ and $R^3$, independently of each other, are hydrogen or trifluoromethyl;
$R^4$ and $R^5$, independently of each other, are selected from the group consisting of:
(1) hydrogen;
(2) fluoro or chloro;
(3) methyl, ethyl, propyl, isopropyl, butyl, sec-butyl, or tert-butyl; and
(4) methoxy, ethoxy, or isopropoxy;
and W, $R^1$ and n are as defined previously.

In another embodiment the present invention is directed to the compounds of formula I or pharmaceutically acceptable salts or esters thereof wherein:
X is a direct bond;
$R^2$ and $R^3$, independently of each other, are hydrogen or trifluoromethyl;
$R^4$ and $R^5$, independently of each other, are selected from the group consisting of:
(1) hydrogen;
(2) chloro;
(3) methyl, ethyl, propyl, isopropyl, butyl, sec-butyl, or tert-butyl;
(4) trifluoromethyl;
(5) methoxy, ethoxy, isopropoxy or trifluoromethoxy;
(6) trimethylsilyl; and
(7) methylsulfonyl or ethylsulfonyl;
wherein Q, W, $R^1$ and n are as defined previously.

In particular embodiments, preferred positions of $R^2$, $R^3$, $R^4$, $R^5$ and X are hereafter indicated by the following numbered positions (2, 3, 4, 5, 6, 8, 9, 10, 11 and 12) of formula I as shown below:

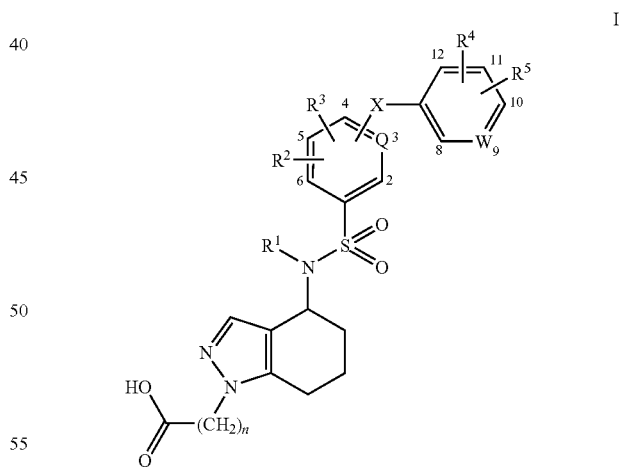

In a preferred embodiment, when X is oxygen it is attached to the 3, 4, or 5 position on the ring containing Q. In a more particular preferred embodiment, when X is oxygen it is attached to the 4 position on the ring containing Q. In another preferred embodiment, when X is $-S(O)_2-$ or a direct bond it is attached to the 3, 4, or 5 position on the ring containing Q. In a more specific embodiment, when X is a direct bond it is attached to the 4 position on the ring containing Q. In another specific embodiment, when X is $-S(O)_2-$ it is attached to the 3 or 5 position on the ring containing Q.

In another particular embodiment, when X is oxygen, at least one of $R^2$ or $R^3$ is attached to the 2, 3, or 5 positions on the ring containing Q and at least one of $R^4$ or $R^5$ is attached to the 8 or 10 position on the ring containing W.

In another particular embodiment, when X is —S(O)$_2$—, at least one of $R^2$ or $R^3$ is attached to the 5 position on the ring containing Q and at least one of $R^4$ or $R^5$ is attached to the 10 position on the ring containing W.

In another particular embodiment, when X is a direct bond, at least one of $R^2$ or $R^3$ is attached to the 5 position on the ring containing Q and at least one of $R^4$ or $R^5$ is attached to the 9 or 11 positions on the ring containing W.

In a more specific embodiment, the present invention is directed to a compound of formula I selected from the group consisting of:

{(R)-4-[4-(2-Chloro-phenoxy)-benzenesulfonylamino]-4,5, 6,7-tetrahydro-indazol-1-yl}-acetic acid;
[(R)-4-(Biphenyl-4-sulfonylamino)-4,5,6,7-tetrahydro-indazol-1-yl]-acetic acid;
[4-(4-Phenoxy-benzenesulfonylamino)-4,5,6,7-tetrahydro-indazol-1-yl]-acetic acid;
[4-(3-Phenoxy-benzenesulfonylamino)-4,5,6,7-tetrahydro-indazol-1-yl]-acetic acid;
3-[4-(Biphenyl-4-sulfonylamino)-4,5,6,7-tetrahydro-indazol-1-yl]-propionic acid;
{4-[5-Bromo-6-(4-chloro-phenoxy)-pyridine-3-sulfonylamino]-4,5,6,7-tetrahydro-indazol-1-yl}-acetic acid;
{4-[5-Bromo-6-(4-fluoro-phenoxy)-pyridine-3-sulfonylamino]-4,5,6,7-tetrahydro-indazol-1-yl}-acetic acid;
{4-[5-Bromo-6-(3-chloro-phenoxy)-pyridine-3-sulfonylamino]-4,5,6,7-tetrahydro-indazol-1-yl}-acetic acid;
{4-[5-Bromo-6-(4-cyano-phenoxy)-pyridine-3-sulfonylamino]-4,5,6,7-tetrahydro-indazol-1-yl}-acetic acid;
{4-[5-Bromo-6-(4-methanesulfonyl-phenoxy)-pyridine-3-sulfonylamino]-4,5,6,7-tetrahydro-indazol-1-yl}-acetic acid;
[4-(5-Bromo-6-p-tolyloxy-pyridine-3-sulfonylamino)-4,5,6, 7-tetrahydro-indazol-1-yl]-acetic acid;
{4-[5-Bromo-6-(4-trifluoromethyl-phenoxy)-pyridine-3-sulfonylamino]-4,5,6,7-tetrahydro-indazol-1-yl}-acetic acid;
{(R)-4-[5-Bromo-6-(4-chloro-phenoxy)-pyridine-3-sulfonylamino]-4,5,6,7-tetrahydro-indazol-1-yl}-acetic acid;
{(R)-4-[5-Bromo-6-(2-chloro-phenoxy)-pyridine-3-sulfonylamino]-4,5,6,7-tetrahydro-indazol-1-yl}-acetic acid;
{4-[5-Bromo-6-(3,4-difluoro-phenoxy)-pyridine-3-sulfonylamino]-4,5,6,7-tetrahydro-indazol-1-yl}-acetic acid;
3-{(R)-4-[5-Bromo-6-(2-chloro-phenoxy)-pyridine-3-sulfonylamino]-4,5,6,7-tetrahydro-indazol-1-yl}-propionic acid;
3-{(R)-4-[5-Bromo-6-(4-chloro-phenoxy)-pyridine-3-sulfonylamino]-4,5,6,7-tetrahydro-indazol-1-yl}-propionic acid;
{4-[6-(4-Chloro-phenoxy)-5-methyl-pyridine-3-sulfonylamino]-4,5,6,7-tetrahydro-indazol-1-yl}-acetic acid;
{4-[6-(4-Fluoro-phenoxy)-pyridine-3-sulfonylamino]-4,5,6, 7-tetrahydro-indazol-1-yl}-acetic acid;
{(R)-4-[3-Chloro-4-(2-chloro-phenoxy)-benzenesulfonylamino]-4,5,6,7-tetrahydro-indazol-1-yl}-acetic acid;
{4-[4-(3-Chloro-phenoxy)-benzenesulfonylamino]-4,5,6,7-tetrahydro-indazol-1-yl}-acetic acid;
{4-[4-(4-Chloro-phenoxy)-benzenesulfonylamino]-4,5,6,7-tetrahydro-indazol-1-yl}-acetic acid;
[4-(3-Phenoxy-5-trifluoromethyl-benzenesulfonylamino)-4, 5,6,7-tetrahydro-indazol-1-yl]-acetic acid;
{(R)-4-[2-Chloro-4-(2-chloro-phenoxy)-benzenesulfonylamino]-4,5,6,7-tetrahydro-indazol-1-yl}-acetic acid;
{(R)-4-[2-Chloro-5-fluoro-4-(4-fluoro-phenoxy)-benzenesulfonylamino]-4,5,6,7-tetrahydro-indazol-1-yl}-acetic acid;
3-{(R)-4-[3-Chloro-4-(2-chloro-phenoxy)-benzenesulfonylamino]-4,5,6,7-tetrahydro-indazol-1-yl}-propionic acid;
((R)-4-{[5-Bromo-6-(4-chloro-phenoxy)-pyridine-3-sulfonyl]-methyl-amino}-4,5,6,7-tetrahydro-indazol-1-yl)-acetic acid;
((R)-4-{[5-Bromo-6-(2-chloro-phenoxy)-pyridine-3-sulfonyl]-methyl-amino}-4,5,6,7-tetrahydro-indazol-1-yl)-acetic acid;
((R)-4-{[5-Bromo-6-(3,5-dichloro-phenoxy)-pyridine-3-sulfonyl]-methyl-amino}-4,5,6,7-tetrahydro-indazol-1-yl)-acetic acid;
((R)-4-{[5-Bromo-6-(2,4-dichloro-phenoxy)-pyridine-3-sulfonyl]-methyl-amino}-4,5,6,7-tetrahydro-indazol-1-yl)-acetic acid;
((R)-4-{[5-Bromo-6-(2,5-dichloro-phenoxy)-pyridine-3-sulfonyl]-methyl-amino}-4,5,6,7-tetrahydro-indazol-1-yl)-acetic acid;
((R)-4-{[5-Bromo-6-(2-chloro-4-fluoro-phenoxy)-pyridine-3-sulfonyl]-methyl-amino}-4,5,6,7-tetrahydro-indazol-1-yl)-acetic acid;
((R)-4-{[5-Bromo-6-(2,4-difluoro-phenoxy)-pyridine-3-sulfonyl]-methyl-amino}-4,5,6,7-tetrahydro-indazol-1-yl)-acetic acid;
((R)-4-{[5-Bromo-6-(3-chloro-phenoxy)-pyridine-3-sulfonyl]-methyl-amino}-4,5,6,7-tetrahydro-indazol-1-yl)-acetic acid;
((R)-4-{[5-Bromo-6-(4-chloro-2-fluoro-phenoxy)-pyridine-3-sulfonyl]-methyl-amino}-4,5,6,7-tetrahydro-indazol-1-yl)-acetic acid;
((R)-4-{[5-Bromo-6-(4-chloro-3-fluoro-phenoxy)-pyridine-3-sulfonyl]-methyl-amino}-4,5,6,7-tetrahydro-indazol-1-yl)-acetic acid;
((R)-4-{[5-Bromo-6-(4-isopropyl-phenoxy)-pyridine-3-sulfonyl]-methyl-amino}-4,5,6,7-tetrahydro-indazol-1-yl)-acetic acid;
((R)-4-{[5-Bromo-6-(4-fluoro-phenoxy)-pyridine-3-sulfonyl]-methyl-amino}-4,5,6,7-tetrahydro-indazol-1-yl)-acetic acid;
((R)-4-{[5-Bromo-6-(4-fluoro-2-methoxy-phenoxy)-pyridine-3-sulfonyl]-methyl-amino}-4,5,6,7-tetrahydro-indazol-1-yl)-acetic acid;
((R)-4-{[5-Bromo-6-(4-cyano-phenoxy)-pyridine-3-sulfonyl]-methyl-amino}-4,5,6,7-tetrahydro-indazol-1-yl)-acetic acid;
((R)-4-{[6-(4-Chloro-phenoxy)-5-isopropyl-pyridine-3-sulfonyl]-methyl-amino}-4,5,6,7-tetrahydro-indazol-1-yl)-acetic acid;
((R)-4-{[6-(4-Chloro-phenoxy)-5-(1-methyl-cyclopropyl)-pyridine-3-sulfonyl]-methyl-amino}-4,5,6,7-tetrahydro-indazol-1-yl)-acetic acid;
((R)-4-{[3-Chloro-4-(2-chloro-phenoxy)-benzenesulfonyl]-methyl-amino}-4,5,6,7-tetrahydro-indazol-1-yl)-acetic acid;
((R)-4-{[3-Chloro-4-(3-chloro-phenoxy)-benzenesulfonyl]-methyl-amino}-4,5,6,7-tetrahydro-indazol-1-yl)-acetic acid;
((R)-4-{[3-Chloro-4-(4-chloro-phenoxy)-benzenesulfonyl]-methyl-amino}-4,5,6,7-tetrahydro-indazol-1-yl)-acetic acid;
((R)-4-{[2-Chloro-4-(4-chloro-phenoxy)-benzenesulfonyl]-methyl-amino}-4,5,6,7-tetrahydro-indazol-1-yl)-acetic acid;

((R)-4-{[4-(4-Chloro-phenoxy)-3-trifluoromethyl-benzenesulfonyl]-methyl-amino}-4,5,6,7-tetrahydro-indazol-1-yl)-acetic acid;
((R)-4-{[3-Chloro-4-(2,4-dichloro-phenoxy)-benzenesulfonyl]-methyl-amino}-4,5,6,7-tetrahydro-indazol-1-yl)-acetic acid;
((R)-4-{[4-(4-tert-Butyl-phenoxy)-3-chloro-benzenesulfonyl]-methyl-amino}-4,5,6,7-tetrahydro-indazol-1-yl)-acetic acid;
((R)-4-{[2-Chloro-4-(2,4-dichloro-phenoxy)-benzenesulfonyl]-methyl-amino}-4,5,6,7-tetrahydro-indazol-1-yl)-acetic acid;
((R)-4-{[2-Chloro-4-(2-chloro-4-fluoro-phenoxy)-benzenesulfonyl]-methyl-amino}-4,5,6,7-tetrahydro-indazol-1-yl)-acetic acid;
((R)-4-{[2-Chloro-4-(2-chloro-phenoxy)-benzenesulfonyl]-methyl-amino}-4,5,6,7-tetrahydro-indazol-1-yl)-acetic acid;
((R)-4-{[3-Chloro-4-(4-chloro-2-fluoro-phenoxy)-benzenesulfonyl]-methyl-amino}-4,5,6,7-tetrahydro-indazol-1-yl)-acetic acid;
((R)-4-{[4-(4-Chloro-phenoxy)-3-fluoro-benzenesulfonyl]-methyl-amino}-4,5,6,7-tetrahydro-indazol-1-yl)-acetic acid;
{(R)-4-[(3-Chloro-4-phenoxy-benzenesulfonyl)-methyl-amino]-4,5,6,7-tetrahydro-indazol-1-yl}-acetic acid;
((R)-4-{[3-Chloro-4-(4-fluoro-phenoxy)-benzenesulfonyl]-methyl-amino}-4,5,6,7-tetrahydro-indazol-1-yl)-acetic acid;
{(R)-4-[(3-Chloro-4-p-tolyloxy-benzenesulfonyl)-methyl-amino]-4,5,6,7-tetrahydro-indazol-1-yl}-acetic acid;
((R)-4-{[3-Chloro-4-(2-chloro-4-fluoro-phenoxy)-benzenesulfonyl]-methyl-amino}-4,5,6,7-tetrahydro-indazol-1-yl)-acetic acid;
((R)-4-{[3-Chloro-4-(4-fluoro-2-methoxy-phenoxy)-benzenesulfonyl]-methyl-amino}-4,5,6,7-tetrahydro-indazol-1-yl)-acetic acid;
((R)-4-{[3-Chloro-4-(2-chloro-5-methyl-phenoxy)-benzenesulfonyl]-methyl-amino}-4,5,6,7-tetrahydro-indazol-1-yl)-acetic acid;
((R)-4-{[3-Chloro-4-(2,4-dimethyl-phenoxy)-benzenesulfonyl]-methyl-amino}-4,5,6,7-tetrahydro-indazol-1-yl)-acetic acid;
((R)-4-{[3-Chloro-4-(4-chloro-2-methoxy-phenoxy)-benzenesulfonyl]-methyl-amino}-4,5,6,7-tetrahydro-indazol-1-yl)-acetic acid;
((R)-4-{[3-Chloro-4-(4-chloro-3-fluoro-phenoxy)-benzenesulfonyl]-methyl-amino}-4,5,6,7-tetrahydro-indazol-1-yl)-acetic acid;
((R)-4-{[3-Chloro-4-(2,5-difluoro-phenoxy)-benzenesulfonyl]-methyl-amino}-4,5,6,7-tetrahydro-indazol-1-yl)-acetic acid;
((R)-4-{[4-(4-Bromo-phenoxy)-3-chloro-benzenesulfonyl]-methyl-amino}-4,5,6,7-tetrahydro-indazol-1-yl)-acetic acid;
((R)-4-{[3-Chloro-4-(3-chloro-4-fluoro-phenoxy)-benzenesulfonyl]-methyl-amino}-4,5,6,7-tetrahydro-indazol-1-yl)-acetic acid;
((R)-4-{[3-Chloro-4-(4-methanesulfonyl-phenoxy)-benzenesulfonyl]-methyl-amino}-4,5,6,7-tetrahydro-indazol-1-yl)-acetic acid;
{(R)-4-[(3-Chloro-4-o-tolyloxy-benzenesulfonyl)-methyl-amino]-4,5,6,7-tetrahydro-indazol-1-yl}-acetic acid;
((R)-4-{[4-(4-Acetylamino-phenoxy)-3-chloro-benzenesulfonyl]-methyl-amino}-4,5,6,7-tetrahydro-indazol-1-yl)-acetic acid;
((R)-4-{[3-Chloro-4-(4-trifluoromethoxy-phenoxy)-benzenesulfonyl]-methyl-amino}-4,5,6,7-tetrahydro-indazol-1-yl)-acetic acid;
((R)-4-{[2-Chloro-5-fluoro-4-(4-fluoro-phenoxy)-benzenesulfonyl]-methyl-amino}-4,5,6,7-tetrahydro-indazol-1-yl)-acetic acid;
((R)-4-{[5-Chloro-2-fluoro-4-(4-fluoro-phenoxy)-benzenesulfonyl]-methyl-amino}-4,5,6,7-tetrahydro-indazol-1-yl)-acetic acid;
((R)-4-{[3-Chloro-4-(4-methoxy-phenoxy)-benzenesulfonyl]-methyl-amino}-4,5,6,7-tetrahydro-indazol-1-yl)-acetic acid;
((R)-4-{[3-Chloro-4-(2,4-difluoro-phenoxy)-benzenesulfonyl]-methyl-amino}-4,5,6,7-tetrahydro-indazol-1-yl)-acetic acid;
((R)-4-{[3-Chloro-4-(2,6-difluoro-phenoxy)-benzenesulfonyl]-methyl-amino}-4,5,6,7-tetrahydro-indazol-1-yl)-acetic acid;
((R)-4-{[3-Chloro-4-(4-cyano-phenoxy)-benzenesulfonyl]-methyl-amino}-4,5,6,7-tetrahydro-indazol-1-yl)-acetic acid;
((R)-4-{[4-(4-Fluoro-phenoxy)-3-methyl-benzenesulfonyl]-methyl-amino}-4,5,6,7-tetrahydro-indazol-1-yl)-acetic acid;
((R)-4-{[4-(4-Carbamoyl-phenoxy)-3-chloro-benzenesulfonyl]-methyl-amino}-4,5,6,7-tetrahydro-indazol-1-yl)-acetic acid;
((R)-4-{[3-Chloro-4-(2-fluoro-phenoxy)-benzenesulfonyl]-methyl-amino}-4,5,6,7-tetrahydro-indazol-1-yl)-acetic acid;
((R)-4-{[3-Chloro-4-(4-fluoro-2-methyl-phenoxy)-benzenesulfonyl]-methyl-amino}-4,5,6,7-tetrahydro-indazol-1-yl)-acetic acid;
((R)-4-{[3,5-Difluoro-4-(4-fluoro-phenoxy)-benzenesulfonyl]-methyl-amino}-4,5,6,7-tetrahydro-indazol-1-yl)-acetic acid;
((R)-4-{[3-Bromo-4-(4-fluoro-phenoxy)-benzenesulfonyl]-methyl-amino}-4,5,6,7-tetrahydro-indazol-1-yl)-acetic acid;
((R)-4-{[4-(4-Fluoro-phenoxy)-3-trifluoromethyl-benzenesulfonyl]-methyl-amino}-4,5,6,7-tetrahydro-indazol-1-yl)-acetic acid;
((R)-4-{[5-(4-Fluoro-phenoxy)-3-trifluoromethyl-benzenesulfonyl]-methyl-amino}-4,5,6,7-tetrahydro-indazol-1-yl)-acetic acid;
[4-(4'-Methoxy-biphenyl-4-sulfonylamino)-4,5,6,7-tetrahydro-indazol-1-yl]-acetic acid;
[4-(4-Pyridin-3-yl-benzenesulfonylamino)-4,5,6,7-tetrahydro-indazol-1-yl]-acetic acid;
[4-(4'-Ethoxy-biphenyl-4-sulfonylamino)-4,5,6,7-tetrahydro-indazol-1-yl]-acetic acid;
[4-(2'-Chloro-biphenyl-4-sulfonylamino)-4,5,6,7-tetrahydro-indazol-1-yl]-acetic acid;
[4-(4'-Methoxy-biphenyl-3-sulfonylamino)-4,5,6,7-tetrahydro-indazol-1-yl]-acetic acid;
[4-(4'-Chloro-biphenyl-4-sulfonylamino)-4,5,6,7-tetrahydro-indazol-1-yl]-acetic acid;
[4-(4'-Fluoro-biphenyl-4-sulfonylamino)-4,5,6,7-tetrahydro-indazol-1-yl]-acetic acid;
[4-(2-Fluoro-biphenyl-4-sulfonylamino)-4,5,6,7-tetrahydro-indazol-1-yl]-acetic acid;
[4-(2-Trifluoromethyl-biphenyl-4-sulfonylamino)-4,5,6,7-tetrahydro-indazol-1-yl]-acetic acid;
[4-(3'-Methoxy-biphenyl-4-sulfonylamino)-4,5,6,7-tetrahydro-indazol-1-yl]-acetic acid;
[4-(3'-Cyano-biphenyl-4-sulfonylamino)-4,5,6,7-tetrahydro-indazol-1-yl]-acetic acid;

[4-(2'-Chloro-biphenyl-3-sulfonylamino)-4,5,6,7-tetrahydro-indazol-1-yl]-acetic acid;
[(R)-4-(3'-Chloro-biphenyl-4-sulfonylamino)-4,5,6,7-tetrahydro-indazol-1-yl]-acetic acid;
[4-(3'-Trifluoromethoxy-biphenyl-4-sulfonylamino)-4,5,6,7-tetrahydro-indazol-1-yl]-acetic acid;
[4-(3'-Chloro-4'-fluoro-biphenyl-4-sulfonylamino)-4,5,6,7-tetrahydro-indazol-1-yl]-acetic acid;
[4-(5-Trifluoromethyl-biphenyl-3-sulfonylamino)-4,5,6,7-tetrahydro-indazol-1-yl]-acetic acid;
[4-(2'-Trifluoromethyl-biphenyl-4-sulfonylamino)-4,5,6,7-tetrahydro-indazol-1-yl]-acetic acid;
[4-(3',5'-Dimethyl-biphenyl-4-sulfonylamino)-4,5,6,7-tetrahydro-indazol-1-yl]-acetic acid;
[4-(3'-Hydroxy-biphenyl-4-sulfonylamino)-4,5,6,7-tetrahydro-indazol-1-yl]-acetic acid;
[4-(3'-Ethoxy-biphenyl-4-sulfonylamino)-4,5,6,7-tetrahydro-indazol-1-yl]-acetic acid;
[4-(3'-Isopropoxy-biphenyl-4-sulfonylamino)-4,5,6,7-tetrahydro-indazol-1-yl]-acetic acid;
[4-(3'-Acetyl-biphenyl-4-sulfonylamino)-4,5,6,7-tetrahydro-indazol-1-yl]-acetic acid;
[4-(3'-Nitro-biphenyl-4-sulfonylamino)-4,5,6,7-tetrahydro-indazol-1-yl]-acetic acid;
[4-(3',5'-Bis-trifluoromethyl-biphenyl-4-sulfonylamino)-4,5,6,7-tetrahydro-indazol-1-yl]-acetic acid;
[(R)-4-(3'-Trifluoromethyl-biphenyl-4-sulfonylamino)-4,5,6,7-tetrahydro-indazol-1-yl]-acetic acid;
[(R)-4-(3'-Trimethylsilanyl-biphenyl-4-sulfonylamino)-4,5,6,7-tetrahydro-indazol-1-yl]-acetic acid;
[(R)-4-(3'-Isopropyl-biphenyl-4-sulfonylamino)-4,5,6,7-tetrahydro-indazol-1-yl]-acetic acid;
[(R)-4-(3'-Methanesulfonyl-biphenyl-4-sulfonylamino)-4,5,6,7-tetrahydro-indazol-1-yl]-acetic acid;
[(R)-4-(3'-Methanesulfinyl-biphenyl-4-sulfonylamino)-4,5,6,7-tetrahydro-indazol-1-yl]-acetic acid;
(R)-3-[4-(biphenyl-4-sulfonylamino)-4,5,6,7-tetrahydro-indazol-1-yl]-propionic acid;
3-[(R)-4-(3'-Trifluoromethyl-biphenyl-4-sulfonylamino)-4,5,6,7-tetrahydro-indazol-1-yl]-propionic acid;
{(R)-4-[Methyl-(3'-trifluoromethyl-biphenyl-4-sulfonyl)-amino]-4,5,6,7-tetrahydro-indazol-1-yl}-acetic acid;
3-{(R)-4-[Methyl-(3'-trifluoromethyl-biphenyl-4-sulfonyl)-amino]-4,5,6,7-tetrahydro-indazol-1-yl}-propionic acid;
{(R)-4-[(4'-Fluoro-5-trifluoromethyl-biphenyl-3-sulfonyl)-methyl-amino]-4,5,6,7-tetrahydro-indazol-1-yl}-acetic acid;
((R)-4-{[3-(4-Chloro-phenylsulfonyl)-5-trifluoromethyl-benzenesulfonyl]-methyl amino}-4,5,6,7-tetrahydro-indazol-1-yl)-acetic acid;
((R)-4-{Methyl-[3-(toluene-4-sulfonyl)-5-trifluoromethyl-benzenesulfonyl]-amino}-4,5,6,7-tetrahydro-indazol-1-yl)-acetic acid;
3-((R)-4-{[3-(4-Fluoro-benzenesulfonyl)-5-trifluoromethyl-benzenesulfonyl]-methyl-amino}-4,5,6,7-tetrahydro-indazol-1-yl)-propionic acid;
3-((R)-4-{[3-(4-Chloro-benzenesulfonyl)-5-trifluoromethyl-benzenesulfonyl]-methyl-amino}-4,5,6,7-tetrahydro-indazol-1-yl)-propionic acid;
3-((R)-4-{[3-(4-Methoxy-benzenesulfonyl)-5-trifluoromethyl-benzenesulfonyl]-methyl-amino}-4,5,6,7-tetrahydro-indazol-1-yl)-propionic acid;
3-((R)-4-{Methyl-[3-(toluene-4-sulfonyl)-5-trifluoromethyl-benzenesulfonyl]-amino}-4,5,6,7-tetrahydro-indazol-1-yl)-propionic acid;
and any pharmaceutically acceptable salt or ester thereof.

In another embodiment, the present invention is directed to a compound selected from the group consisting of:
{4-[3-(5-Methyl-[1,3,4]oxadiazol-2-yl)-benzenesulfonylamino]-4,5,6,7-tetrahydro-indazol-1-yl}-acetic acid;
[4-(3-Benzoylamino-benzenesulfonylamino)-4,5,6,7-tetrahydro-indazol-1-yl]-acetic acid;
[(R)-4-(3-Benzenesulfonylamino-benzenesulfonylamino)-4,5,6,7-dihydro-indazol-1-yl]-acetic acid;
and any pharmaceutically acceptable salt or ester thereof.

General Synthesis of Compounds According to the Invention

The compounds of the present invention can be prepared by any conventional means. Suitable processes for synthesizing these compounds are provided in the examples. Generally, compounds of formula I can be prepared according to the schemes illustrated below.

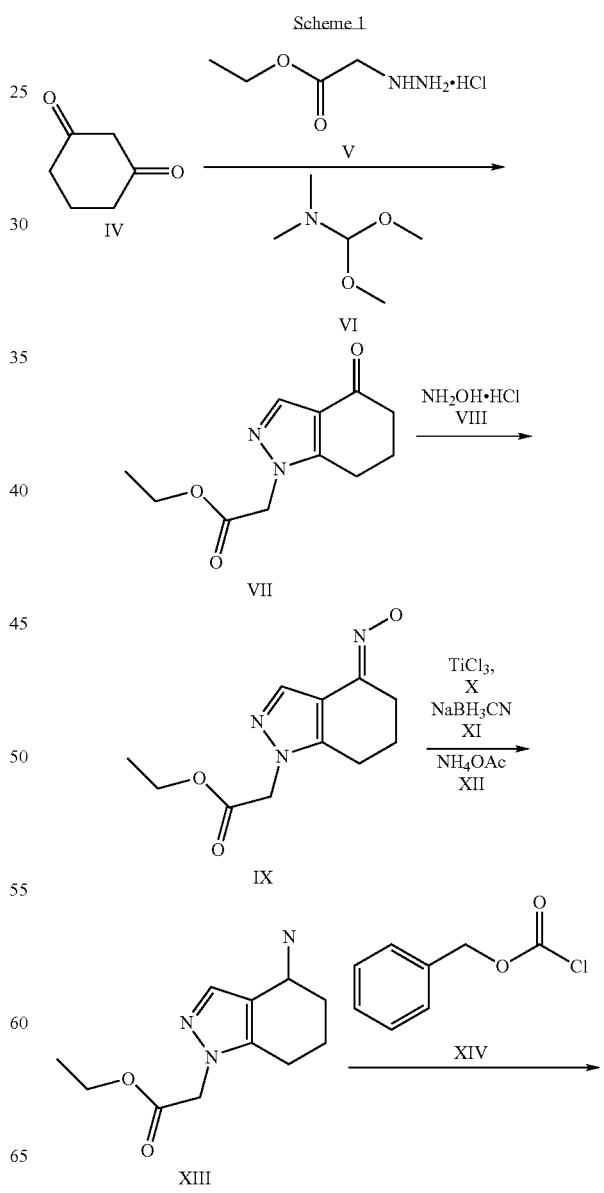

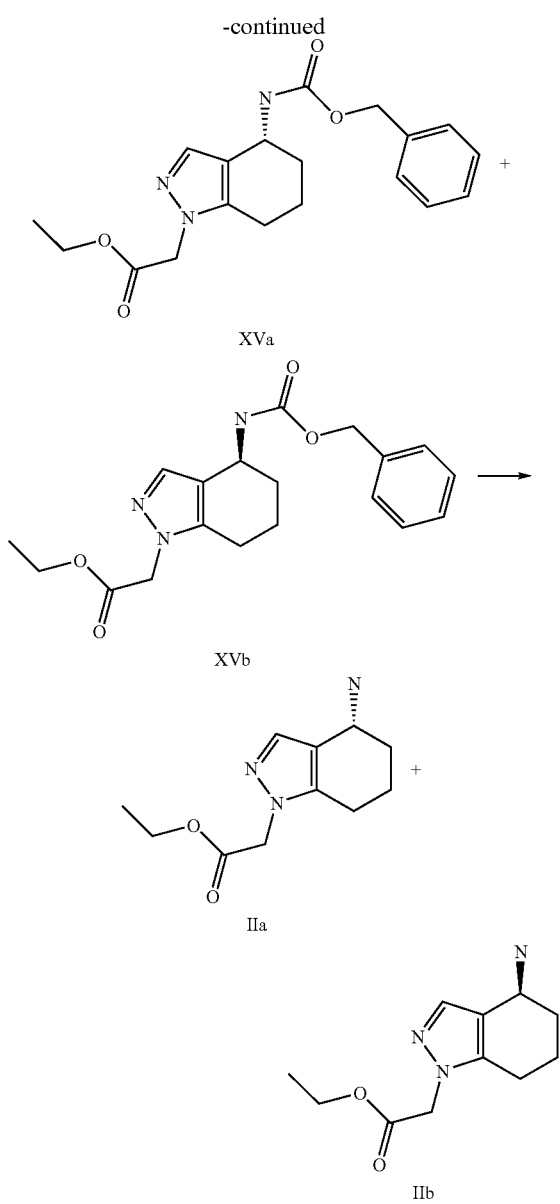

quently heating at 190° C. for 2 minutes under microwave irradiation (reference: Molteni, V. et al., *Synthesis* (2002) 1669).

Condensation of the ketone VII with hydroxylamine hydrochloride (VIII) to give the oxime IX can be achieved by heating the reaction mixture at a temperature between 70 and 90° C. (reflux temperature) for 1 to 3 hours in an alcohol solvent, such as methanol, ethanol, or n-butanol. The reaction can be carried out in the presence or absence of a base such as pyridine, sodium hydroxide, or sodium acetate.

Reduction of the oxime IX to the corresponding amine XIII can be achieved by using titanium (III) chloride (X), sodium cyanoborohydride (XI), and ammonium acetate (XII). The reaction can be carried out at room temperature for several hours, under an atmosphere of an inert gas such as nitrogen or argon (reference: Leeds, J. P. et al., *Synth. Comm.* 18 (1988) 777).

The racemic mixture of carbamates XVa and XVb can be prepared by the condensation of the intermediate XIII with benzyl chloroformate (XIV), in the presence of an inorganic base (such as sodium carbonate, sodium bicarbonate, or sodium hydroxide) or an organic base (such as triethylamine, diisopropylethylamine or the like). The reaction solvent can be a suitable inert solvent such as tetrahydrofuran, toluene, or 1,4-dioxane when an organic base is used, or a mixture of above solvent with water when an inorganic base is used. The reaction can initially be carried out at 0° C. temperature, and then slowly allowed to warm up to room temperature during several hours. The enantiomers from the racemic mixture thus prepared can be separated at this stage to XVa and XVb using a chiral column (CHIRALPAK AS-H, 5 um, 20×250 mm) on a Gilson instrument.

Hydrogenolysis of each single enantiomer XVa or XVb (or the racemic mixture of the two) to the corresponding amine of formula IIa or IIb with retained chirality can be conveniently carried out in the presence of 10% palladium on carbon under an atmospheric pressure of hydrogen, at room temperature for several hours, in an organic solvent such as ethyl acetate, methanol, or ethanol.

The key intermediates of formula IIa and IIb can be prepared according to Scheme 1. In this process, a cyclization reaction involving commercially available materials, cyclohexane-1,3-dione (IV), ethyl hydrazinoacetate hydrochloride (V), and dimethoxymethyl-dimethyl-amine (VI), gives the intermediate of formula VII, which is subsequently treated with hydroxylamine hydrochloride (VIII) to produce the oxime IX. Compound IX is then converted to the corresponding amino analogue XIII, which is further functionalized to the racemic mixture of its carbamate derivatives XVa and XVb. Hydrogenolysis of either XVa or XVb (or the mixture of the two) then provides the corresponding IIa or IIb separately (or as the mixture of the two).

In the first step outlined in Scheme 1, the intermediate VII can be prepared by treating cyclohexane-1,3-dione (IV) with an equimolar amount of ethyl hydrazinoacetate hydrochloride (V) in an inert solvent such as N,N-dimethylformamide at room temperature for about 5 minutes, followed by addition of dimethoxymethyl-dimethyl-amine (VI), and subse- Scheme 2

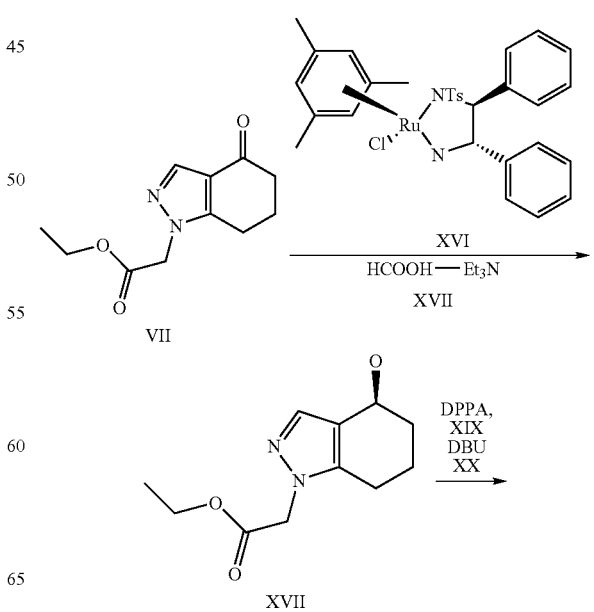

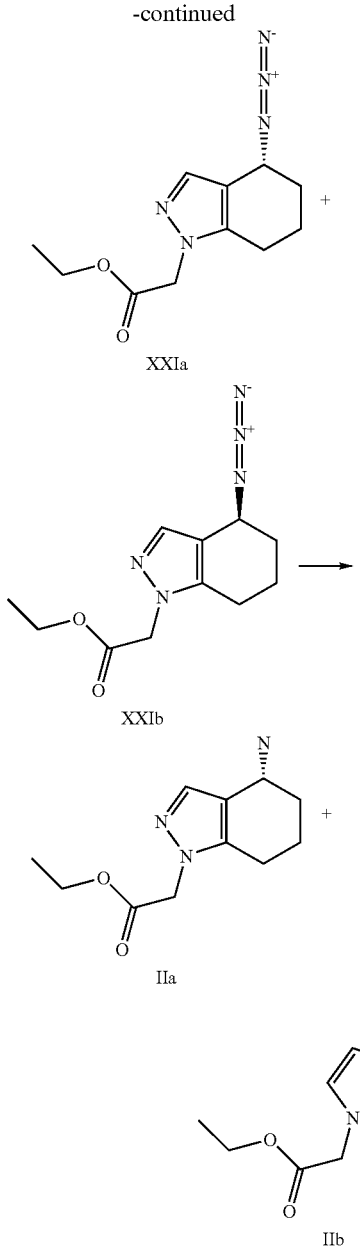

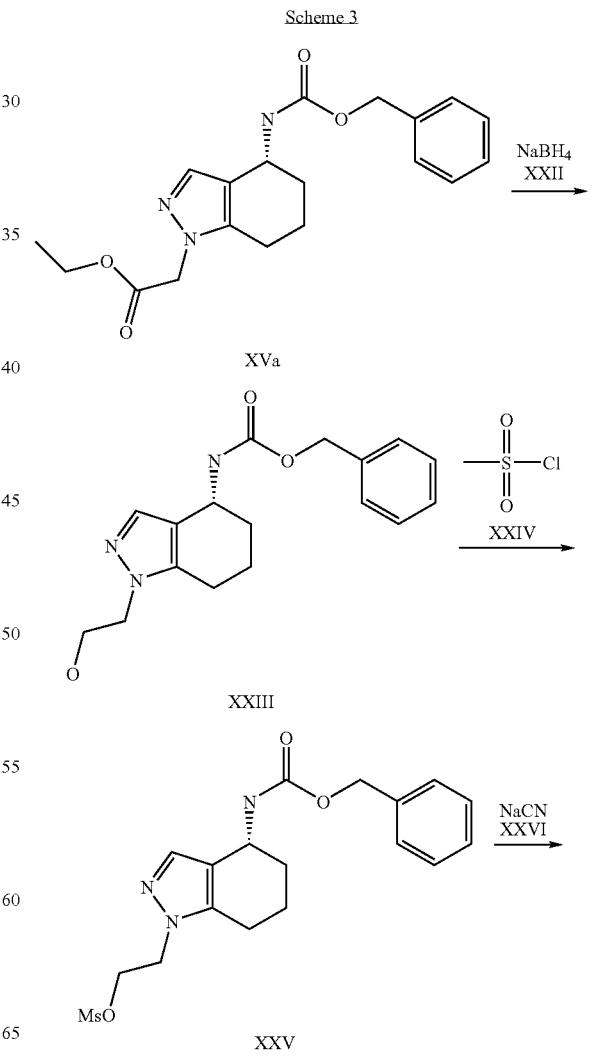

Scheme 3 acid-triethylamine azeoptropes (molar fraction of triethylamine: 0.2857) at room temperature for several hours, and then at 45° C. for another few hours (reference: Fuji, A. et al., *J. Am. Chem. Soc.* 118 (1996) 2521; Wagner, K. *Angew. Chem., Int. Ed. Engl.* 9 (1970), 50).

Conversion of the hydroxyl compound XVIII to its corresponding azido analogues XXIa and XXIb (with a high selectivity for XXIa) can be achieved by treating a mixture of compound XVIII and diphenylphosphoryl azide (DPPA) (XIX) with 1,8-diazabicyclo[5,4,0]-undec-7-ene (DBU) (XX) under anhydrous conditions at a temperature between −6 and 10° C. for 16 hours, in an inert solvent such as toluene or N,N-dimethylformamide. The enantiomers from the mixture thus prepared can be separated by preparative HPLC with a Chiralpak IA column (reference: Ho, W-B. et al., *J. Org. Chem.* 65 (2000) 6743).

Hydrogenation of each enantiomer XXIa or XXIb to give the corresponding amine IIa or IIb with retained chirality can be carried out in the presence of 10% palladium on carbon under 30 psi pressure of hydrogen, at room temperature for 1 hour, in an organic solvent such as ethyl acetate, methanol, or ethanol.

Alternatively, the key intermediate IIa or IIb can be prepared via an asymmetric synthesis approach shown in Scheme 2. This process gives predominately the enantiomer of structure IIa, which is the more preferable in this invention. Reduction of the ketone VII to the hydroxyl compound XVIII can be done enantioselectively by using the chiral catalyst of formula XVI in the presence of formic acid-triethylamine azeotropes (XVII). The hydroxyl compound XVIII is then converted to the corresponding azido analogue XXIa or XXIb with high selectivity for the formation of XXIa using diphenylphosphoryl azide (DPPA) (XIX) and 1,8-diazabicyclo[5,4,0]-undec-7-ene (DBU) (XX). Hydrogenation of either XXIa or XXIb gives the corresponding amine IIa or IIb with chirality intact.

Reduction of the ketone VII to the hydroxyl compound XVIII can be done enantioselectively by using a catalyst such as chloro-[(1S,2S)-N-(p-tolunenesulfonyl)-1,2-diphenylethane diamine](mesitylene) ruthenium(II) (XVI) in formic

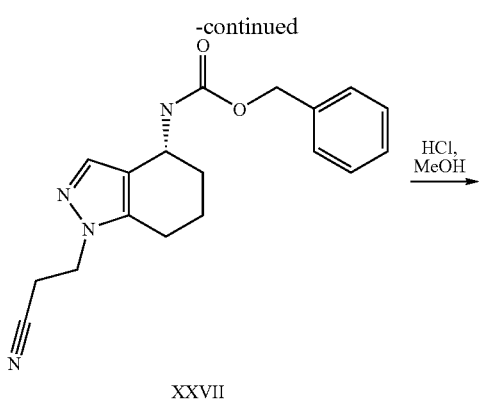

XXVII

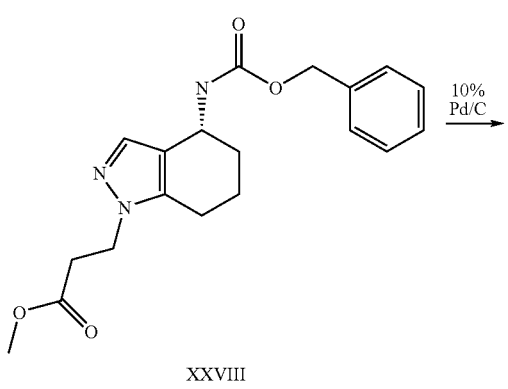

XXVIII

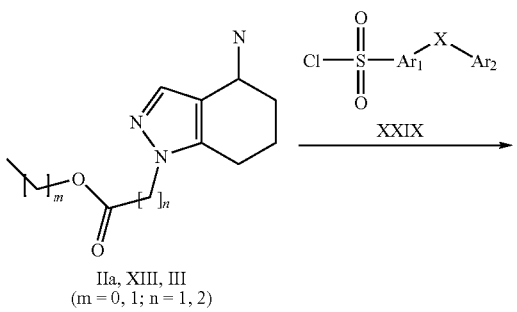

III

The key intermediate III can be prepared according to Scheme 3, starting with the intermediate XVa (synthesis shown in Scheme 1). Sodium borohydride reduction of the ester XVa gives the corresponding hydroxyl compound XXIII. Mesylation of the alcohol XXIII, followed by treatment with sodium cyanide (XXVI) generates the cyano derivative XXVII. Conversion of the cyanide XXVII to the methyl ester analogue XXVIII can be accomplished easily by alcoholysis. Hydrogenolysis of the benzyl carbamate XXVIII affords the intermediate III.

Reduction of the ester XVa to the corresponding alcohol XXIII can be easily done with a hydride-donor reagent such as sodium borohydride in an alcoholic solvent such as methanol or ethanol, at the reflux temperature of the solvent for several hours.

Reaction of the alcohol XXIII with methanesulfonyl chloride XXIV leads to the formation of the mesylate XXV. The reaction can be carried out in the presence of a base such as pyridine, triethylamine or diisopropylethylamine, in an inert solvent such as 1,4-dioxane, dichloromethane or tetrahydrofuran, at a temperature between 0° C. and room temperature for several hours.

Transformation of the mesylate XXV to the cyano derivative XXVII can be achieved by using sodium cyanide or potassium cyanide in a polar solvent such as dimethyl sulfoxide, N,N-dimethylformamide, or a mixture of ethanol and water at a temperature between 55 and 80° C. for 2 to 4 hours.

The methyl ester XXVIII can be prepared by acid catalyzed alcoholysis of the cyano derivative XXVII in a solution of hydrogen chloride in methanol at room temperature for 30 hours, or at a higher temperature (reflux temperature) for a shorter period of time.

Hydrogenolysis of the benzyl carbamate XXVIII gives the key intermediate III. The reaction can be carried out in the presence of 10% palladium on carbon under an atmospheric pressure of hydrogen in a solvent such as ethanol, ethyl acetate, or methanol at room temperature for several hours.

Scheme 4

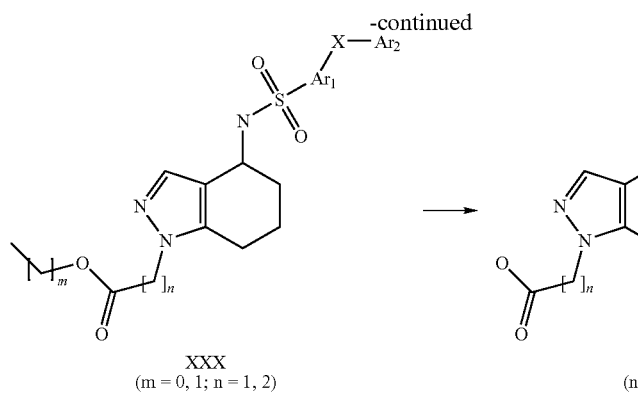

XXX
(m = 0, 1; n = 1, 2)

Ia
(n = 1, 2)

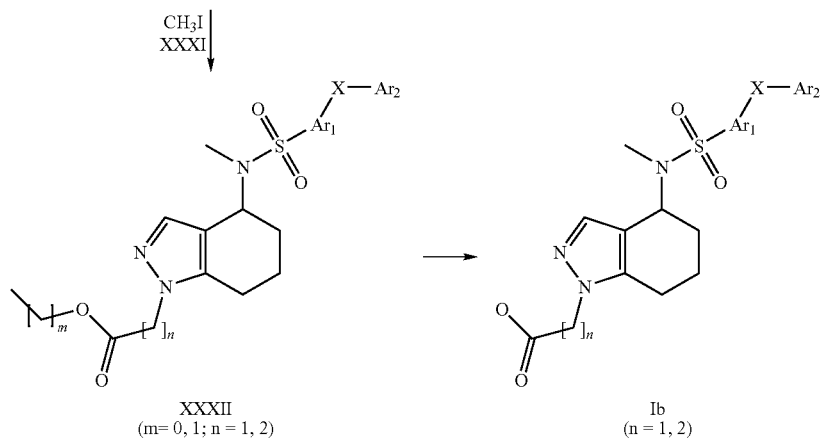

XXXII
(m = 0, 1; n = 1, 2)

Ib
(n = 1, 2)

The compounds of interest of formula Ia or Ib can be prepared according to Scheme 4. Sulfonylation of the amines IIa, XIII or III leads to the corresponding sulfonamides XXX. Hydrolysis of the ester XXX gives the compounds of interest Ia. The N-methyl derivatives Ib can be obtained through methylation of the intermediates XXX, followed by a hydrolysis reaction.

Sulfonylation of the amines IIa, IIb or III with the aromatic sulfonyl chlorides XXIX (where X could be a direct bond or oxygen.) to give the sulfonamides XXX can be easily accomplished using methods well known to someone skilled in the art. The reaction is typically carried out in the presence of a base such as triethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

The compounds of interest of formula Ia can be conveniently prepared via hydrolysis of the esters XXX. The reaction can be carried out in the presence of an aqueous inorganic base such as sodium hydroxide or potassium hydroxide, in an organic solvent such as 1,4-dioxane or tetrahydrofuran, at room temperature for several hours.

N-Methylation of compounds XXX to produce the derivatives XXXII can be achieved by treating compounds XXX with methyl iodide (XXXI) in the presence of a base such as potassium carbonate or sodium carbonate, in an inert solvent such as N,N-dimethylformamide, acetonitrile, or tetrahydrofuran, at 65° C. for 5 hours.

Hydrolysis of compounds XXXII gives the compounds of interest of formula Ib. The reaction can be carried out in the presence of an aqueous inorganic base such as sodium hydroxide or potassium hydroxide, in an organic solvent such as 1,4-dioxane or tetrahydrofuran, at room temperature for several hours.

Scheme 5

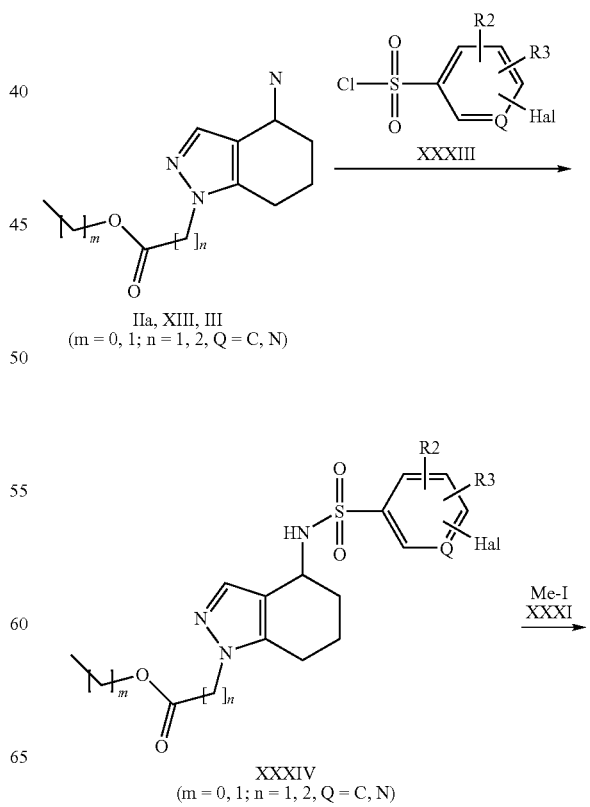

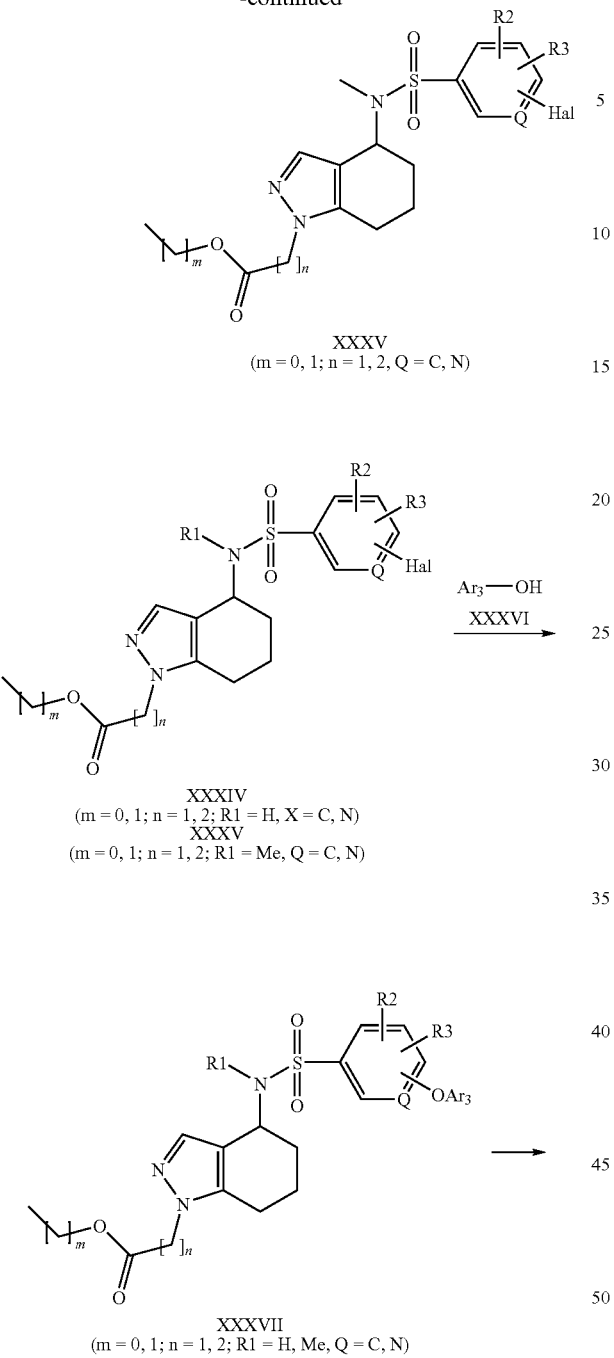

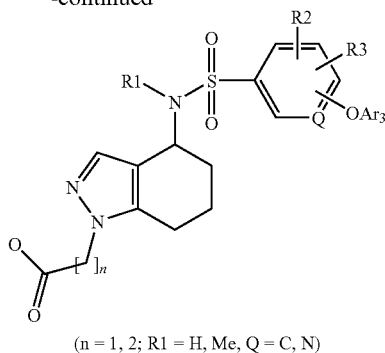

The compounds of interest of formula Ic, where a second aromatic ring ($Ar_3$) is linked to the aromatic sulfonamide through an ether linkage, can also be prepared according to Scheme 5. In this sequence, the first step involves a sulfonylation reaction (similar to Scheme 4), where the sulfonyl chlorides XXXIII used contain a halogen group (Cl or F) on the aromatic ring. Methylation of compounds XXXIV generates the corresponding N-methyl derivatives XXXV. Nucleophilic substitution of the halogen group of compounds XXXIV or XXXV with phenols XXXVI, followed by a hydrolysis reaction, produces compounds Ic.

Sulfonylation of the amines IIa, IIb or III with the aromatic sulfonyl chlorides XXXIII to give the sulfonamides XXXIV can be easily done using methods well known to someone skilled in the art. The reaction is typically carried out in the presence of a base such as triethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

The corresponding N-methyl compounds XXXV can be easily formed by methylation of compounds XXXIV with methyl iodide (XXXI). The reaction can be carried out in the presence of a weak base such as potassium carbonate or sodium carbonate, in an inert solvent such as N,N-dimethylformamide, acetonitrile or tetrahydrofuran, at 65° C. for 5 hours.

Conversion of compounds XXXIV or XXXV (where $R_1$ could be H, or $CH_3$) to the ethers XXXVII can be achieved by a nucleophilic substitution reaction with the phenols XXXVI, which is well known to those skilled in the art, in the presence of a base such as sodium hydride or potassium carbonate, in an inert solvent such as N,N-dimethylformamide at a temperature between 100 and 150° C. for 15 to 60 minutes under microwave irradiation.

Hydrolysis of compounds XXXVII (where $R_1$ could be H or $CH_3$) gives the compounds of interest of formula Ic. The reaction can be carried out in the presence of an aqueous inorganic base such as sodium hydroxide or potassium hydroxide, in an organic solvent such as 1,4-dioxane or tetrahydrofuran, at room temperature for several hours.

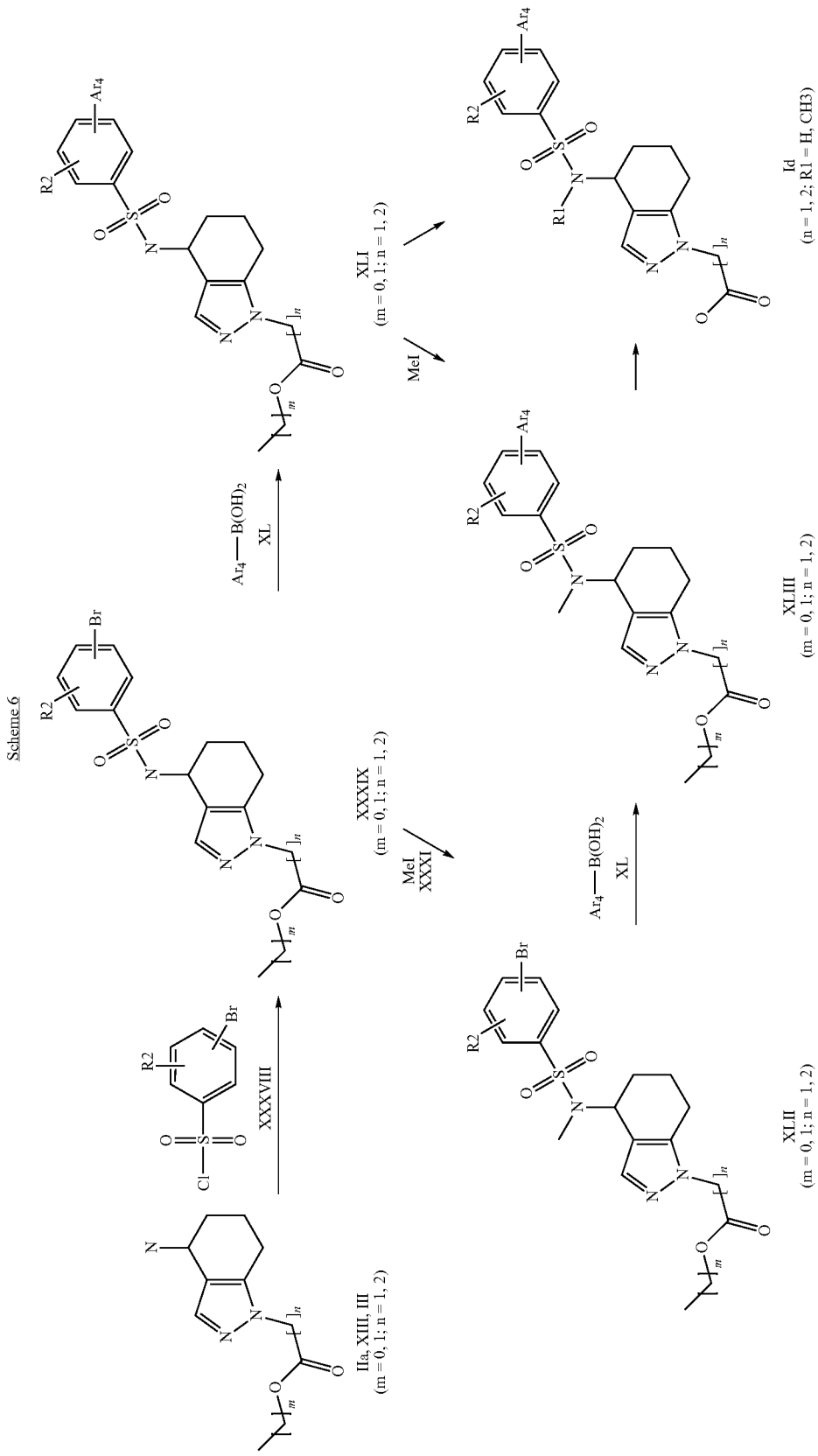

Synthesis of the compounds of interest of formula Id containing bi-aryl sulfonamides is illustrated in Scheme 6. In this process, the first step involves a sulfonylation reaction similar to that described in Scheme 4 utilizing the sulfonyl chlorides XXXVIII. Suzuki coupling of compounds XXXIX with the aryl boronic acids XL, followed by hydrolysis can afford the compounds of interest Id (where $R_1$=H). N-Methylated derivatives Id (where $R_1$=$CH_3$) can be prepared by two routes. One route is to methylate the N—H intermediates XXXIX first, followed by Suzuki coupling with aryl boronic acids XL, and subsequent hydrolysis. The alternative method is to perform the Suzuki coupling of compounds XXXIX with the aryl boronic acids XL first, followed by methylation, and subsequent hydrolysis.

Sulfonylation of the amines IIa, Ib or III with the aromatic sulfonyl chlorides of structures XXXVIII to give the sulfonamides XXXIX can be easily accomplished using methods well known to someone skilled in the art. For example, the reaction can be carried out in the presence of a base such as triethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

Suzuki coupling reactions between the aryl boronic acids XL and the aryl halides XXXIX to give compounds XLI can be easily done in the presence of a palladium catalyst such as [1,1'-bis(diphenylphosphino)ferrocene]dichloropalladium (II) ($PdCl_2$(dppf)), or tetrakis(triphenylphosphine)palladium (0), and a base such as potassium tert-butoxide, sodium carbonate, or sodium hydroxide, in an inert solvent such as N,N-dimethylformamide or dimethyl sulfoxide, at a temperature between 130 and 180° C. for 15 to 30 minutes under microwave irradiation (Lee S. et al., *Bioorg. Med. Chem. Lett.* 15 (2005) 2998). Alternatively, the reactions can be carried out without the use of a microwave at a heated temperature such as 130° C. for a longer reaction time.

The corresponding N-methyl derivatives XLII can be easily formed by methylation of compounds XXXIX with methyl iodide (XXXI). The reaction can be carried out in the presence of a weak base such as potassium carbonate or sodium carbonate, in an inert solvent such as N,N-dimethylformamide, acetonitrile or tetrahydrofuran, at 65° C. for 5 hours. In the same fashion as described above, Suzuki coupling reactions between the aryl boronic acids XL and compounds XLII to give compounds XLIII can be easily done in the presence of a palladium catalyst such as tetrakis(triphenylphosphine)palladium(0), or [1,1'-bis(diphenylphosphino)ferrocene]dichloropalladium(II) ($PdCl_2$(dppf)), and a base such as potassium tert-butoxide, sodium carbonate, or sodium hydroxide, in an inert solvent such as N,N-dimethylformamide or dimethyl sulfoxide, at a temperature between 130 and 180° C. for 15 to 30 minutes under microwave irradiation. Alternatively, the reactions can be carried out without the use of a microwave at a heated temperature such as 130° C. for a longer reaction time.

Compounds XLIII can also be obtained through methylation of the N—H intermediates XLI, which are obtained via Suzuki coupling between compound XXXIX and the boronic acids XL as described above. The methylation can be carried out in the presence of a weak base such as potassium carbonate or sodium carbonate, in an inert solvent such as N,N-dimethylformamide, acetonitrile, or tetrahydrofuran, at 65° C. for 5 hours.

Hydrolysis of compounds XLI or XLIII gives the compounds of interest of formula Id. The reaction can be carried out in the presence of an aqueous inorganic base such as sodium hydroxide or potassium hydroxide, in an organic solvent such as 1,4-dioxane or tetrahydrofuran, at room temperature for several hours.

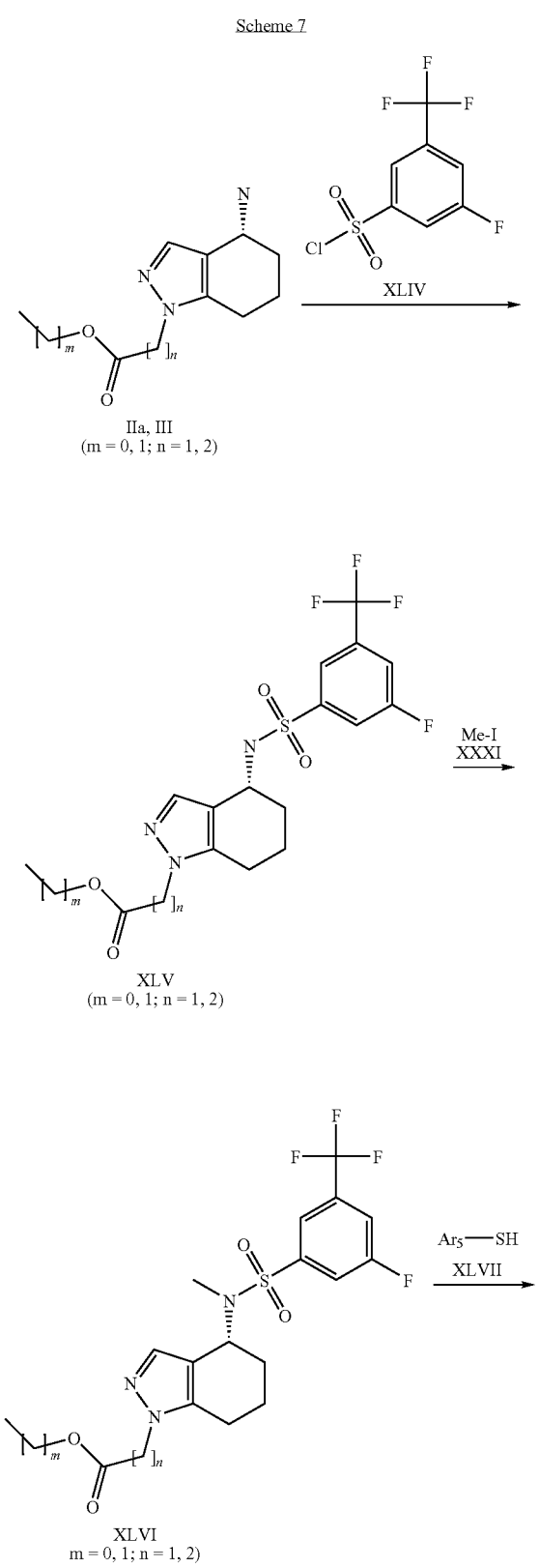

Scheme 7

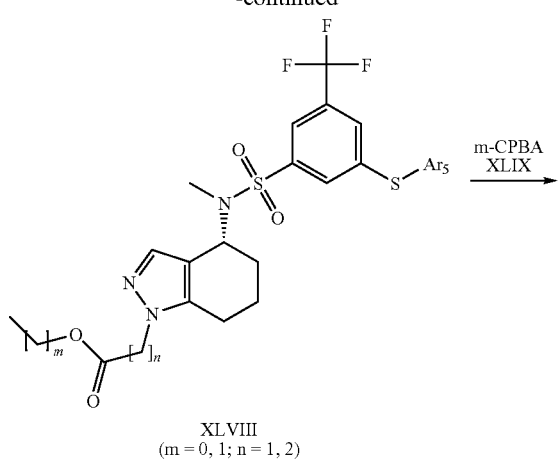

XLVIII
(m = 0, 1; n = 1, 2)

m-CPBA
XLIX
→

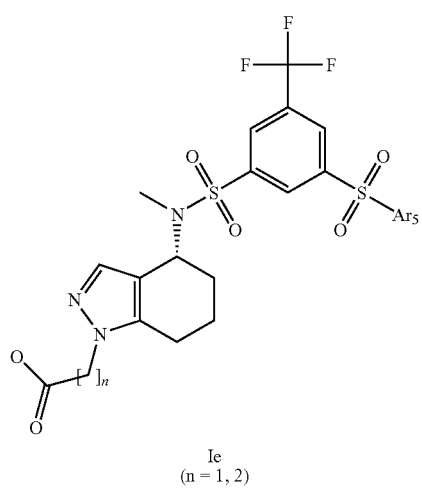

L
(m = 0, 1; n = 1, 2)

Ie
(n = 1, 2)

The compounds of interest of structures Ie, where two aromatic rings are linked through a sulfone group, can be prepared according to Scheme 7. In this process, compounds XLVI can be obtained as described in Scheme 5, via sulfonylation of the amines IIa or III with the sulfonyl chlorides XLIV, followed by methylation. Further transformation of the fluoro derivatives XLVI to generate compounds Ie can be accomplished by nucleophilic substitution with the aryl thiols XLVII, followed by oxidation to the corresponding sulfones, and subsequent hydrolysis.

Sulfonylation of the amines IIa or III with 3-fluoro-5-trifluoromethyl-benzenesulfonyl chloride (XLIV) to give the sulfonamides XLV can be easily done using methods well known to someone skilled in the art. The reaction is typically carried out in the presence of a base such as triethylamine, pyridine, or dimethyl-pyridin-4-yl-amine, in a suitable inert solvent such as dichloromethane, acetonitrile, 1,4-dioxane, tetrahydrofuran or mixtures thereof, at room temperature for 16 hours.

The corresponding N-methyl compounds XLVI can be easily formed by methylation of compounds XLV with methyl iodide (XXXI). The reaction can be carried out in the presence of a weak base such potassium carbonate or sodium carbonate, in an inert solvent such as N,N-dimethylformamide, acetonitrile, or tetrahydrofuran, at 65° C. for 5 hours.

Nucleophilic substitution of the fluoro compounds XLVI with the aryl thiols XLVII to give the 3-aryl sulfanyl analogues XLVIII can be accomplished in the presence of a base, such as potassium carbonate, cesium carbonate, potassium hydroxide, sodium acetate, or triethylamine, in a solvent such as N,N-dimethylformamide, dimethyl sulfoxide, ethanol, water or mixtures thereof, at a temperature between 100 and 150° C. for about 30 to 60 minutes under microwave irradiation. Alternatively, the reaction can be also carried out without the use of a microwave at a moderately heated temperature for a longer period of time.

Oxidation of the sulfanyl compounds XLVIII to the sulfonyl analogues L can be achieved using an oxidant such as hydrogen peroxide or m-chloroperoxybenzoic acid (m-CPBA) (XLIX), in an inert solvent such as dichloromethane or dichloroethane (or an aqueous solution if hydrogen peroxide is used), at a temperature between 0° C. and room temperature for several hours.

Hydrolysis of the esters L gives the compounds of interest Ie. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 8

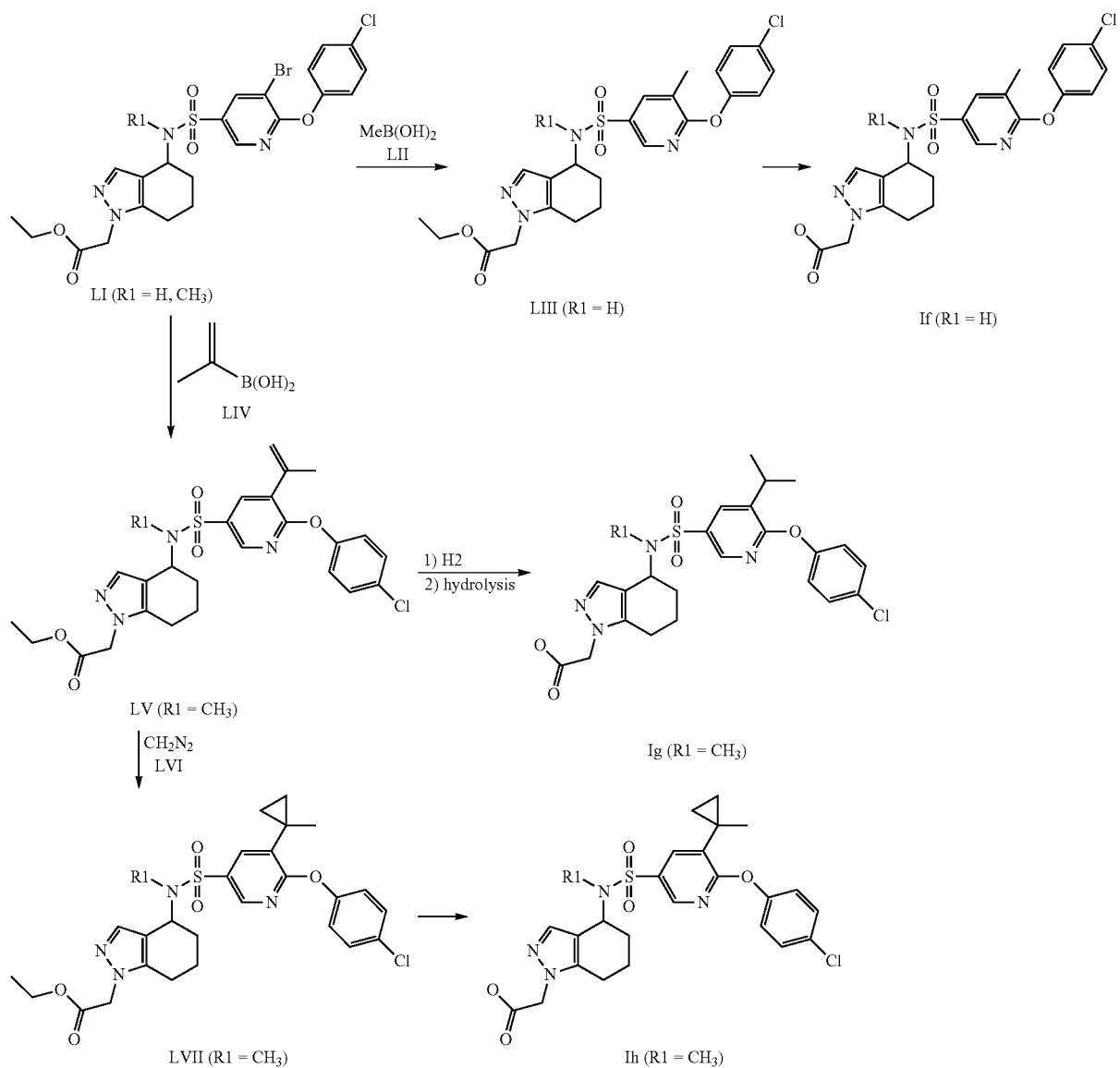

The compounds of interest of formula If-Ih can be prepared according to Scheme 8. Starting from the bromo derivatives LI, which are prepared in the same manner as intermediates XXXVII in Scheme 5, Suzuki coupling with methyl boronic acid (LII) gives compounds LIII. Further hydrolysis of the esters LIII generates compounds If. Suzuki coupling of compounds LI with isobutenyl boronic acid LIV produces the intermediates LV. Hydrogenation of the olefins LV, followed by ester hydrolysis affords compounds Ig. Treatment of the olefins LV with diazomethane, followed by ester hydrolysis generates compounds Ih.

Suzuki coupling reactions between compounds LI and methyl boronic acid (LII) or isobutenyl boronic acid (LIV) to give compounds LIII or LV, respectively, can be done in the presence of a palladium catalyst such as tetrakis(triphenylphosphine)palladium(0), or [1,1'-bis(diphenylphosphino)ferrocene]dichloropalladium(II) (PdCl$_2$(dppf)), and a base such as potassium tert-butoxide, sodium carbonate, or sodium hydroxide, in an inert solvent such as N,N-dimethylformamide or dimethyl sulfoxide, at a temperature between 130 and 180° C. for 15 to 30 minutes under microwave irradiation. Alternatively, the reaction can be carried out without the use of a microwave at a heated temperature such as 130° C. for a longer reaction time.

Hydrolysis of compounds LIII gives the compounds of interest of formula If. The reaction can be carried out in the presence of an aqueous inorganic base such as sodium hydroxide or potassium hydroxide, in an inert solvent such as 1,4-dioxane or tetrahydrofuran, at room temperature for several hours.

Conversion of the olefins LV to the corresponding saturated intermediates via hydrogenation can be carried out in the presence of 10% palladium on carbon under atmospheric pressure of hydrogen in a solvent such as ethanol, ethyl acetate, or methanol, at room temperature for several hours. The compounds of interest of formula Ig can be obtained through base-catalyzed hydrolysis in the presence of an aqueous inorganic base such as sodium hydroxide or potassium hydroxide, in an inert solvent such as dichloromethane or tetrahydrofuran, at room temperature for several hours.

Transformation of the olefins LV to the corresponding cyclopropyl derivatives LVII can be accomplished by treating compounds LV with diazomethane (LVI) in the presence of a palladium catalyst such as palladium acetate, palladium(II) acetylacetone, or palladium dichloride bis(benzonitrile), in a solvent such as dichloromethane, diethyl ether, tetrahydrofuran, or mixtures thereof, at a temperature between 0° C. and room temperature for several hours (reference: Staas, D. D. et al. *Bioorg. Med. Chem.* 14 (2006) 6900). Further hydrolysis of the cyclopropyl compounds LVII gives compounds of interest of formula Ih. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 9

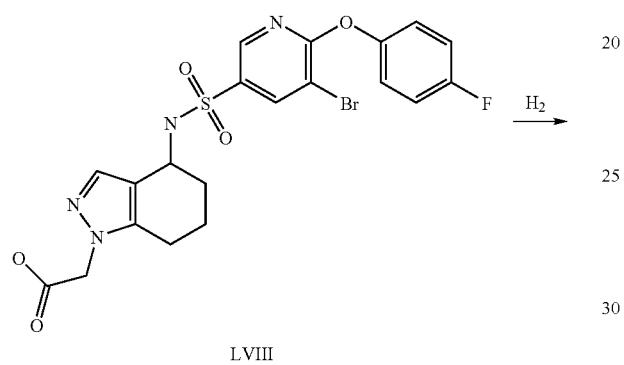

LVIII

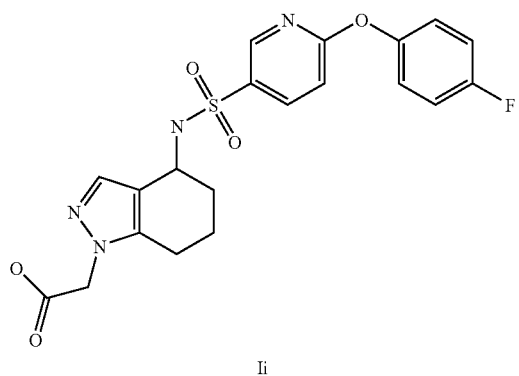

Ii

The compound of interest of formula Ii can be synthesized as illustrated in Scheme 9, starting from the compound LVIII, which can be prepared according to Scheme 5.

Catalytic hydrogenation/debromination of compound LVIII to produce compound Ii can be achieved in the presence of 10% palladium on carbon under 30 psi pressure of hydrogen in a solvent such as ethanol, ethyl acetate, or methanol, at room temperature for several hours.

Scheme 10

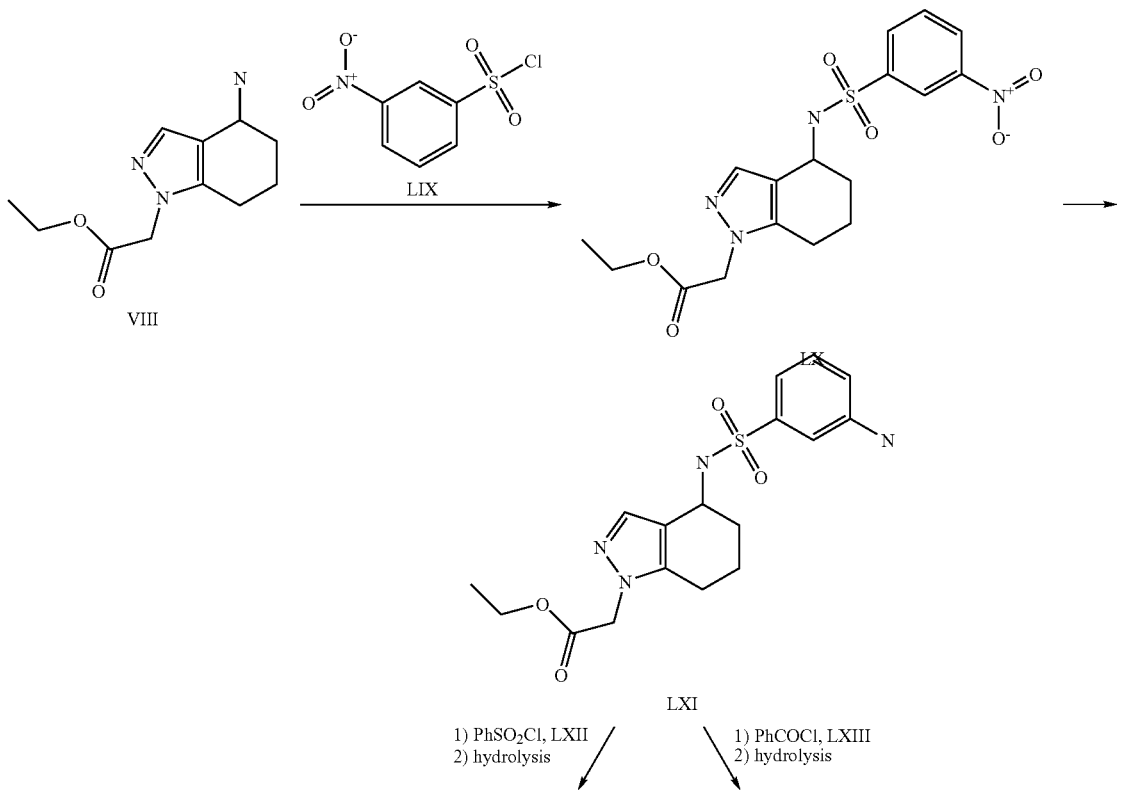

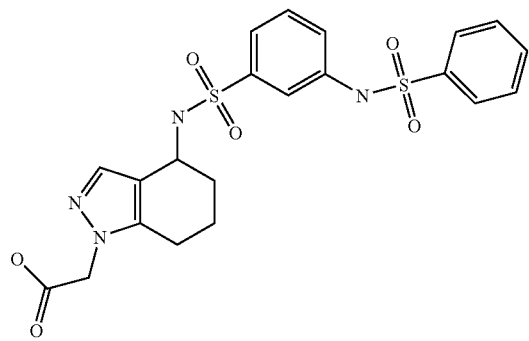

Ij

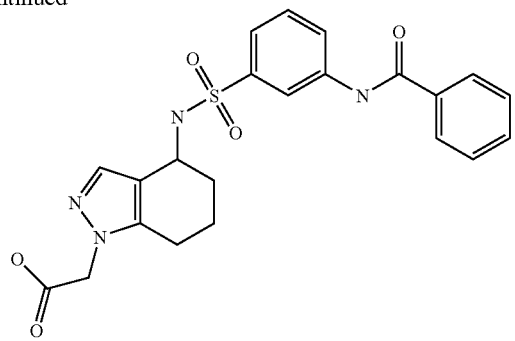

Ik

The compounds of interest of formula Ij and Ik can be synthesized as illustrated in Scheme 10. The aniline intermediate LXI can be generated by treating compound VIII with 3-nitrobenzensulfonyl chloride (LIX), followed by reduction of the nitro group to the corresponding amine. Sulfonylation of the aniline LXI, followed by hydrolysis of the ester produces the compound of interest Ij. Alternatively, acylation of compound LXI, followed by hydrolysis afford the compound of interest Ik.

Sulfonylation of the amine compound IIa with 3-nitrobenzensulfonyl chloride (LIX) to give the sulfonamide LX can be easily accomplished using methods well known to someone skilled in the art. For example, the reaction can be carried out in the presence of a base such as triethylamine, pyridine, or dimethyl-pyridin-4-yl-amine, in a suitable inert solvent such as dichloromethane, acetonitrile, 1,4-dioxane, or tetrahydrofuran and mixtures thereof, at room temperature for 16 hours.

Reduction of the nitro compound LX to the corresponding amine derivative LXI can be done using methods well known to someone skilled in the art. For example, Zinc reduction can be employed. The reaction typically is carried out under acidic conditions by using acetic acid, hydrochloric acid, or ammonium chloride in a suitable solvent such as methanol, ethanol, tetrahydrofuran, water or mixtures thereof, at a temperature between room temperature and reflux temperature of the solvent used for several hours.

Following the same procedure as the step 1 of this sequence, sulfonylation of the amine compound LXI with benzenesulfonyl chloride (LXII) provides the corresponding benzene sulfonamide. Hydrolysis of this sulfonamide leads to the final compound of interest Ij. The reaction can be carried out in the presence of an aqueous inorganic base such as sodium hydroxide or potassium hydroxide, in an inert solvent such as dichloromethane or tetrahydrofuran, at room temperature for several hours.

In the same fashion, acylation of the amine compound LXI with benzoyl chloride (LXIII) can be carried out in the presence of a base such as triethylamine, pyridine, or dimethyl-pyridin-4-yl-amine in a suitable inert solvent such as dichloromethane, acetonitrile, 1,4-dioxane, or tetrahydrofuran and mixtures thereof, at room temperature for 16 hours. Further hydrolysis of the above acetylated compound produces the compound of interest Ik. The reaction can be carried out in the presence of an aqueous inorganic base such as sodium hydroxide or potassium hydroxide, in an inert solvent such as 1,4-dioxane or tetrahydrofuran, at room temperature for several hours.

EXAMPLES

Although certain exemplary embodiments are depicted and described herein, the compounds of the present invention can be prepared using appropriate starting materials according to the methods described generally herein and/or by methods available to one of ordinary skill in the art.

Materials and Instrumentation in General

Intermediates and final compounds were purified by either flash chromatography and/or preparative HPLC (high performance liquid chromatography). Flash chromatography was performed using (1) the Biotage SP1™ system and the Quad 12/25 Cartridge module (from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 µm, OBD™ 30×100 mm) column (from Waters Corporation), or a SunFire™ Prep $C_{18}$ (5 µm, OBD™ 30×100 mm) column (from Waters Corporation)

Mass spectrometry (MS) was performed using a Waters® Alliance® 2795-ZQ™2000 (from Waters Corporation). Mass spectra data generally only indicates the parent ions unless otherwise stated. MS data is provided for a particular intermediate or compound where indicated.

Nuclear magnetic resonance spectroscopy (NMR) was performed using a Bruker Avance™ 400 MHZ Digital NMR Spectrometer (for the $^1$H NMR spectrum acquired at 400 MHz) (from Bruker BioSpin AG Ltd.). NMR data is provided for a particular intermediate or compound where indicated.

The microwave assisted reactions were carried out in a Biotage Initiator™ Sixty (or its early models) (from Biotage AB).

Chiral separation was performed by Preparative HPLC. Preparative HPLC was performed using an Agilent 1200 HPLC with a Chiral pak® IA (5 µm, 20×250 mm) column and a Chiral pak® AS-H (5 µm, 20×250 mm) column both from Daicel Chiral Technologies (China) co., Ltd.

All reactions involving air-sensitive reagents were performed under an inert atmosphere. Reagents were used as received from commercial suppliers unless otherwise noted.

Part I: Preparation of Preferred Intermediates

Preparation of ((R)-4-amino-4,5,6,7-tetrahydro-indazol-1-yl)-acetic acid ethyl ester (IIa) and ((S)-4-amino-4,5,6,7-tetrahydro-indazol-1-yl)-acetic acid ethyl ester (IIb)

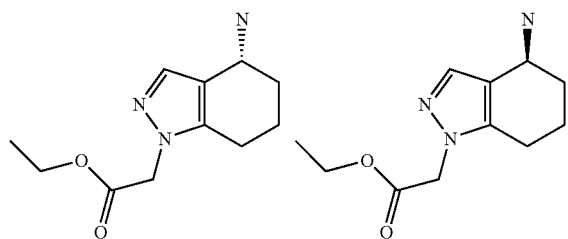

(4-Oxo-4,5,6,7-tetrahydro-indazol-1-yl)-acetic acid ethyl ester (VII)

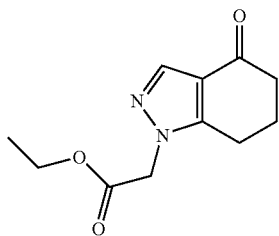

To a solution of cyclohexane-1,3-dione (50.7 g, 45.2 mmol) in N,N-dimethylformamide (700 mL) was added ethyl hydrazinoacetate hydrochloride (70 g, 45.2 mmol). The reaction mixture was stirred for 5 minutes, then dimethoxymethyl-dimethyl-amine (53.9 g, 45.2 mmol) was added. The reaction mixture was divided into 50 vials, which were heated in a microwave at 190° C. for 2 minutes. After cooling to room temperature, the combined reaction mixture was concentrated in vacuo to remove most of N,N-dimethylformamide. Water (200 mL) was added, and the resulting dark brown mixture was extracted with ethyl acetate (200 mL×3). The organic layers were combined, washed with brine (600 mL), dried over sodium sulfate and concentrated in vacuo to afford a brown oil, which was placed in a fridge overnight. The resulting yellow precipitate was filtered and washed with petroleum ether to give (4-oxo-4,5,6,7-tetrahydro-indazol-1-yl)-acetic acid ethyl ester (79 g, 79%) as yellow crystals. $^1$H NMR (400 MHz, CDCl$_3$) δ ppm 7.92 (s, 1 H), 4.89 (s, 2 H), 4.26 (m, 2 H), 2.80 (t, J=6.4 Hz, 2 H), 2.51 (t, J=6.4 Hz, 2 H), 2.20 (t, J=6.4 Hz, 2 H), 1.31 (t, J=7.2 Hz, 3 H). MS calcd. for C$_{11}$H$_{14}$N$_2$O$_3$ 222, obsd. (ESI$^+$) (M+H)$^+$223.

(4-Hydroxyimino-4,5,6,7-tetrahydro-indazol-1-yl)-acetic acid ethyl ester (IX)

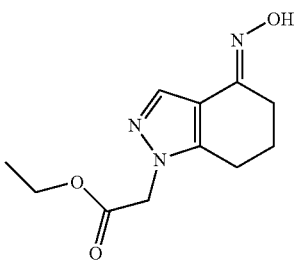

To a stirred solution of (4-oxo-4,5,6,7-tetrahydro-indazol-1-yl)-acetic acid ethyl ester (222 mg, 10 mmol) in ethanol (10 mL) was added hydroxylammonium chloride (74 mg, 10.5 mmol). The reaction mixture was heated at reflux for 1 hour. After cooling to room temperature, a solution of concentrated ammonia and saturated ammonium chloride (10 mL, 1:5, v/v) was added to the reaction mixture. The resulting solution was extracted with ethyl acetate (25 mL×3). The combined organic layers were washed with brine (30 mL), dried over sodium sulfate and concentrated in vacuo to give 4-hydroxyimino-4,5,6,7-tetrahydro-indazol-1-yl)-acetic acid ethyl ester (203 mg, 85%) as a white solid, which was used for the next step without further purification. The above white solid contained a pair of isomers in 10 to 1 ratio as determined by $^1$HNMR. for the major isomer, $^1$H NMR (400 MHz, CDCl$_3$) δ ppm 8.29 (s, 1 H), 4.89 (s, 2 H), 4.26 (m, 2 H), 2.73 (t, J=6.4 Hz, 2 H), 2.58 (t, J=6.4 Hz, 2 H), 2.10 (t, J=6.4 Hz, 2 H), 1.31 (t, J=7.2 Hz, 3 H). MS calcd. for C$_{11}$H$_{15}$N$_3$O$_3$ 237, obsd. (ESI$^+$) [(M+H)$^+$] 238.

(4-Amino-4,5,6,7-tetrahydro-indazol-1-yl)-acetic acid ethyl ester (XIII)

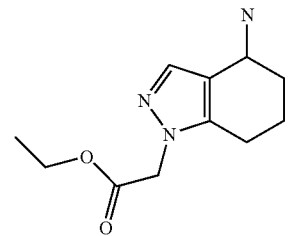

To a solution of (4-hydroxyimino-4,5,6,7-tetrahydro-indazol-1-yl)-acetic acid ethyl ester (132 mg, 0.59 mmol), sodium cyanoborohydride (110 mg, 1.76 mmol), and ammonium acetate (0.5 g, 7.2 mmol) in methanol (10 mL) was added titanium (III) chloride (0.99 mL, 20% wt in water, 1.68 mmol) dropwise. The reaction mixture was stirred at room temperature for 2 hours under an argon atmosphere. To the above mixture were added water (10 mL) and a solution of concentrated ammonia and saturated ammonium chloride (10 mL, 1:5, v/v). The resulting mixture was filtered through a pad of Celite® (a diatomite filter from World Minerals Inc.) with dichloromethane (30 mL). The separated aqueous layer was extracted with dichloromethane (20 mL×3). The combined organic layers were washed with brine (30 mL), dried over sodium sulfate and concentrated in vacuo to afford 4-amino-4,5,6,7-tetrahydro-indazol-1-yl)-acetic acid ethyl ester (131 mg, 99%) as a viscous light brown oil. $^1$H NMR (400 MHz, CD$_3$OD) δ ppm 7.76 (s, 1 H), 5.34 (s, 2 H), 4.60 (m, 2 H), 4.34 (m, 2 H), 2.70 (m, 2 H), 2.20 (m, 1 H), 1.98 (m, 3 H), 1.32 (t, J=7.2 Hz, 3 H). MS calcd. for C$_{11}$H$_{17}$N$_3$O$_2$ 223, obsd. (ESI$^+$) [(M+H)$^+$] 224.

((R)-4-Benzyloxycarbonylamino-4,5,6,7-tetrahydro-indazol-1-yl)-acetic acid ethyl ester (XVa) and ((S)-4-Benzyloxycarbonylamino-4,5,6,7-tetrahydro-indazol-1-yl)-acetic acid ethyl ester (XVb)

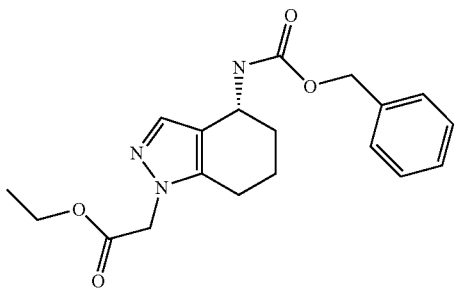

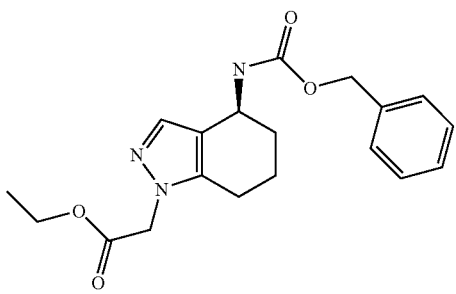

To a solution of (4-amino-4,5,6,7-tetrahydro-indazol-1-yl)-acetic acid ethyl ester (60 mg, 0.27 mmol) in 5% sodium carbonate (0.57 mL) and 1,4-1,4-dioxane (1 mL) was added benzyl chloroformate (58 uL, 0.40 mmol) at 0° C. The reaction mixture was allowed to warm to room temperature slowly, and stirred overnight. The reaction mixture was partitioned between water (10 mL) and dichloromethane (20 mL×3). The combined organic layers were collected and dried over sodium sulfate, filtered and concentrated in vacuo. The residue was purified by column chromatography (50% ethyl acetate in hexanes) to afford racemic (4-benzyloxycarbonylamino-4,5,6,7-tetrahydro-indazol-1-yl)-acetic acid ethyl ester (94.2 mg, 98.2%) as a white solid. $^1$H NMR (400 MHz, CDCl$_3$) δ ppm 7.54 (s, 1 H), 7.49-7.35 (m, 4 H), 5.18 (s, 2 H), 5.23 (s, 2 H), 4.92-4.80 (m, 3 H), 4.23 (dd, J=7.2 Hz, 2 H), 2.52 (m, 2 H), 2.05-1.88 (m, 4 H), 1.30 (t, J=7.2 Hz, 3 H). MS calcd. for C$_{19}$H$_{23}$N$_3$O$_4$ 357, obsd. (ESI$^+$) [(M+H)$^+$] 358. The chrial separation (Gilson instrument: column: AS-H; flow rate: 15 mL/min; gradient: 55% hexane in propan-2-ol) gave ((R)-4-benzyloxycarbonylamino-4,5,6,7-tetrahydro-indazol-1-yl)-acetic acid ethyl ester (retention time 7.2 minutes) and ((S)-4-benzyloxycarbonylamino-4,5,6,7-tetrahydro-indazol-1-yl)-acetic acid ethyl ester (retention time 8.7 minutes). The recovery for both isomers together was 70%.

((R)-4-Amino-4,5,6,7-tetrahydro-indazol-1-yl)-acetic acid ethyl ester (IIa)

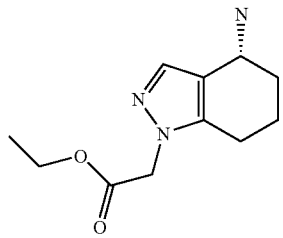

A solution of ((R)-4-amino-4,5,6,7-tetrahydro-indazol-1-yl)-acetic acid ethyl ester (357 mg, 1.0 mmol) in ethanol was hydrogenated over 10% palladium on carbon (40 mg) under atmospheric pressure at room temperature for 3 hours. The reaction mixture was then filtered through a pad of Celite® (diatomite filter). The filtrate was collected and concentrated in vacuo to afford ((R)-4-amino-4,5,6,7-tetrahydro-indazol-1-yl)-acetic acid ethyl ester (224 mg, 99%) as a light yellow oil. MS calcd. for C$_{11}$H$_{17}$N$_3$O$_2$ 223, obsd. (ESI$^+$) [(M+H)$^+$] 224.

The stereochemistry of the R-configuration of the compounds of the present invention was further confirmed by x-ray crystallography of [(R)-4-(3-bromo-5-tert-butyl-benzenesulfonylamino)-4,5,6,7-tetrahydro-indazol-1-yl]-acetic acid ethyl ester, prepared from IIa according to methods described herein.

((S)-4-Amino-4,5,6,7-tetrahydro-indazol-1-yl)-acetic acid ethyl ester (IIb)

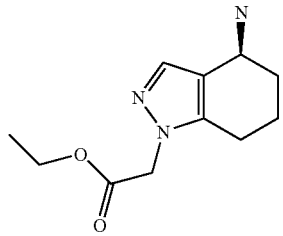

A solution of ((S)-4-amino-4,5,6,7-tetrahydro-indazol-1-yl)-acetic acid ethyl ester (357 mg, 1.0 mmol) in ethanol was hydrogenated over 10% palladium on carbon (40 mg) under atmospheric pressure at room temperature for 3 hours. The reaction mixture was then filtered through a pad of Celite® (diatomite filter). The filtrate was collected and concentrated in vacuo to afford ((S)-4-amino-4,5,6,7-tetrahydro-indazol-1-yl)-acetic acid ethyl ester (224 mg, 99%). MS calcd. for C$_{11}$H$_{17}$N$_3$O$_2$ 223, obsd. (ESI$^+$) [(M+H)$^+$] 224.

Alternatively, ((R)-4-amino-4,5,6,7-tetrahydro-indazol-1-yl)-acetic acid ethyl ester (IIa) and ((S)-4-amino-4,5,6,7-tetrahydro-indazol-1-yl)-acetic acid ethyl ester (IIb) can be synthesized according to Scheme 2. The detailed experimental procedures are described below.

((S)-4-Hydroxy-4,5,6,7-tetrahydro-indazol-1-yl)-acetic acid ethyl ester (XVIII)

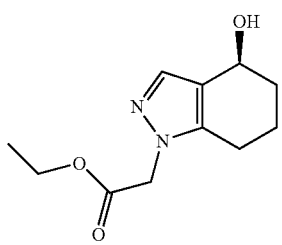

To a stirred solution of (4-oxo-4,5,6,7-tetrahydro-indazol-1-yl)-acetic acid ethyl ester (16.7 g, 75.0 mmol) in formic acid-triethylamine azeotropes (molar fraction of triethylamine: 0.2857, 45 mL) was added chloro-[(1S,2S)-N-(p-tolunenesulfonyl)-1,2-diphenylethanediamine](mesitylene)ruthenium(II) (1.86 g, 3.0 mmol). The reaction mixture was stirred at room temperature for 3 hours and then at 45° C. for 2.5 hours with occasional venting. After cooling to room temperature, 1N hydrochloric acid (50 mL) was added, followed by extraction with ethyl acetate (200 mL×3). The organic layers were combined, washed with brine (300 mL), dried over sodium sulfate, filtered and concentrated in vacuo. The residue was purified by column chromatography (gradient elution, 0-4% methanol in dichloromethane) to afford ((S)-4-hydroxy-4,5,6,7-tetrahydro-indazol-1-yl)-acetic acid ethyl ester (14.3 g, 85%) as a white solid with enantiomerical purity ≧99% as determined by Chiralpak™ IA column (condition: gradient: 50% hexane in ethanol, flow rate: 15 mL/min and retention time: 5.8 min for A enantiomer and 8.1 min for B enantiomer).

$^1$H NMR (400 MHz, CD$_3$OD) δ ppm 7.47 (s, 1 H), 4.89(d, 4 H), 4.76 (d, 1 H), 4.20 (q, J=7.2 Hz, 2 H), 2.52 (m, 2 H), 2.06-1.84 (m, 4 H), 1.29 (t, J=7.2 Hz, 3 H). MS calcd. for C$_{11}$H$_{16}$N$_2$O$_3$ 224, obsd. (ESI$^+$) [(M+H)$^+$] 225.

((R)-4-Azido-4,5,6,7-tetrahydro-indazol-1-yl)-acetic acid ethyl ester (XXIa) and (S)-(4-Azido-4,5,6,7-tetrahydro-indazol-1-yl)-acetic acid ethyl ester (XXIb)

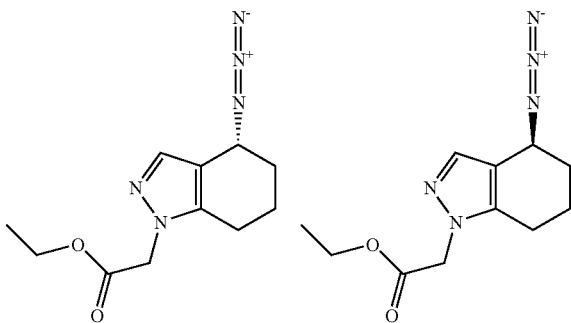

An oven dried flask was charged with ((S)-4-hydroxy-4,5,6,7-tetrahydro-indazol-1-yl)-acetic acid ethyl ester (14.3 g, 63.8 mmol), diphenylphosphoryl azide (DPPA) (15.1 mL, 70.1 mmol) and anhydrous toluene (100 mL). The mixture was cooled to −6° C. in an ice bath. 1,8-diazabicyclo[5,4,0]-undec-7-ene (DBU) (9.53 mL, 63.8 mmol) was added dropwise, while maintaining the internal temperature of the reaction below 5° C. The reaction mixture was stirred below 10° C. for 16 hours. After the reaction was complete, a solution of saturated ammonium chloride (50 mL) was added, and the aqueous layer was extracted with dichloromethane (100 mL×3). The combined organic layers were dried over sodium sulfate, filtered and concentrated in vacuo. The residue was purified by column chromatography (gradient elution, 15-30% ethyl acetate in petroleum ether) to afford a mixture of two enantiomers (10.7 g, 67.4%). The ratio of (R)-enantiomer to (S)-enantiomer was 8:2 as determined by HPLC with Chiralpak™ IA column).

The two enantiomers were further separated by HPLC with Chiralpak™ IA column (separation condition: gradient: 70% hexane in ethanol; flow rate: 15 mL/min; retention time: 7.4 min for (R)-enantiomer and 8.9 min for (S)-enantiomer) to afford ((R)-4-azido-4,5,6,7-tetrahydro-indazol-1-yl)-acetic acid ethyl ester (7.1 g, e.e. % ≧99%) as a viscous oil.

$^1$H NMR (400 MHz, CD$_3$OD) δ ppm 7.51 (s, 1 H), 4.91(s, 4 H), 4.63 (s, 1 H), 4.20 (q, J=7.2 Hz, 2 H), 2.52 (m, 2 H), 1.97-1.88 (m, 4 H), 1.29 (t, J=7.2 Hz, 3 H). MS calcd. for C$_{11}$H$_{15}$N$_5$O$_2$ 249, obsd. (ESI$^+$) [(M+H)$^+$] 250.

((R)-4-Amino-4,5,6,7-tetrahydro-indazol-1-yl)-acetic acid ethyl ester (IIa)

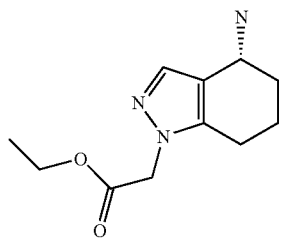

A solution of ((R)-4-azido-4,5,6,7-tetrahydro-indazol-1-yl)-acetic acid ethyl ester (1.25 g, 5.0 mmol) in ethanol (40 mL) was hydrogenated over 10% palladium on carbon (130 mg) under 30 psi in a 150 mL parr bottle at room temperature for 1 hour. The reaction mixture was filtered through a pad of Celite® (diatomite filter). The filtrate was collected and concentrated in vacuo to afford ((R)-4-amino-4,5,6,7-tetrahydro-indazol-1-yl)-acetic acid ethyl ester as an oil (1.10 g, 98%), which was used in the next step without further purification. MS calcd. for $C_{11}H_{17}N_3O_2$ 223, obsd. (ESI$^+$) [(M+H)$^+$] 224.

Preparation of 3-((R)-4-amino-4,5,6,7-tetrahydro-indazol-1-yl)-propionic acid methyl ester (III)

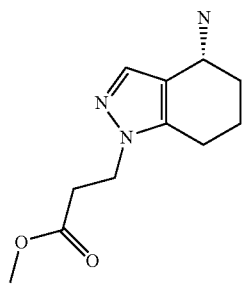

[(R)-1-(2-Hydroxy-ethyl)-4,5,6,7-tetrahydro-1H-indazol-4-yl]-carbamic acid benzyl ester (XXIII)

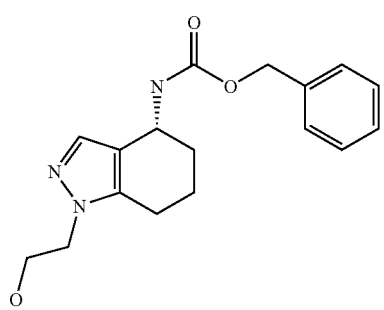

To a solution of ((R)-4-benzyloxycarbonylamino-4,5,6,7-tetrahydro-indazol-1-yl)-acetic acid ethyl ester (2.00 g, 5.60 mmol) in methanol (150 mL) was added sodium borohydride (1.61 g, 39.5 mmol). The mixture was stirred at 70° C. for 2 hours. After being cooled to room temperature, the reaction mixture was acidified to pH 7 with 5N hydrochloric acid, and then concentrated to remove methanol. The resulting mixture was extracted with dichloromethane (20 mL). After filtering out any insoluble materials from the organic layer, the filtrate was concentrated in vacuo to give [(R)-1-(2-hydroxy-ethyl)-4,5,6,7-tetrahydro-1H-indazol-4-yl]-carbamic acid benzyl ester (1.68 g, 95%) as a white solid. MS calcd. for $C_{17}H_{21}N_3O_3$ 315, obsd. (ESI$^+$) [(M+H)$^+$] 316.

Methanesulfonic acid 2-((R)-4-benzyloxycarbonylamino-4,5,6,7-tetrahydroindazol-1-yl)-ethyl ester (XXV)

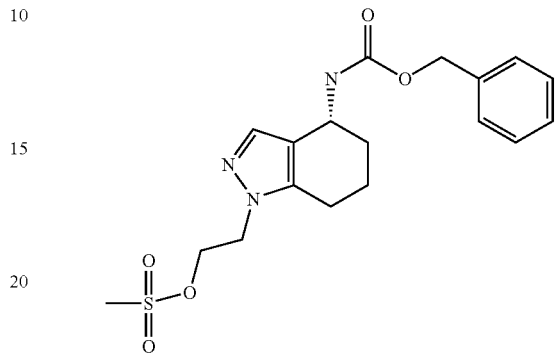

To a solution of [(R)-1-(2-hydroxy-ethyl)-4,5,6,7-tetrahydro-1H-indazol-4-yl]-carbamic acid benzyl ester (755 mg, 2.40 mmol) and pyridine (1.45 mL, 18.0 mmol) in dichloromethane was added methanesulfonyl chloride (1.40 mL, 18.0 mmol) dropwise at 0° C. The mixture was warmed to room temperature and stirred for 6 hours The resulting mixture was poured into ice (10 g). The organic layer was then separated and washed with 0.1 N hydrochloric acid and saturated sodium bicarbonate, dried over sodium sulfate, filtered and concentrated in vacuo. The residue was purified by column chromatography (10% methanol in dichloromethane) to afford methanesulfonic acid 2-((R)-4-benzyloxycarbonylamino-4,5,6,7-tetrahydroindazol-1-yl)-ethyl ester (880 mg, 90%) as a white solid. MS calcd. for $C_{18}H_{23}N_3O_5S$ 393, obsd. (ESI$^+$) [(M+H)$^+$] 394.

[(R)-1-(2-Cyano-ethyl)-4,5,6,7-tetrahydro-1H-indazol-4-yl]-carbamic acid benzyl ester (XXVII)

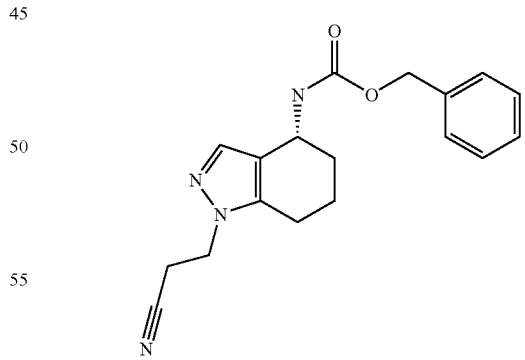

To a solution of methanesulfonic acid 2-((R)-4-benzyloxycarbonylamino-4,5,6,7-tetrahydroindazol-1-yl)-ethyl ester (850 mg, 2.16 mmol) in dimethyl sulfoxide (20 mL) was added sodium cyanide (540 mg, 10.8 mmol). The mixture was stirred at 55° C. for 4 hours. After cooling, the mixture was poured into water, and the aqueous layer was extracted with ethyl acetate (20 mL×4). The combined organic layers were dried over sodium sulfate, filtered and concentrated in vacuo.

The residue was purified by flash column chromatography (10% methanol in dichloromethane) to afford [(R)-1-(2-cyano-ethyl)-4,5,6,7-tetrahydro-1H-indazol-4-yl]-carbamic acid benzyl ester (600 mg, 85%) as a white solid. MS calcd. for $C_{18}H_{20}N_4O_2$ 324, obsd. (ESI$^+$) [(M+H)$^+$] 325.

3-((R)-4-Benzyloxycarbonylamino-4,5,6,7-tetrahydro-indazol-1-yl)-propionic acid methyl ester (XXVIII)

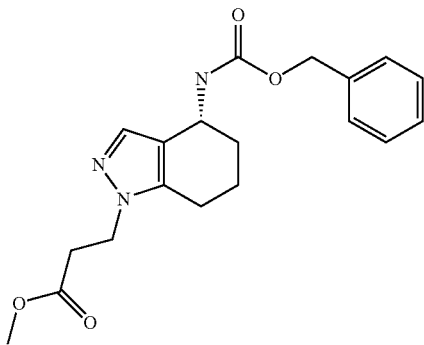

A solution of [(R)-1-(2-cyano-ethyl)-4,5,6,7-tetrahydro-1H-indazol-4-yl]-carbamic acid benzyl ester (700 mg, 1.96 mmol) in 2M solution of hydrogen chloride in methanol (60 mL) was stirred at room temperature for 32 hours. The pH of the reaction mixture was then adjusted to 7.5-8 with solid sodium bicarbonate, and resulting mixture was concentrated in vacuo. To the residue was added dichloromethane. Filtration and concentration gave (R)-3-(4-benzyloxycarbonyl-amino-4,5,6,7-tetrahydro-indazol-1-yl)-propionic acid methyl ester (770 mg, 99%) as a yellow solid. MS calcd. for $C_{19}H_{23}N_3O_4$ 357, obsd. (ESI$^+$) [(M+H)$^+$] 358.

3-((R)-4-Amino-4,5,6,7-tetrahydro-indazol-1-yl)-propionic acid methyl ester (III)

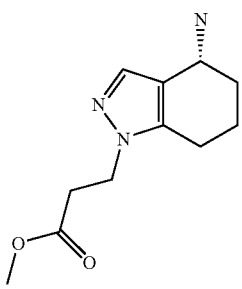

A solution of 3-((R)-4-benzyloxycarbonyl-amino-4,5,6,7-tetrahydro-indazol-1-yl)-propionic acid methyl ester (150 mg, 0.42 mmol) in methanol was hydrogenated over 10% palladium on carbon (30 mg) under atmospheric pressure at room temperature for 3 hours. The reaction mixture was filtered and the filtrate was concentrated in vacuo to give 3-((R)-4-amino-4,5,6,7-tetrahydro-indazol-1-yl)-propionic acid methyl ester (93 mg, 99%) as a yellow oil, MS calcd. for $C_{11}H_{17}N_3O_2$ 223, obsd. (ESI$^+$) [(M+H)$^+$] 224.

3-(4-Amino-4,5,6,7-tetrahydro-indazol-1-yl)-propionic acid methyl ester was obtained starting with racemic (4-benzyloxycarbonylamino-4,5,6,7-tetrahydro-indazol-1-yl)-acetic acid ethyl ester, in a method analogous to the one described for 3-((R)-4-Amino-4,5,6,7-tetrahydro-indazol-1-yl)-propionic acid methyl ester.

Preparation of 4-fluoro-3-methyl-benzenesulfonyl chloride

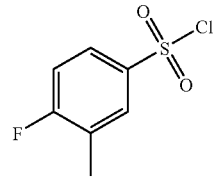

4-Fluoro-3-methyl-phenylamine (10 g, 79.9 mmol) was mixed with trifluoroacetic acid (100 mL) in a 250 mL flask. After the mixture was cooled to 0° C., concentrated hydrochloric acid (10 mL) was added slowly, followed by addition of a solution of sodium nitrite (6.95 g, 100.67 mmol) in water (5 mL) dropwise over 20 minutes at 0° C. The mixture was stirred for another 10 minutes, and then poured into a stirred mixture of acetic acid (120 mL), sulfurous acid (0.94 N aqueous sulfur dioxide solution, 120 mL), copper(II) chloride (13.6 g, 79.9 mmol) and copper(I) chloride (100 mg) at 0° C. The resulting mixture was allowed to warm to room temperature and stirred for 15 hours, and then poured into water (200 mL). The aqueous layer was extracted with ethyl acetate (100 mL×3). The combined organic layers were dried over sodium sulfate and concentrated in vacuo. The residue was purified by column chromatography (20% ethyl acetate in petroleum ether) to afford 4-fluoro-3-methyl-benzenesulfonyl chloride (5.2 g, 31.2%) (reference: Cherney, R. J. et al., *J. Med. Chem.* 46 (2003) 1811). $^1$H NMR (400 MHz, CDCl$_3$) δ ppm 7.96-7.90 (m, 2 H), 7.284-7.229 (m, 1 H), 2.42 (d, J=1.6 Hz, 3 H).

The following examples were prepared in an analogous manner as described for 4-fluoro-3-methyl-benzenesulfonyl chloride starting from commercially available substituted phenyl amines.

| Starting amine | Sulfonyl chloride | $^1$H NMR (400 MHz, CDCl$_3$) δ ppm |
|---|---|---|
| 4-Fluoro-3-trifluoromethylphenylamine | 4-Fluoro-3-trifluoromethyl-benezensulfonyl chloride | 8.35-8.37 (d, J = 6.0 Hz, 1H), 8.29-8.33 (m, 1H), 7.50-7.54 (t, J = 6.0 Hz, 1H) |
| 3-Fluoro-5-trifluoromethylphenylamine | 3-Fluoro-5-trifluoromethyl-benezensulfonyl chloride | 8.15 (s, 1H), 7.97-7.99 (d, J = 4.0 Hz, 1H), 7.74-7.76 (d, J = 4.0 Hz, 1H) |

Part II: Preparation of Compounds of Interest

Example 1-1

{(R)-4-[4-(2-Chloro-phenoxy)-benzenesulfonylamino]-4,5,6,7-tetrahydro-indazol-1-yl}-acetic acid ethyl ester

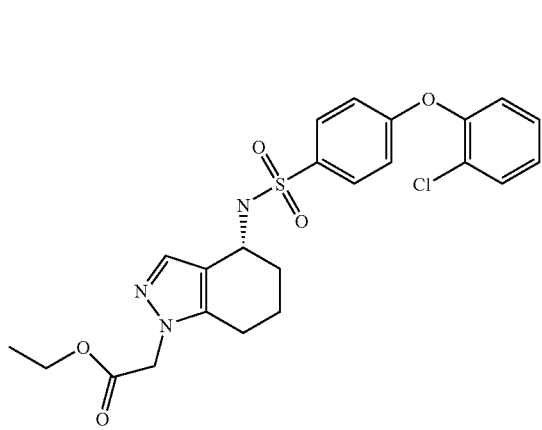

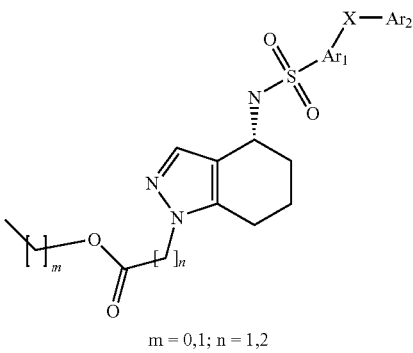

m = 0,1; n = 1,2

A solution of dimethyl-pyridin-4-yl-amine (122 mg, 1.00 mmol) in tetrahydrofuran (2 mL) was added dropwise to a solution of 3-((R)-4-amino-4,5,6,7-tetrahydro-indazol-1-yl)-acetic acid ethyl ester (112 mg, 0.5 mmol) and 4-(2-chlorophenoxy)-benzenesulfonyl chloride (364 mg, 0.60 mmol) in tetrahydrofuran (2 mL). The reaction mixture was stirred at room temperature overnight, and then concentrated. The residue was purified by column chromatography (gradient elution, 0-5% methanol in dichloromethane) to afford {(R)-4-[4-(2-chloro-phenoxy)-benzenesulfonylamino]-4,5,6,7-tetrahydro-indazol-1-yl}-acetic acid ethyl ester (167 mg, 68%) as a white solid. MS calcd. for $C_{23}H_{24}ClN_3O_5S$ 489, obsd (ESI$^+$) [(M+H)$^+$] 490.

Examples 1-2 to 1-6

The following examples 1-2 to 1-6 were prepared in an analogous manner as described for example 1-1 using 3-((R)-4-amino-4,5,6,7-tetrahydro-indazol-1-yl)-acetic acid ethyl ester or 3-(4-amino-4,5,6,7-tetrahydro-indazol-1-yl)-acetic acid ethyl ester or 3-((R)-4-amino-4,5,6,7-tetrahydro-indazol-1-yl)-propionic acid methyl ester and the appropriate commercially available substituted benzenesulfonyl chlorides

| Example No. | Systematic Name | MS (ESI+, M + H) | Structure |
|---|---|---|---|
| 1-2 | [(R)-4-(Biphenyl-4-sulfonylamino)-4,5,6,7-tetrahydro-indazol-1-yl]-acetic acid ethyl ester | 440 | 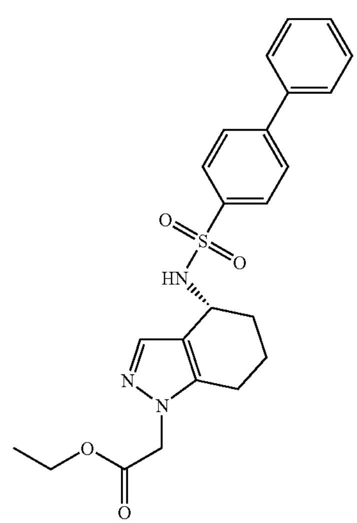 |

-continued

| Example No. | Systematic Name | MS (ESI+, M + H) | Structure |
|---|---|---|---|
| 1-3 | [4-(4-Phenoxy-benzenesulfonylamino)-4,5,6,7-tetrahydro-indazol-1-yl]-acetic acid ethyl ester | 456 | 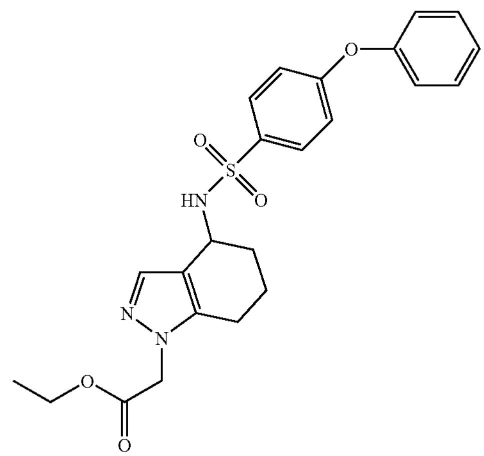 |
| 1-4 | {4-[3-(5-Methyl-[1,3,4]oxadiazol-2-yl)-benzenesulfonylamino]-4,5,6,7-tetrahydro-indazol-1-yl}-acetic acid ethyl ester | 446 | 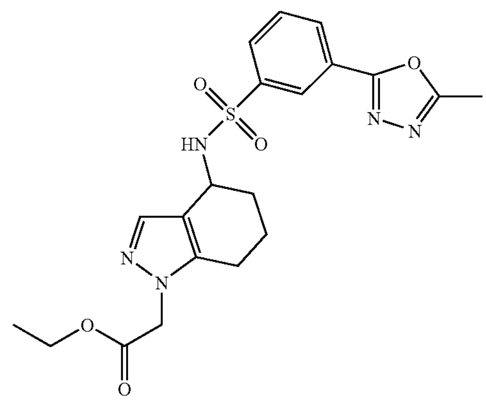 |
| 1-5 | [4-(3-Phenoxy-benzenesulfonylamino)-4,5,6,7-tetrahydro-indazol-1-yl]-acetic acid ethyl ester | 456 | 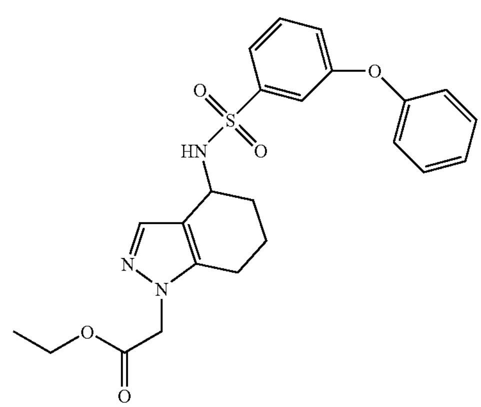 |

-continued

| Example No. | Systematic Name | MS (ESI+, M + H) | Structure |
|---|---|---|---|
| 1-6 | 3-[4-(Biphenyl-4-sulfonylamino)-4,5,6,7-tetrahydro-indazol-1-yl]-propionic acid methyl ester | 440 | 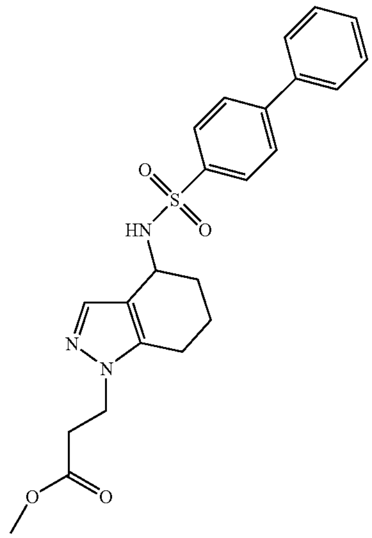 |

Example 1-1a

{(R)-4-[4-(2-Chloro-phenoxy)-benzenesulfonylamino]-4,5,6,7-tetrahydro-indazol-1-yl}-acetic acid To a solution of {(R)-4-[4-(2-chloro-phenoxy)-benzenesulfonylamino]-4,5,6,7-tetrahydro-indazol-1-yl}-acetic acid ethyl ester (example 1-1) (167 mg, 0.34 mmol) in tetrahydrofuran (3 mL) was added 1N sodium hydroxide (3 mL). The reaction mixture was stirred at room temperature for 2 hours, and then extracted with diethyl ether (10 mL). The organic layer was discarded. The aqueous layer was acidified with concentrated hydrochloric acid to pH 4 and stirred with diethyl ether (3 mL) and petroleum ether (9 mL) at room temperature for 2 hours. The resulting mixture was filtered through a glass funnel to afford {(R)-4-[4-(2-chloro-phenoxy)-benzenesulfonylamino]-4,5,6,7-tetrahydro-indazol-1-yl}-acetic acid (124 mg, 79%) as a white powder. $^1$H NMR (400 MHz, CD$_3$OD) δ ppm 7.94 (d, 2 H), 7.60 (q, 1 H), 7.43 (m, 1 H), 7.26 (m, 2 H), 7.07 (d, 2 H), 6.70 (s, 1 H), 4.80 (s, 2 H), 4.37 (t, 1 H), 2.60-2.48 (m, 2 H), 1.94-1.75 (m, 4 H). MS cald. (calculated) for C$_{21}$H$_{20}$ClN$_3$O$_5$S 461, obsd. (observed) (ESI$^+$) [(M+H)$^+$] 462.

Examples 1-2a to 1-6a

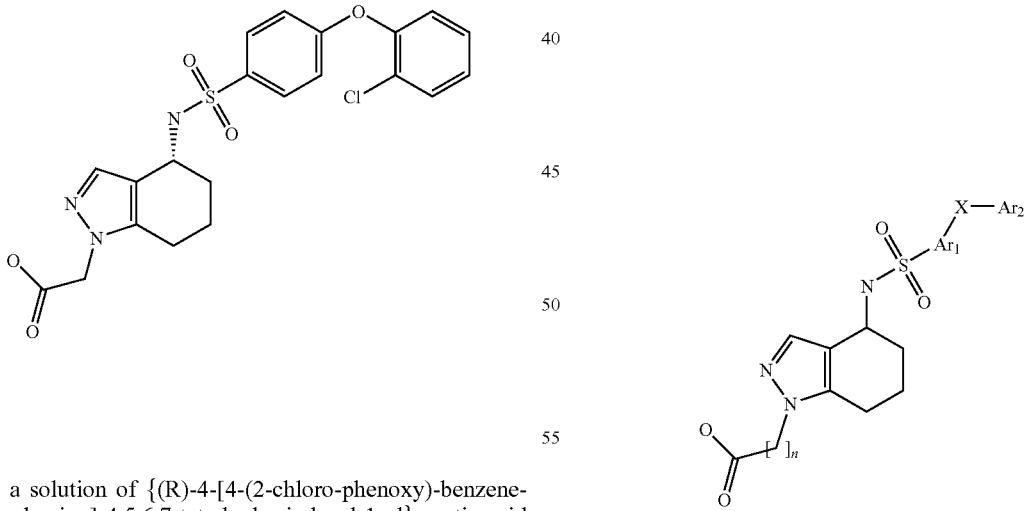

n = 1, 2

The following examples 1-2a to 1-6a were prepared in an analogous manner as described for example 1-1a from the corresponding esters 1-2 to 1-6.

| Example No. | Systematic Name | $^1$H NMR (400 MHz, CD$_3$OD) δ ppm | MS (ESI+, M + H) | Structure |
|---|---|---|---|---|
| 1-2a | [(R)-4-(Biphenyl-4-sulfonylamino)-4,5,6,7-tetrahydro-indazol-1-yl]-acetic acid | 8.04 (d, J = 7.83 Hz, 1 H) 7.94 (dd, J = 3.92, 2.65 Hz, 3 H) 7.77 (d, J = 7.83 Hz, 2 H) 7.52 (td, J = 7.64, 1.89 Hz, 2 H) 7.45 (dd, J = 7.83, 1.77 Hz, 1 H) 6.69 (d, J = 2.53 Hz, 1 H) 4.76 (s, 2 H) 4.28 (d, J = 6.82 Hz, 1 H) 2.32-2.48 (m, 2 H) 1.82 (s., 1 H) 1.68 (d, J = 4.04 Hz, 2 H) 1.51 (s, 1 H) | 412 | 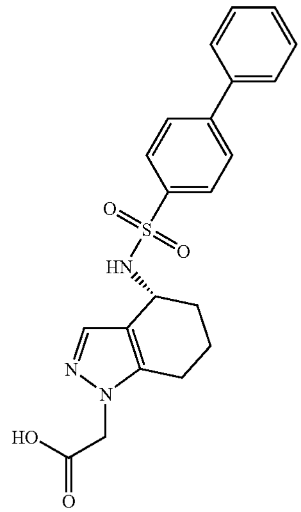 |
| 1-3a | [4-(4-Phenoxy-benzenesulfonyl amino)-4,5,6,7-tetrahydro-indazol-1-yl]-acetic acid | 7.93 (d, 2 H), 7.49 (t, 2 H), 7.27 (t, 1 H), 6.70 (s, 1 H), 4.80 (s, 2 H), 4.36 (t, 1 H), 2.61-2.45 (m, 2 H), 1.96-1.75 (m, 4 H) | 428 | 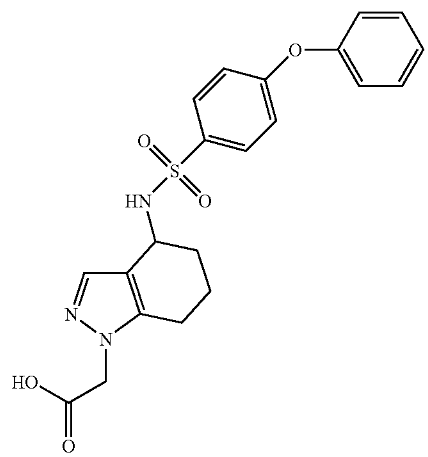 |
| 1-4a | {4-[3-(5-Methyl-[1,3,4]oxadiazol-2-yl)-benzenesulfonyl amino]-4,5,6,7-tetrahydro-indazol-1-yl}-acetic acid | 8.57 (t, J = 1.52 Hz, 1 H), 8.34-8.30 (m, 1 H), 8.19-8.14 (m, 1 H), 7.84 (t, J = 7.83 Hz, 1 H), 6.75 (s, 1 H), 4.79 (s, 2 H), 4.45 (s, 1 H), 2.67 (s, 3 H), 2.61-247 (m, 2 H), 2.00-1.90 (m, 1 H), 1.88-1.69 (m, 3 H) | 418 | 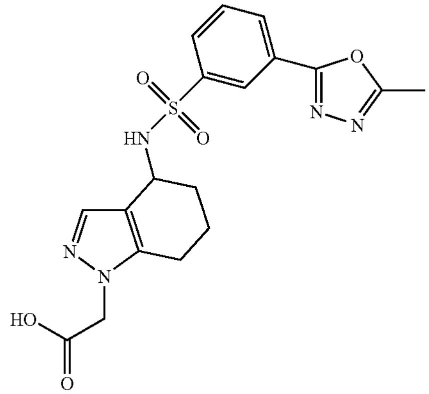 |

| Example No. | Systematic Name | ¹H NMR (400 MHz, CD₃OD) δ ppm | MS (ESI+, M + H) | Structure |
|---|---|---|---|---|
| 1-5a | [4-(3-Phenoxy-benzenesulfonyl amino)-4,5,6,7-tetrahydro-indazol-1-yl]-acetic acid | 7.68-7.65 (m, 1 H), 7.59 (t, J = 7.96 Hz, 1 H), 7.46-7.39 (m, 3 H), 7.31-7.25 (m, 1 H), 7.19 (t, J = 7.45 Hz, 1 H), 7.07 (dd, 2 H), 6.62 (dd, 2 H), 4.76 (s, 2 H), 4.33 (t, 1 H), 2.60-2.38 (m, 2 H), 1.98-1.86 (m, 1 H), 1.87-1.61 (m, 3 H) | 428 | 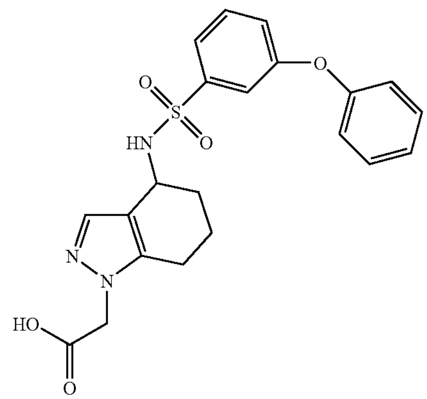 |
| 1-6a | 3-[4-(Biphenyl-4-sulfonylamino)-4,5,6,7-tetrahydro-indazol-1-yl]-propionic acid | 7.99 (d, 2 H), 7.86 (d, 2 H), 7.72 (d, 2 H), 7.49 (t, 2 H), 7.42 (t, 1 H), 6.67 (s, 1 H) 4.37 (t, 1 H), 4.15 (t, 2 H), 2.75 (t, 2 H), 2.72-2.52 (m, 2 H), 1.98-1.88 (m, 1 H), 1.83-1.68 (m, 3 H) | 426 | 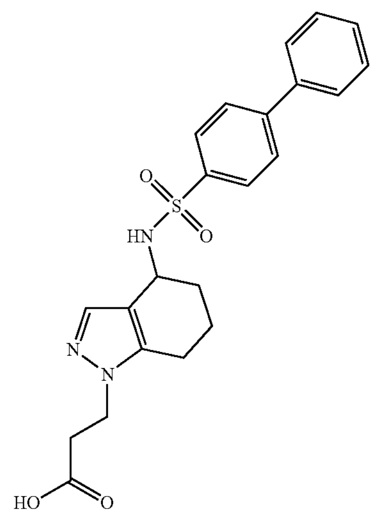 |

Example 2-1

{4-[5-Bromo-6-(4-chloro-phenoxy)-pyridine-3-sulfonylamino]-4,5,6,7-tetrahydro-indazol-1-yl}-acetic acid ethyl ester

[4-(5-Bromo-6-chloro-pyridine-3-sulfonylamino)-4,5,6,7-tetrahydro-indazol-1-yl]-acetic acid ethyl ester

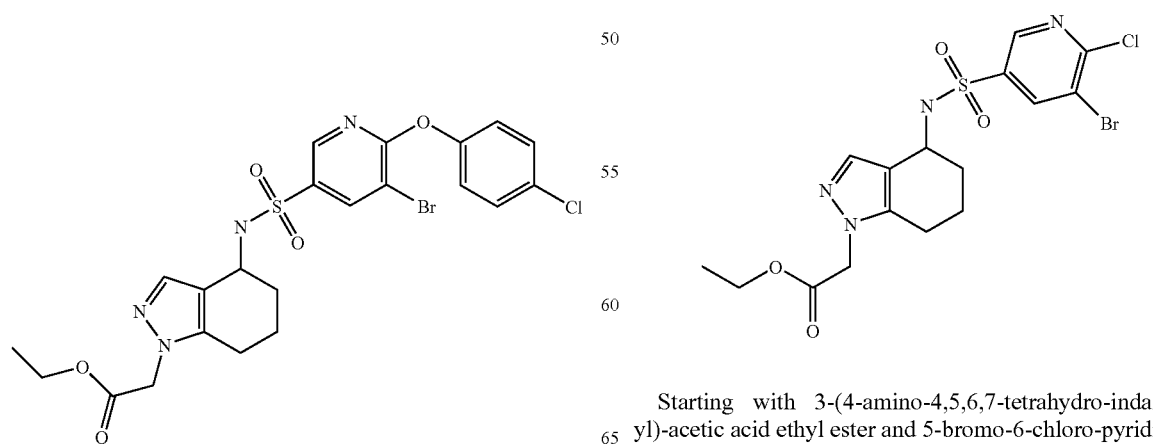

Starting with 3-(4-amino-4,5,6,7-tetrahydro-indazol-1-yl)-acetic acid ethyl ester and 5-bromo-6-chloro-pyridine-3-sulfonyl chloride, and using the method described for example 1-1, [4-(5-bromo-6-chloro-pyridine-3-sulfonylamino)-4,5,6,7-tetrahydro-indazol-1-yl]-acetic acid ethyl ester was prepared. MS calcd. for $C_{16}H_{18}BrClN_4O_4S$ 476, obsd (ESI$^+$) [(M+H)$^+$] 477.

{4-[5-Bromo-6-(4-chloro-phenoxy)-pyridine-3-sulfonylamino]-4,5,6,7-tetrahydro-indazol-1-yl}-acetic acid ethyl ester

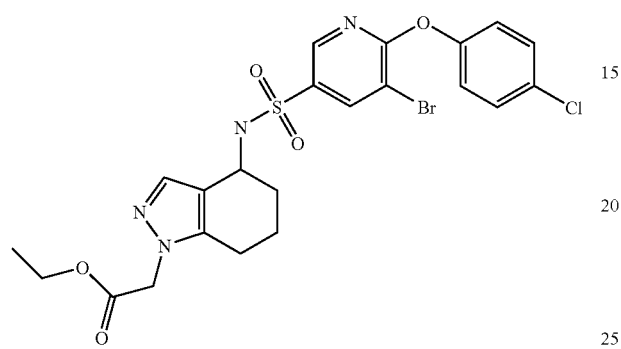

The mixture of [4-(5-Bromo-6-chloro-pyridine-3-sulfonylamino)-4,5,6,7-tetrahydro-indazol-1-yl]-acetic acid ethyl ester (50 mg, 0.10 mmol), sodium hydride (60% dispersed in mineral oil, 20 mg, 0.50 mmol) and 4-chlorophenol (0.4 mL, 3.79 mmol) in N,N-dimethylformamide (1.5 mL) was heated in a microwave oven at 100° C. for 15 minutes, then acidified with acetic acid to pH 5, filtered through a glass funnel and purified by preparative HPLC to afford {4-[5-bromo-6-(4-chloro-phenoxy)-pyridine-3-sulfonylamino]-4,5,6,7-tetrahydro-indazol-1-yl}-acetic acid ethyl ester (30 mg, 52.6%) as a white powder. MS calcd for $C_{22}H_{22}BrClN_4O_5S$ 548, obsd (ESI$^+$) [(M+H)$^+$]: 569.

Examples 2-2 to 2-12

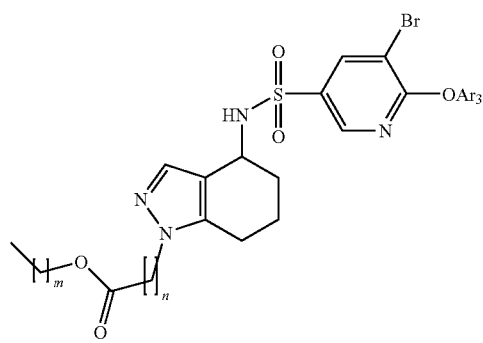

m = 0, 1; n = 1, 2

The following examples 2-2 to 2-12 were prepared in an analogous manner as described for example 2-1 using 3-((R)-4-amino-4,5,6,7-tetrahydro-indazol-1-yl)-acetic acid ethyl ester or 3-(4-amino-4,5,6,7-tetrahydro-indazol-1-yl)-acetic acid ethyl ester, or 3-((R)-4-amino-4,5,6,7-tetrahydro-indazol-1-yl)-propionic acid methyl ester, 5-bromo-6-chloro-pyridine-3-sulfonyl chloride and the appropriate commercially available substituted phenols (Ar$_3$OH).

| Example No. | Systematic Name | MS (ESI+, M + H | Structure |
|---|---|---|---|
| 2-2 | {4-[5-Bromo-6-(4-fluoro-phenoxy)-pyridine-3-sulfonylamino]-4,5,6,7-tetrahydro-indazol-1-yl}-acetic acid ethyl ester | 553 | 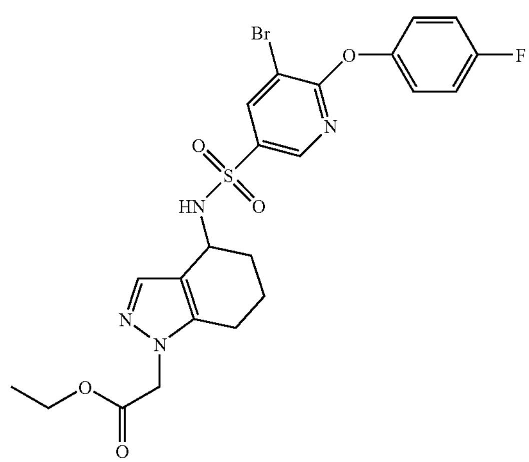 |

-continued

| Example No. | Systematic Name | MS (ESI+, M + H) | Structure |
|---|---|---|---|
| 2-3 | {4-[5-Bromo-6-(3-chloro-phenoxy)-pyridine-3-sulfonylamino]-4,5,6,7-tetrahydro-indazol-1-yl}-acetic acid ethyl ester | 569 | 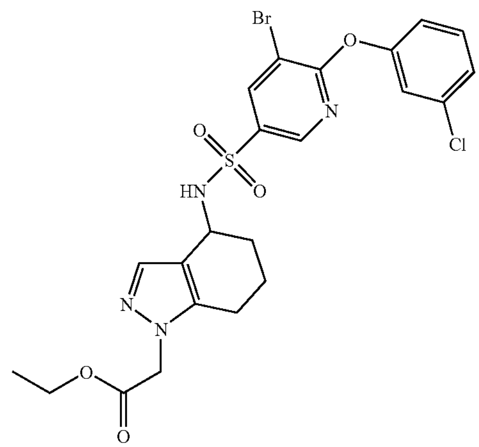 |
| 2-4 | {4-[5-Bromo-6-(4-cyano-phenoxy)-pyridine-3-sulfonylamino]-4,5,6,7-tetrahydro-indazol-1-yl}-acetic acid ethyl ester | 560 | 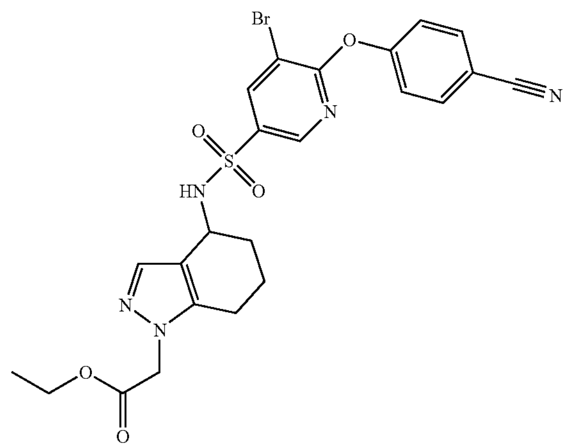 |
| 2-5 | {4-[5-Bromo-6-(4-methanesulfonyl-phenoxy)-pyridine-3-sulfonylamino]-4,5,6,7-tetrahydro-indazol-1-yl}-acetic acid ethyl ester | 613 | 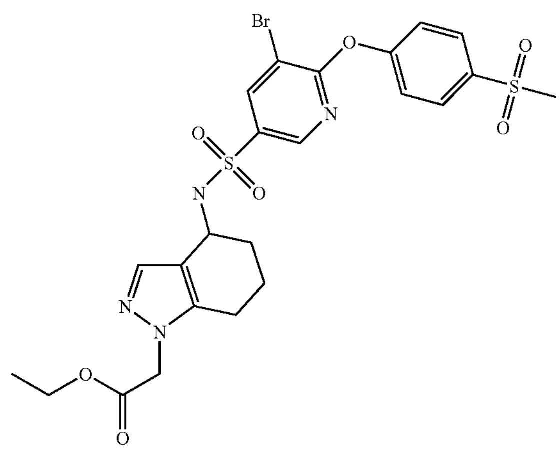 |

-continued

| Example No. | Systematic Name | MS (ESI+, M + H) | Structure |
|---|---|---|---|
| 2-6 | [4-(5-Bromo-6-p-tolyloxy-pyridine-3-sulfonylamino)-4,5,6,7-tetrahydro-indazol-1-yl]-acetic acid ethyl ester | 549 | 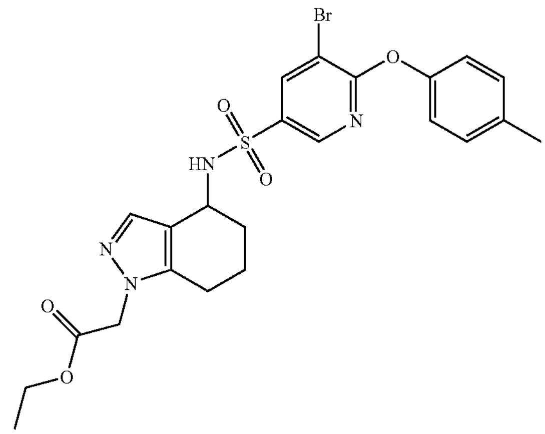 |
| 2-7 | {4-[5-Bromo-6-(4-trifluoromethyl-phenoxy)-pyridine-3-sulfonylamino]-4,5,6,7-tetrahydro-indazol-1-yl}-acetic acid ethyl ester | 603 | 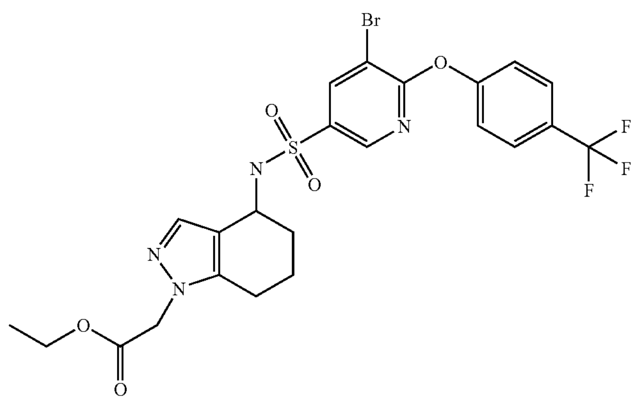 |
| 2-8 | {(R)-4-[5-Bromo-6-(4-chloro-phenoxy)-pyridine-3-sulfonylamino]-4,5,6,7-tetrahydro-indazol-1-yl}-acetic acid ethyl ester | 569 | 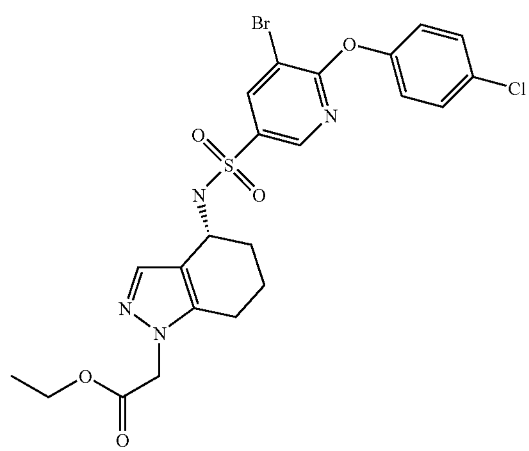 |

| Example No. | Systematic Name | MS (ESI+, M + H | Structure |
|---|---|---|---|
| 2-9 | {(R)-4-[5-Bromo-6-(2-chloro-phenoxy)-pyridine-3-sulfonylamino]-4,5,6,7-tetrahydro-indazol-1-yl}-acetic acid ethyl ester | 569 | 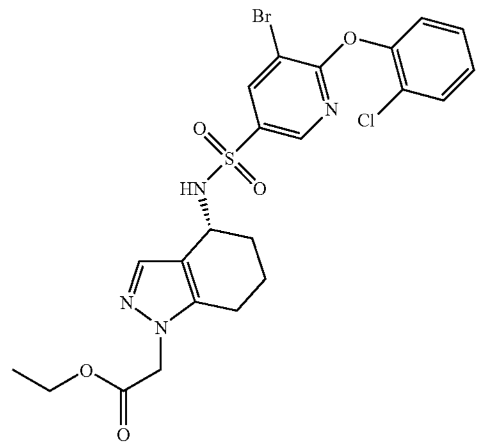 |
| 2-10 | {4-[5-Bromo-6-(3,4-difluoro-phenoxy)-pyridine-2-sulfonylamino]-4,5,6,7-tetrahydro-indazol-1-yl}-acetic acid ethyl ester | 571 | 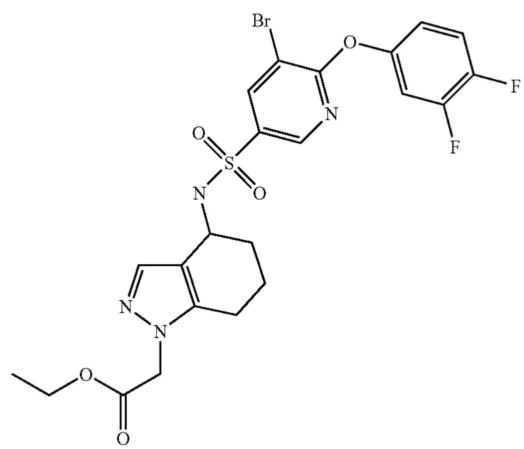 |
| 2-11 | 3-{(R)-4-[5-Bromo-6-(2-chloro-phenoxy)-pyridine-3-sulfonylamino]-4,5,6,7-tetrahydro-indazol-1-yl}-propionic acid methyl ester | 569 | 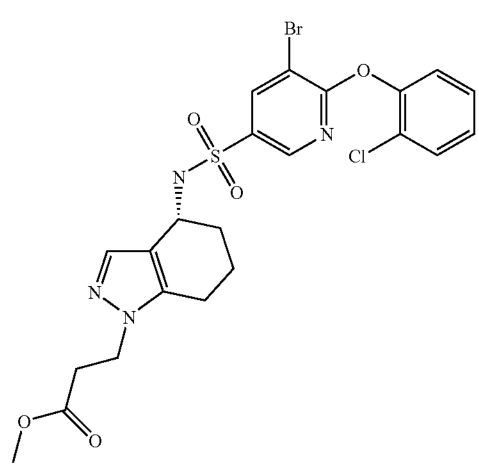 |

| Example No. | Systematic Name | MS (ESI+, M + H | Structure |
|---|---|---|---|
| 2-12 | 3-{(R)-4-[5-Bromo-6-(4-chloro-phenoxy)-pyridine-3-sulfonylamino]-4,5,6,7-tetrahydro-indazol-1-yl}-propionic acid methyl ester | 569 | 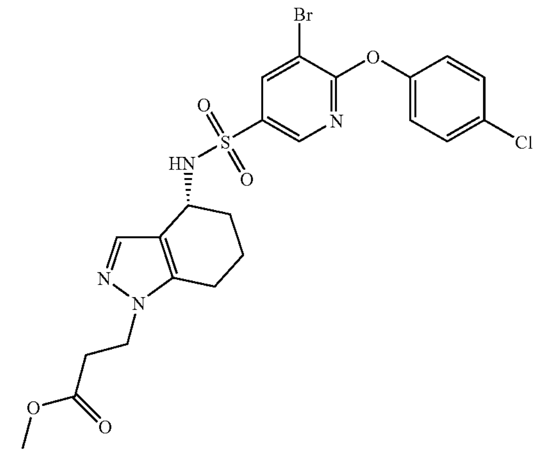 |

Example 2-1a

{4-[5-Bromo-6-(4-chloro-phenoxy)-pyridine-3-sulfonylamino]-4,5,6,7-tetrahydro-indazol-1-yl}-acetic acid Starting with {4-[5-bromo-6-(4-chloro-phenoxy)-pyridine-3-sulfonylamino]-4,5,6,7-tetrahydro-indazol-1-yl}-acetic acid ethyl ester, and using the method described for example 1-1a, {4-[5-bromo-6-(4-chloro-phenoxy)-pyridine-3-sulfonylamino]-4,5,6,7-tetrahydro-indazol-1-yl}-acetic acid (10 mg, 52.7%) was obtained as a white solid. $^1$H NMR (400 MHz, CD$_3$OD) δ ppm 8.49 (t, 2 H), 7.44 (dd, 4 H), 6.88 (s, 1 H), 4.41 (t, 1 H), 4.19 (s, 2 H), 2.79-2.57 (m, 2 H), 2.03-1.71 (m, 4 H). MS cald. for C$_{20}$H$_{18}$BrClN$_4$O$_5$S 540, obsd. (ESI$^+$) [(M+H)$^+$] 541.

Examples 2-2a to 2-12a

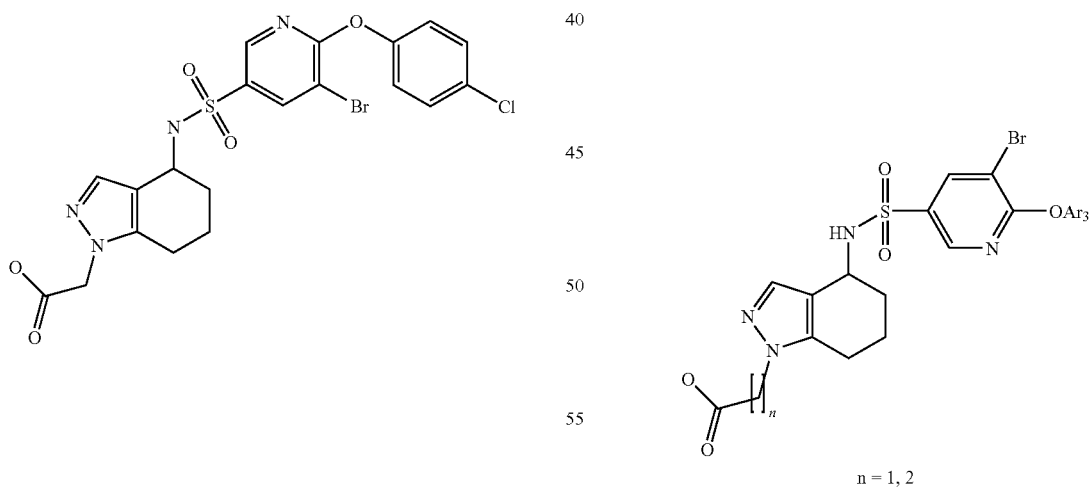

n = 1, 2

The following examples 2-2a to 2-12a were prepared in an analogous manner as described for example 1-1a from the corresponding esters 2-2 to 2-12.

| Example No. | Systematic Name | $^1$H NMR (400 MHz, CD$_3$OD) δ ppm | MS (ESI+, M + H) | Structure |
|---|---|---|---|---|
| 2-2a | {4-[5-Bromo-6-(4-fluoro-phenoxy)-pyridine-3-sulfonylamino]-4,5,6,7-tetrahydro-indazol-1-yl}-acetic acid | 8.50 (s, 2H), 7.24-7.16 (m, 4H), 6.90 (s, 1H), 4.80 (s, 2H), 4.42 (t, 1H), 2.63-2.44 (m, 2H), 1.99-1.89 (m, 1H), 1.87-1.69 (m, 3H) | 525 | 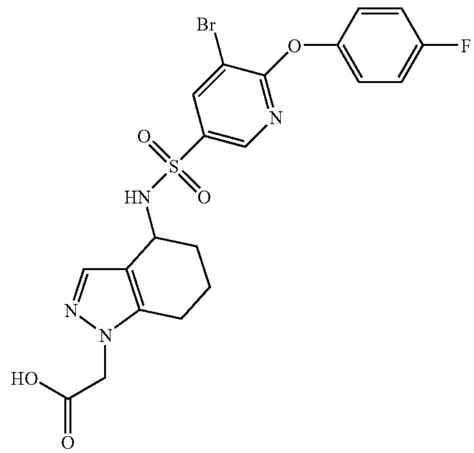 |
| 2-3a | {4-[5-Bromo-6-(3-chloro-phenoxy)-pyridine-3-sulfonylamino]-4,5,6,7-tetrahydro-indazol-1-yl}-acetic acid | 8.55 (d, J = 1.52 Hz, 1H), 8.41 (d, J = 1.01 Hz, 1H), 7.39 (t, J = 8.08 Hz, 2H), 7.29 (d, J = 8.34 Hz, 1H), 7.24 (d, J = 1.77 Hz, 1H), 7.11 (d, J = 6.06 Hz, 1H), 5.45 (s, 1H) 4.76 (d, 2H), 4.50-4.41 (m, 1H), 2.59-2.41 (m, 2H), 1.99-1.89 (m, 1H), 1.87-1.69 (m, 3H) | 541 | 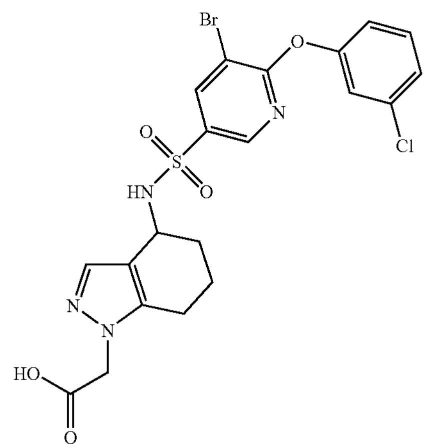 |
| 2-4a | {4-[5-Bromo-6-(4-cyano-phenoxy)-pyridine-3-sulfonylamino]-4,5,6,7-tetrahydro-indazol-1-yl}-acetic acid | 8.78 (t, 2H), 8.55-7.42 (dd, 4H), 6.92 (s, 1H), 4.80 (s, 2H), 4.46 (t, 1H), 2.58-2.52 (m, 2H), 2.05-1.74 (m, 4H) | 532 | 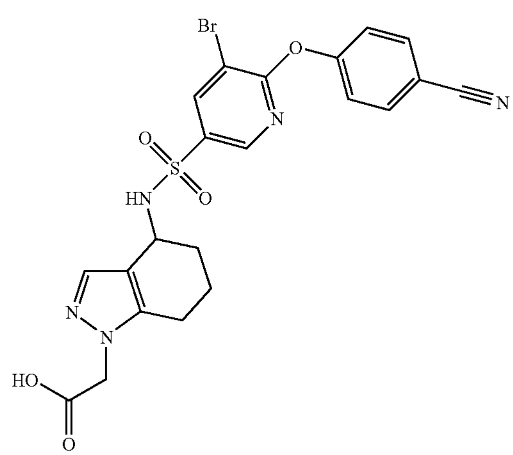 |

| Example No. | Systematic Name | $^1$H NMR (400 MHz, CD$_3$OD) δ ppm | MS (ESI+, M + H) | Structure |
| --- | --- | --- | --- | --- |
| 2-5a | {4-[5-Bromo-6-(4-methanesulfonyl-phenoxy)-pyridine-3-sulfonylamino]-4,5,6,7-tetrahydro-indazol-1-yl}-acetic acid | 8.56 (d, 2H), 8.06 (d, 2H), 7.49 (d, 2H), 6.90 (s, 1H), 4.77 (s, 2H), 4.45 (s, 1H), 3.17 (s, 3H), 2.54 (d, 2H), 1.98-1.90 (m, 1H), 1.88-1.71 (m, 3H) | 585 | 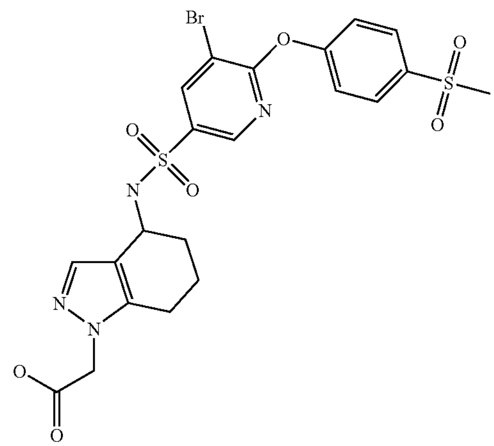 |
| 2-6a | [4-(5-Bromo-6-p-tolyloxy-pyridine-3-sulfonylamino)-4,5,6,7-tetrahydro-indazol-1-yl]-acetic acid | 8.48 (s, 1H), 8.45 (s, 1H), 8.08 (s, 1H), 7.24 (dd, 4H), 6.90 (s, 1H), 4.79 (s, 2H), 4.42 (s, 1H), 2.9 (q, 2H), 2.37 (s, 3H), 2.04-1.72 (m, 4H) | 521 | 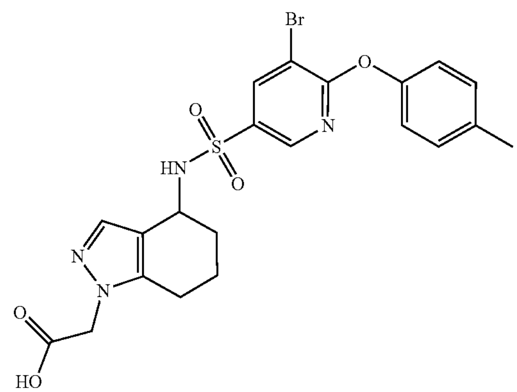 |
| 2-7a | {4-[5-Bromo-6-(4-trifluoromethyl-phenoxy)-pyridine-3-sulfonylamino]-4,5,6,7-tetrahydro-indazol-1-yl}-acetic acid | 8.55 (s, 2H), 7.79 (d, 2H), 7.43 (d, 2H), 6.86 (s, 1H), 4.71 (s, 2H), 4.43 (s, 1H), 2.57-2.51 (m, 2H), 2.00-1.76 (m, 4H) | 575 | 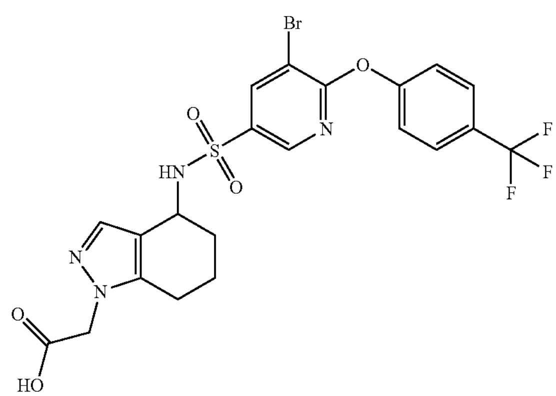 |

-continued

| Example No. | Systematic Name | $^1$H NMR (400 MHz, CD$_3$OD) δ ppm | MS (ESI+, M + H) | Structure |
|---|---|---|---|---|
| 2-8a | {(R)-4-[5-Bromo-6-(4-chloro-phenoxy)-pyridine-3-sulfonylamino]-4,5,6,7-tetrahydro-indazol-1-yl}-acetic acid | 8.49 (t, 2H), 7.44 (dd, 4H), 6.88 (s, 1H), 4.41 (t, 1H), 4.19 (s, 2H), 2.79-2.57 (m, 2H), 2.03-1.71 (m, 4H) | 541 | 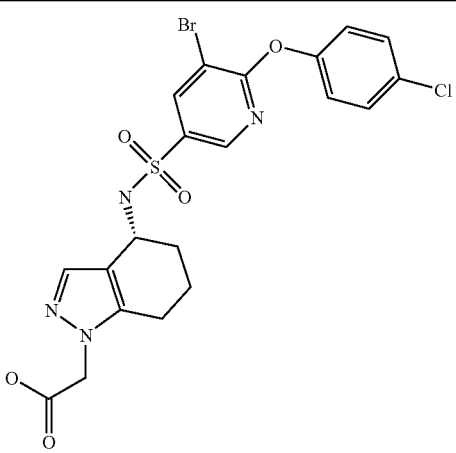 |
| 2-9a | {(R)-4-[5-Bromo-6-(2-chloro-phenoxy)-pyridine-3-sulfonylamino]-4,5,6,7-tetrahydro-indazol-1-yl}-acetic acid | 8.54 (d, 1H), 8.50 (d, 1H), 7.54 (m, 1H), 7.44 (m, 1H), 7.35 (m, 2H), 7.21 (s, 1H), 4.58 (s, 2H), 4.46 (t, J = 5.43 Hz, 1H), 2.67-2.51 (m, 2H), 2.02-1.93 (m, 1H), 1.83 (d, J = 2.53 Hz, 1H), 1.76-1.66 (m, 1H) | 541 | 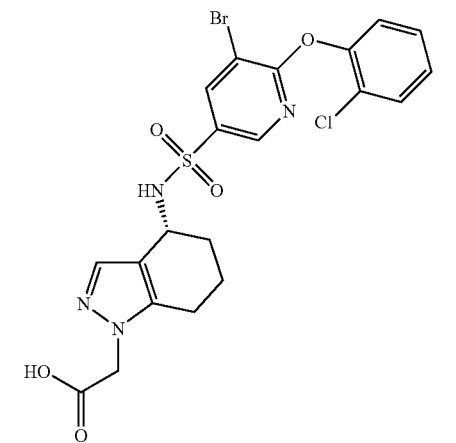 |
| 2-10a | {4-[5-Bromo-6-(3,4-difluoro-phenoxy)-pyridine-3-sulfonylamino]-4,5,6,7-tetrahydro-indazol-1-yl}-acetic acid | 8.56-8.48 (m, 2H), 7.74 (s, 1H), 7.37 (q, 1H), 7.27 (ddd, J = 10.93, 6.76, 2.78 Hz, 1H), 7.08-7.03 (m, 1H), 5.09 (s, 2H), 4.49 (t, J = 5.68 Hz, 1H), 2.74-2.58 (m, 2H), 2.06-1.95 (m, 1H), 1.86 (d, J = 5.05 Hz, 2H), 1.71 (dd, J = 13.89, 6.82 Hz, 1H) | 543 | 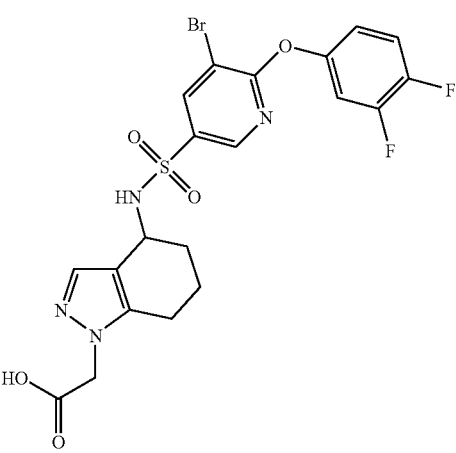 |

-continued

| Example No. | Systematic Name | $^1$H NMR (400 MHz, CD$_3$OD) δ ppm | MS (ESI+, M + H) | Structure |
|---|---|---|---|---|
| 2-11a | 3-{(R)-4-[5-Bromo-6-(2-chloro-phenoxy)-pyridine-3-sulfonylamino]-4,5,6,7-tetrahydro-indazol-1-yl}-propionic acid | 8.50 (d, 2H), 7.53 (t, 1H), 7.40 (m, 1H), 7.31 (m, 2H), 6.82 (s, 1H), 4.40 (s, 1H), 4.16 (s, 2H), 2.60 (m, 4H), 1.90-1.66 (m, 4H) | 555 | 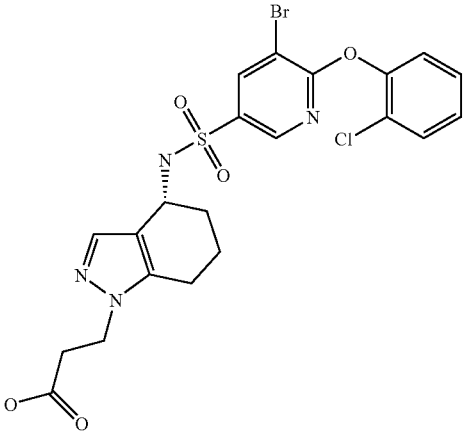 |
| 2-12a | 3-{(R)-4-[5-Bromo-6-(4-chloro-phenoxy)-pyridine-3-sulfonylamino]-4,5,6,7-tetrahydro-indazol-1-yl}-propionic acid | 8.49 (t, 2H), 7.46-7.19 (dd, 4H), 6.88 (s, 1H), 4.38 (t, 1H), 4.20 (s, 2H), 2.60 (m, 4H), 1.93-1.71 (m, 4H) | 555 | 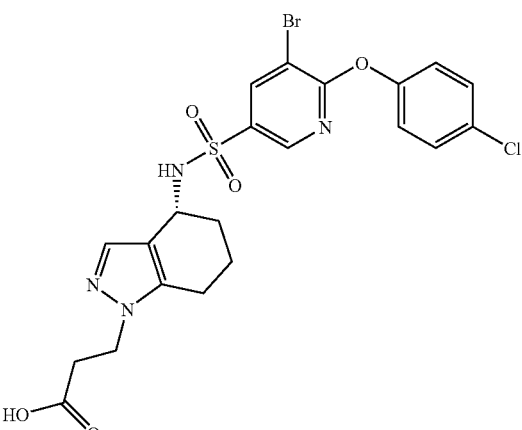 |

Example 3-1

{4-[6-(4-Chloro-phenoxy)-5-methyl-pyridine-3-sulfonylamino]-4,5,6,7-tetrahydro-indazol-1-yl}-acetic acid ethyl ester

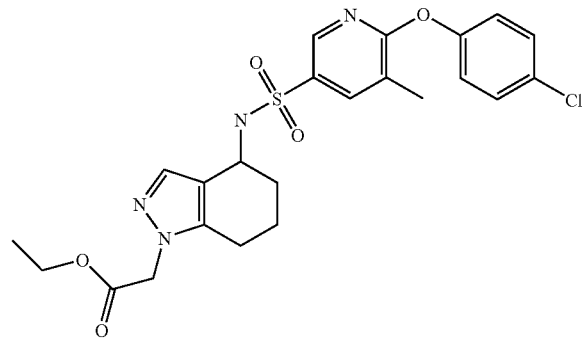

A mixture of {4-[5-bromo-6-(4-chloro-phenoxy)-pyridine-3-sulfonylamino]-4,5,6,7-tetra-hydro-indazol-1-yl}-acetic acid ethyl ester (70 mg, 0.123 mmol, prepared as described above in example 2-1), tetrakis(triphenylphosphine)palladium(0) (1 mg, 0.012 mmol), potassium tert-butoxide (2.5 mg, 0.29 mmol), methylboronic acid (12 mg, 0.184 mmol) in N,N-dimethylformamide (1.5 ml) was heated in a microwave oven at 160° C. for 30 minutes, then acidified to pH 6 by addition of acetic acid. The resulting precipitate was filtered through a glass funnel to afford {4-[6-(4-chloro-phenoxy)-5-methyl-pyridine-3-sulfonylamino]-4,5,6,7-tetrahydro-indazol-1-yl}-acetic acid ethyl ester (30 mg, 48%) as a white solid. MS cald. for $C_{23}H_{25}ClN_4O_5S$ 504, obsd. (ESI$^+$) [(M+H)$^+$] 505.

Example 3-1a

{4-[6-(4-Chloro-phenoxy)-5-methyl-pyridine-3-sulfonylamino]-4,5,6,7-tetrahydro-indazol-1-yl}-acetic acid

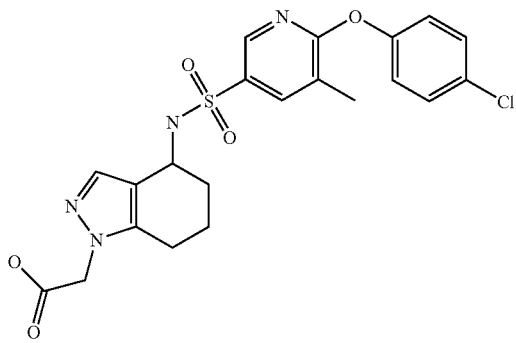

Starting with {4-[6-(4-chloro-phenoxy)-5-methyl-pyridine-3-sulfonylamino]-4,5,6,7-tetrahydro-indazol-1-yl}-acetic acid ethyl ester, and using the method described for example 1-1a, {4-[6-(4-chloro-phenoxy)-5-methyl-pyridine-3-sulfonylamino]-4,5,6,7-tetrahy-dro-indazol-1-yl}-acetic acid (10 mg, 36%) was obtained as a white solid. $^1$H NMR (400 MHz, CD$_3$OD) δ ppm 8.38 (s, 1 H), 8.09 (s, 1 H), 7.40 (dd, 4 H), 6.81 (s, 1 H), 4.78 (S, 2 H), 4.36 (s, 1 H), 2.68-2.40 (m, 5 H), 2.03-1.69 (m, 4 H). MS cald. for $C_{21}H_{21}ClN_4O_5S$ 476, obsd. (ESI$^+$) [(M+H)$^+$] 477.

Example 4-1a

{4-[6-(4-Fluoro-phenoxy)-pyridine-3-sulfonylamino]-4,5,6,7-tetrahydro-indazol-1-yl}-acetic acid

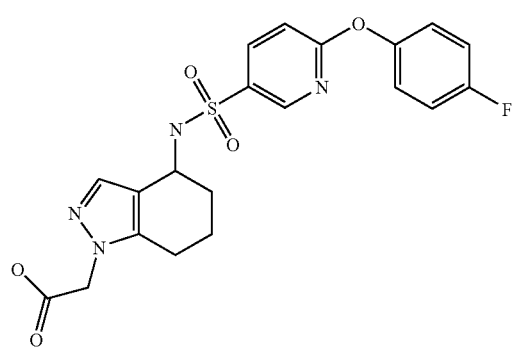

A solution of {4-[5-bromo-6-(4-fluoro-phenoxy)-pyridine-3-sulfonylamino]-4,5,6,7-tetra-hydro-indazol-1-yl}-acetic acid (example 2-2a) (20 mg, 0.038 mmol) in methanol (5 mL) was hydrogenated over 10% palladium on carbon (2 mg) under 30 psi in a 50 mL parr at room temperature for 3 hours. The mixture was filtered through a glass funnel. The filtrate was concentrated in vacuo and then purified by preparative HPLC to afford {4-[6-(4-fluoro-phenoxy)-pyridine-3-sulfonylamino]-4,5,6,7-tetrahydro-indazol-1-yl}-acetic acid (5 mg, 30%) as a white solid. $^1$H NMR (400 MHz, CD$_3$OD) δ ppm 8.62 (d, 1 H), 8.28 (dd, 1 H), 7.20 (m, 5 H), 6.87 (s, 1 H), 4.79 (s, 2 H), 4.42 (m, 1 H), 2.57 (m, 2 H), 2.01-1.72 (m, 4 H). MS cald. for $C_{20}H_{19}FN_4O_5S$ 446, obsd. (ESI$^+$) [(M+H)$^+$] 447.

Example 5-1

{(R)-4-[3-Chloro-4-(2-chloro-phenoxy)-benzenesulfonylamino]-4,5,6,7-tetrahydro-indazol-1-yl}-acetic acid ethyl ester

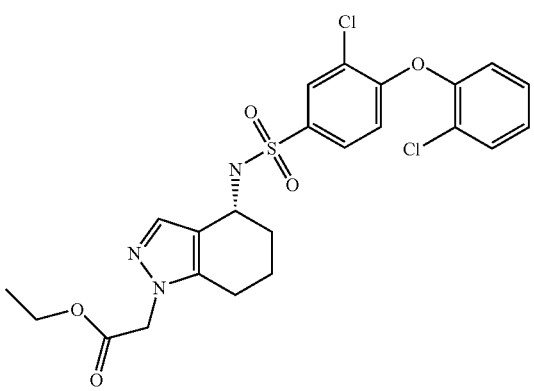

[(R)-4-[(3-Chloro-4-fluoro-benzenesulfonylamino)-4,5,6,7-tetrahydro-indazol-1-yl]-acetic acid ethyl ester

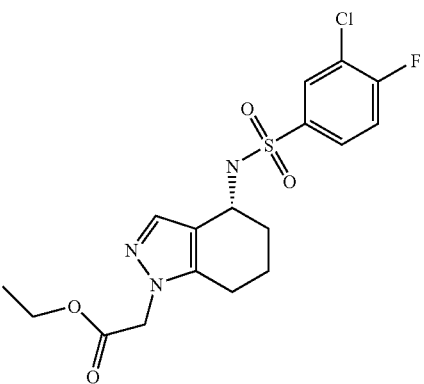

[(R)-4-[(3-chloro-4-fluoro-benzenesulfonylamino)-4,5,6,7-tetrahydro-indazol-1-yl]-acetic acid ethyl ester was prepared by a method analogous to example 1-1, starting with 3-((R)-4-amino-4,5,6,7-tetrahydro-indazol-1-yl)-acetic acid ethyl ester and 3-chloro-4-fluoro-benzene-sulfonyl chloride. MS calcd. for $C_{17}H_{19}ClFN_3O_4S$ 415, obsd (ESI$^+$) [(M+H)$^+$] 416.

{(R)-4-[3-Chloro-4-(2-chloro-phenoxy)-benzene-sulfonylamino]-4,5,6,7-tetrahydro-indazol-1-yl}-acetic acid ethyl ester A mixture of [(R)-4-[(3-chloro-4-fluoro-benzenesulfony-lamino)-4,5,6,7-tetrahydro-indazol-1-yl]-acetic acid ethyl ester (24.0 mg, 0.058 mmol), sodium hydride (60% dispersed in mineral oil, 11.6 mg, 0.29 mmol) and 2-chlorophenol (51.9 mg, 0.40 mmol) in N,N-dimethylformamide (2 mL) was heated in a microwave oven at 150° C. for 40 minutes. The resulting mixture was acidified with 0.1N hydrochloric acid to pH 5 and extracted with ethyl acetate. The organic layer was washed with brine, dried over sodium sulfate, and concentrated in vacuo and purified by column chromatography (gradient elution, 0-5% methanol in dichloromethane) to afford {(R)-4-[3-chloro-4-(2-chloro-phenoxy)-benzene-sulfonylamino]-4,5,6,7-tetrahydro-indazol-1-yl}-acetic acid ethyl ester (26.0 mg, 46.4%), MS calcd. for $C_{23}H_{23}Cl_2N_3O_5S$ 523, obsd. (ESI$^+$) [(M+H)$^+$] 524.

Examples 5-2 to 5-7

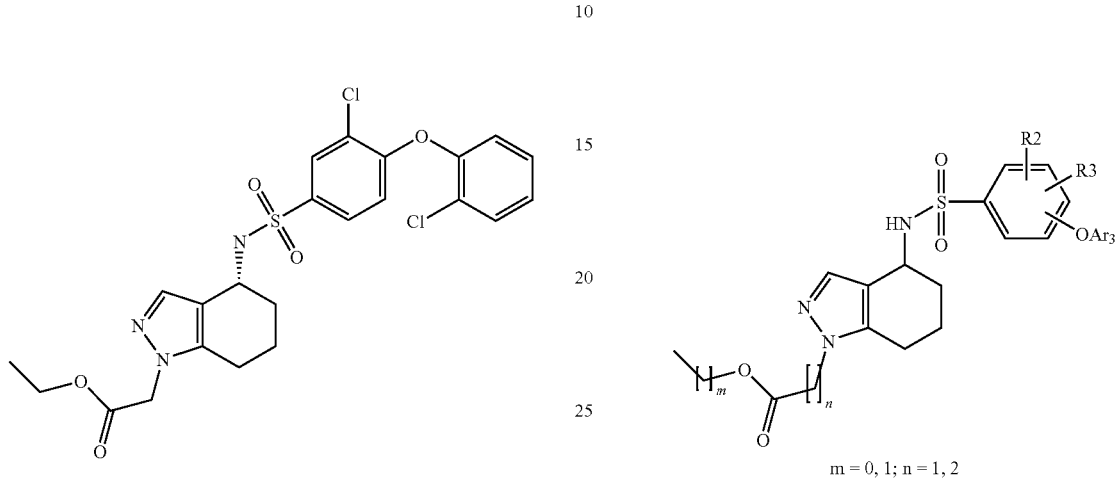

m = 0, 1; n = 1, 2

The following examples 5-2 to 5-7 were prepared in an analogous manner as described for example 5-1 using 3-((R)-4-amino-4,5,6,7-tetrahydro-indazol-1-yl)-acetic acid ethyl ester or 3-(4-amino-4,5,6,7-tetrahydro-indazol-1-yl)-acetic acid ethyl ester, or 3-((R)-4-amino-4,5,6,7-tetrahydro-indazol-1-yl)-propionic acid methyl ester, appropriate commercially available or prepared substituted benzenesulfonyl chlorides XXXIII and substituted phenols (Ar$_3$OH).

| Example No. | Systematic Name | MS (ESI+, M + H) | Structure |
|---|---|---|---|
| 5-2 | {4-[4-(3-Chloro-phenoxy)-benzenesulfonylamino]-4,5,6,7-tetrahydro-indazol-1-yl}-acetic acid ethyl ester | 490 | 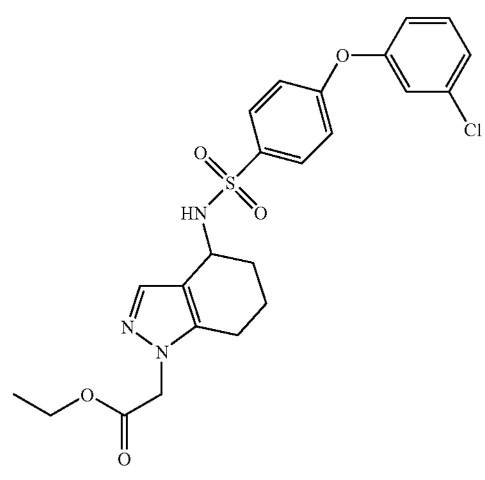 |

| Example No. | Systematic Name | MS (ESI+, M + H) | Structure |
|---|---|---|---|
| 5-3 | {4-[4-(4-Chloro-phenoxy)-benzenesulfonylamino]-4,5,6,7-tetrahydro-indazol-1-yl}-acetic acid ethyl ester | 490 | 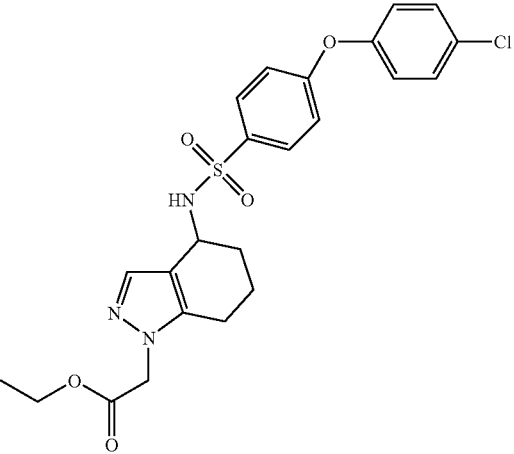 |
| 5-4 | [4-(3-Phenoxy-5-trifluoromethyl-benzenesulfonylamino)-4,5,6,7-tetrahydro-indazol-1-yl]-acetic acid ethyl ester | 524 | 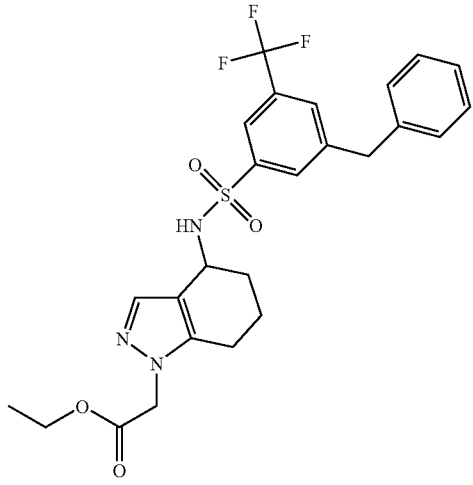 |
| 5-5 | {(R)-4-[2-Chloro-4-(2-chloro-phenoxy)-benzenesulfonylamino]-4,5,6,7-tetrahydro-indazol-1-yl}-acetic acid ethyl ester | 525 | 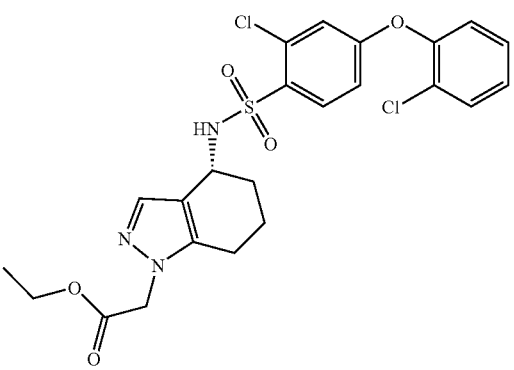 |

-continued

| Example No. | Systematic Name | MS (ESI+, M + H) | Structure |
|---|---|---|---|
| 5-6 | {(R)-4-[2-Chloro-5-fluoro-4-(4-fluoro-phenoxy)-benzenesulfonylamino]-4,5,6,7-tetrahydro-indazol-1-yl}-acetic acid ethyl ester | 526 | 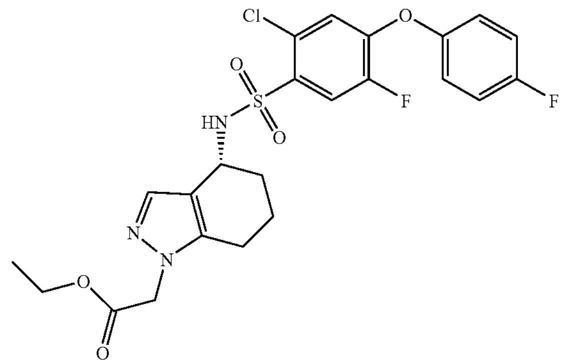 |
| 5-7 | 3-{(R)-4-[3-Chloro-4-(2-chloro-phenoxy)-benzenesulfonylamino]-4,5,6,7-tetrahydro-indazol-1-yl}-propionic acid methyl ester | 525 | 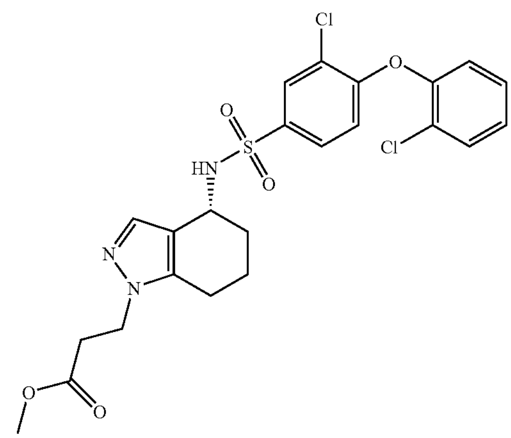 |

Example 5-1a

{(R)-4-[3-Chloro-4-(2-chloro-phenoxy)-benzene-sulfonylamino]-4,5,6,7-tetrahydro-indazol-1-yl}-acetic acid Starting with {(R)-4-[3-chloro-4-(2-chloro-phenoxy)-benzenesulfonylamino]-4,5,6,7-tetrahydro-indazol-1-yl}-acetic acid ethyl ester, and using the method described for example 1-1a, {(R)-4-[3-chloro-4-(2-chloro-phenoxy)-benzenesulfonyl-amino]-4,5,6,7-tetra-hydro-indazol-1-yl}-acetic acid (12.0 mg, 50.8%) was obtained as a white solid. $^1$H NMR (400 MHz, CD$_3$OD) δ ppm 8.08 (s, 1 H), 7.81 (d, 1 H), 7.62 (d, 1 H), 7.46 (t, 1 H), 7.32 (t, 1 H), 7.23 (d, 1 H), 6.88 (d, 1 H), 6.77 (s, 1 H), 4.79 (s, 2 H), 4.40 (s, 1 H), 2.55 (d, 2 H), 1.77-1.96 (m, 4 H). MS cald. for C$_{21}$H$_{19}$Cl$_2$N$_3$O$_5$S 495, obsd. (ESI$^+$) [(M+H)$^+$] 496.

Examples 5-2a to 5-7a

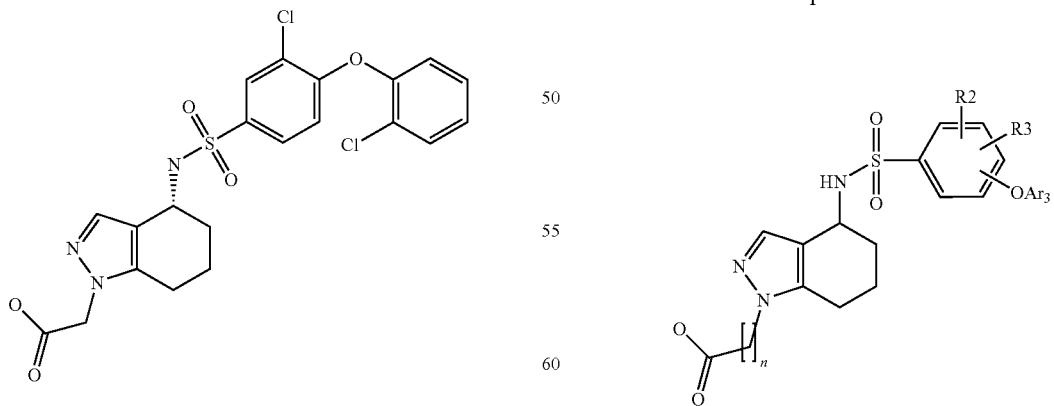

n = 1, 2

The following examples 5-2a to 5-7a were prepared in an analogous manner as described for example 1-1a from the corresponding esters 5-2 to 5-7.

| Example No. | Systematic Name | ¹H NMR (400 MHz, CD₃OD) δ ppm | MS (ESI+, M + H) | Structure |
|---|---|---|---|---|
| 5-2a | {4-[4-(3-Chloro-phenoxy)-benzenesulfonyl amino]-4,5,6,7-tetrahydro-indazol-1-yl}-acetic acid | 7.94 (d, J = 8.84 Hz, 2H), 7.43 (t, J = 8.08 Hz, 1H), 7.25 (dd, J = 7.71, 1.64 Hz, 1H), 7.19-7.16 (m, 3H) 7.05 (dd, J = 7.07, 1.26 Hz, 1H), 4.81 (s, 2H), 2.60-2.43 (m, 2H), 1.99-1.90 (m, 1H), 1.85-1.67 (m, 3H) | 462 | 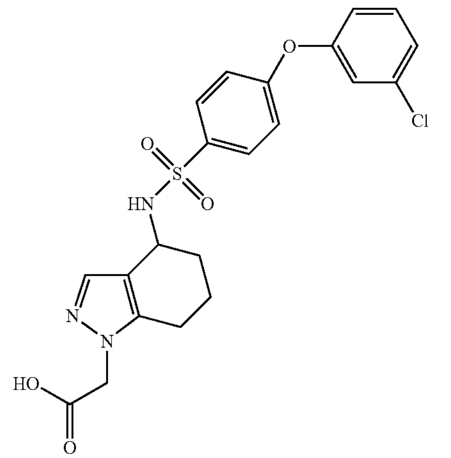 |
| 5-3a | {4-[4-(4-Chloro-phenoxy)-benzenesulfonyl amino]-4,5,6,7-tetrahydro-indazol-1-yl}-acetic acid | 7.92 (d, J = 8.84 Hz, 2H), 7.44 (d, J = 8.84 Hz, 2H), 7.13 (dd, J = 12.88, 8.84 Hz, 4H), 6.67 (s, 1H), 4.77 (s, 2H), 4.35 (t, 1H), 2.61-2.42 (m, 2H), 2.00-1.88 (m, 1H), 1.84-1.76 (m, 2H), 1.76-1.68 (m, 1H) | 462 | 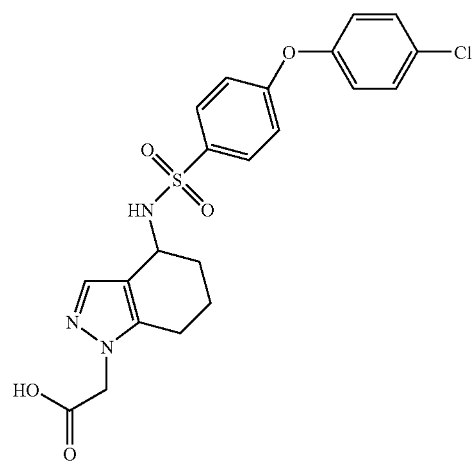 |
| 5-4a | [4-(3-Phenoxy-5-trifluoromethyl-benzenesulfonyl amino)-4,5,6,7-tetrahydro-indazol-1-yl]-acetic acid | 7.88 (s, 1H), 7.63 (s, 1H), 7.54-7.45 (m, 3H), 7.29 (t, 1H), 7.19-7.09 (m, 2H), 6.73 (s, 1H), 4.36 (s, 1H), 2.66-2.38 (m, 2H), 1.99-1.57 (m, 4H) | 496 | 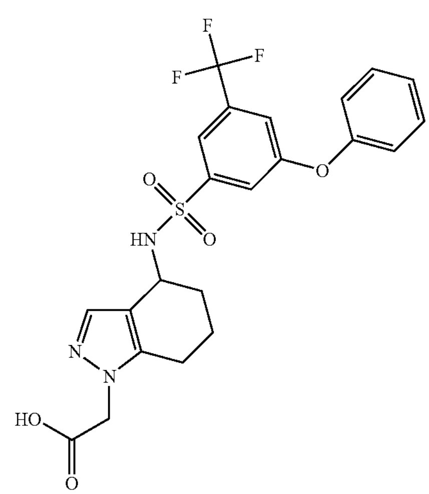 |

-continued

| Example No. | Systematic Name | $^1$H NMR (400 MHz, CD$_3$OD) δ ppm | MS (ESI+, M + H) | Structure |
|---|---|---|---|---|
| 5-5a | {(R)-4-[2-Chloro-4-(2-chloro-phenoxy)-benzenesulfonyl amino]-4,5,6,7-tetrahydro-indazol-1-yl}-acetic acid | 8.12 (d, 1H), 7.60 (d, 1H), 7.46 (t, 1H), 7.33 (m, 2H), 7.12 (s, 1H), 7.058 (s, 1H), 6.96 (d, 1H), 4.83 (s, 2H), 4.36 (s, 1H) 2.55 (m, 2H), 2.05 (s, 1H), 1.78 (s, 3H) | 496 | 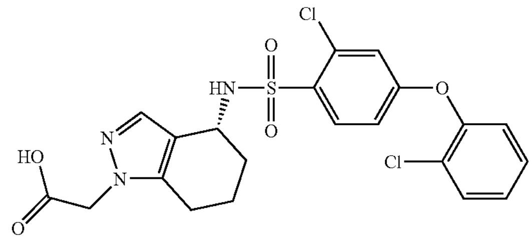 |
| 5-6a | {(R)-4-[2-Chloro-5-fluoro-4-(4-fluoro-phenoxy)-benzenesulfonyl amino]-4,5,6,7-tetrahydro-indazol-1-yl}-acetic acid | 8.03 (d, 1H), 7.24 (m, 4H), 7.12 (m, 2H), 4.45 (d, 2H), 2.58 (m, 2H), 2.01 (s, 1H), 1.78 (m, 3H) | 498 | 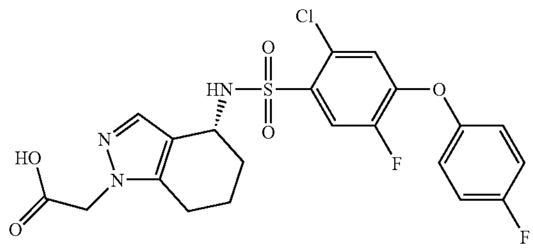 |
| 5-7a | 3-{(R)-4-[3-Chloro-4-(2-chloro-phenoxy)-benzenesulfonyl amino]-4,5,6,7-tetrahydro-indazol-1-yl}-propionic acid | 7.80 (q, 1H), 7.61 (q, 1H), 7.45 (m, 1H), 7.33 (m, 1H), 7.23 (q, 1H), 6.88 (d, J = 8.8 Hz, 1H), 6.78 (s, 1H), 4.37 (t, J = 10.4, 1H), 4.21 (m, 2H), 2.81 (t, J = 13.2, 3H), 2.58-2.70 (m, 2H), 2.06-1.71 (m, 4H) | 510 | 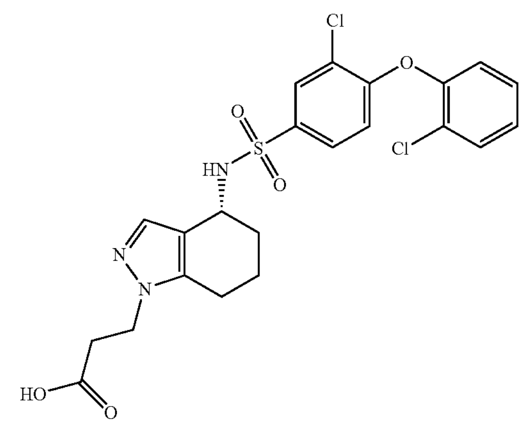 |

Example 6-1

((R)-4-{[5-Bromo-6-(4-chloro-phenoxy)-pyridine-3-sulfonyl]-methyl-amino}-4,5,6,7-tetrahydro-indazol-1-yl)-acetic acid ethyl ester {(R)-4-[(5-Bromo-6-chloro-pyridine-3-sulfonyl)-methyl-amino]-4,5,6,7-tetrahydro-indazol-1-yl}-acetic acid ethyl ester

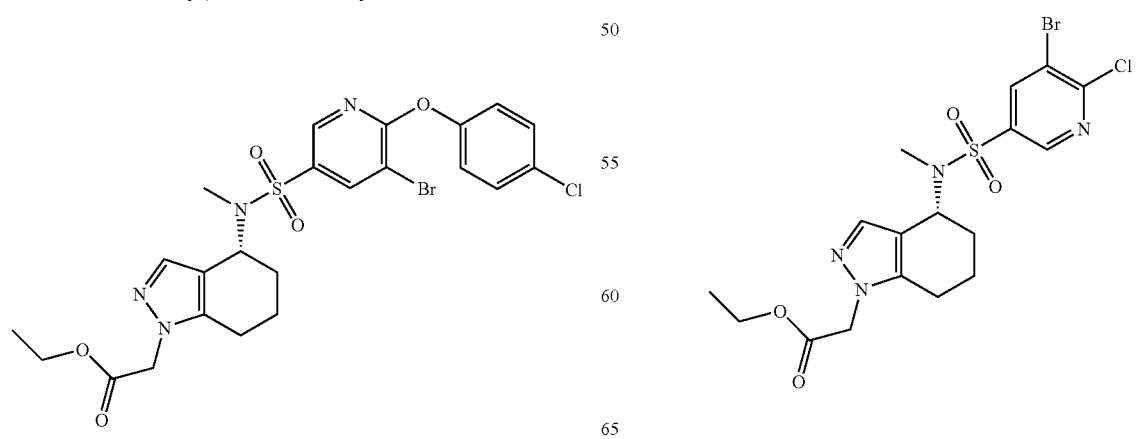

To a solution of [(R)-4-(5-bromo-6-chloro-pyridine-3-sulfonylamino)-4,5,6,7-tetrahydro-indazol-1-yl]-acetic acid ethyl ester (prepared as described above in example 2-1, 1$^{st}$ step) (740 mg, 1.55 mmol) in acetonitrile (15 mL) was added methyl iodide (655 mg, 4.65 mmol) and potassium carbonate (641 mg, 4.65 mmol). The reaction mixture was stirred at 65° C. for 5 hours, then cooled to room temperature and filtered through a glass funnel. The filtrate was concentrated in vacuo and the residue was purified by column chromatography (gradient elution, 0-10% methanol in dichloromethane) to afford {(R)-4-[(5-bromo-6-chloro-pyridine-3-sulfonyl)-methyl-amino]-4,5,6,7-tetrahydro-indazol-1-yl}-acetic acid ethyl ester (680 mg, 89%) as a yellow solid. Ms cald. for C$_{17}$H$_{20}$BrClN$_4$O$_4$S 490, obsd. (ESI$^+$) [(M+H)$^+$] 491.

((R)-4-{[5-Bromo-6-(4-chloro-phenoxy)-pyridine-3-sulfonyl]-methyl-amino}-4,5,6,7-tetrahydro-indazol-1-yl)-acetic acid ethyl ester

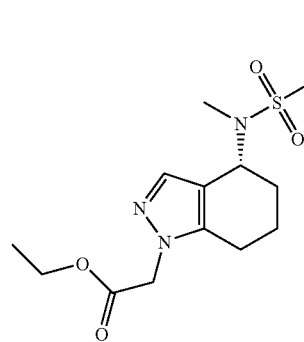

The mixture of {(R)-4-[(5-Bromo-6-chloro-pyridine-3-sulfonyl)-methyl-amino]-4,5,6,7-tetrahydro-indazol-1-yl}-acetic acid ethyl ester (80 mg, 0.16 mmol), sodium hydride (60% dispersed in mineral oil, 40 mg) and 4-chlorophenol (315 mg, 2.45 mmol) in N,N-dimethylformamide (2 mL) was heated in a microwave oven at 100° C. for 15 minutes, and then acidified with 0.1N hydrochloric acid to pH 5. The precipitate was filtered through a glass funnel and purified by preparative HPLC to afford ((R)-4-{[5-bromo-6-(4-chloro-phenoxy)-pyridine-3-sulfonyl]-methyl-amino}-4,5,6,7-tetrahydro-indazol-1-yl)-acetic acid ethyl ester (70 mg, 75%) as a white powder. MS cald. for C$_{23}$H$_{24}$BrClN$_4$O$_5$S 582, obsd. (ESI$^+$) [(M+H)$^+$]: 583.

Examples 6-2 to 6-14

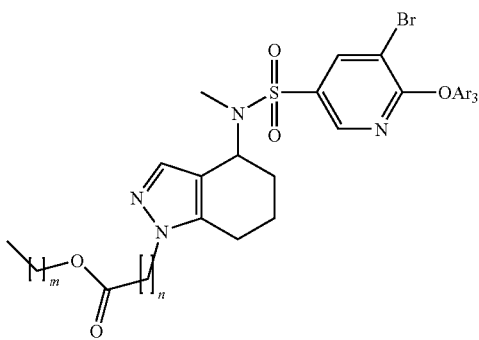

m = 0, 1; n = 1, 2

The following examples 6-2 to 6-14 were prepared in an analogous manner as described for example 6-1 using 3-((R)-4-amino-4,5,6,7-tetrahydro-indazol-1-yl)-acetic acid ethyl ester, 5-bromo-6-chloro-pyridine-3-sulfonyl chloride and the appropriate commercially available substituted phenols (Ar$_3$OH).

| Example No. | Systematic Name | MS (ESI+, M + H) | Structure |
|---|---|---|---|
| 6-2 | ((R)-4-{[5-Bromo-6-(2-chloro-phenoxy)-pyridine-3-sulfonyl]-methyl-amino}-4,5,6,7-tetrahydro-indazol-1-yl)-acetic acid ethyl ester ethyl ester | 583 | 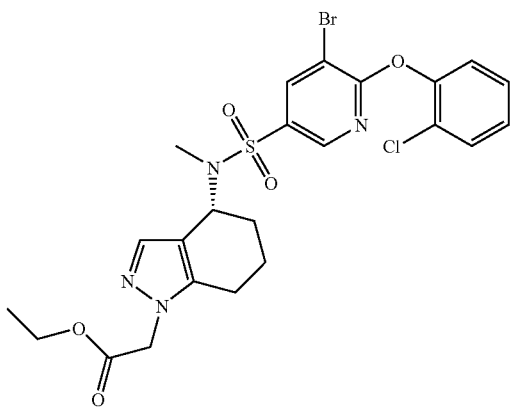 |

-continued

| Example No. | Systematic Name | MS (ESI+, M + H) | Structure |
|---|---|---|---|
| 6-3 | ((R)-4-{[5-Bromo-6-(3,5-dichloro-phenoxy)-pyridine-3-sulfonyl]-methyl-amino}-4,5,6,7-tetrahydro-indazol-1-yl)-acetic acid ethyl ester | 617 | 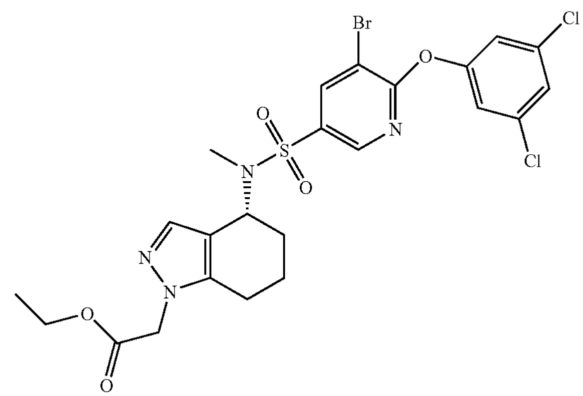 |
| 6-4 | ((R)-4-{[5-Bromo-6-(2,4-dichloro-phenoxy)-pyridine-3-sulfonyl]-methyl-amino}-4,5,6,7-tetrahydro-indazol-1-yl)-acetic acid ethyl ester | 617 | 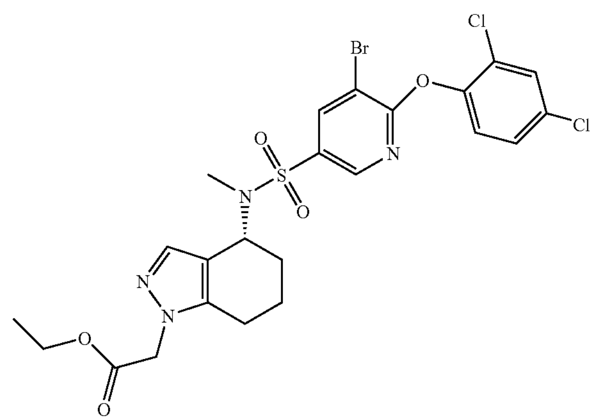 |
| 6-5 | ((R)-4-{[5-Bromo-6-(2,5-dichloro-phenoxy)-pyridine-3-sulfonyl]-methyl-amino}-4,5,6,7-tetrahydro-indazol-1-yl)-acetic acid ethyl ester | 617 | 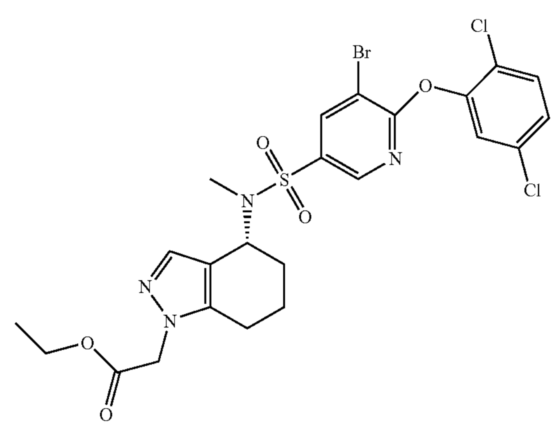 |

| Example No. | Systematic Name | MS (ESI+, M + H) | Structure |
|---|---|---|---|
| 6-6 | ((R)-4-{[5-Bromo-6-(2-chloro-4-fluoro-phenoxy)-pyridine-3-sulfonyl]-methyl-amino}-4,5,6,7-tetrahydro-indazol-1-yl)-acetic acid ethyl ester | 601 | 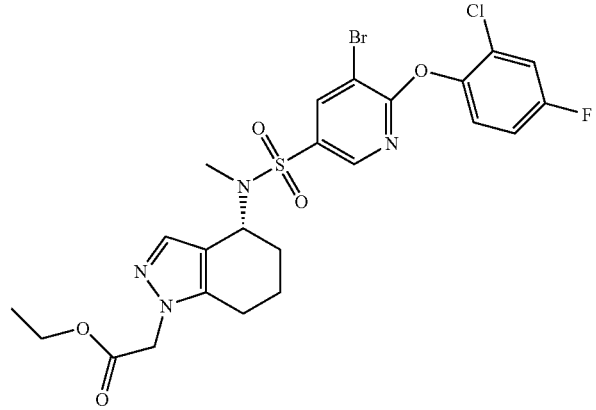 |
| 6-7 | ((R)-4-{[5-Bromo-6-(2,4-difluoro-phenoxy)-pyridine-3-sulfonyl]-methyl-amino}-4,5,6,7-tetrahydro-indazol-1-yl)-acetic acid ethyl ester | 585 | 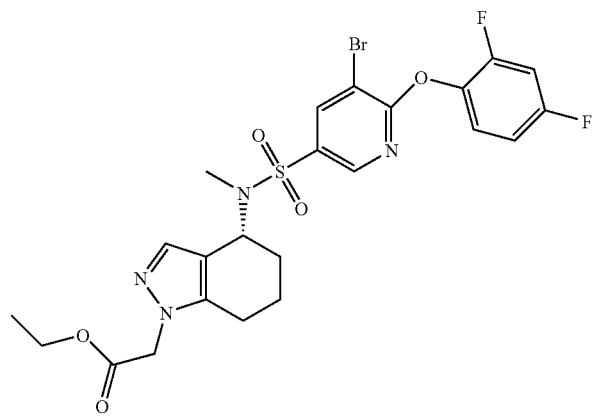 |
| 6-8 | ((R)-4-{[5-Bromo-6-(3-chloro-phenoxy)-pyridine-3-sulfonyl]-methyl-amino}-4,5,6,7-tetrahydro-indazol-1-yl)-acetic acid ethyl ester | 583 | 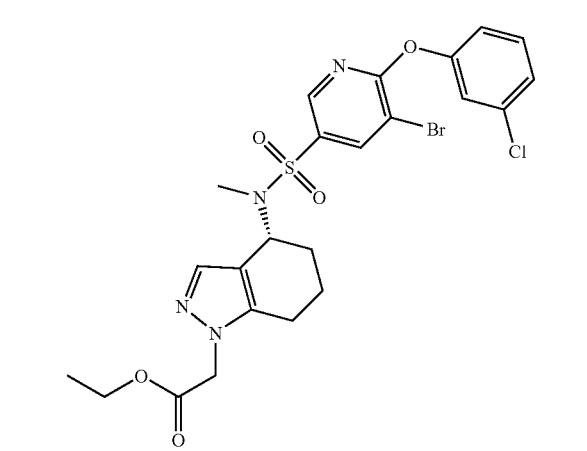 |

-continued

| Example No. | Systematic Name | MS (ESI+, M + H) | Structure |
|---|---|---|---|
| 6-9 | ((R)-4-{[5-Bromo-6-(4-chloro-2-fluoro-phenoxy)-pyridine-3-sulfonyl]-methyl-amino}-4,5,6,7-tetrahydro-indazol-1-yl)-acetic acid ethyl ester | 601 | 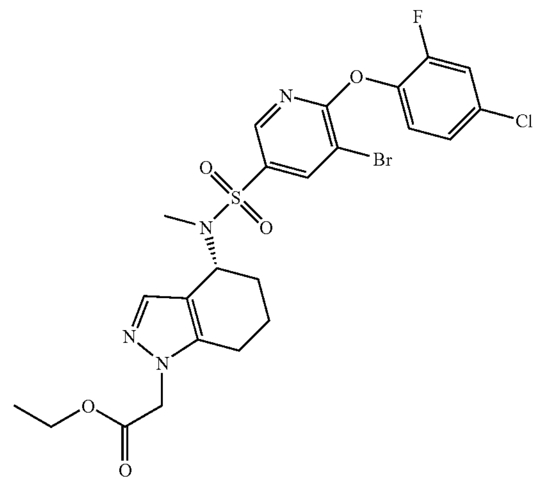 |
| 6-10 | ((R)-4-{[5-Bromo-6-(4-chloro-3-fluoro-phenoxy)-pyridine-3-sulfonyl]-methyl-amino}-4,5,6,7-tetrahydro-indazol-1-yl)-acetic acid ethyl ester | 601 | 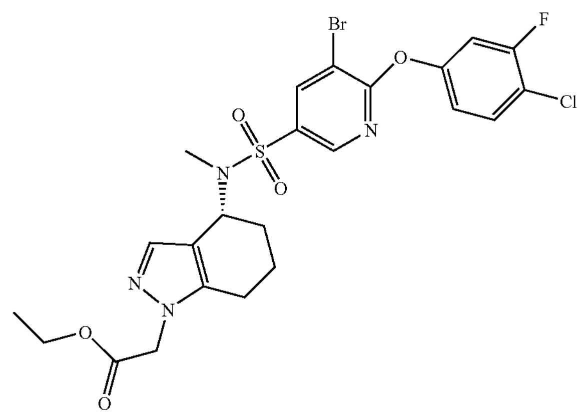 |
| 6-11 | ((R)-4-{[5-Bromo-6-(4-isopropyl-phenoxy)-pyridine-3-sulfonyl]-methyl-amino}-4,5,6,7-tetrahydro-indazol-1-yl)-acetic acid ethyl ester | 591 | 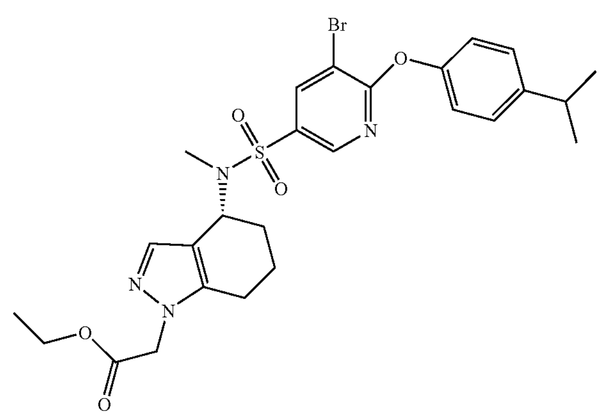 |

| Example No. | Systematic Name | MS (ESI+, M + H) | Structure |
|---|---|---|---|
| 6-12 | ((R)-4-{[5-Bromo-6-(4-fluoro-phenoxy)-pyridine-3-sulfonyl]-methyl-amino}-4,5,6,7-tetrahydro-indazol-1-yl)-acetic acid ethyl ester | 567 | 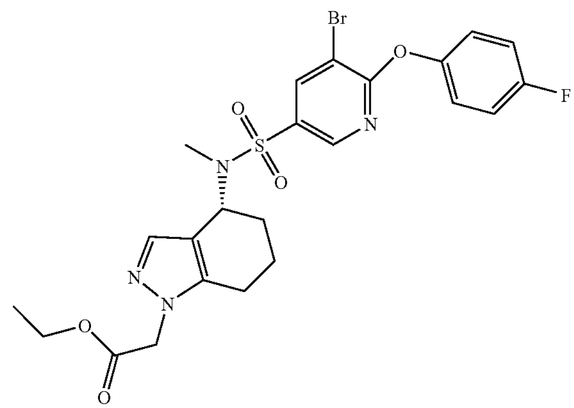 |
| 6-13 | ((R)-4-{[5-Bromo-6-(4-fluoro-2-methoxy-phenoxy)-pyridine-3-sulfonyl]-methyl-amino}-4,5,6,7-tetrahydro-indazol-1-yl)-acetic acid ethyl ester | 597 | 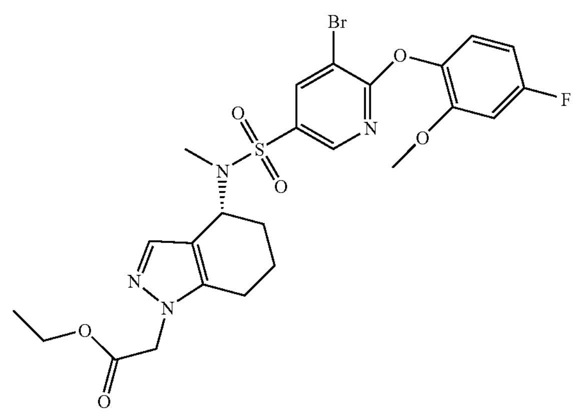 |
| 6-14 | ((R)-4-{[5-Bromo-6-(4-cyano-phenoxy)-pyridine-3-sulfonyl]-methyl-amino}-4,5,6,7-tetrahydro-indazol-1-yl)-acetic acid ethyl ester | 574 | 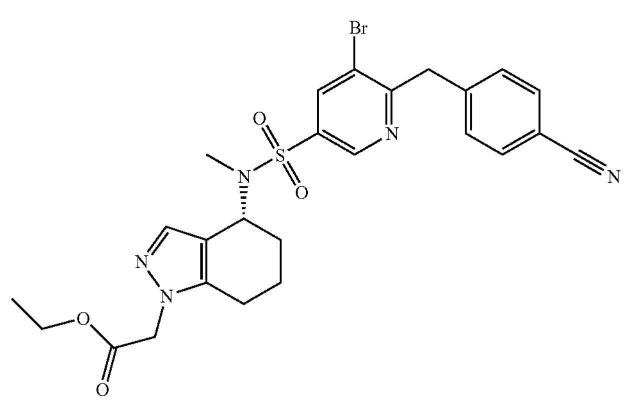 |

Example 6-1a ((R)-4-{[5-Bromo-6-(4-chloro-phenoxy)-pyridine-3-sulfonyl]-methyl-amino}-4,5,6,7-tetrahydro-indazol-1-yl)-acetic acid

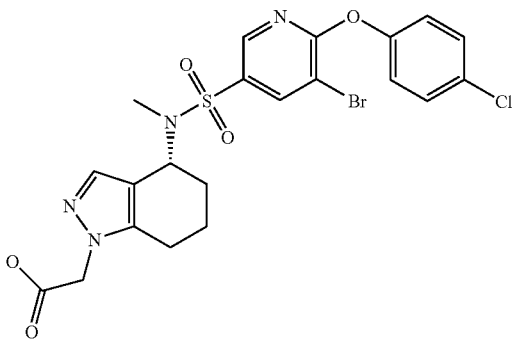

Starting with ((R)-4-{[5-bromo-6-(4-chloro-phenoxy)-pyridine-3-sulfonyl]-methyl-amino}-4,5,6,7-tetrahydro-indazol-1-yl)-acetic acid ethyl ester, and using the method described for example 1-1a, ((R)-4-{[5-bromo-6-(4-chloro-phenoxy)-pyridine-3-sulfonyl]-methyl-amino}-4,5,6,7-tetrahydro-indazol-1-yl)-acetic acid (50 mg, 75%) was obtained as a white solid. $^1$H NMR (400 MHz, CD$_3$OD) δ ppm 8.54 (q, 2 H), 7.47-7.18(m, 4 H), 6.75 (s, 1 H), 5.13 (q, 1 H), 4.81 (s, 2 H), 2.65 (s, 3 H), 2.55 (m, 2 H), 2.06-1.65 (m, 4 H). MS cald. for $C_{21}H_{20}BrClN_4O_5S$ 554, obsd. (ESI$^+$) [(M+H)$^+$] 555.

Examples 6-2a to 6-14a

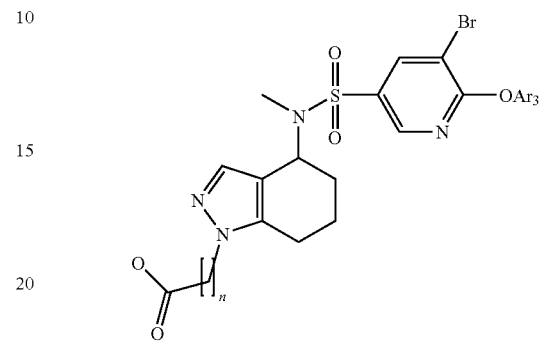

n = 1, 2

The following examples 6-2a to 6-14a were prepared in an analogous manner as described for example 1-1a from the corresponding esters 6-2 to 6-14.

| Example No. | Systematic Name | $^1$H NMR (400 MHz, CD$_3$OD) δ ppm | MS (ESI+, M + H) | Structure |
|---|---|---|---|---|
| 6-2a | ((R)-4-{[5-Bromo-6-(2-chloro-phenoxy)-pyridine-3-sulfonyl]-methyl-amino}-4,5,6,7-tetrahydro-indazol-1-yl)-acetic acid | 8.58 (s, 1H), 8.50 (s, 1H), 7.54 (d, 1H), 7.42 (t, 1H), 7.35-7.31 (m, 2H), 6.71 (s, 1H), 5.12 (d, 1H), 4.82 (s, 2H), 2.64 (s, 3H), 2.54 (m, 2H), 2.05-1.82 (m, 4H) | 555 | 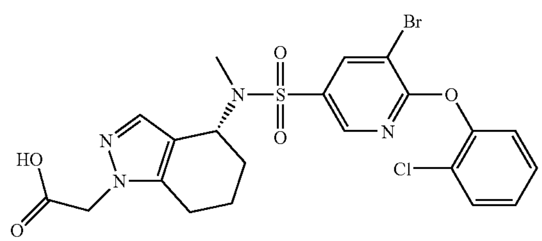 |
| 6-3a | ((R)-4-{[5-Bromo-6-(3,5-dichloro-phenoxy)-pyridine-3-sulfonyl]-methyl-amino}-4,5,6,7-tetrahydro-indazol-1-yl)-acetic acid | 8.60 (d, 2H), 7.42 (t, 1H), 7.31 (d, 2H), 6.82 (m, 1H), 5.14 (t, 1H), 2.68 (s, 3H), 2.57 (s, 2H), 2.05-1.67 (m, 4H) | 589 | 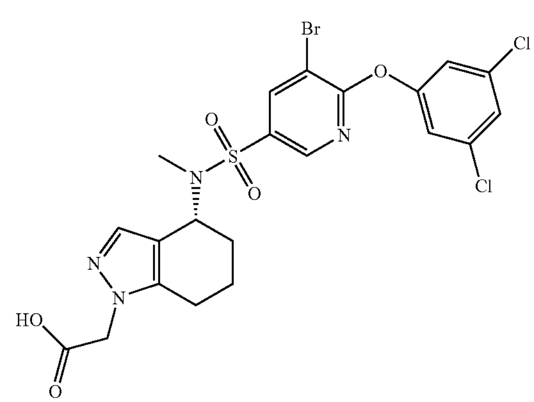 |

| Example No. | Systematic Name | $^1$H NMR (400 MHz, CD$_3$OD) δ ppm | MS (ESI+, M + H) | Structure |
|---|---|---|---|---|
| 6-4a | ((R)-4-{[5-Bromo-6-(2,4-dichloro-phenoxy)-pyridine-3-sulfonyl]-methyl-amino}-4,5,6,7-tetrahydro-indazol-1-yl)-acetic acid | 8.61 (d, 1H), 8.54 (d, 1H), 7.64 (d, 1H), 7.49-7.44 (m, 1H), 7.38 (d, 1H), 6.72 (s, 1H) 5.10-5.17 (m, 1H), 4.84 (s, 2H), 2.66 (s, 3H) 2.63-2.48 (m, 2H), 2.10-2.01 (m, 1H), 1.90-1.75 (m, 2H), 1.75-1.64 (m, 1H) | 589 | 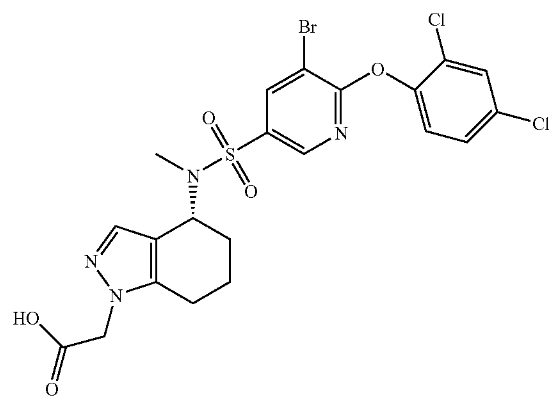 |
| 6-5a | ((R)-4-{[5-Bromo-6-(2,5-dichloro-phenoxy)-pyridine-3-sulfonyl]-methyl-amino}-4,5,6,7-tetrahydro-indazol-1-yl)-acetic acid | 8.61 (d, 1H), 8.55 (d, 1H), 7.56 (d, 1H), 7.49 (d, 1H), 7.37 (dd, 1H), 6.74 (s, 1H), 5.16-5.10 (m, 1H), 4.80 (s, 2H), 2.67 (s, 3H), 2.63-2.49 (m, 2H), 2.10-2.00 (m, 1H), 1.89-1.75 (m, 2H), 1.75-1.64 (m, 1H) | 589 | 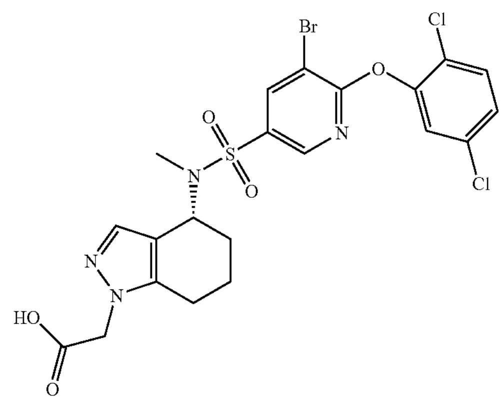 |
| 6-6a | ((R)-4-{[5-Bromo-6-(2-chloro-4-fluoro-phenoxy)-pyridine-3-sulfonyl]-methyl-amino}-4,5,6,7-tetrahydro-indazol-1-yl)-acetic acid | 8.60 (d, 1H), 8.55 (d, 1H), 7.42 (m, 1H), 7.21 (m, 1H), 7.07 (m, 1H), 6.74 (s, 1H), 5.16 (t, 1H), 4.76 (s, 2H), 2.68 (s, 3H), 2.54 (s, 2H), 2.05-1.67 (m, 4H) | 573 | 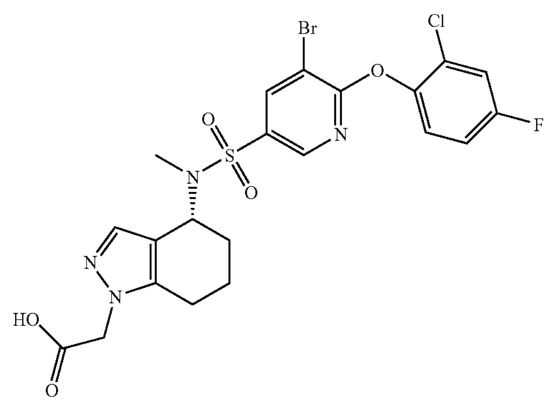 |
| 6-7a | ((R)-4-{[5-Bromo-6-(2,4-difluoro-phenoxy)-pyridine-3-sulfonyl]-methyl-amino}-4,5,6,7-tetrahydro-indazol-1-yl)-acetic acid | 8.60 (d, 1H), 8.55 (d, 1H), 7.42-7.35 (m, 1H), 7.22-7.15 (m, 1H), 7.07 (t, 1H), 6.74 (s, 1H), 5.17-5.11 (m, 1H), 4.75 (s, 2H), 2.68 (s, 3H) 2.49-2.62 (m, 2H), 2.09-2.00 (m, 1H), 1.89-1.76 (m, 2H), 1.75-1.63 (m, 1H) | | |

-continued

| Example No. | Systematic Name | $^1$H NMR (400 MHz, CD$_3$OD) δ ppm | MS (ESI+, M + H) | Structure |
|---|---|---|---|---|
| 6-8a | ((R)-4-{[5-Bromo-6-(3-chloro-phenoxy)-pyridine-3-sulfonyl]-methyl-amino}-4,5,6,7-tetrahydro-indazol-1-yl)-acetic acid | 8.57 (dd, 2H), 7.46 (t, 1H), 7.36-7.31 (m, 2H), 7.18 (d, 1H), 6.79 (s, 1H), 5.18-5.12 (m, 1H), 4.83 (s, 2H), 2.67 (s, 3H), 2.62-2.49 (m, 2H), 2.10-2.02 (m, 1H), 1.90-1.76 (m, 2H), 1.74-1.64 (m, 1H) | 555 | 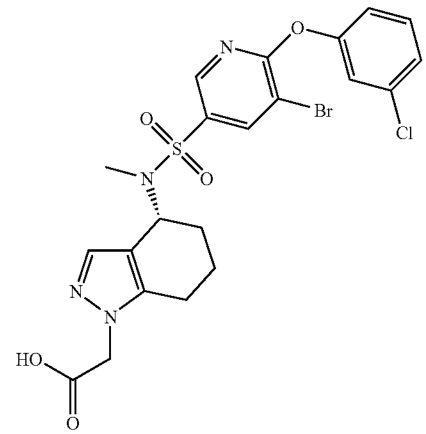 |
| 6-9a | ((R)-4-{[5-Bromo-6-(4-chloro-2-fluoro-phenoxy)-pyridine-3-sulfonyl]-methyl-amino}-4,5,6,7-tetrahydro-indazol-1-yl)-acetic acid | 8.61 (d, 1H), 8.56 (d, 1H), 7.44-7.30 (m, 3H), 6.77 (s, 1H), 5.18-5.11 (m, 1H), 4.84 (s, 2H), 2.67 (s, 3H), 2.63-2.48 (m, 2H), 2.10-2.01 (m, 1H), 1.88-1.76 (m, 2H), 1.74-1.63 (m, 1H) | 573 | 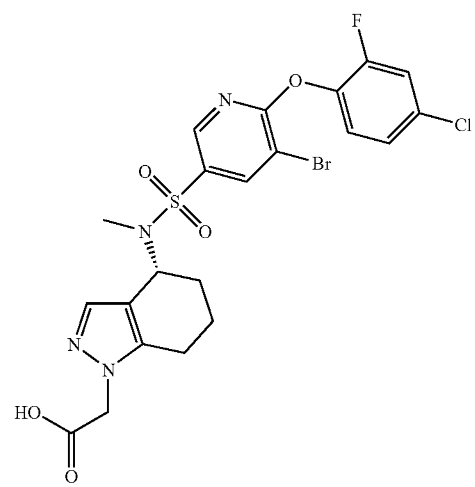 |
| 6-10a | ((R)-4-{[5-Bromo-6-(4-chloro-3-fluoro-phenoxy)-pyridine-3-sulfonyl]-methyl-amino}-4,5,6,7-tetrahydro-indazol-1-yl)-acetic acid | 8.58 (d, 2H), 7.58 (t, 1H), 7.28 (dd, 1H), 7.10 (d, 1H), 6.79 (s, 1H), 5.18-5.12 (m, 1H), 4.81 (s, 2H), 2.67 (s, 3H), 2.64-2.48 (m, 2H), 2.10-2.02 (m, 1H), 1.90-1.76 (m, 2H), 1.69 (q, 1H) | 573 | 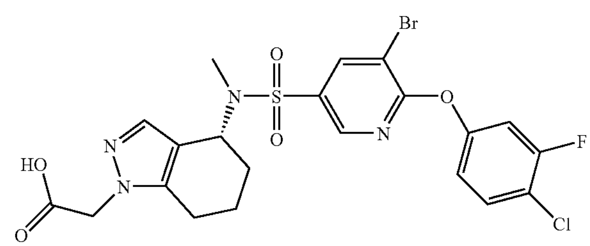 |
| 6-11a | ((R)-4-{[5-Bromo-6-(4-isopropyl-phenoxy)-pyridine-3-sulfonyl]-methyl-amino}-4,5,6,7-tetrahydro-indazol-1-yl)-acetic acid | 8.54 (dd, 2H), 7.34 (d, 2H), 7.11 (d, 2H), 6.76 (s, 1H), 5.17-5.11 (m, 1H), 4.80 (s, 2H), 3.03-2.92 (m, 1H), 2.67 (s, 3H), 2.63-2.49 (m, 2H), 2.10-2.02 (m, 1H), 1.89-1.76 (m, 2H), 1.74-1.64 (m, 1H), 1.30 (d, 6H) | 563 | 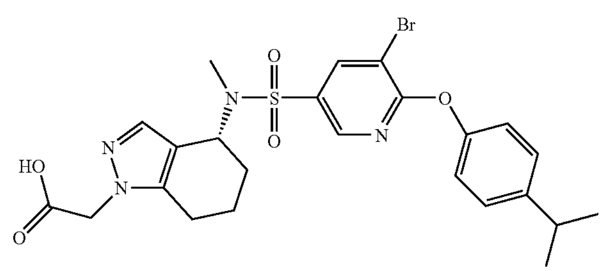 |

-continued

| Example No. | Systematic Name | ¹H NMR (400 MHz, CD₃OD) δ ppm | MS (ESI+, M + H) | Structure |
|---|---|---|---|---|
| 6-12a | ((R)-4-{[5-Bromo-6-(4-fluoro-phenoxy)-pyridine-3-sulfonyl]-methyl-amino}-4,5,6,7-tetrahydro-indazol-1-yl)-acetic acid | 8.57 (d, 1H), 8.54 (s, 1H), 7.23 (m, 4H), 6.73 (s, 1H), 5.15 (t, 1H), 4.72 (s, 2H), 2.68 (s, 3H), 2.57 (s, 2H), 2.04-1.67 (m, 4H) | 539 | 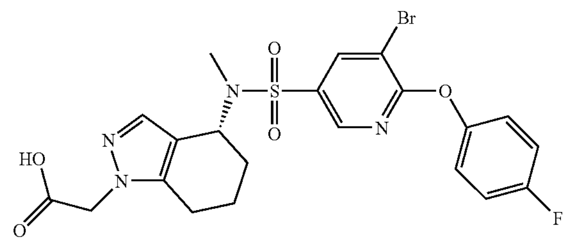 |
| 6-13a | ((R)-4-{[5-Bromo-6-(4-fluoro-2-methoxy-phenoxy)-pyridine-3-sulfonyl]-methyl-amino}-4,5,6,7-tetrahydro-indazol-1-yl)-acetic acid | 8.53 (d, 1H), 8.49 (d, 1H), 7.19 (dd, 1H), 6.95 (dd, 1H), 6.75 (td, 1H), 6.67 (s, 1H), 5.14-5.08 (m, 1H), 4.76 (s, 2H), 3.75 (s, 3H), 2.66 (s, 3H), 2.63-2.49 (m, 2H), 2.10-2.01 (m, 1H), 1.90-1.76 (m, 2H), 1.75-1.64 (m, 1H) | 569 | 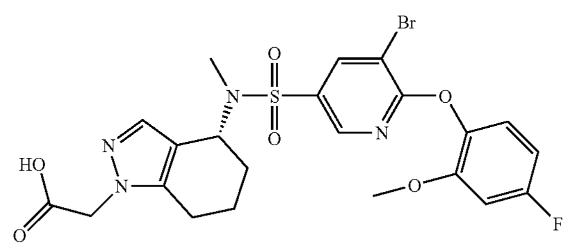 |
| 6-14a | ((R)-4-{[5-Bromo-6-(4-cyano-phenoxy)-pyridine-3-sulfonyl]-methyl-amino}-4,5,6,7-tetrahydro-indazol-1-yl)-acetic acid | 8.60 (dd, 2H), 7.87 (d, 2H), 7.44 (d, 2H), 6.71 (s, 1H), 5.18-5.11 (m, 1H), 4.67 (s, 2H), 2.69 (s, 3H), 2.64-2.49 (m, 2H), 2.09-2.00 (m, 1H), 1.89-1.77 (m, 2H), 1.76-1.65 (m, 1H) | 546 | 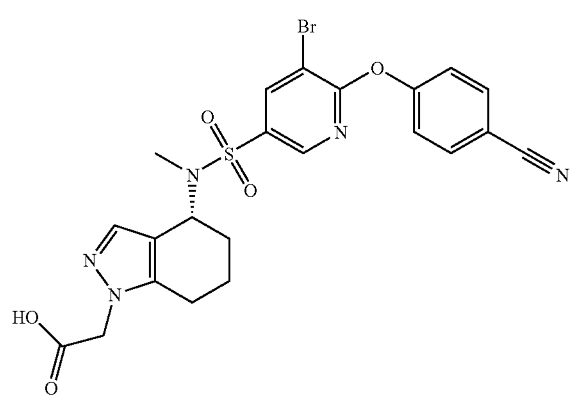 |

Example 7-1

((R)-4-{[6-(4-Chloro-phenoxy)-5-isopropyl-pyridine-3-sulfonyl]-methyl-amino}-4,5,6,7-tetrahydro-indazol-1-yl)-acetic acid ethyl ester

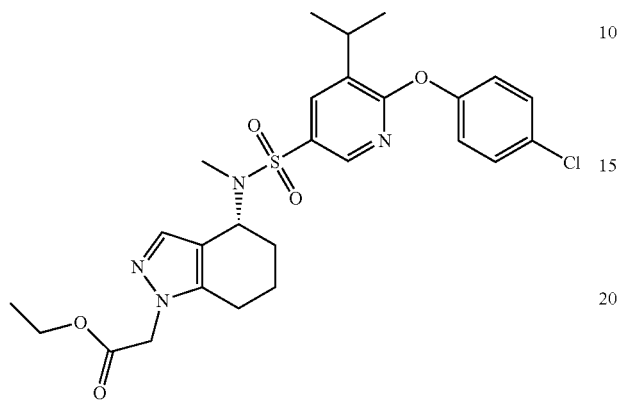

((R)-4-{[6-(4-Chloro-phenoxy)-5-isopropenyl-pyridine-3-sulfonyl]-methyl-amino}-4,5,6,7-tetrahydro-indazol-1-yl)-acetic acid ethyl ester

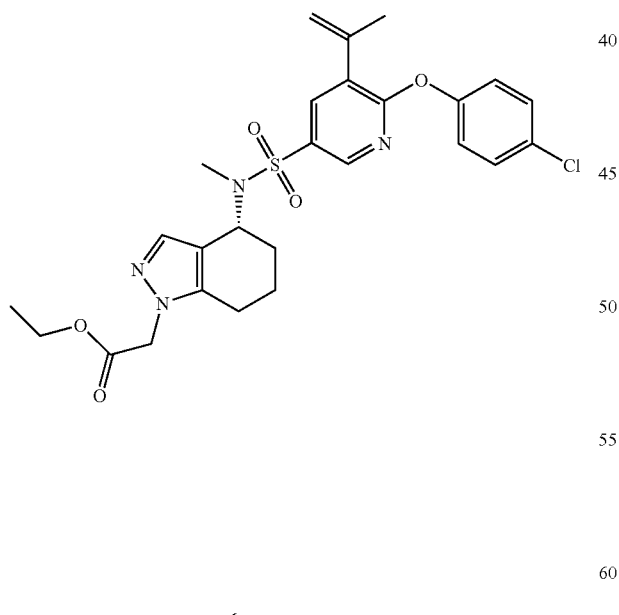

Starting with ((R)-4-{[5-bromo-6-(4-chloro-phenoxy)-pyridine-3-sulfonyl]-methyl-amino}-4,5,6,7-tetrahydro-indazol-1-yl)-acetic acid ethyl ester and isopropenyl-boric acid, and using the method described for example 3-1, ((R)-4-{[6-(4-chloro-phenoxy)-5-isopropenyl-pyridine-3-sulfonyl]-methyl-amino}-4,5,6,7-tetrahydro-indazol-1-yl)-acetic acid ethyl ester (42 mg, 73%) was prepared as a white solid. MS cald. for $C_{26}H_{29}ClN_4O_5S$ 544, obsd. (ESI$^+$) [(M+H)$^+$] 545.

((R)-4-{[6-(4-Chloro-phenoxy)-5-isopropyl-pyridine-3-sulfonyl]-methyl-amino}-4,5,6,7-tetrahydro-indazol-1-yl)-acetic acid ethyl ester

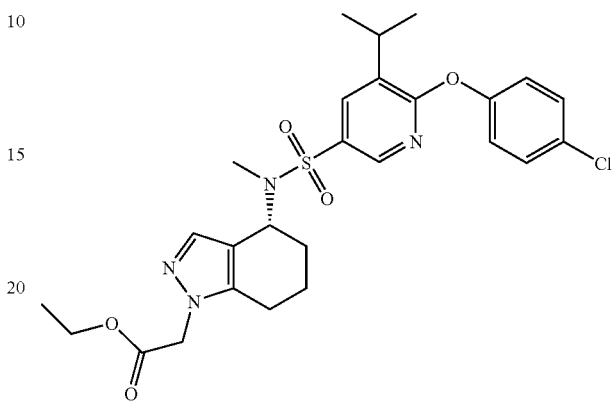

A solution of ((R)-4-{[6-(4-chloro-phenoxy)-5-isopropenyl-pyridine-3-sulfonyl]-methyl-amino}-4,5,6,7-tetrahydro-indazol-1-yl)-acetic acid ethyl ester (42 mg, 0.077 mmol) in methanol was hydrogenated over 10% palladium on carbon (6 mg) under atmospheric pressure for 2.5 hours at room temperature. The reaction mixture was filtered through a glass funnel and the filtrate was purified by preparative HPLC to afford ((R)-4-{[6-(4-chloro-phenoxy)-5-isopropyl-pyridine-3-sulfonyl]-methyl-amino}-4,5,6,7-tetrahydro-indazol-1-yl)-acetic acid ethyl ester (22.4 mg, 53%) as a white solid. MS cald. for $C_{26}H_{31}ClN_4O_5S$ 546, obsd. (ESI$^+$) [(M+H)$^+$] 547.

Example 7-1a ((R)-4-{[6-(4-Chloro-phenoxy)-5-isopropyl-pyridine-3-sulfonyl]-methyl-amino}-4,5,6,7-tetrahydro-indazol-1-yl)-acetic acid Starting with ((R)-4-{[6-(4-chloro-phenoxy)-5-isopropyl-pyridine-3-sulfonyl]-methyl-amino}-4,5,6,7-tetrahydro-indazol-1-yl)-acetic acid ethyl ester, and using the method described for example 1-1a, ((R)-4-{[6-(4-chloro-phenoxy)-

5-isopropyl-pyridine-3-sulfonyl]-methyl-amino}-4,5,6,7-tetrahydro-indazol-1-yl)-acetic acid (16 mg, 75%) was obtained as a white solid. ¹H NMR (400 MHz, CD₃OD) δ ppm 8.43 (d, 1 H), 8.12 (d, 1 H), 7.47-7.17 (dd, 4 H), 6.56 (s, 1 H), 5.13 (t, 1 H), 4.78 (s, 2 H), 3.50 (m, 1 H), 2.65 (s, 3 H), 2.57 (s, 2 H), 2.04-1.67 (m, 4 H), 1.41, (t, 6 H). MS cald. for C₂₄H₂₇ClN₄O₅S 518, obsd. (ESI⁺) [(M+H)⁺] 519.

Example 8-1

((R)-4-{[6-(4-Chloro-phenoxy)-5-(1-methyl-cyclopropyl)-pyridine-3-sulfonyl]-methyl-amino}-4,5,6,7-tetrahydro-indazol-1-yl)-acetic acid ethyl ester

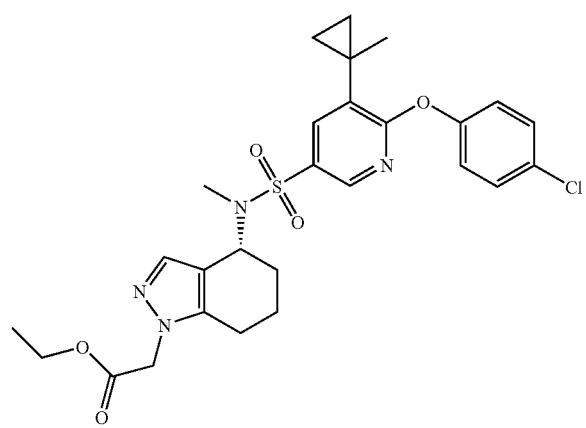

To a solution of ((R)-4-{[5-bromo-6-(4-chloro-phenoxy)-pyridine-3-sulfonyl]-methyl-amino}-4,5,6,7-tetrahydro-indazol-1-yl)-acetic acid ethyl ester (87.6 mg, 0.15 mmol) in tetrahydrofuran (2 mL) was added a solution of diazomethane in diethyl ether (1M, 8 mL) slowly at 0° C. under an argon atmosphere, followed by palladium acetate (5 mg). After the mixture was stirred for 10 minutes, a second portion of palladium acetate (5 mg) was added and the mixture was stirred for 20 minutes, followed by the addition of a second portion of a solution of diazomethane in diethyl ether (1M, 5 mL). After being stirred at 0° C. for 2 hours under an argon atmosphere, the reaction mixture was quenched by the addition of a few drops of acetic acid, filtered through a glass funnel and concentrated in vacuo. The residue was purified by flash column (gradient elution, 0-10% methanol in dichloromethane) to afford ((R)-4-{methyl-[3-(1-methyl-cyclopropyl)-5-trifluoromethyl-benzenesulfonyl]-amino}-4,5,6,7-tetrahydro-indazol-1-yl)-acetic acid ethyl ester (67.9 mg, 81.0%) as a colorless semisolid. MS cald. for C₂₇H₃₁ClN₄O₅S 558, obsd. (ESI⁺) [(M+H)⁺] 559.

Example 8-1a ((R)-4-{[6-(4-Chloro-phenoxy)-5-(1-methyl-cyclopropyl)-pyridine-3-sulfonyl]-methyl-amino}-4,5,6,7-tetrahydro-indazol-1-yl)-acetic acid

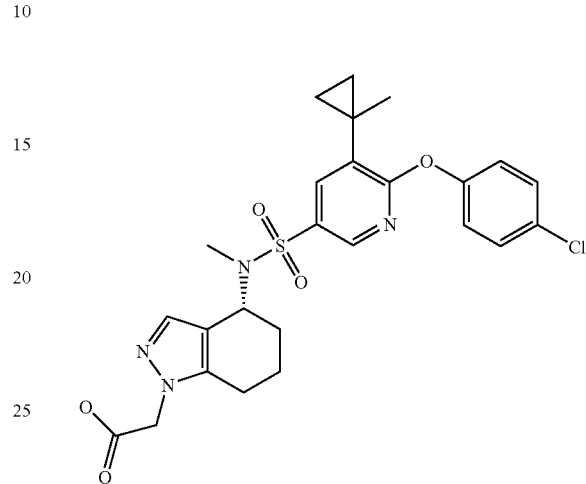

Starting with ((R)-4-{methyl-[3-(1-methyl-cyclopropyl)-5-trifluoromethyl-benzenesulfonyl]-amino}-4,5,6,7-tetrahydro-indazol-1-yl)-acetic acid ethyl ester, and using the method described for example 1-1a, ((R)-4-{methyl-[3-(1-methyl-cyclopropyl)-5-trifluoromethyl-benzenesulfonyl]-amino}-4,5,6,7-tetrahydro-indazol-1-yl)-acetic acid (41 mg, 55.6%) was obtained as a white solid. ¹H NMR (400 MHz, CD₃OD) δ ppm 8.44 (d, 1 H), 8.15 (d, 1 H), 7.47-7.19 (dd, 4 H), 6.52 (s, 1 H), 5.13 (t, 1 H), 4.84 (s, 2 H), 2.63 (s, 3 H), 2.57 (m, 2 H), 2.08-1.64 (m, 4 H), 1.49 (s, 3 H), 0.95-0.88 (m, 4 H). MS cald. for C₂₅H₂₇ClN₄O₅S 530, obsd. (ESI⁺) [(M+H)⁺] 531.

Example 9-1

((R)-4-{[3-Chloro-4-(2-chloro-phenoxy)-benzenesulfonyl]-methyl-amino}-4,5,6,7-tetrahydro-indazol-1-yl)-acetic acid ethyl ester

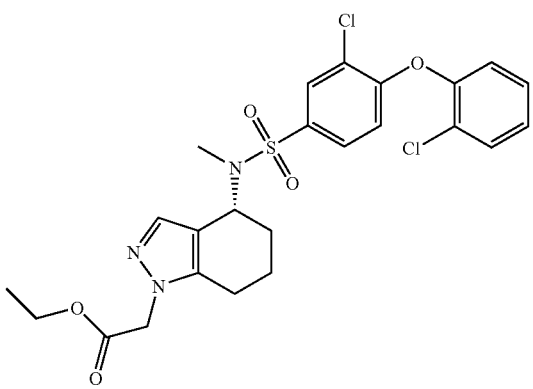

{(R)-4-[(3-Chloro-4-fluoro-benzenesulfonyl)-methyl-amino]-4,5,6,7-tetrahydro-indazol-1-yl}-acetic acid ethyl ester

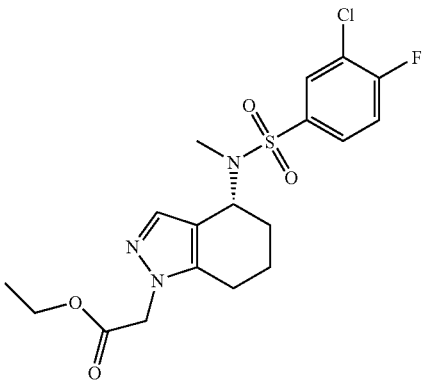

To a solution of [(R)-4-(3-chloro-4-fluoro-benzenesulfonylamino)-4,5,6,7-tetrahydro-indazol-1-yl]-acetic acid ethyl ester (150 mg, 0.36 mmol, prepared as described in example 4-1, 1$^{st}$ step) in acetonitrile (10 mL) was added methyl iodide (154 mg, 1.1 mmol) and potassium carbonate (151 mg, 1.1 mmol). The reaction mixture was stirred at 65° C. for 5 hours, then cooled to room temperature and filtered through a glass funnel. The filtrate was evaporated under reduced pressure and purified by column chromatography (gradient elution, 0-10% methanol in dichloromethane) to afford {(R)-4-[(3-chloro-4-fluoro-benzenesulfonyl)-methyl-amino]-4,5,6,7-tetrahydro-indazol-1-yl}-acetic acid ethyl ester (150 mg, 96%) as a yellow solid. MS cald for $C_{18}H_{21}ClN_3O_4S$ 429, obsd. (ESI$^+$) [(M+H)$^+$]: 430.

((R)-4-{[3-Chloro-4-(2-chloro-phenoxy)-benzenesulfonyl]-methyl-amino}-4,5,6,7-tetrahydro-indazol-1-yl)-acetic acid ethyl ester

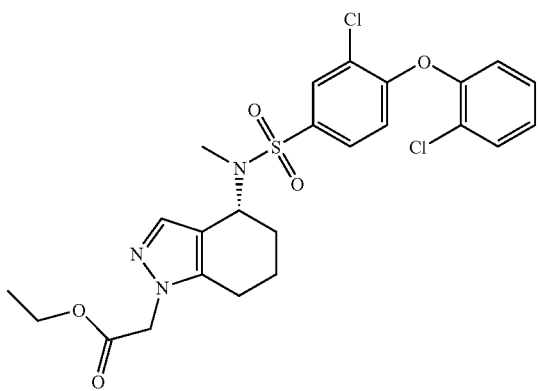

{(R)-4-[(3-Chloro-4-fluoro-benzenesulfonyl)-methylamino]-4,5,6,7-tetrahydro-indazol-1-yl}-acetic acid ethyl ester (24 mg, 0.058 mmol), sodium hydride (60% dispersed in mineral oil, 11.6 mg) and 4-chlorophenol (0.52 mg, 0.40 mmol) were dissolved in N,N-dimethylformamide (2 mL). After being heated in a microwave oven at 100° C. for 15 minutes, the resulting mixture was acidified with acetic acid to pH 5, and filtered through a glass funnel. The precipitate was purified by preparative HPLC to afford ((R)-4-{[3-chloro-4-(2-chloro-phenoxy)-benzenesulfonyl]-methyl-amino}-4,5,6,7-tetrahydro-indazol-1-yl)-acetic acid ethyl ester (24 mg, 77%) as a white powder. MS cald. for $C_{24}H_{25}Cl_2N_3O_5S$ 537, obsd. (ESI$^+$) [(M+H)$^+$]: 538.

Examples 9-2 to 9-42

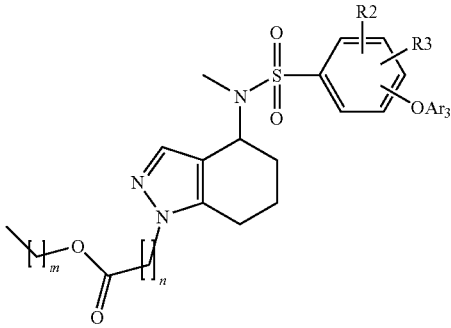

m = 0, 1; n = 1, 2

The following examples 9-2 to 9-42 were prepared in an analogous manner as described for example 8-1 using 3-((R)-4-amino-4,5,6,7-tetrahydro-indazol-1-yl)-acetic acid ethyl ester, and the appropriate commercially available or prepared fluoro-substituted benzenesulfonyl chlorides XXXIII and substituted phenols (Ar$_3$OH).

| Example No. | Systematic Name | MS (ESI+, M + H) | Structure |
|---|---|---|---|
| 9-2 | ((R)-4-{[3-Chloro-4-(3-chloro-phenoxy)-benzenesulfonyl]-methyl-amino}-4,5,6,7-tetrahydro-indazol-1-yl)-acetic acid ethyl ester | 538 | 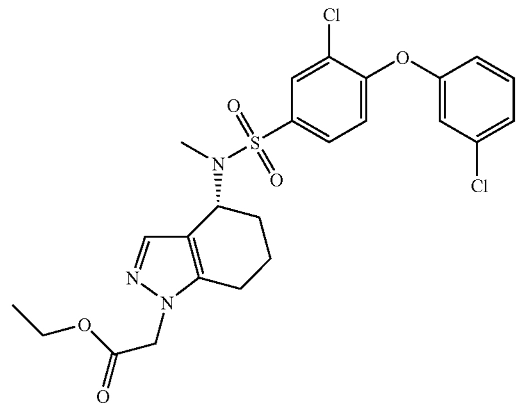 |
| 9-3 | ((R)-4-{[3-Chloro-4-(4-chloro-phenoxy)-benzenesulfonyl]-methyl-amino}-4,5,6,7-tetrahydro-indazol-1-yl)-acetic acid ethyl ester | 538 | 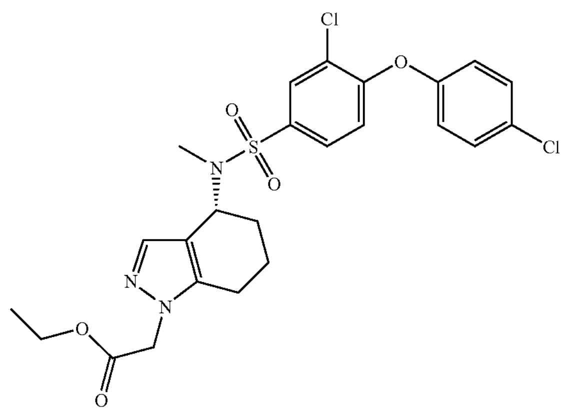 |
| 9-4 | ((R)-4-{[2-Chloro-4-(4-chloro-phenoxy)-benzenesulfonyl]-methyl-amino}-4,5,6,7-tetrahydro-indazol-1-yl)-acetic acid ethyl ester | 538 | 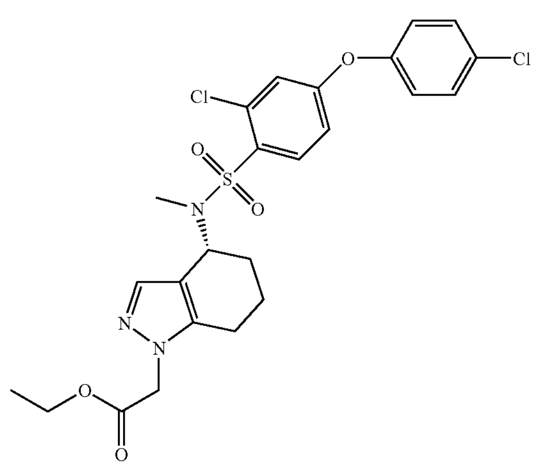 |

-continued

| Example No. | Systematic Name | MS (ESI+, M + H) | Structure |
|---|---|---|---|
| 9-5 | ((R)-4-{[4-(4-Chloro-phenoxy-3-trifluoromethyl-benzenesulfonyl]-methyl-amino}-4,5,6,7-tetrahydro-indazol-1-yl)-acetic acid ethyl ester | 572 | 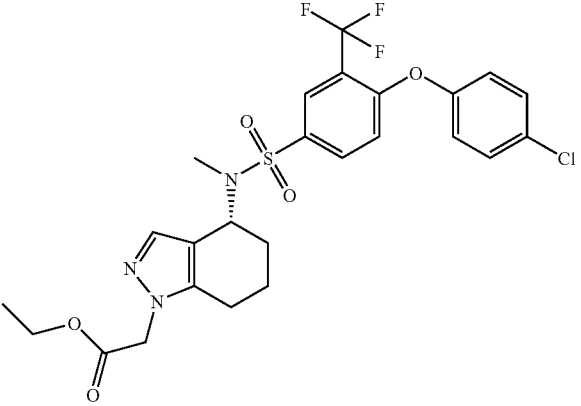 |
| 9-6 | ((R)-4-{[3-Chloro-4-(2,4-dichloro-phenoxy)-benzenesulfonyl]-methyl-amino}-4,5,6,7-tetrahydro-indazol-1-yl)-acetic acid ethyl ester | 572 | 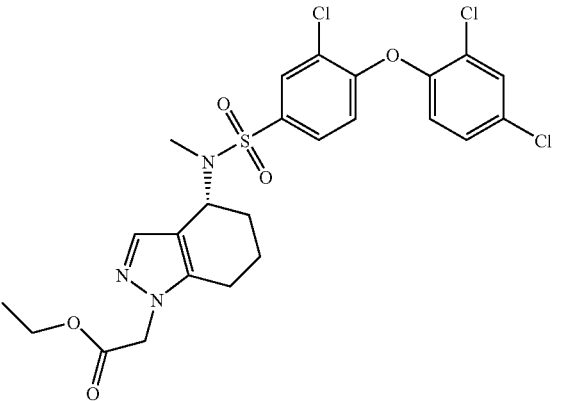 |
| 9-7 | ((R)-4-{[4-(4-tert-Butyl-phenoxy)-3-chloro-benzenesulfonyl]-methyl-amino}-4,5,6,7-tetrahydro-indazol-1-yl)-acetic acid ethyl ester | 560 | 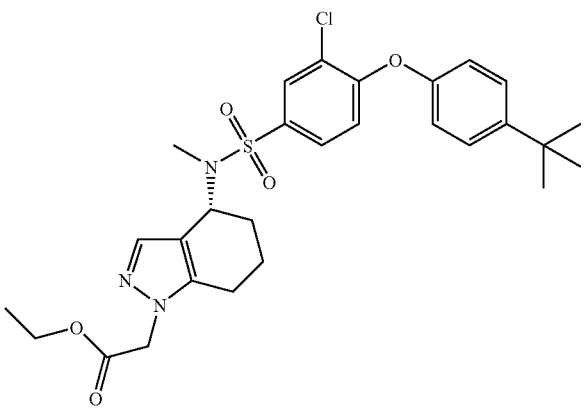 |

-continued

| Example No. | Systematic Name | MS (ESI+, M + H) | Structure |
|---|---|---|---|
| 9-8 | ((R)-4-{[2-Chloro-4-(2,4-dichloro-phenoxy)-benzenesulfonyl]-methyl-amino}-4,5,6,7-tetrahydro-indazol-1-yl)-acetic acid ethyl ester | 572 | 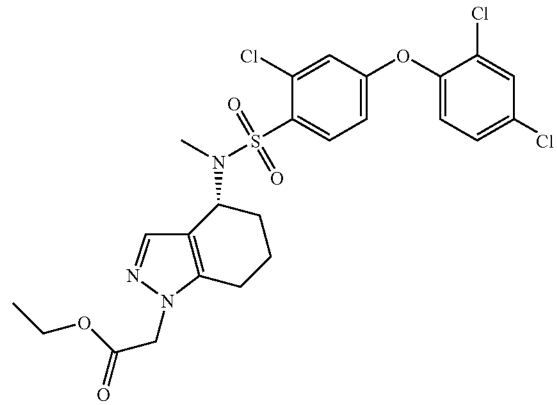 |
| 9-9 | ((R)-4-{[2-Chloro-4-(2-chloro-4-fluoro-phenoxy)-benzenesulfonyl]-methyl-amino}-4,5,6,7-tetrahydro-indazol-1-yl)-acetic acid ethyl ester | 556 | 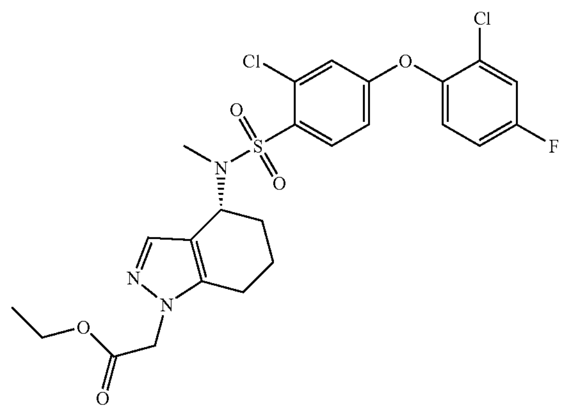 |
| 9-10 | ((R)-4-{[2-Chloro-4-(2-chloro-phenoxy)-benzenesulfonyl]-methyl-amino}-4,5,6,7-tetrahydro-indazol-1-yl)-acetic acid ethyl ester | 538 | 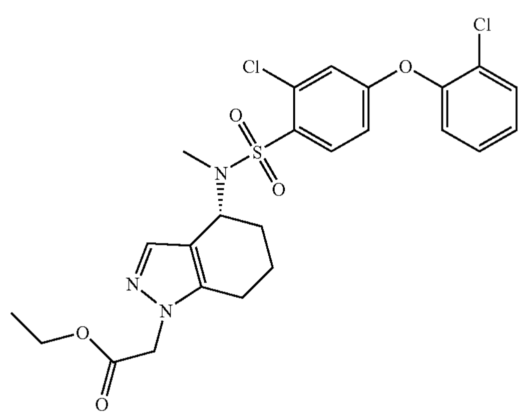 |

| Example No. | Systematic Name | MS (ESI+, M + H) | Structure |
|---|---|---|---|
| 9-11 | ((R)-4-{[3-Chloro-4-(4-chloro-2-fluoro-phenoxy)-benzenesulfonyl]-methyl-amino}-4,5,6,7-tetrahydro-indazol-1-yl)-acetic acid ethyl ester | 556 | 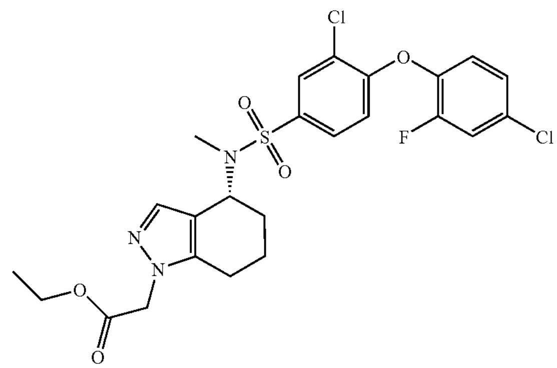 |
| 9-12 | ((R)-4-{[4-(4-Chloro-phenoxy)-3-fluoro-benzenesulfonyl]-methyl-amino}-4,5,6,7-tetrahydro-indazol-1-yl)-acetic acid ethyl ester | 522 | 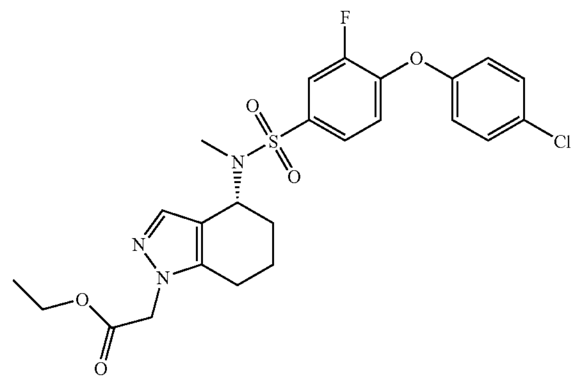 |
| 9-13 | {(R)-4-[(3-Chloro-4-phenoxy-benzenesulfonyl)-methyl-amino]-4,5,6,7-tetrahydro-indazol-1-yl}-acetic acid ethyl ester | 504 | 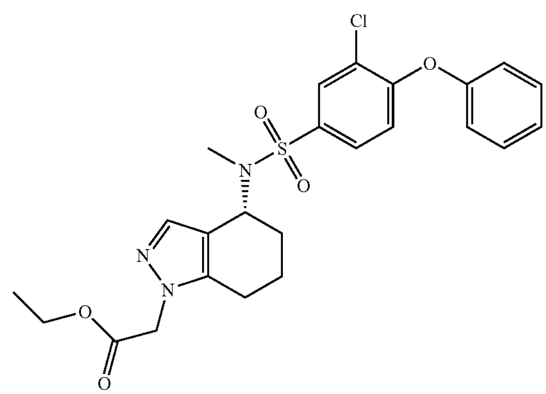 |
| 9-14 | ((R)-4-{[3-Chloro-4-(4-fluoro-phenoxy)-benzenesulfonyl]-methyl-amino}-4,5,6,7-tetrahydro-indazol-1-yl)-acetic acid ethyl ester | 522 | 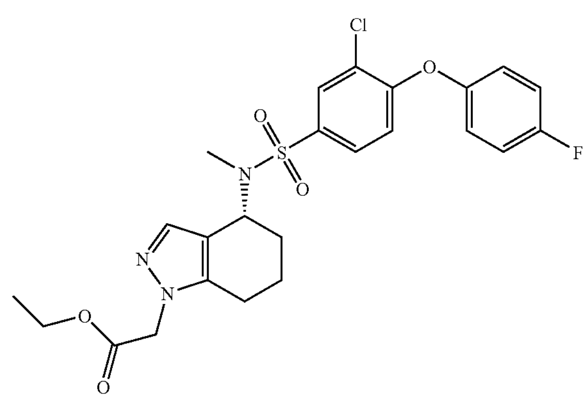 |

-continued

| Example No. | Systematic Name | MS (ESI+, M + H) | Structure |
|---|---|---|---|
| 9-15 | {(R)-4-[(3-Chloro-4-p-tolyloxy-benzenesulfonyl)-methyl-amino]-4,5,6,7-tetrahydro-indazol-1-yl}-acetic acid ethyl ester | 518 | 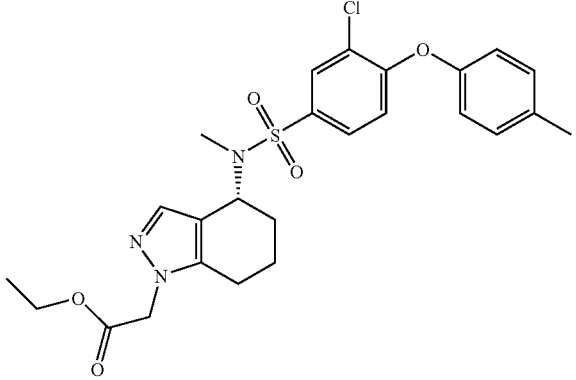 |
| 9-16 | ((R)-4-{[3-Chloro-4-(2-chloro-4-fluoro-phenoxy)-benzenesulfonyl]-methyl-amino}-4,5,6,7-tetrahydro-indazol-1-yl)-acetic acid ethyl ester | 556 | 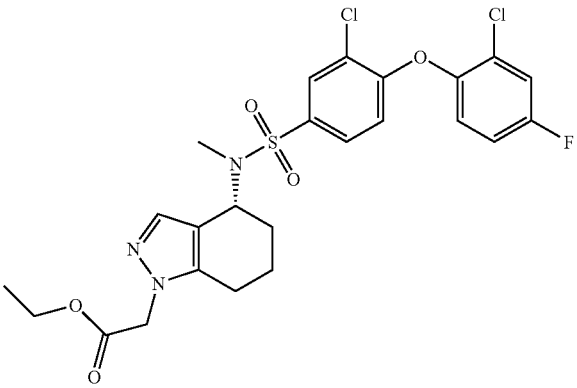 |
| 9-17 | ((R)-4-{[3-Chloro-4-(4-fluoro-2-methoxy-phenoxy)-benzenesulfonyl]-methyl-amino}-4,5,6,7-tetrahydro-indazol-1-yl)-acetic acid ethyl ester | 552 | 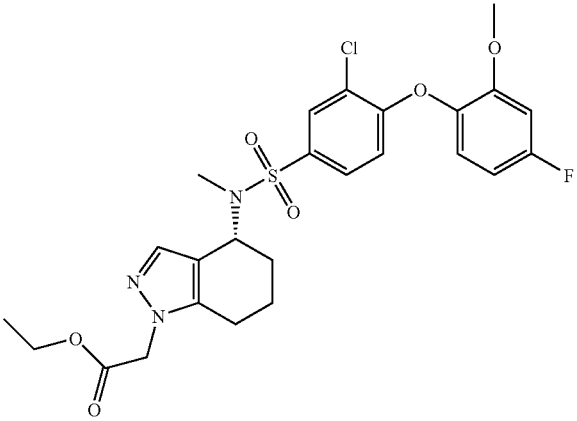 |

-continued

| Example No. | Systematic Name | MS (ESI+, M + H) | Structure |
|---|---|---|---|
| 9-18 | ((R)-4-{[3-Chloro-4-(2-chloro-5-methyl-phenoxy)-benzenesulfonyl]-methyl-amino}-4,5,6,7-tetrahydro-indazol-1-yl)-acetic acid ethyl ester | 552 | 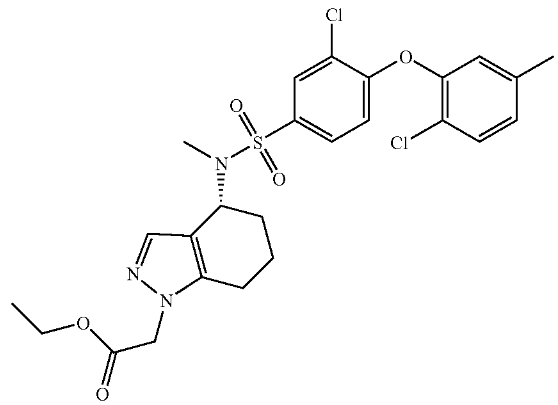 |
| 9-19 | ((R)-4-{[3-Chloro-4-(2,4-dimethyl-phenoxy)-benzenesulfonyl]-methyl-amino}-4,5,6,7-tetrahydro-indazol-1-yl)-acetic acid ethyl ester | 532 | 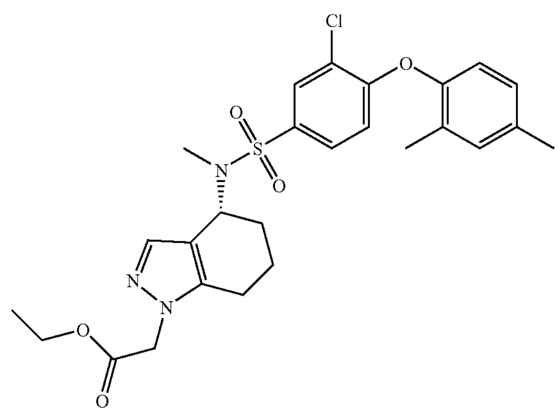 |
| 9-20 | ((R)-4-{[3-Chloro-4-(4-chloro-2-methoxy-phenoxy)-benzenesulfonyl]-methyl-amino}-4,5,6,7-tetrahydro-indazol-1-yl)-acetic acid ethyl ester | 568 | 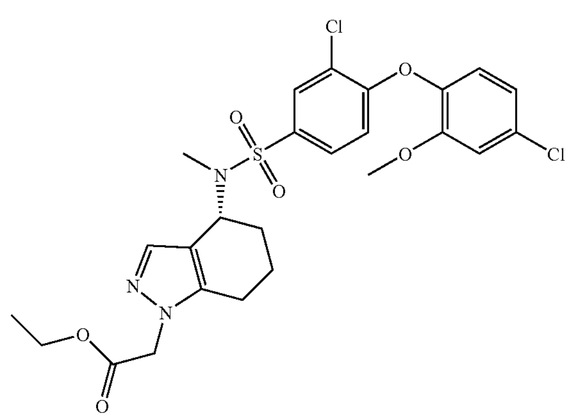 |

| Example No. | Systematic Name | MS (ESI+, M + H) | Structure |
|---|---|---|---|
| 9-21 | ((R)-4-{[3-Chloro-4-(4-chloro-3-fluoro-phenoxy)-benzenesulfonyl]-methyl-amino}-4,5,6,7-tetrahydro-indazol-1-yl)-acetic acid ethyl ester | 556 | 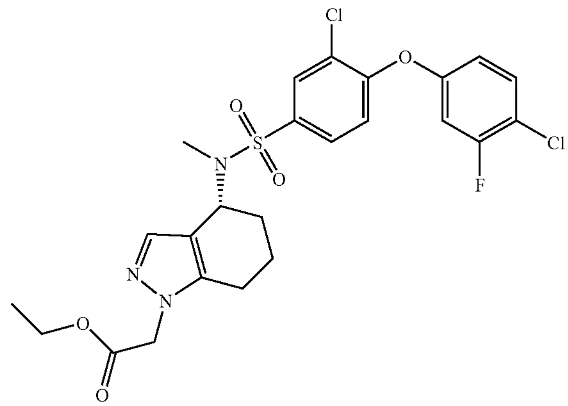 |
| 9-22 | ((R)-4-{[3-Chloro-4-(2,5-difluoro-phenoxy)-benzenesulfonyl]-methyl-amino}-4,5,6,7-tetrahydro-indazol-1-yl)-acetic acid ethyl ester | 540 | 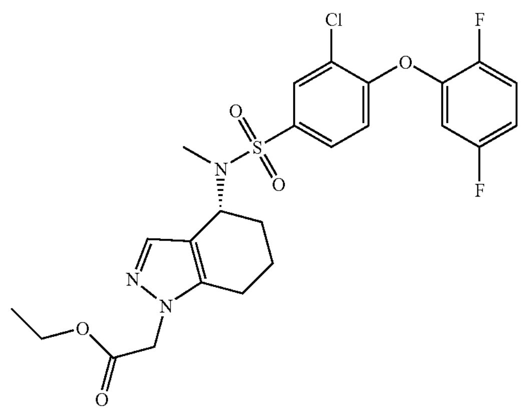 |
| 9-23 | ((R)-4-{[4-(4-Bromo-phenoxy)-3-chloro-benzenesulfonyl]-methyl-amino}-4,5,6,7-tetrahydro-indazol-1-yl)-acetic acid ethyl ester | 582 | 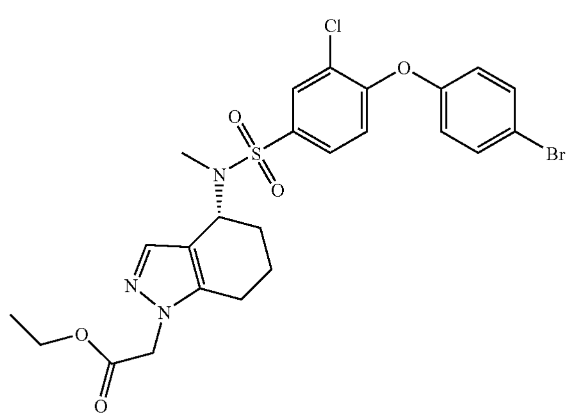 |

| Example No. | Systematic Name | MS (ESI+, M + H) | Structure |
|---|---|---|---|
| 9-24 | ((R)-4-{[3-Chloro-4-(3-chloro-4-fluoro-phenoxy)-benzenesulfonyl]-methyl-amino}-4,5,6,7-tetrahydro-indazol-1-yl)-acetic acid ethyl ester | 556 | 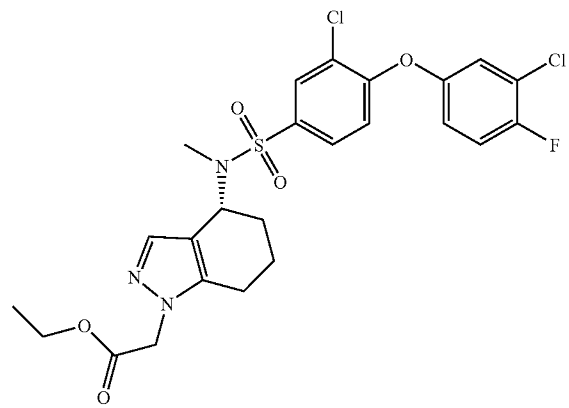 |
| 9-25 | ((R)-4-{[3-Chloro-4-(4-methanesulfonyl-phenoxy)-benzenesulfonyl]-methyl-amino}-4,5,6,7-tetrahydro-indazol-1-yl)-acetic acid ethyl ester | 582 | 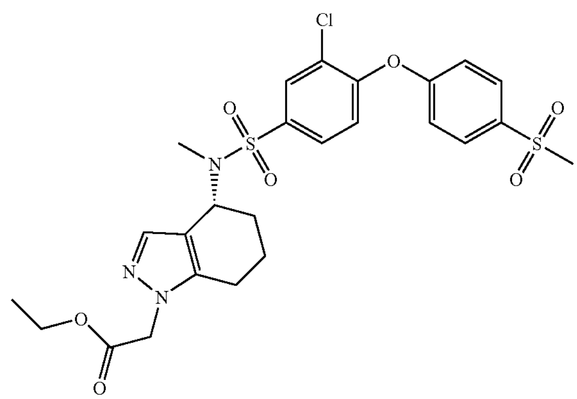 |
| 9-26 | {(R)-4-[(3-Chloro-4-o-tolyloxy-benzenesulfonyl)-methyl-amino]-4,5,6,7-tetrahydro-indazol-1-yl}-acetic acid ethyl ester | 518 | 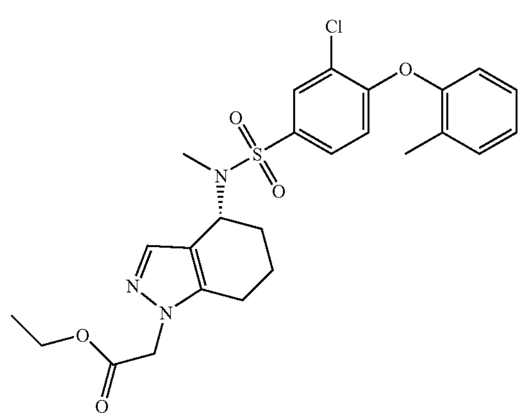 |

| Example No. | Systematic Name | MS (ESI+, M + H) | Structure |
|---|---|---|---|
| 9-27 | ((R)-4-{[4-(4-Acetylamino-phenoxy)-3-chloro-benzenesulfonyl]-methyl-amino}-4,5,6,7-tetrahydro-indazol-1-yl)-acetic acid ethyl ester | 561 | 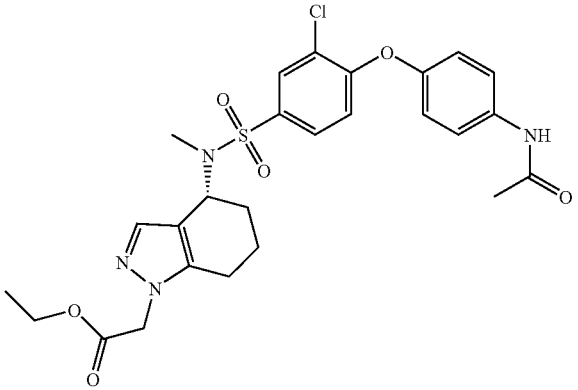 |
| 9-28 | ((R)-4-{[3-Chloro-4-(4-trifluoromethoxy-phenoxy)-benzenesulfonyl]-methyl-amino}-4,5,6,7-tetrahydro-indazol-1-yl)-acetic acid ethyl ester | 588 | 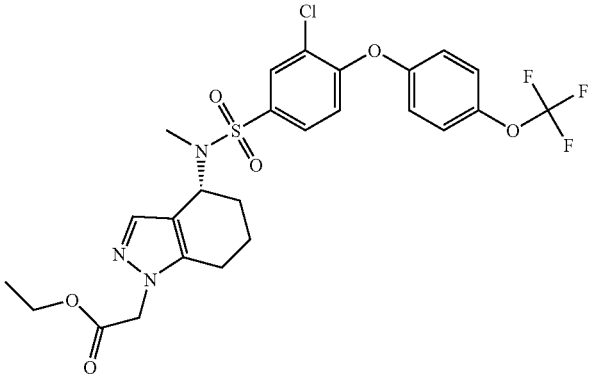 |
| 9-29 | ((R)-4-{[2-Chloro-5-fluoro-4-(4-fluoro-phenoxy)-benzenesulfonyl]-methyl-amino}-4,5,6,7-tetrahydro-indazol-1-yl)-acetic acid ethyl ester | 540 | 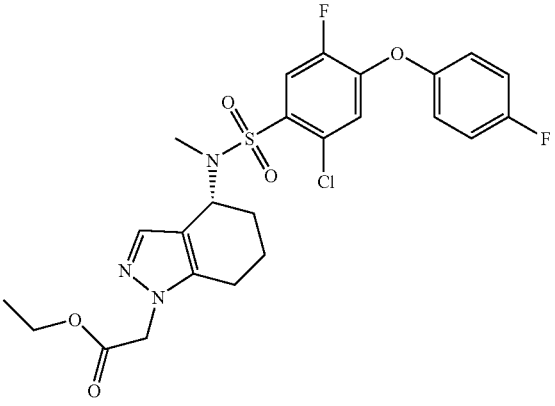 |

-continued

| Example No. | Systematic Name | MS (ESI+, M + H) | Structure |
|---|---|---|---|
| 9-30 | ((R)-4-{[5-Chloro-2-fluoro-4-(4-fluoro-phenoxy)-benzenesulfonyl]-methyl-amino}-4,5,6,7-tetrahydro-indazol-1-yl)-acetic acid ethyl ester | 540 | 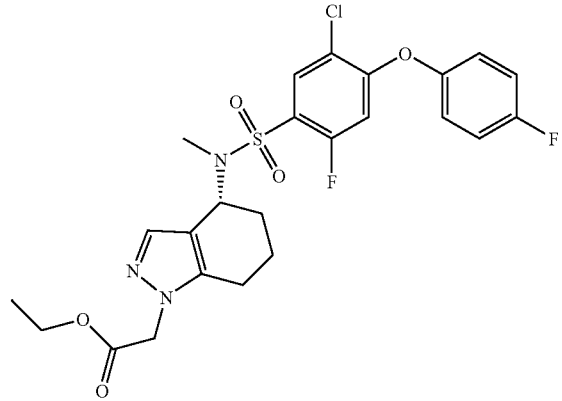 |
| 9-31 | ((R)-4-{[3-Chloro-4-(4-methoxy-phenoxy)-benzenesulfonyl]-methyl-amino}-4,5,6,7-tetrahydro-indazol-1-yl)-acetic acid ethyl ester | 534 | 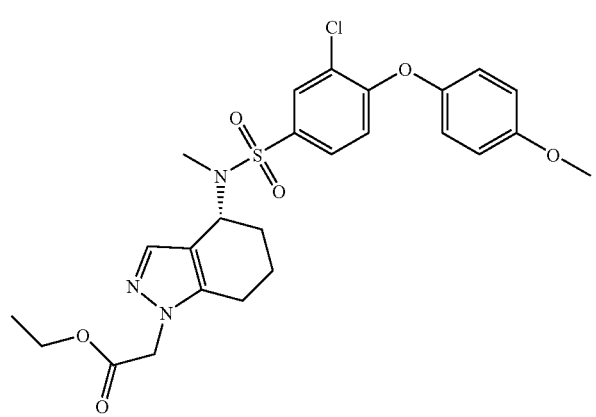 |
| 9-32 | ((R)-4-{[3-Chloro-4-(2,4-difluoro-phenoxy)-benzenesulfonyl]-methyl-amino}-4,5,6,7-tetrahydro-indazol-1-yl)-acetic acid ethyl ester | 540 | 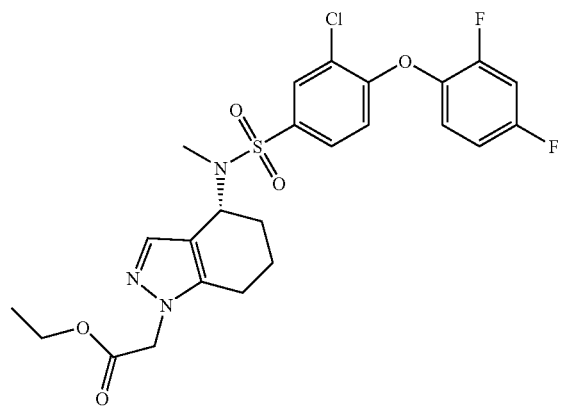 |

-continued

| Example No. | Systematic Name | MS (ESI+, M + H) | Structure |
|---|---|---|---|
| 9-33 | ((R)-4-{[3-Chloro-4-(2,6-difluoro-phenoxy)-benzenesulfonyl]-methyl-amino}-4,5,6,7-tetrahydro-indazol-1-yl)-acetic acid ethyl ester | 540 | 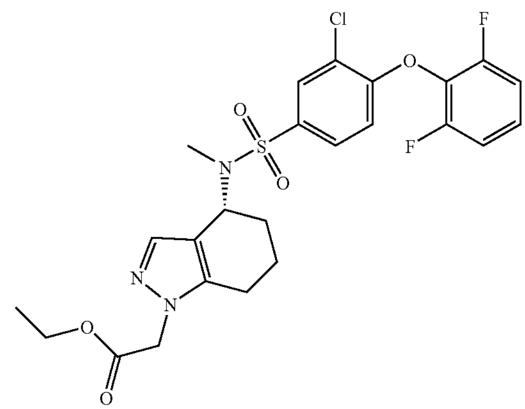 |
| 9-34 | ((R)-4-{[3-Chloro-4-(4-cyano-phenoxy)-benzenesulfonyl]-methyl-amino}-4,5,6,7-tetrahydro-indazol-1-yl)-acetic acid ethyl ester | 529 | 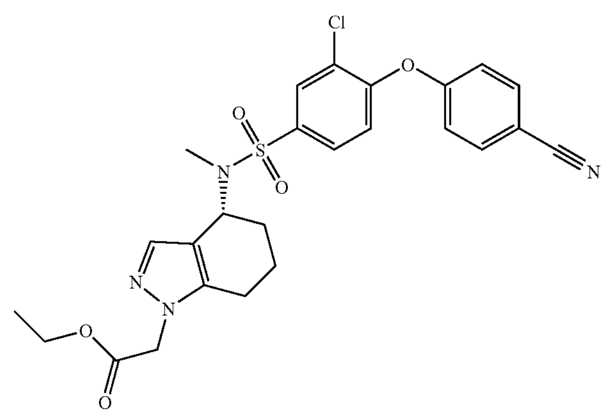 |
| 9-35 | ((R)-4-{[4-(4-Fluoro-phenoxy)-3-methyl-benzenesulfonyl]-methyl-amino}-4,5,6,7-tetrahydro-indazol-1-yl)-acetic acid ethyl ester | 502 | 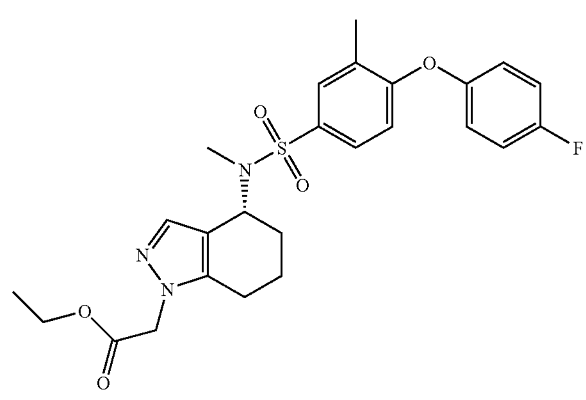 |

-continued

| Example No. | Systematic Name | MS (ESI+, M + H) | Structure |
|---|---|---|---|
| 9-36 | ((R)-4-{[4-(4-Carbamoyl-phenoxy)-3-chloro-benzenesulfonyl]-methyl-amino}-4,5,6,7-tetrahydro-indazol-1-yl)-acetic acid ethyl ester | 547 | 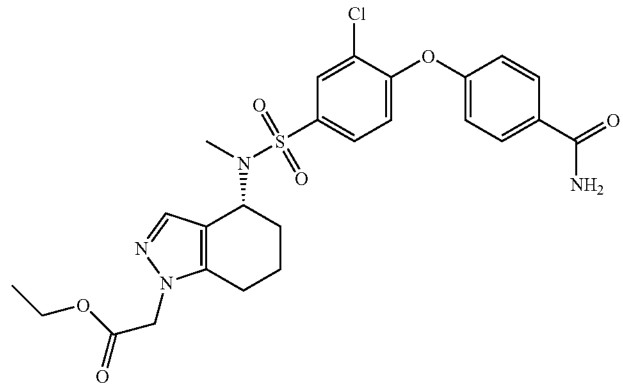 |
| 9-37 | ((R)-4-{[3-Chloro-4-(2-fluoro-phenoxy)-benzenesulfonyl]-methyl-amino}-4,5,6,7-tetrahydro-indazol-1-yl)-acetic acid ethyl ester | 522 | 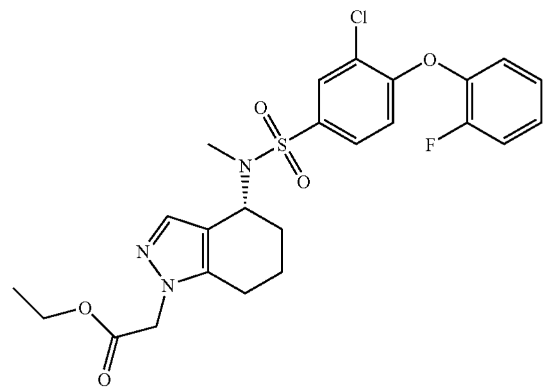 |
| 9-38 | ((R)-4-{[3-Chloro-4-(4-fluoro-2-methyl-phenoxy)-benzenesulfonyl]-methyl-amino}-4,5,6,7-tetrahydro-indazol-1-yl)-acetic acid ethyl ester | 536 | 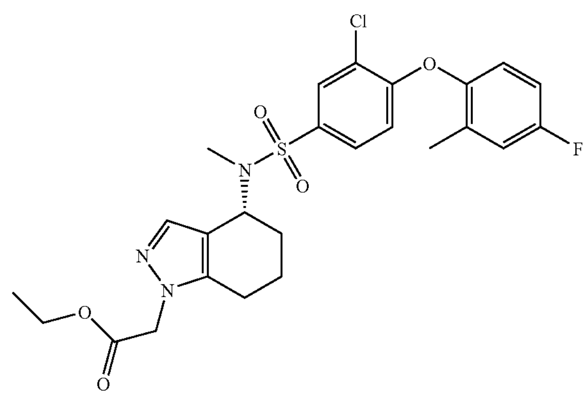 |
| 9-39 | ((R)-4-{[3,5-Difluoro-4-(4-fluoro-phenoxy)-benzenesulfonyl]-methyl-amino}-4,5,6,7-tetrahydro-indazol-1-yl)-acetic acid ethyl ester | 524 | 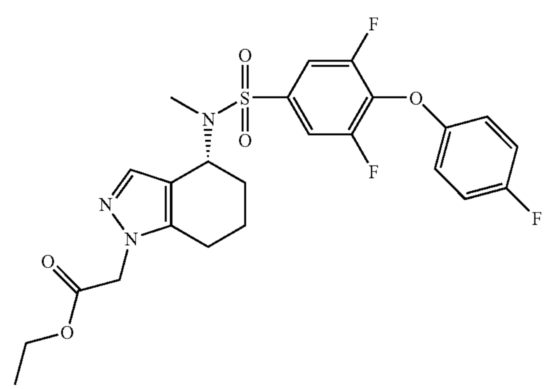 |

| Example No. | Systematic Name | MS (ESI+, M + H) | Structure |
|---|---|---|---|
| 9-40 | ((R)-4-{[3-Bromo-4-(4-fluoro-phenoxy)-benzenesulfonyl]-methyl-amino}-4,5,6,7-tetrahydro-indazol-1-yl)-acetic acid ethyl ester | 566 | 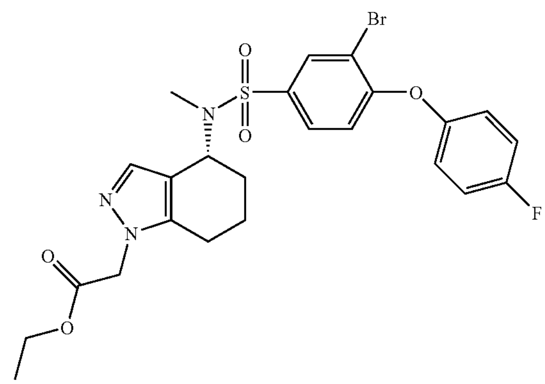 |
| 9-41 | ((R)-4-{[4-(4-Fluoro-phenoxy)-3-trifluoromethyl-benzenesulfonyl]-methyl-amino}-4,5,6,7-tetrahydro-indazol-1-yl)-acetic acid ethyl ester | 556 | 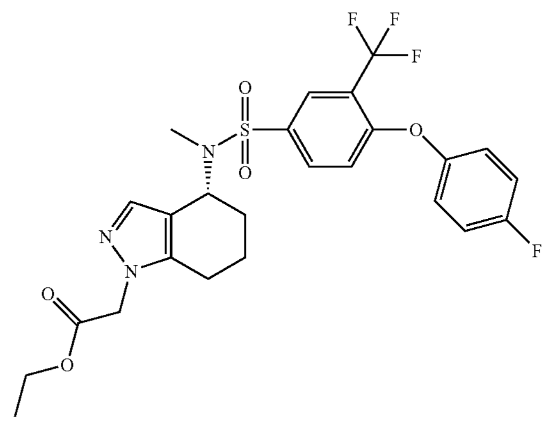 |
| 9-42 | ((R)-4-{[3-(4-Fluoro-phenoxy)-5-trifluoromethyl-benzenesulfonyl]-methyl-amino}-4,5,6,7-tetrahydro-indazol-1-yl)-acetic acid ethyl ester | 556 | 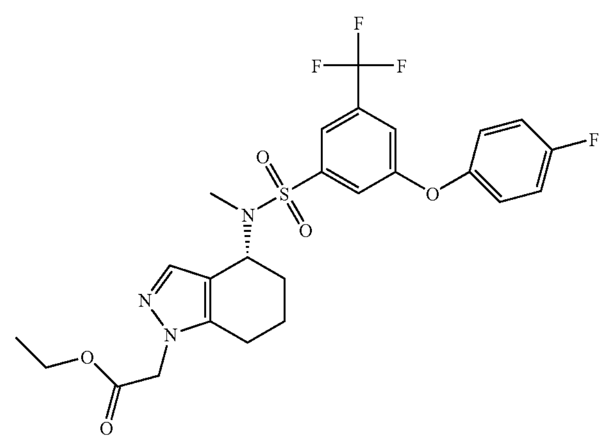 |

Example 9-1a ((R)-4-{[3-Chloro-4-(2-chloro-phenoxy)-benzene-sulfonyl]-methyl-amino}-4,5,6,7-tetrahydro-indazol-1-yl)-acetic acid

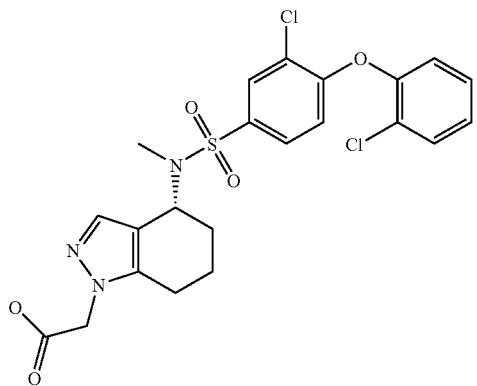

Starting with ((R)-4-{[3-chloro-4-(2-chloro-phenoxy)-benzenesulfonyl]-methyl-amino}-4,5,6,7-tetrahydro-indazol-1-yl)-acetic acid ethyl ester, and using the method described for example 1-1a, ((R)-4-{[3-chloro-4-(2-chloro-phenoxy)-benzenesulfonyl]-methyl-amino}-4,5,6,7-tetrahydro-indazol-1-yl)-acetic acid (39 mg, 52.6%) was obtained as a white solid.

$^1$H NMR (400 MHz, CD$_3$OD) δ ppm 8.07 (d, 1 H), 7.80 (d, 1 H), 7.60 (d, 1 H), 7.44 (t, 1 H), 7.32 (t, 1 H), 7.24 (d, 1 H), 6.89 (d, 1 H), 6.77 (s, 1 H), 5.09 (d, 1 H), 4.83 (s, 2 H), 2.64 (d, 3 H), 2.55 (s, 2 H), 2.05 (d, 1 H), 1.67-1.89 (m, 3 H). MS cald. for C$_{22}$H$_{21}$Cl$_2$N$_3$O$_5$S 509, obsd. (ESI$^+$) [(M+H)$^+$] 510.

Examples 9-2a to 9-42a

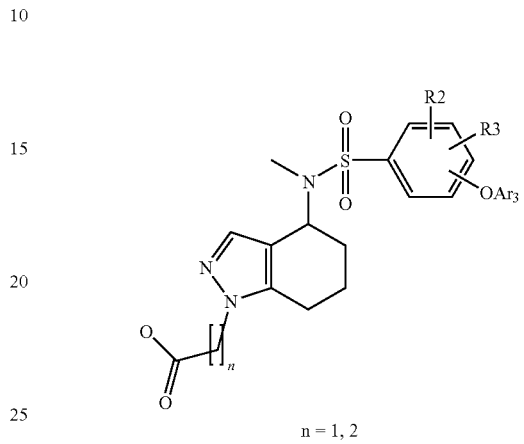

n = 1, 2

The following examples 9-2a to 9-42a were prepared in an analogous manner as described for example 1-1a from the corresponding esters 9-2 to 9-42.

| Example No. | Systematic Name | $^1$H NMR (400 MHz, CD$_3$OD) δ ppm | MS (ESI+, M + H) | Structure |
|---|---|---|---|---|
| 9-2a | ((R)-4-{[3-Chloro-4-(3-chloro-phenoxy)-benzenesulfonyl]-methyl-amino}-4,5,6,7-tetrahydro-indazol-1-yl)-acetic acid | 8.08 (s, 1H), 7.87 (d, 1H), 7.44 (t, 1H), 7.26 (d, 1H), 7.18 (m, 2H), 7.02 (d, 1H), 6.61 (s, 1H), 5.10 (t, 1H), 4.83 (s, 2H), 2.66 (s, 3H), 2.56 (s, 2H), 2.05 (t, 1H), 1.88-1.67 (m, 3H) | 510 | 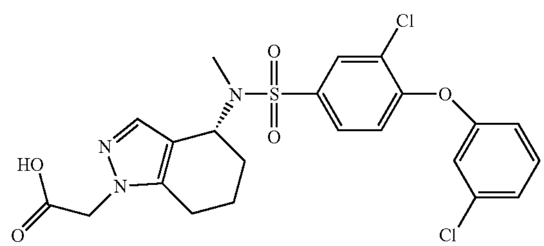 |
| 9-3a | ((R)-4-{[3-Chloro-4-(4-chloro-phenoxy)-benzenesulfonyl]-methyl-amino}-4,5,6,7-tetrahydro-indazol-1-yl)-acetic acid | 8.07 (d, 1H), 7.84 (m, 1H), 7.46 (m, 2H), 7.11 (m, 3H), 6.55 (s, 1H), 5.10 (d, 1H), 4.84 (s, 2H), 2.65 (d, 3H), 2.56 (s, 2H), 2.05 (d, 1H), 1.89-1.67 (m, 3H) | 510 | 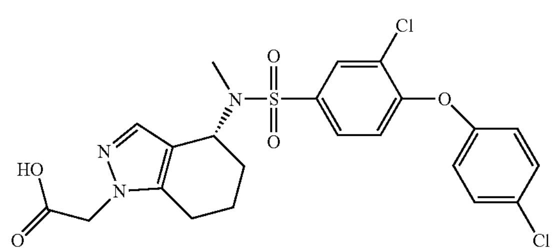 |

| Example No. | Systematic Name | $^1$H NMR (400 MHz, CD$_3$OD) δ ppm | MS (ESI+, M + H) | Structure |
|---|---|---|---|---|
| 9-4a | ((R)-4-{[2-Chloro-4-(4-chloro-phenoxy)-benzenesulfonyl]-methyl-amino}-4,5,6,7-tetrahydro-indazol-1-yl)-acetic acid | 8.09 (d, 1H), 7.44 (d, 2H), 7.20 (s, 1H), 7.16-7.05 (m, 3H), 7.00 (d, 1H), 4.96-4.89 (m, 1H), 4.80-4.69 (m, 2H), 2.68 (s, 3H), 2.59-2.47 (m, 2H), 2.09-2.00 (m, 1H), 1.94-1.83 (m, 1H), 1.80-1.65 (m, 2H) | 510 | 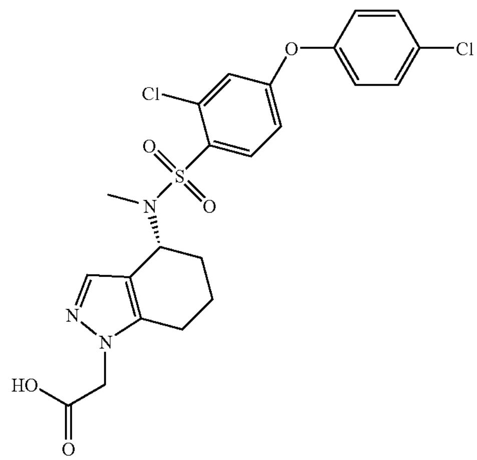 |
| 9-5a | ((R)-4-{[4-(4-Chloro-phenoxy)-3-trifluoromethyl-benzenesulfonyl]-methyl-amino}-4,5,6,7-tetrahydro-indazol-1-yl)-acetic acid | 7.53-7.49 (m, 2H), 7.21-7.16 (m, 3H), 6.58 (s, 1H), 5.14-5.09 (m, 1H), 4.84 (s, 2H), 2.65 (s, 3H), 2.62-2.47 (m, 2H), 2.09-2.02 (m, 1H), 1.90-1.67 (m, 3H) | 544 | 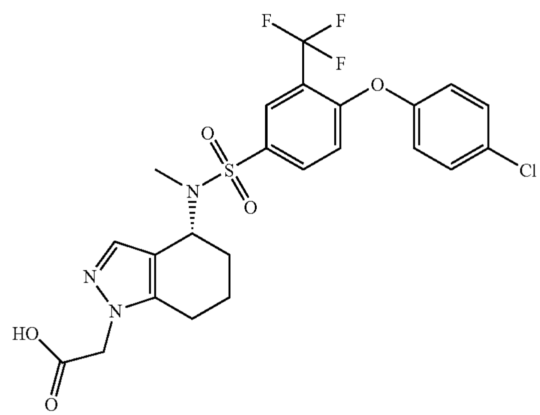 |
| 9-6a | ((R)-4-{[3-Chloro-4-(2,4-dichloro-phenoxy)-benzenesulfonyl]-methyl-amino}-4,5,6,7-tetrahydro-indazol-1-yl)-acetic acid | 8.09 (d, 1H), 7.83 (dd, 1H), 7.68 (t, 1H), 7.48-7.42 (m, 1H), 7.23 (d, 1H), 6.99 (d, 1H), 6.54 (s, 1H), 5.09 (t, 1H), 4.82 (m, 2H), 2.65 (s, 3H), 2.58-2.51 (m, 2H), 2.09-2.01 (m, 1H), 1.91-1.75 (m, 2H), 1.73-1.63 (m, 1H) | 544 | 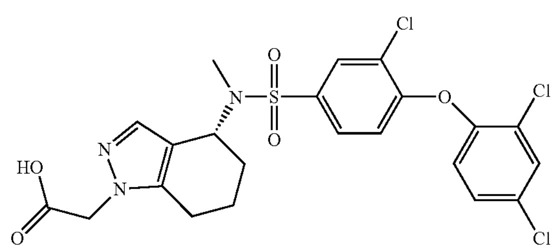 |
| 9-7a | ((R)-4-{[4-(4-tert-Butyl-phenoxy)-3-chloro-benzenesulfonyl]-methyl-amino}-4,5,6,7-tetrahydro-indazol-1-yl)-acetic acid | 8.04 (d, 1H), 7.79 (dd, 1H), 7.52 (d, 2H), 7.05 (d, 3H), 6.54 (s, 1H), 5.08 (t, 1H), 4.73 (s, 2H), 2.65 (s, 3H), 2.55 (s, 2H), 2.10-2.00 (m, 1H), 1.90-1.74 (m, 2H), 1.73-1.63 (m, 1H), 1.36 (s, 9H) | 532 | 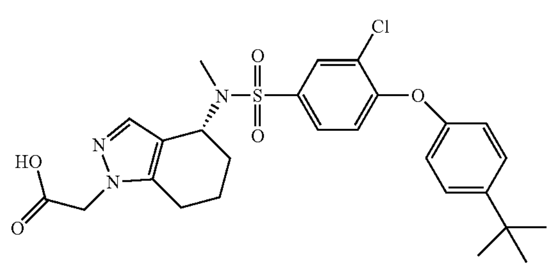 |

-continued

| Example No. | Systematic Name | $^1$H NMR (400 MHz, CD$_3$OD) δ ppm | MS (ESI+, M + H) | Structure |
|---|---|---|---|---|
| 9-8a | ((R)-4-{[2-Chloro-4-(2,4-dichloro-phenoxy)-benzenesulfonyl]-methyl-amino}-4,5,6,7-tetrahydro-indazol-1-yl)-acetic acid | 8.16 (d, 1H), 7.69 (d, 1H), 7.48 (dd, 1H), 7.32 (d, 1H), 7.22 (d, 1H), 7.11 (s, 1H), 6.98 (dd, 1H), 4.98 (s, 1H), 4.82 (s, 2H), 2.81 (s, 3H), 2.58 (s, 2H), 2.09-1.80 (m, 4H) | 544 | 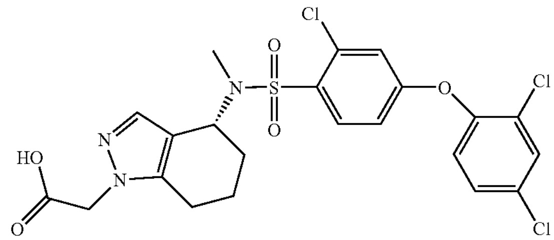 |
| 9-9a | ((R)-4-{[2-Chloro-4-(2-chloro-4-fluoro-phenoxy)-benzenesulfonyl]-methyl-amino}-4,5,6,7-tetrahydro-indazol-1-yl)-acetic acid | 8.14 (d, 1H), 7.46 (dd, 1H), 7.36 (q, 1H), 7.24 (dt, 1H), 7.18 (d, 1H), 7.11 (s, 1H), 6.95 (dd, 1H), 4.97 (t, 1H), 4.84 (s, 2H), 2.72 (s, 3H), 2.63-2.49 (m, 2H), 2.11-2.04 (m, 1H), 1.98-1.89 (m, 1H), 1.84-1.73 (m, 2H) | 528 | 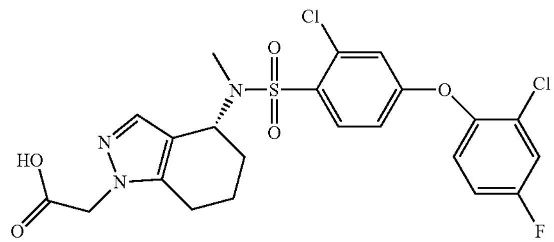 |
| 9-10a | ((R)-4-{[2-Chloro-4-(2-chloro-phenoxy)-benzenesulfonyl]-methyl-amino}-4,5,6,7-tetrahydro-indazol-1-yl)-acetic acid | 8.13 (d, 1H), 7.61 (d, 1H), 7.46 (t, 1H), 7.38-7.30 (m, 2H), 7.15 (d, 1H), 7.12 (s, 1H), 6.95 (dd, 1H), 4.98 (t, 1H), 4.85 (s, 2H), 2.72 (s, 3H), 2.61-2.54 (m, 2H), 2.11-2.03 (m, 1H), 1.99-1.88 (m, 1H), 1.84-1.73 (m, 2H) | 510 | 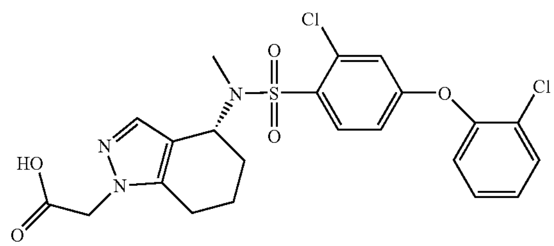 |
| 9-11a | ((R)-4-{[3-Chloro-4-(4-chloro-2-fluoro-phenoxy)-benzenesulfonyl]-methyl-amino}-4,5,6,7-tetrahydro-indazol-1-yl)-acetic acid | 8.13 (s, 1H), 7.85 (d, 1H), 7.49 (dd, 1H), 7.30 (m, 2H), 7.10 (d, 1H), 6.56 (s, 1H), 5.09 (t, 1H), 4.81 (s, 2H), 2.66 (s, 3H), 2.57 (s, 2H), 2.05 (s, 1H), 1.88-1.64 (m, 3H) | 528 | 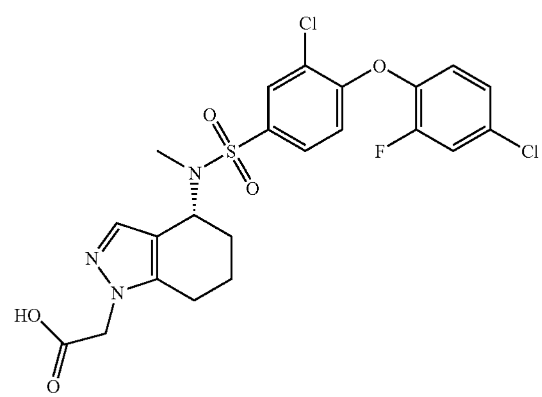 |
| 9-12a | ((R)-4-{[4-(4-Chloro-phenoxy)-3-fluoro-benzenesulfonyl]-methyl-amino}-4,5,6,7-tetrahydro-indazol-1-yl)-acetic acid | 7.88 (q, 1H), 7.76 (d, 1H), 7.46-7.10 (dd, 4H), 7.18 (m, 2H), 7.26 (t, 1H), 6.55 (s, 1H), 5.10 (t, 1H), 4.84 (s, 2H), 2.66 (s, 3H), 2.56 (m, 2H), 2.05 (m, 1H), 1.91-1.64 (m, 3H) | 494 | 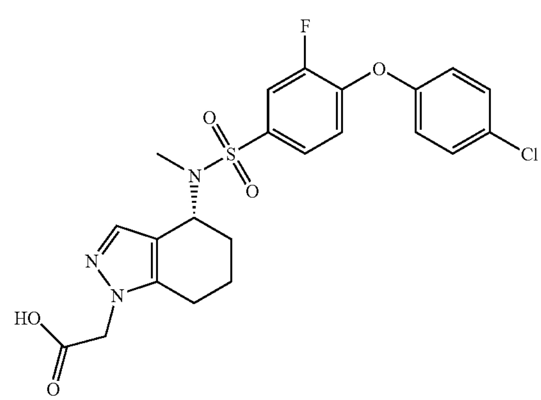 |

| Example No. | Systematic Name | ¹H NMR (400 MHz, CD₃OD) δ ppm | MS (ESI+, M + H) | Structure |
|---|---|---|---|---|
| 9-13a | {(R)-4-[(3-Chloro-4-phenoxy-benzenesulfonyl)-methyl-amino]-4,5,6,7-tetrahydro-indazol-1-yl}-acetic acid | 8.07 (d, 1H), 7.82 (dd, 1H), 7.48 (t, 2H), 7.28 (t, 1H), 7.11 (q, 3H), 6.55 (s, 1H), 5.09 (t, 1H), 4.83 (s, 2H), 2.65 (s, 3H), 2.62-2.48 (m, 2H), 2.10-2.02 (m, 1H), 1.91-1.75 (m, 2H), 1.74-1.63 (m, 1H) | 476 | 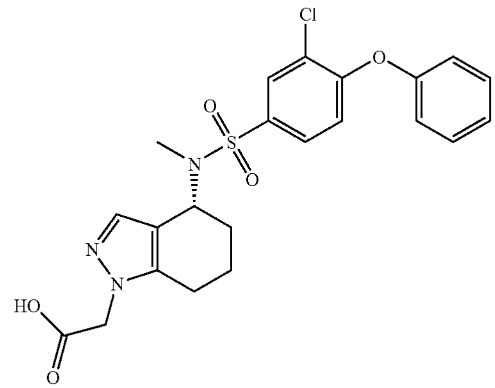 |
| 9-14a | ((R)-4-{[3-Chloro-4-(4-fluoro-phenoxy)-benzenesulfonyl]-methyl-amino}-4,5,6,7-tetrahydro-indazol-1-yl)-acetic acid | 8.10 (s, 1H), 7.8 (dd, 1H), 7.22 (t, 2H), 7.17 (m, 2H), 7.06 (d, 1H), 6.53 (s, 1H), 5.10 (t, 1H), 4.83 (s, 2H), 2.65 (s, 3H), 2.56 (s, 2H), 2.05 (m, 1H), 2.01-1.64 (m, 3H) | 474 | 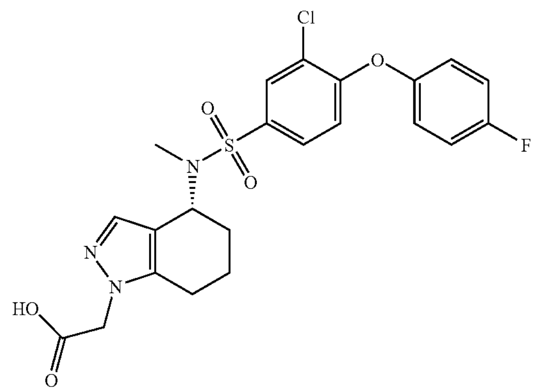 |
| 9-15a | {(R)-4-[(3-Chloro-4-p-tolyloxy-benzenesulfonyl)-methyl-amino]-4,5,6,7-tetrahydro-indazol-1-yl}-acetic acid | 8.04 (d, 1H), 7.79 (dd, 1H), 7.29 (d, 2H), 7.02 (q, 3H), 6.54 (s, 1H), 5.08 (t, 1H), 4.78 (s, 2H), 2.65 (s, 3H), 2.62-2.48 (m, 2H), 2.39 (s, 3H), 2.10-2.01 (m, 1H), 1.90-1.74 (m, 2H), 1.73-1.63 (m, 1H) | 490 | 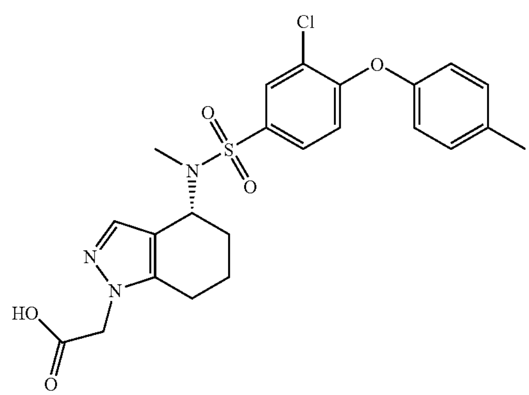 |
| 9-16a | ((R)-4-{[3-Chloro-4-(2-chloro-4-fluoro-phenoxy)-benzenesulfonyl]-methyl-amino}-4,5,6,7-tetrahydro-indazol-1-yl)-acetic acid | 8.07 (d, 1H), 7.81 (dd, 1H), 7.47 (dd, 1H), 7.32 (q, 1H), 7.24 (td, 1H), 6.91 (d, 1H), 6.52 (s, 1H), 5.08 (t, 1H), 4.79 (s, 2H), 2.65 (s, 3H), 2.55 (s, 2H), 2.09-2.01 (m, 1H), 1.90-1.74 (m, 2H), 1.73-1.63 (m, 1H) | 528 | 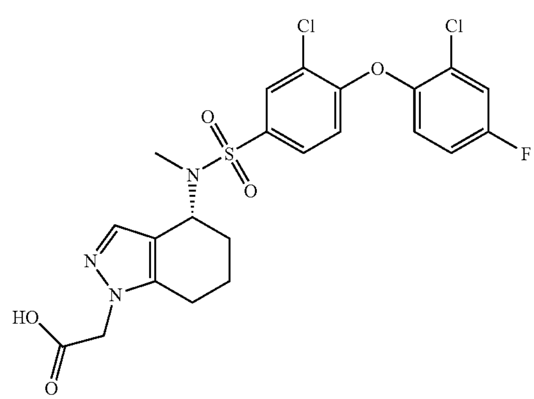 |

-continued

| Example No. | Systematic Name | ¹H NMR (400 MHz, CD₃OD) δ ppm | MS (ESI+, M + H) | Structure |
|---|---|---|---|---|
| 9-17a | ((R)-4-{[3-Chloro-4-(4-fluoro-2-methoxy-phenoxy)-benzenesulfonyl]-methyl-amino}-4,5,6,7-tetrahydro-indazol-1-yl)-acetic acid | 8.00 (d, 1H), 7.73 (dd, 1H), 7.21 (dd, 1H), 7.01 (dd, 1H), 6.83-6.77 (m, 2H), 6.50 (s, 1H), 5.09-5.02 (m, 1H), 4.77 (s, 2H), 3.81 (s, 3H), 2.63 (s, 3H), 2.60-2.46 (m, 2H), 2.09-2.00 (m, 1H), 1.90-1.74 (m, 2H), 1.68 (q, 1H) | 524 | 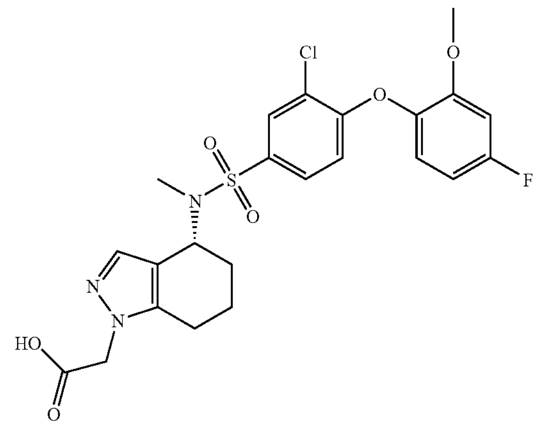 |
| 9-18a | ((R)-4-{[3-Chloro-4-(2-chloro-5-methyl-phenoxy)-benzenesulfonyl]-methyl-amino}-4,5,6,7-tetrahydro-indazol-1-yl)-acetic acid | 8.06 (d, 1H), 7.80 (dd, 1H), 7.46 (d, 1H), 7.16 (d, 1H), 7.08 (s, 1H) 6.89 (d, 1H) 6.55 (s, 1H), 5.09 (t, 1H), 4.79 (s, 2H), 2.64 (s, 3H), 2.56 (s, 2H), 2.36 (s, 3H), 2.05 (s, 1H), 1.90-1.64 (m, 3H) | 524 | 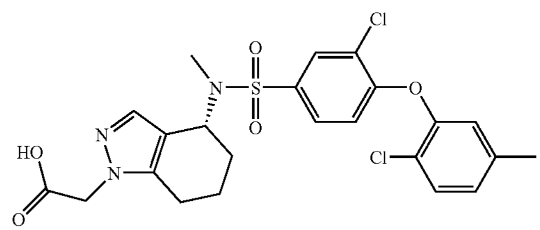 |
| 9-19a | ((R)-4-{[3-Chloro-4-(2,4-dimethyl-phenoxy)-benzenesulfonyl]-methyl-amino}-4,5,6,7-tetrahydro-indazol-1-yl)-acetic acid | 8.03 (d, 1H), 7.76 (dd, 1H), 7.19 (s, 1H), 7.13 (d, 1H), 6.94 (d, 1H 6.83 (m, 1H 6.55 (s, 1H), 5.09 (t, 1H), 4.83 (s, 2H), 2.64 (s, 3H), 2.56 (s, 2H), 2.36 (s, 3H), 2.20 (s, 3H), 2.05 (m, 1H), 1.90-1.64 (m, 3H) | 504 | 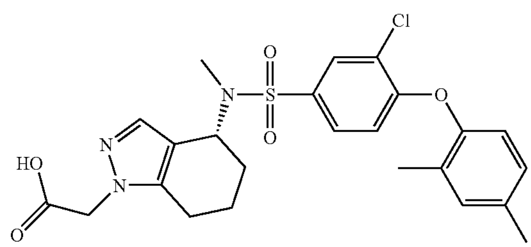 |
| 9-20a | ((R)-4-{[3-Chloro-4-(4-chloro-2-methoxy-phenoxy)-benzenesulfonyl]-methyl-amino}-4,5,6,7-tetrahydro-indazol-1-yl)-acetic acid | 8.01 (d, 1H), 7.74 (dd, 1H), 7.23 (d, 1H), 7.18 (d, 1H), 7.07 (dd, 1H), 6.84 (d, 1H), 6.52 (s, 1H), 5.06 (q, 1H), 4.80 (s, 2H), 3.80 (s, 3H), 2.64 (s, 3H), 2.61-2.47 (m, 2H), 2.09-2.00 (m, 1H), 1.91-1.74 (m, 2H), 1.74-1.63 (m, 1H) | 540 | 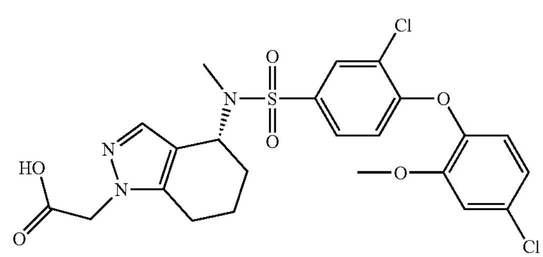 |
| 9-21a | ((R)-4-{[3-Chloro-4-(4-chloro-3-fluoro-phenoxy)-benzenesulfonyl]-methyl-amino}-4,5,6,7-tetrahydro-indazol-1-yl)-acetic acid | 8.08 (d, 1H), 7.80 (dd, 1H), 7.30 (m, 2H), 7.18 (d, 1H), 7.10 (m, 1H), 6.59 (s, 1H), 5.10 (t, 1H), 2.65 (s, 3H), 2.56 (s, 2H), 2.05 (m, 1H), 1.90-1.64 (m, 3H) | 528 | 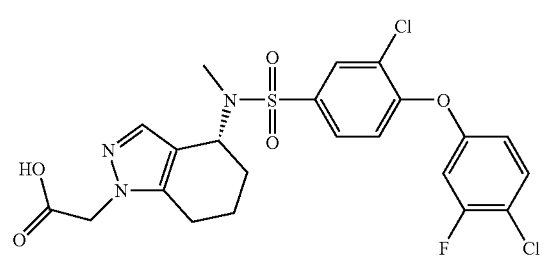 |

-continued

| Example No. | Systematic Name | $^1$H NMR (400 MHz, CD$_3$OD) δ ppm | MS (ESI+, M + H) | Structure |
|---|---|---|---|---|
| 9-22a | ((R)-4-{[3-Chloro-4-(2,5-difluoro-phenoxy)-benzenesulfonyl]-methyl-amino}-4,5,6,7-tetrahydro-indazol-1-yl)-acetic acid | 8.08 (d, 1H), 7.85 (dd, 1H), 7.40-7.34 (m, 1H), 7.14-7.06 (m, 3H), 6.63 (s, 1H), 5.10 (t, 1H), 4.80 (s, 2H), 2.66 (s, 3H), 2.62-2.48 (m, 2H), 2.09-2.00 (m, 1H), 1.89-1.76 (m, 2H), 1.69 (q, 1H) | 512 | 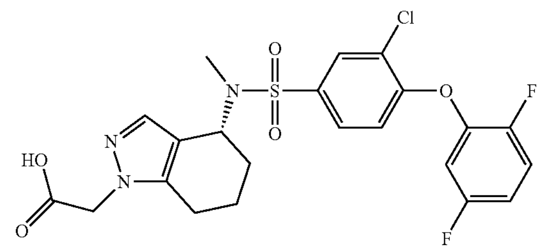 |
| 9-23a | ((R)-4-{[4-(4-Bromo-phenoxy)-3-chloro-benzenesulfonyl]-methyl-amino}-4,5,6,7-tetrahydro-indazol-1-yl)-acetic acid | 8.08 (d, 1H), 7.85 (dd, 1H), 7.61 (d, 2H), 7.17 (d, 1H), 7.05 (d, 2H), 6.56 (s, 1H), 5.10 (t, 1H), 2.66 (s, 3H), 2.63-2.48 (m, 2H), 2.10-2.01 (m, 1H), 1.92-1.75 (m, 2H), 1.75-1.64 (m, 1H) | 554 | 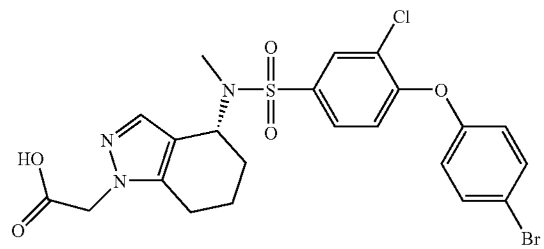 |
| 9-24a | ((R)-4-{[3-Chloro-4-(3-chloro-4-fluoro-phenoxy)-benzenesulfonyl]-methyl-amino}-4,5,6,7-tetrahydro-indazol-1-yl)-acetic acid | 8.03 (s, 1H), 7.78 (d, 1H), 7.09-6.96 (m, 5H), 6.55 (s, 1H), 5.08 (s, 1H), 3.84 (s, 3H), 2.64 (s, 3H), 2.56 (s, 2H), 2.05 (m, 1H), 1.90-1.64 (m, 3H) | 528 | 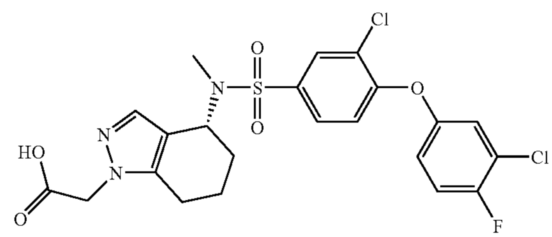 |
| 9-25a | ((R)-4-{[3-Chloro-4-(4-methanesulfonyl-phenoxy)-benzenesulfonyl]-methyl-amino}-4,5,6,7-tetrahydro-indazol-1-yl)-acetic acid | 8.15 (d, 1H), 8.04 (d, 2H), 7.96 (dd, 1H), 7.42 (d, 1H), 7.26 (d, 2H), 6.59 (d, 1H), 5.15 (t, 1H), 3.16 (s, 3H), 2.62 (s, 3H), 2.57 (s, 2H), 2.05 (m, 1H), 1.90-1.64 (m, 3H) | 554 | 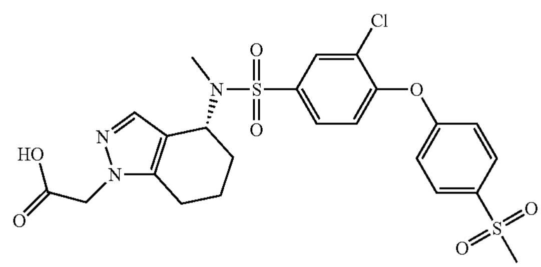 |
| 9-26a | {(R)-4-[(3-Chloro-4-o-tolyloxy-benzenesulfonyl)-methyl-amino]-4,5,6,7-tetrahydro-indazol-1-yl}-acetic acid | 8.05 (d, 1H), 7.77 (dd, 1H), 7.38 (d, 1H), 7.31 (t, 1H), 7.23 (t, 1H), 7.03 (d, 1H), 6.86 (d, 1H), 6.55 (s, 1H), 5.08 (t, 1H), 4.79 (s, 2H), 2.64 (s, 3H), 2.62-2.47 (m, 2H), 2.21 (s, 3H), 2.09-2.01 (m, 1H), 1.90-1.74 (m, 2H), 1.73-1.63 (m, 1H) | 490 | 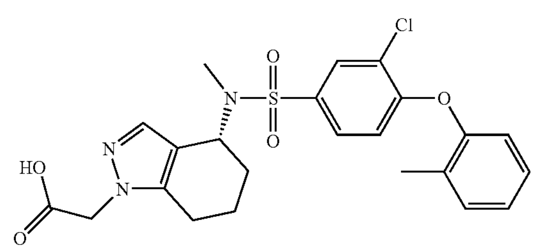 |

-continued

| Example No. | Systematic Name | $^1$H NMR (400 MHz, CD$_3$OD) δ ppm | MS (ESI+, M + H) | Structure |
|---|---|---|---|---|
| 9-27a | ((R)-4-{[4-(4-Acetylamino-phenoxy)-3-chloro-benzenesulfonyl]-methyl-amino}-4,5,6,7-tetrahydro-indazol-1-yl)-acetic acid | 8.05 (s, 1H), 7.81 (d, 1H), 7.66 (d, 2H), 7.10 (d, 2H), 7.08 (s, 1H), 6.54 (s, 1H 5.10 (t, 1H), 4.78 (s, 2H), 2.65 (s, 3H), 2.57 (s, 2H), 2.17 (s, 3H), 2.04 (m, 1H), 1.90-1.74 (m, 2H), 1.73-1.63 (m, 1H) | 533 | 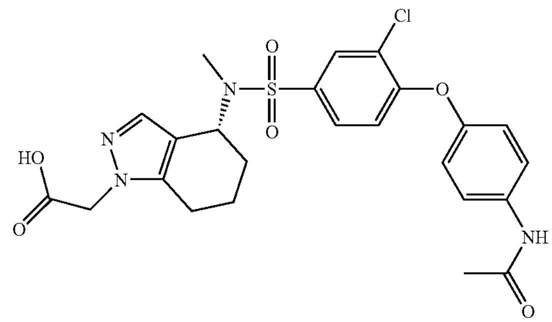 |
| 9-28a | ((R)-4-{[3-Chloro-4-(4-trifluoromethoxy-phenoxy)-benzenesulfonyl]-methyl-amino}-4,5,6,7-tetrahydro-indazol-1-yl)-acetic acid | 8.09 (d, 1H), 7.86 (dd, 1H), 7.39 (d, 2H), 7.20 (d, 3H), 6.56 (s, 1H), 5.10 (t, 1H), 4.80 (s, 2H), 2.66 (s, 3H), 2.63-2.48 (m, 2H), 2.10-2.02 (m, 1H) 1.92-1.75 (m, 2H) 1.75-1.64 (m, 1H) | 560 | 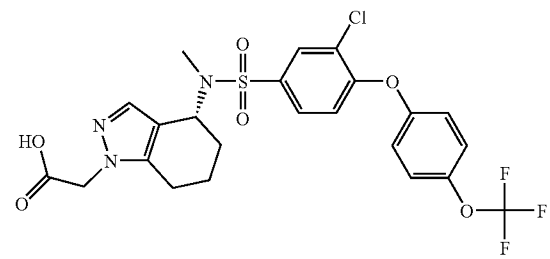 |
| 9-29a | ((R)-4-{[2-Chloro-5-fluoro-4-(4-fluoro-phenoxy)-benzenesulfonyl]-methyl-amino}-4,5,6,7-tetrahydro-indazol-1-yl)-acetic acid | 8.06 (s, 1H), 7.25-7.14 (m, 6H), 5.10 (t, 1H), 2.73 (s, 3H), 2.58 (s, 2H), 2.08 (s, 1H), 1.96 (m, 1H), 1.79 (m, 1H) | 512 | 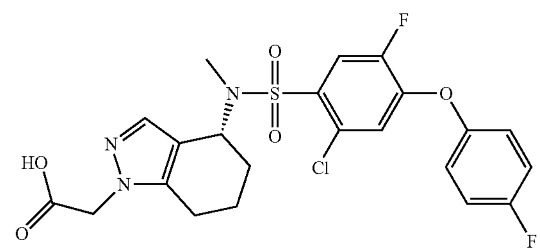 |
| 9-30a | ((R)-4-{[5-Chloro-2-fluoro-4-(4-fluoro-phenoxy)-benzenesulfonyl]-methyl-amino}-4,5,6,7-tetrahydro-indazol-1-yl)-acetic acid | 8.06 (d, 1H), 7.28-7.18 (m, 4H), 6.93 (s, 1H), 6.84 (d, 1H), 5.08 (t, 1H), 2.70 (s, 3H), 2.63-2.50 (m, 2H), 2.11-2.02 (m, 1H), 1.93-1.85 (m, 1H), 1.85-1.70 (m, 2H) | 512 | 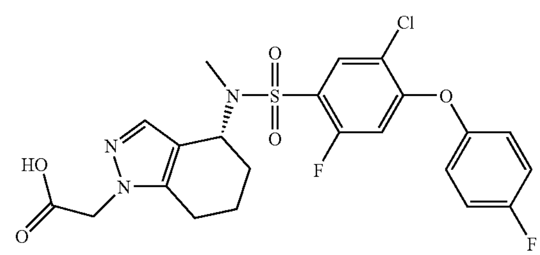 |
| 9-31a | ((R)-4-{[3-Chloro-4-(4-methoxy-phenoxy)-benzenesulfonyl]-methyl-amino}-4,5,6,7-tetrahydro-indazol-1-yl)-acetic acid | 8.00 (m, 1H), 7.76 (m, 1H), 7.06 (dd, 4H), 6.96 (m, 1H), 6.53 (s, 1H), 5.05 (m, 1H), 3.82 (d, J = 3.28 Hz, 3H), 2.62 (d, J = 3.54 Hz, 3H), 2.58-2.45 (m, 2H), 2.05 (m, 1H), 1.90-1.72 (m, 2H), 1.72-1.60 (m, 1H) | 506 | 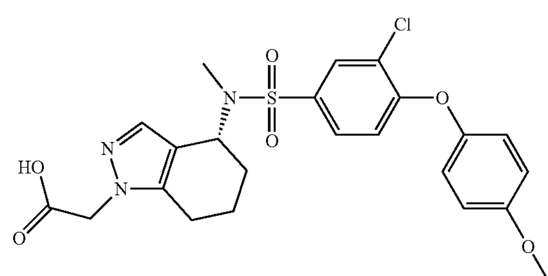 |

-continued

| Example No. | Systematic Name | ¹H NMR (400 MHz, CD₃OD) δ ppm | MS (ESI+, M + H) | Structure |
|---|---|---|---|---|
| 9-32a | ((R)-4-{[3-Chloro-4-(2,4-difluoro-phenoxy)-benzenesulfonyl]-methyl-amino}-4,5,6,7-tetrahydro-indazol-1-yl)-acetic acid | 8.06 (d, 1H), 7.82 (dd, 1H), 7.32 (m, 1H), 7.26 (m, 1H), 7.10 (t, 1H), 7.02 (d, 1H), 6.59 (s, 1H), 5.08 (t, 1H), 4.78 (s, 2H), 2.66 (s, 3H), 2.56 (m, 2H), 2.12-2.00 (m, 1H), 1.90-1.76 (m, 2H), 1.73-1.62 (m, 1H) | 512 | 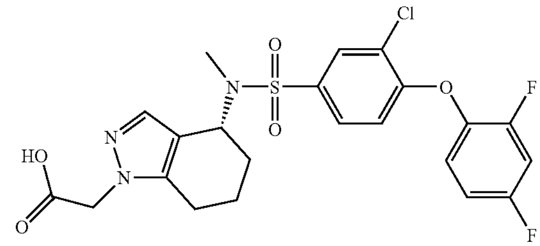 |
| 9-33a | ((R)-4-{[3-Chloro-4-(2,6-difluoro-phenoxy)-benzenesulfonyl]-methyl-amino}-4,5,6,7-tetrahydro-indazol-1-yl)-acetic acid | 8.08 (d, 1H), 7.82 (dd, 1H), 7.46-7.35 (m, 1H), 7.24 (t, 2H), 7.01 (d, 1H), 6.66 (s, 1H), 5.27-5.05 (m, 3H), 2.66 (s, 3H), 2.62-2.46 (m, 2H), 2.10-2.00 (m, 1H), 1.90-1.74 (m, 2H), 1.68 (t, 1H), | 512 | 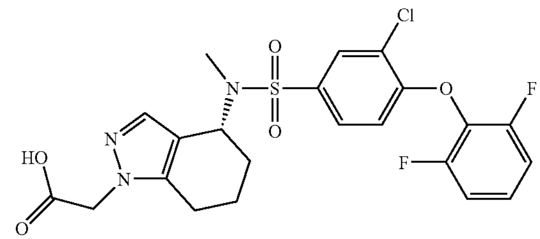 |
| 9-34a | ((R)-4-{[3-Chloro-4-(4-cyano-phenoxy)-benzenesulfonyl]-methyl-amino}-4,5,6,7-tetrahydro-indazol-1-yl)-acetic acid | 8.13 (d, 1H), 7.94 (dd, 1H), 7.81 (d, 2H), 7.39 (d, 1H), 7.17 (d, 2H), 6.56 (s, 1H), 5.11 (t, 1H), 2.69 (s, 3H), 2.64-2.49 (m, 2H) 2.11-2.02 (m, 1H) 1.93-1.72 (m, 3H) | 501 | 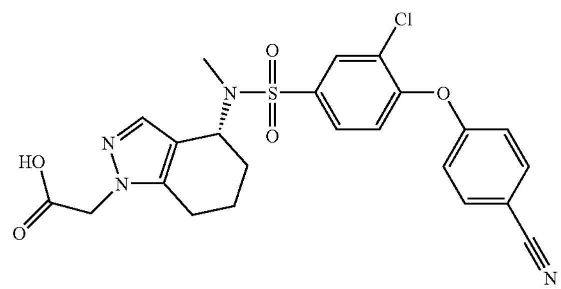 |
| 9-35a | ((R)-4-{[4-(4-Fluoro-phenoxy)-3-methyl-benzenesulfonyl]-methyl-amino}-4,5,6,7-tetrahydro-indazol-1-yl)-acetic acid | 7.85 (s, 1H), 7.70 (dd, 1H), 7.21-7.08 (m, 4H), 6.92 (d, 1H), 6.41 (s, 1H), 5.08 (t, 1H), 2.63 (s, 3H), 2.55 (s, 2H), 2.41 (s, 3H), 2.05 (s, 1H), 1.90-1.66 (m, 3H) | 474 | 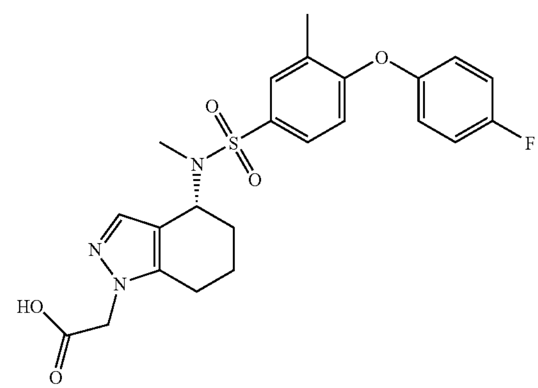 |
| 9-36a | ((R)-4-{[4-(4-Carbamoyl-phenoxy)-3-chloro-benzenesulfonyl]-methyl-amino}-4,5,6,7-tetrahydro-indazol-1-yl)-acetic acid | 8.11 (s, 1H), 7.97 (dd, 2H), 7.89 (d, 1H), 7.27 (d, 1H), 7.12 (d, 2H), 6.56 (s, 1H), 5.15-5.05 (m, 1H), 2.66 (s, 3H), 2.62-2.48 (m, 2H), 2.11-1.98 (m, 1H), 1.91-1.67 (m, 3H) | 519 | 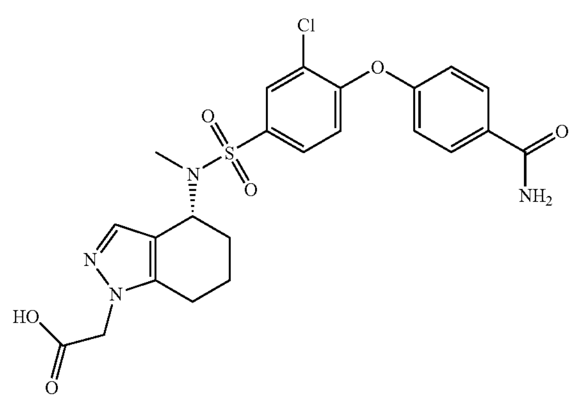 |

| Example No. | Systematic Name | $^1$H NMR (400 MHz, CD$_3$OD) δ ppm | MS (ESI+, M + H) | Structure |
|---|---|---|---|---|
| 9-37a | ((R)-4-{[3-Chloro-4-(2-fluoro-phenoxy)-benzenesulfonyl]-methyl-amino}-4,5,6,7-tetrahydro-indazol-1-yl)-acetic acid | 8.05 (d, 1H), 7.80 (dd, 1H), 7.37-7.24 (m, 4H), 7.00 (d, 1H), 6.60 (s, 1H), 5.08 (t, 1H), 2.64 (s, 3H), 2.59-2.47 (m, 2H), 2.10-2.00 (m, 1H), 1.90-1.74 (m, 2H), 1.73-1.61 (m, 1H) | 494 | 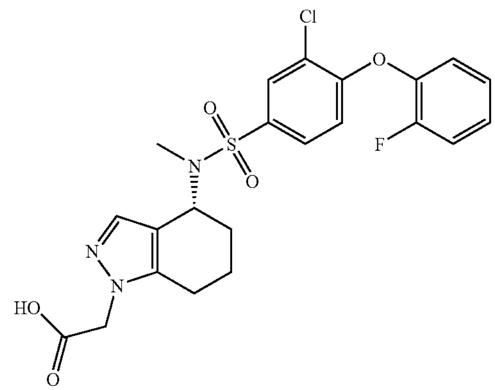 |
| 9-38a | ((R)-4-{[3-Chloro-4-(4-fluoro-2-methyl-phenoxy)-benzenesulfonyl]-methyl-amino}-4,5,6,7-tetrahydro-indazol-1-yl)-acetic acid | 8.05 (d, 1H), 7.78 (dd, 1H), 7.14 (d, 1H), 7.10-7.02 (m, 2H), 6.87 (d, 1H), 6.54 (s, 1H), 5.08 (t, 1H), 4.81 (s, 2H), 2.64 (s, 3H), 2.61-2.47 (m, 2H), 2.21 (s, 3H), 2.09-2.00 (m, 1H), 1.91-1.75 (m, 2H), 1.73-1.66 (m, 1H) | 508 | 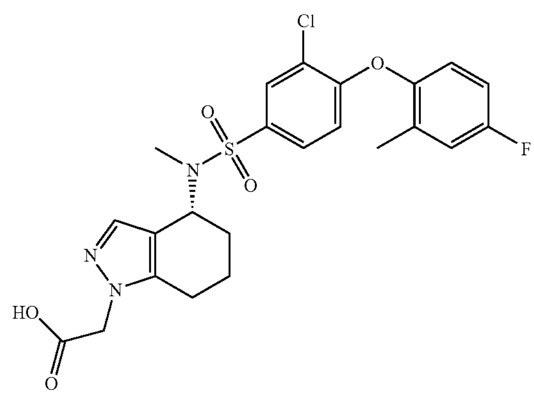 |
| 9-39a | ((R)-4-{[3,5-Difluoro-4-(4-fluoro-phenoxy)-benzenesulfonyl]-methyl-amino}-4,5,6,7-tetrahydro-indazol-1-yl)-acetic acid | 7.78 (m, 2H), 7.14 (m, 2H), 7.05 (m, 2H), 6.67 (s, 1H), 5.14 (t, 1H), 4.82 (s, 2H), 2.70 (s, 3H), 2.64-2.50 (m, 2H), 2.11-2.03 (m, 1H), 1.92-1.78 (m, 2H), 1.76-1.65 (m, 1H) | 496 | 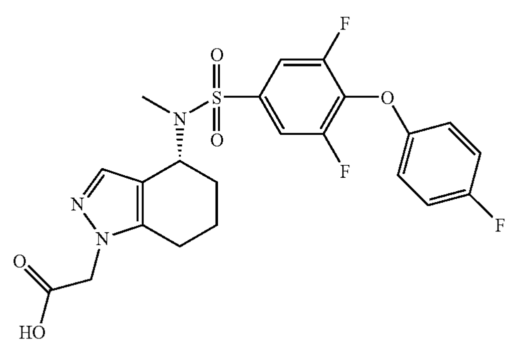 |
| 9-40a | ((R)-4-{[3-Bromo-4-(4-fluoro-phenoxy)-benzenesulfonyl]-methyl-amino}-4,5,6,7-tetrahydro-indazol-1-yl)-acetic acid | 8.19 (s, 1H), 7.85 (d, 1H), 7.26-7.12 (m, 4H), 7.02 (d, 1H), 6.50 (s, 1H), 5.14-5.03 (m, 1H), 4.69-4.56 (m, 2H), 2.73-2.55 (m, 5H), 2.12-1.97 (m, 1H), 1.917-1.67 (m, 3H) | 538 | 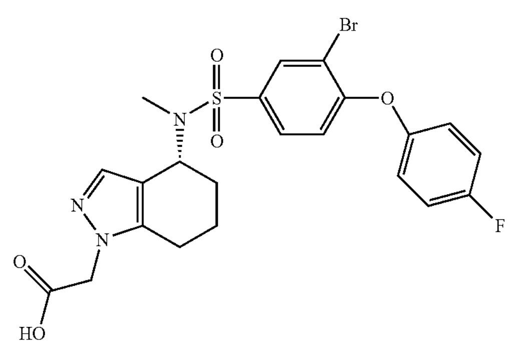 |

| Example No. | Systematic Name | $^1$H NMR (400 MHz, CD$_3$OD) δ ppm | MS (ESI+, M + H) | Structure |
|---|---|---|---|---|
| 9-41a | ((R)-4-{[4-(4-Fluoro-phenoxy)-3-trifluoromethyl-benzenesulfonyl]-methyl-amino}-4,5,6,7-tetrahydro-indazol-1-yl)-acetic acid | 8.20 (s, 1H), 8.12 (dd, 1H), 7.30-7.19 (m, 4H), 7.12 (d, 1H), 6.56 (s, 1H), 5.10 (t, 1H), 4.77 (s, 2H), 2.65 (s, 3H), 2.61-2.47 (m, 2H), 2.09-2.00 (m, 1H), 1.90-1.67 (m, 3H) | 528 | 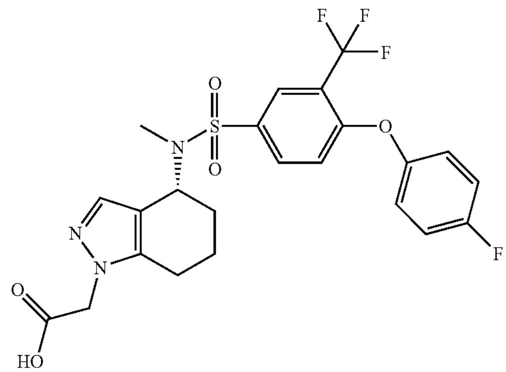 |
| 9-42a | ((R)-4-{[3-(4-Fluoro-phenoxy)-5-trifluoromethyl-benzenesulfonyl]-methyl-amino}-4,5,6,7-tetrahydro-indazol-1-yl)-acetic acid | 7.87 (s, 1H), 7.58 (s, 2H), 7.25-7.15 (m, 4H), 6.48 (s, 1H), 5.08-5.01 (m, 1H), 4.83 (s, 2H), 2.62 (s, 3H), 2.59-2.48 (m, 2H), 2.10-2.02 (m, 1H), 1.86-1.62 (m, 3H) | 528 | 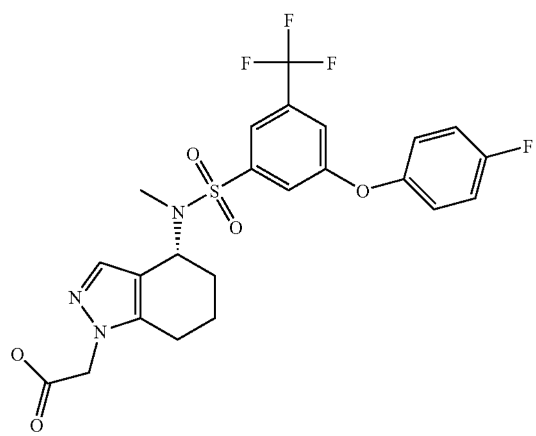 |

Example 10-1

[4-(4'-Methoxy-biphenyl-4-sulfonylamino)-4,5,6,7-tetrahydro-indazol-1-yl]-acetic acid ethyl ester

[4-(4-Bromo-benzenesulfonylamino)-4,5,6,7-tetrahydro-indazol-1-yl]-acetic acid ethyl ester

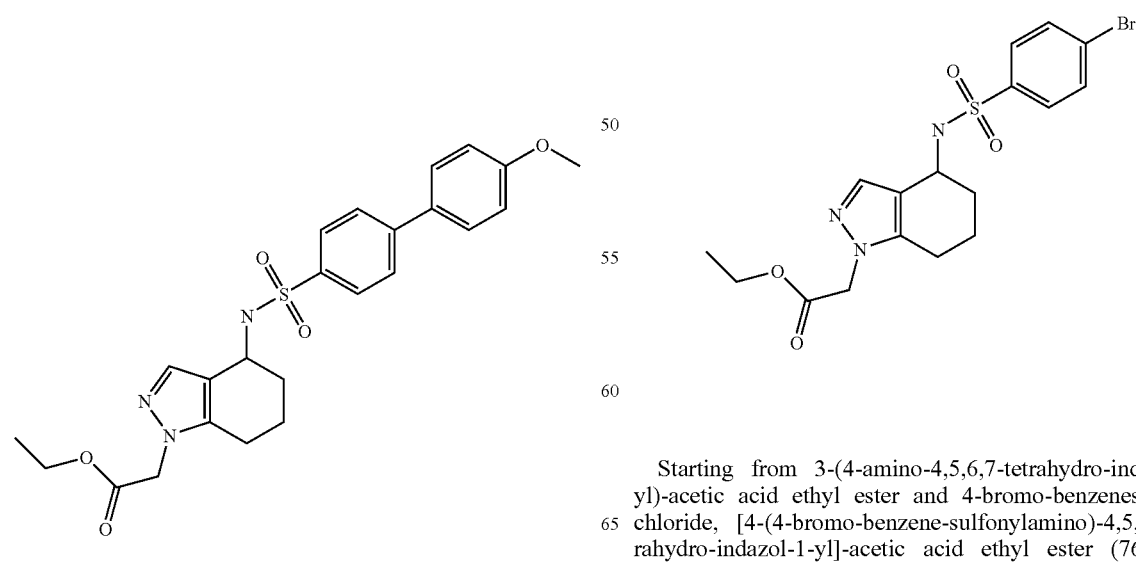

Starting from 3-(4-amino-4,5,6,7-tetrahydro-indazol-1-yl)-acetic acid ethyl ester and 4-bromo-benzenesulfonyl chloride, [4-(4-bromo-benzene-sulfonylamino)-4,5,6,7-tetrahydro-indazol-1-yl]-acetic acid ethyl ester (760 mg, 54.7%) was prepared in an analogous manner as described for example 1-1 as a viscous oil. MS cald. for $C_{17}H_{20}BrN_3O_4S$ 441, obsd. (ESI$^+$) [(M+H)$^+$] 442.

[4-(4'-Methoxy-biphenyl-4-sulfonylamino)-4,5,6,7-tetrahydro-indazol-1-yl]-acetic acid ethyl ester

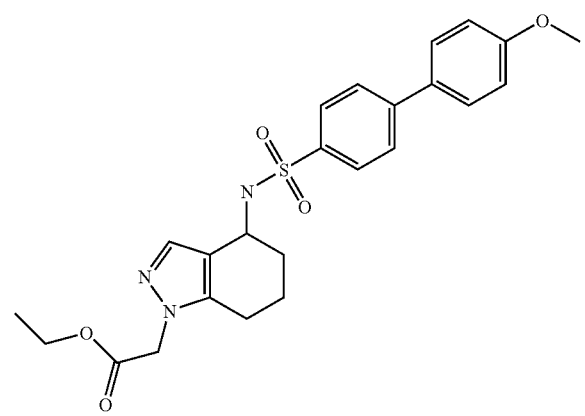

A mixture of [4-(4-bromo-benzenesulfonylamino)-4,5,6,7-tetrahydro-indazol-1-yl]-acetic acid ethyl ester (44 mg, 0.10 mmol), 4-methoxy-phenylboronic acid (3 mg, 0.15 mmol), sodium carbonate (21 mg, 0.20 mmol) and tetrakis(triphenylphosphine)palladium(0) (6 mg, 0.005 mmol) in N,N-dimethylformamide (0.5 mL) was heated in a microwave oven at 150° C. for 30 minutes under an argon atmosphere. The resulting mixture was diluted with water and extracted with ethyl acetate. The organic layer was washed with brine, dried over sodium sulfate and concentrated in vacuo. The residue was purified by preparative HPLC to afford [4-(4'-methoxy-biphenyl-4-sulfonylamino)-4,5,6,7-tetrahydro-indazol-1-yl]-acetic acid ethyl ester (4.7 mg, 10%) as a white solid. MS cald. for $C_{24}H_{27}N_3O_5S$ 469, obsd. (ESI$^+$) [(M+H)$^+$] 470.

Examples 10-2 to 10-31

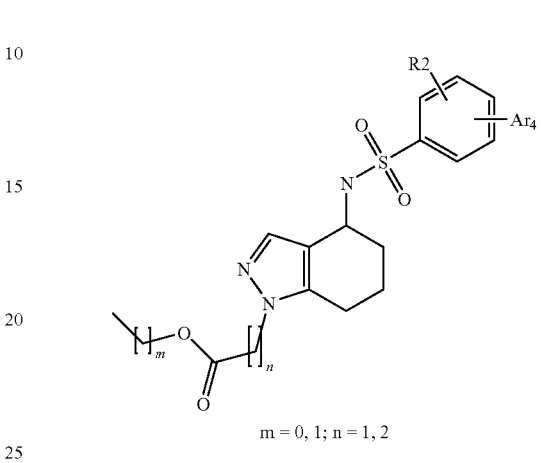

m = 0, 1; n = 1, 2

The following examples 10-2 to 10-31 were prepared in an analogous manner as described for example 10-1 using 3-((R)-4-amino-4,5,6,7-tetrahydro-indazol-1-yl)-acetic acid ethyl ester, or 3-(4-amino-4,5,6,7-tetrahydro-indazol-1-yl)-acetic acid ethyl ester, or 3-((R)-4-amino-4,5,6,7-tetrahydro-indazol-1-yl)-propionic acid methyl ester, or 3-(4-amino-4,5,6,7-tetrahydro-indazol-1-yl)-propionic acid methyl ester and the appropriate commercially available benzenesulfonyl chlorides XXXVIII and aryl boronic acids (Ar$_4$B(OH)$_2$).

| Example No. | Systematic Name | MS (ESI+, M + H) | Structure |
|---|---|---|---|
| 10-2 | [4-(4-Pyridin-3-yl-benzenesulfonylamino)-4,5,6,7-tetrahydro-indazol-1-yl]-acetic acid ethyl ester | 441 | 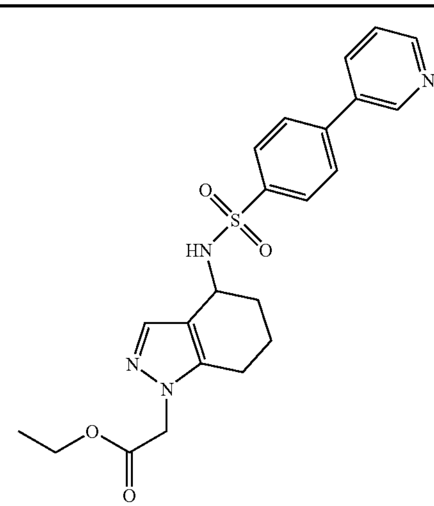 |

-continued
| Example No. | Systematic Name | MS (ESI+, M + H) | Structure |
|---|---|---|---|
| 10-3 | [4-(4'-Ethoxy-biphenyl-4-sulfonylamino)-4,5,6,7-tetrahydro-indazol-1-yl]-acetic acid ethyl ester | 484 | 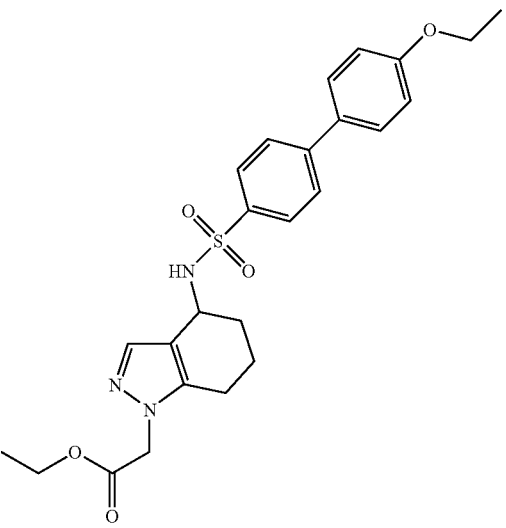 |
| 10-4 | [4-(2'-Chloro-biphenyl-4-sulfonylamino)-4,5,6,7-tetrahydro-indazol-1-yl]-acetic acid ethyl ester | 474 | 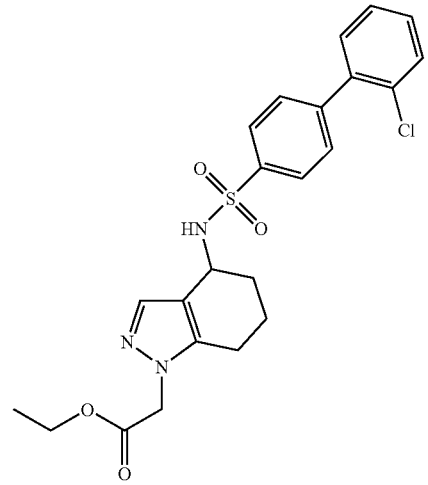 |
| 10-5 | [4-(4'-Methoxy-biphenyl-3-sulfonylamino)-4,5,6,7-tetrahydro-indazol-1-yl]-acetic acid ethyl ester | 470 | 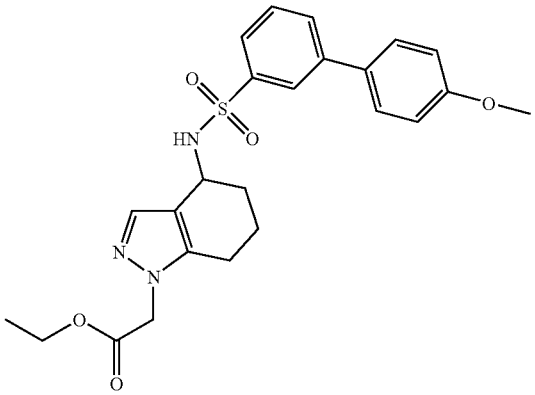 |

-continued

| Example No. | Systematic Name | MS (ESI+, M + H) | Structure |
|---|---|---|---|
| 10-6 | [4-(4'-Chloro-biphenyl-4-sulfonylamino)-4,5,6,7-tetrahydro-indazol-1-yl]-acetic acid ethyl ester | 474 | 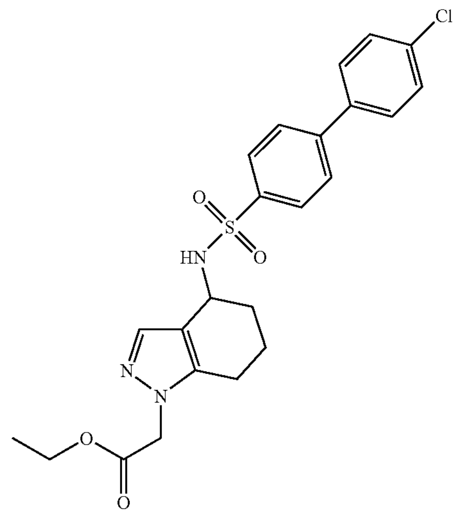 |
| 10-7 | [4-(4'-Fluoro-biphenyl-4-sulfonylamino)-4,5,6,7-tetrahydro-indazol-1-yl]-acetic acid ethyl ester | 458 | 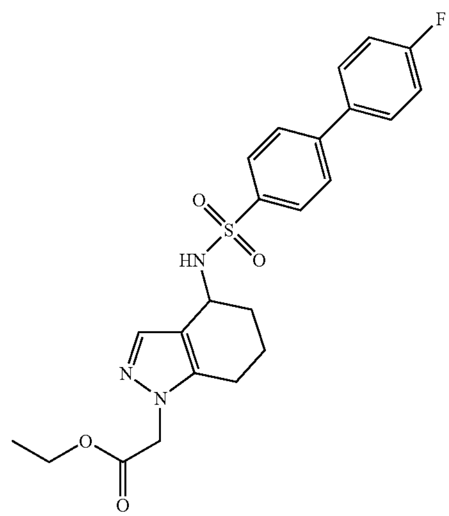 |
| 10-8 | [4-(2-Fluoro-biphenyl-4-sulfonylamino)-4,5,6,7-tetrahydro-indazol-1-yl]-acetic acid ethyl ester | 458 | 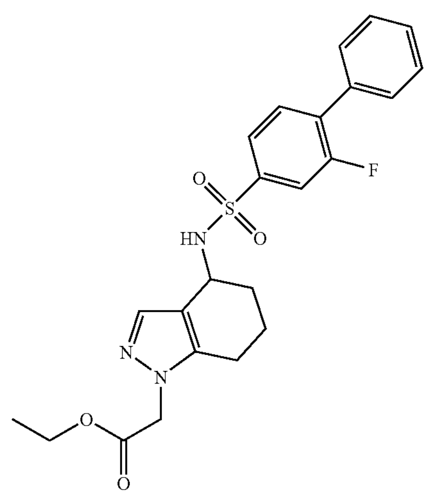 |

-continued
| Example No. | Systematic Name | MS (ESI+, M + H) | Structure |
|---|---|---|---|
| 10-9 | [4-(2-Trifluoromethyl-biphenyl-4-sulfonylamino)-4,5,6,7-tetrahydro-indazol-1-yl]-acetic acid ethyl ester | 508 | 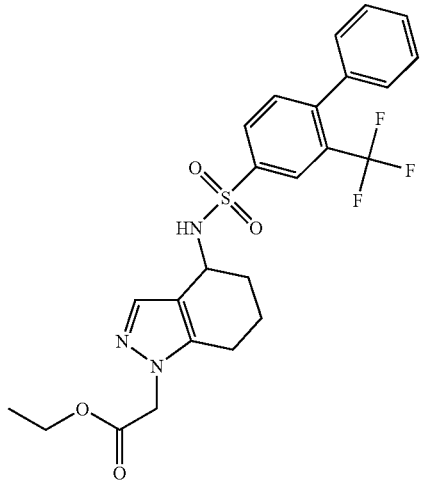 |
| 10-10 | [4-(3'-Methoxy-biphenyl-4-sulfonylamino)-4,5,6,7-tetrahydro-indazol-1-yl]-acetic acid ethyl ester | 470 | 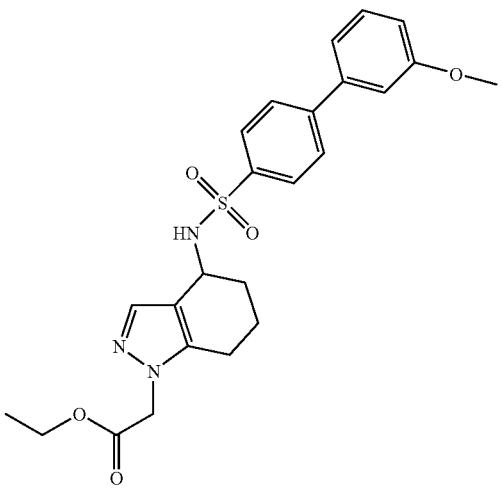 |
| 10-11 | [4-(3'-Cyano-biphenyl-4-sulfonylamino)-4,5,6,7-tetrahydro-indazol-1-yl]-acetic acid ethyl ester | 465 | 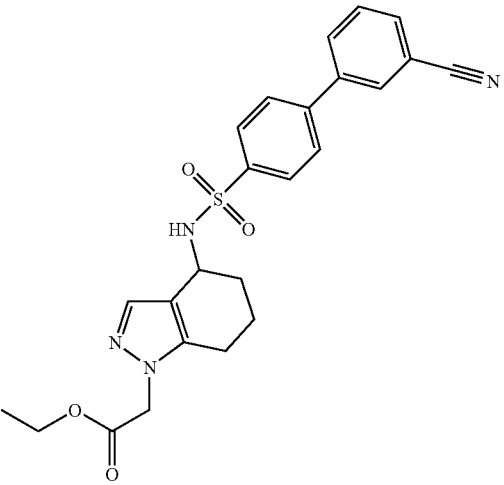 |

-continued
| Example No. | Systematic Name | MS (ESI+, M + H) | Structure |
|---|---|---|---|
| 10-12 | [4-(2'-Chloro-biphenyl-3-sulfonylamino)-4,5,6,7-tetrahydro-indazol-1-yl]-acetic acid ethyl ester | 474 | 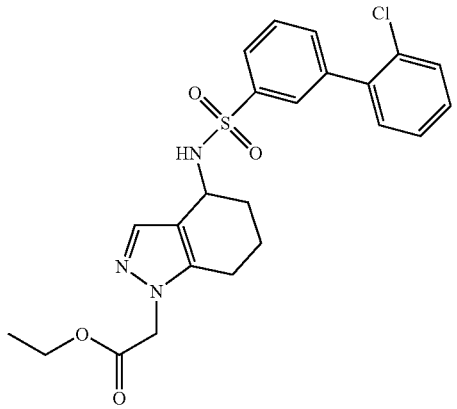 |
| 10-13 | [(R)-4-(3'-Chloro-biphenyl-4-sulfonylamino)-4,5,6,7-tetrahydro-indazol-1-yl]-acetic acid ethyl ester | 474 | 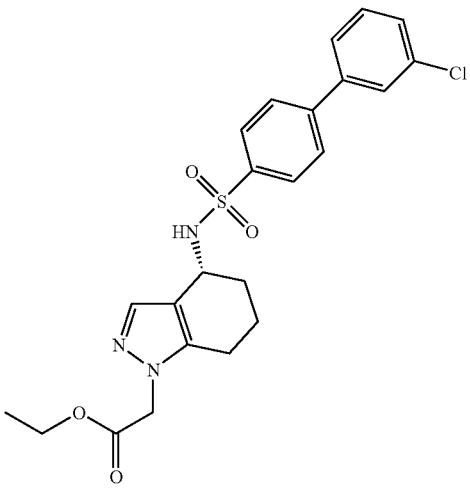 |
| 10-14 | [4-(3'-Trifluoromethoxy-biphenyl-4-sulfonylamino)-4,5,6,7-tetrahydro-indazol-1-yl]-acetic acid ethyl ester | 524 | 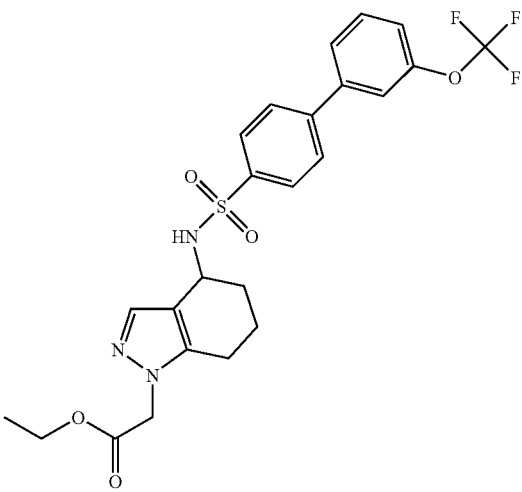 |

-continued

| Example No. | Systematic Name | MS (ESI+, M + H) | Structure |
|---|---|---|---|
| 10-15 | [4-(3'-Chloro-4'-fluoro-biphenyl-4-sulfonylamino)-4,5,6,7-tetrahydro-indazol-1-yl]-acetic acid ethyl ester | 492 | 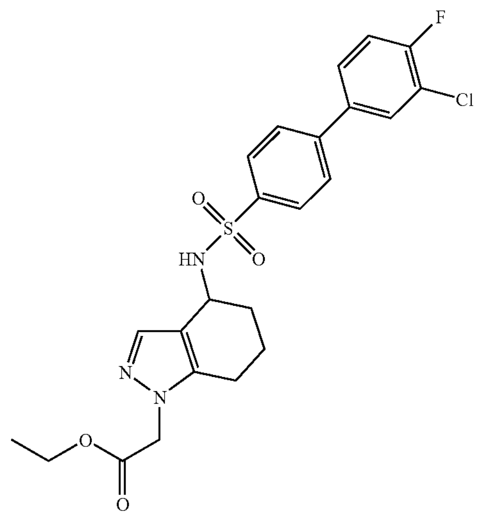 |
| 10-16 | [4-(5-Trifluoromethyl-biphenyl-3-sulfonylamino)-4,5,6,7-tetrahydro-indazol-1-yl]-acetic acid ethyl ester | 508 | 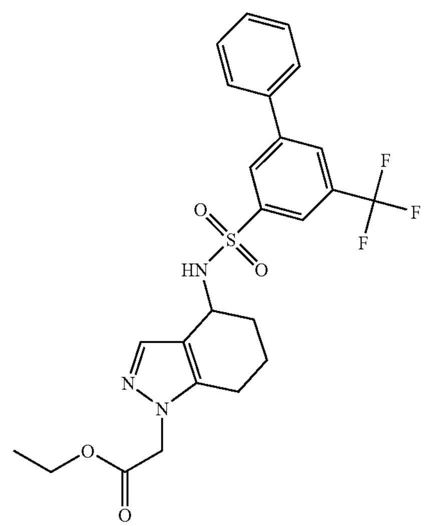 |
| 10-17 | [4-(2'-Trifluoromethyl-biphenyl-4-sulfonylamino)-4,5,6,7-tetrahydro-indazol-1-yl]-acetic acid ethyl ester | 508 | 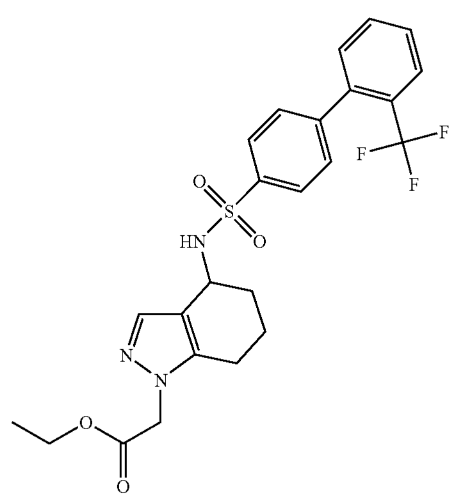 |

-continued

| Example No. | Systematic Name | MS (ESI+, M + H) | Structure |
|---|---|---|---|
| 10-18 | [4-(3',5'-Dimethyl-biphenyl-4-sulfonylamino)-4,5,6,7-tetrahydro-indazol-1-yl]-acetic acid ethyl ester | 468 | 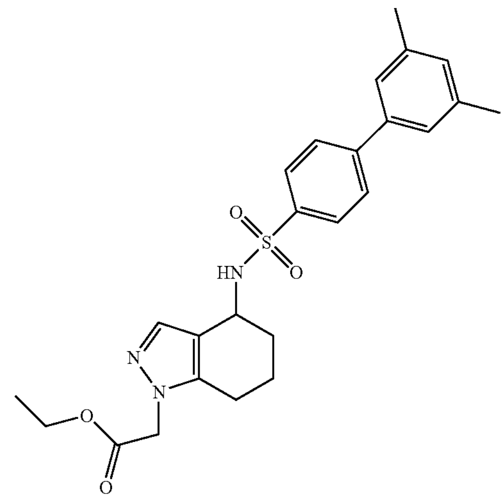 |
| 10-19 | [4-(3'-Hydroxy-biphenyl-4-sulfonylamino)-4,5,6,7-tetrahydro-indazol-1-yl]-acetic acid ethyl ester | 456 | 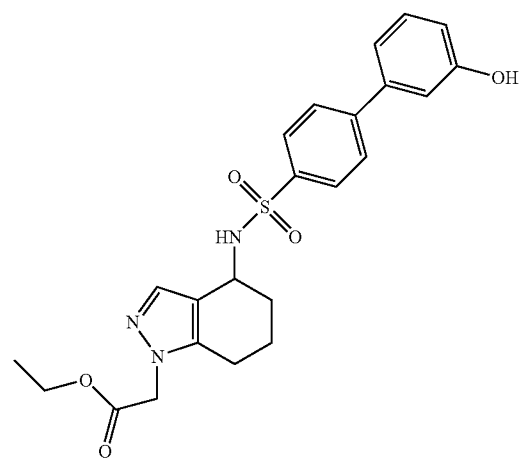 |
| 10-20 | [4-(3'-Ethoxy-biphenyl-4-sulfonylamino)-4,5,6,7-tetrahydro-indazol-1-yl]-acetic acid ethyl ester | 484 | 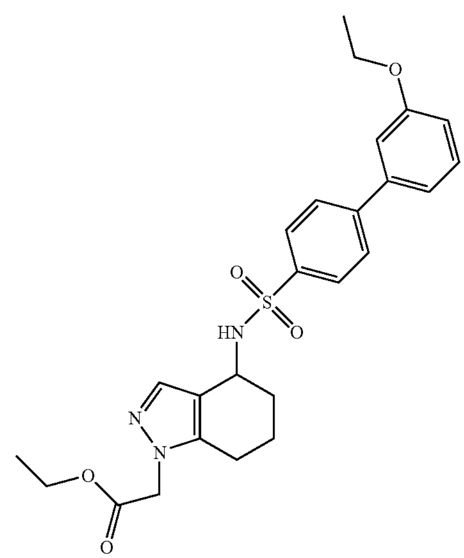 |

| Example No. | Systematic Name | MS (ESI+, M + H) | Structure |
|---|---|---|---|
| 10-21 | [4-(3'-Isopropoxy-biphenyl-4-sulfonylamino)-4,5,6,7-tetrahydro-indazol-1-yl]-acetic acid ethyl ester | 498 | 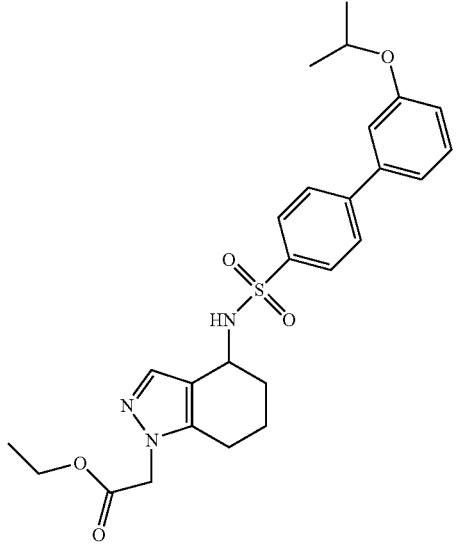 |
| 10-22 | [4-(3'-Acetyl-biphenyl-4-sulfonylamino)-4,5,6,7-tetrahydro-indazol-1-yl]-acetic acid ethyl ester | 482 | 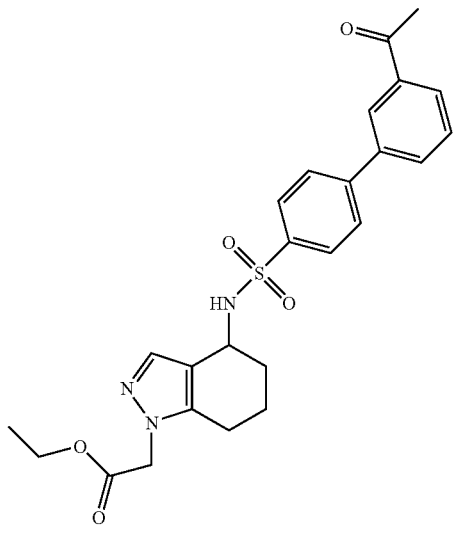 |

-continued

| Example No. | Systematic Name | MS (ESI+, M + H) | Structure |
|---|---|---|---|
| 10-23 | [4-(3'-Nitro-biphenyl-4-sulfonylamino)-4,5,6,7-tetrahydro-indazol-1-yl]-acetic acid ethyl ester | 485 | 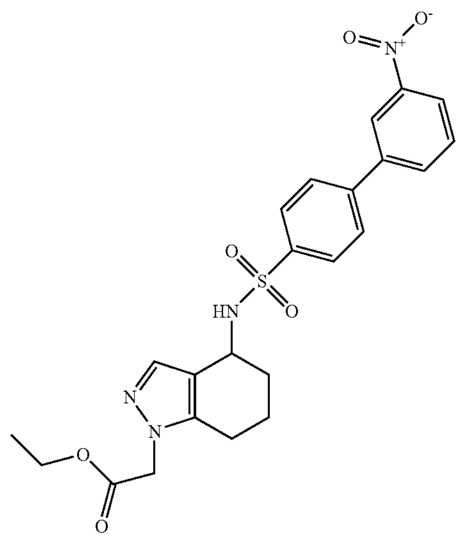 |
| 10-24 | [4-(3',5'-Bis-trifluoromethyl-biphenyl-4-sulfonylamino)-4,5,6,7-tetrahydro-indazol-1-yl]-acetic acid ethyl ester | 576 | 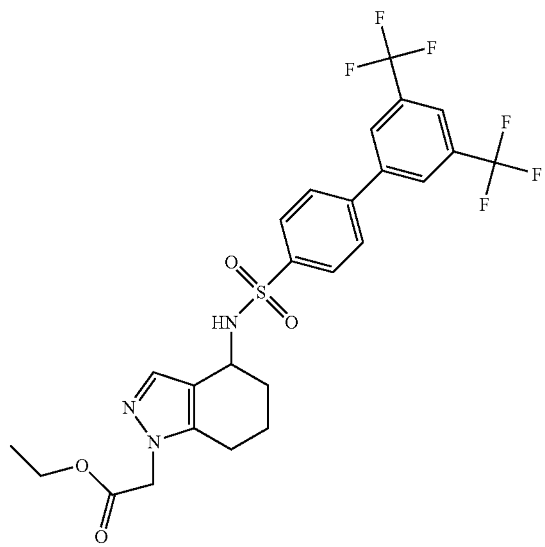 |
| 10-25 | [(R)-4-(3'-Trifluoromethyl-biphenyl-4-sulfonylamino)-4,5,6,7-tetrahydro-indazol-1-yl]-acetic acid ethyl ester | 508 | 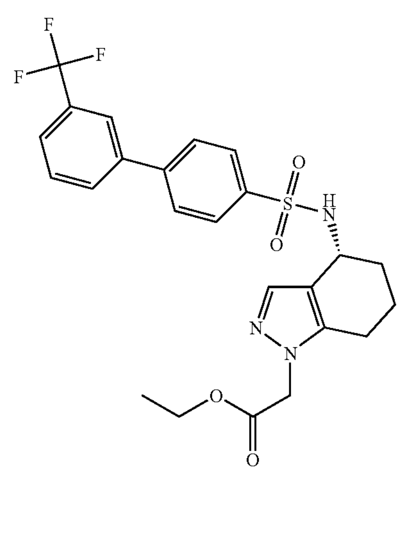 |

-continued

| Example No. | Systematic Name | MS (ESI+, M + H) | Structure |
|---|---|---|---|
| 10-26 | [(R)-4-(3'-Trimethylsilanyl-biphenyl-4-sulfonylamino)-4,5,6,7-tetrahydro-indazol-1-yl]-acetic acid ethyl ester | 512 | 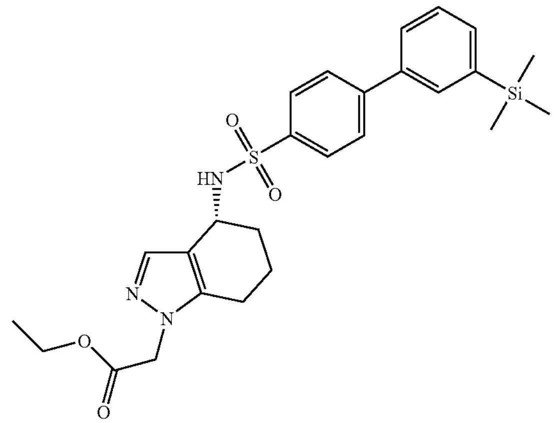 |
| 10-27 | [(R)-4-(3'-Isopropyl-biphenyl-4-sulfonylamino)-4,5,6,7-tetrahydro-indazol-1-yl]-acetic acid ethyl ester | 482 | 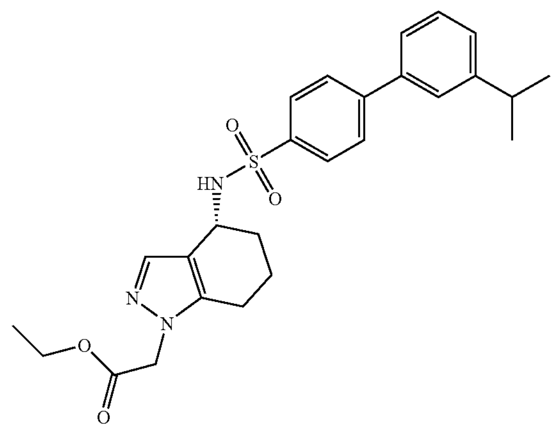 |
| 10-28 | [(R)-4-(3'-Methanesulfonyl-biphenyl-4-sulfonylamino)-4,5,6,7-tetrahydro-indazol-1-yl]-acetic acid ethyl ester | 518 | 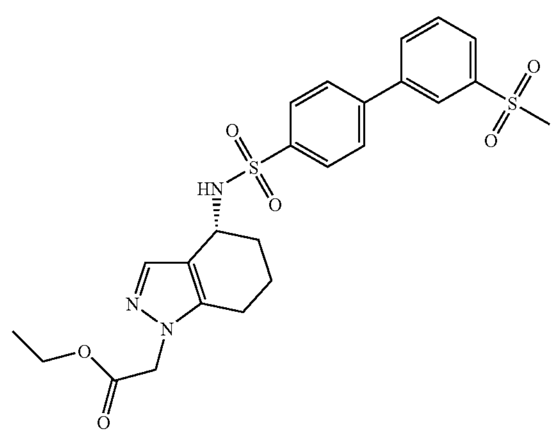 |

| Example No. | Systematic Name | MS (ESI+, M + H) | Structure |
|---|---|---|---|
| 10-29 | [(R)-4-(3'-Methanesulfinyl-biphenyl-4-sulfonylamino)-4,5,6,7-tetrahydro-indazol-1-yl]-acetic acid ethyl ester | 502 | 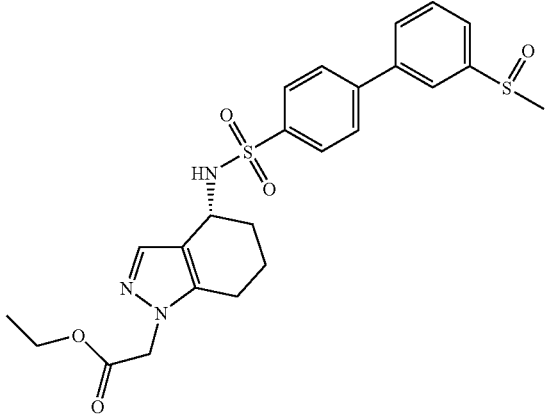 |
| 10-30 | 3-[4-biphenyl-4-sulfonylamino)-4,5,6,7-tetrahydro-indazol-1-yl]-propionic acid ethyl ester | 440 | 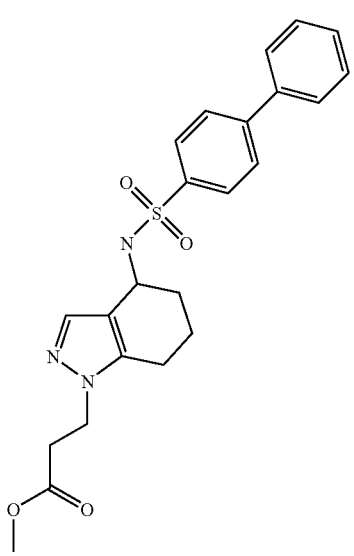 |
| 10-31 | 3-[(R)-4-(3'-Trifluoromethyl-biphenyl-4-sulfonylamino)-4,5,6,7-tetrahydro-indazol-1-yl]-propionic acid methyl ester | 508 | 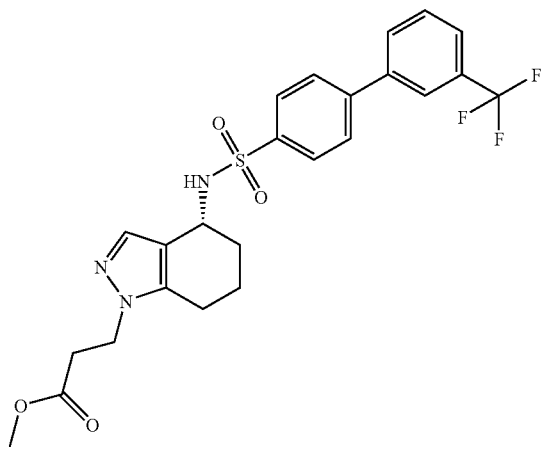 |

Example 10-1a

[4-(4'-Methoxy-biphenyl-4-sulfonylamino)-4,5,6,7-tetrahydro-indazol-1-yl]-acetic acid

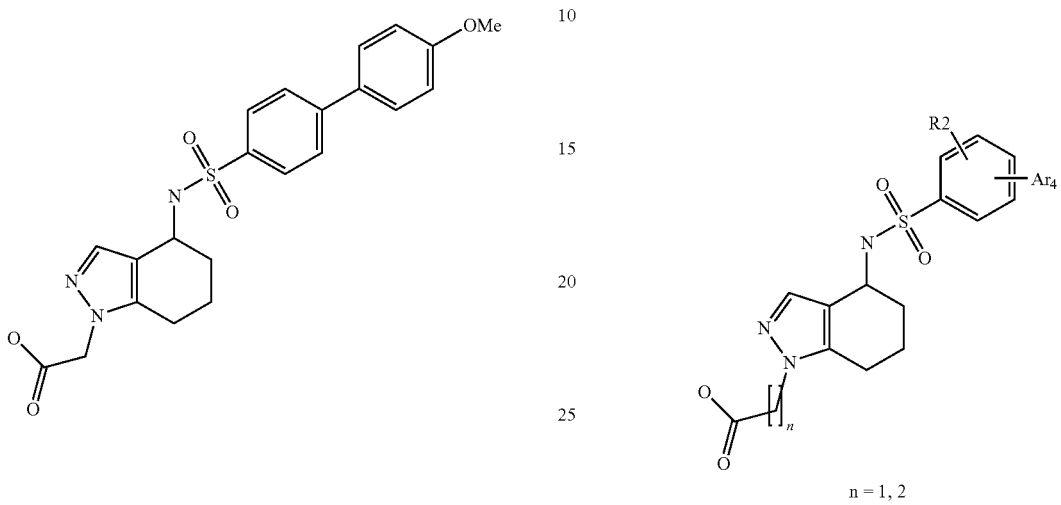

Starting from [4-(4'-methoxy-biphenyl-4-sulfonylamino)-4,5,6,7-tetrahydro-indazol-1-yl]-acetic acid ethyl ester, and using the method described for example 1-1a, [4-(4'-methoxy-biphenyl-4-sulfonylamino)-4,5,6,7-tetrahydro-indazol-1-yl]-acetic acid (2.7 mg, 61.4%) was obtained as a white powder. $^1$H NMR (400 MHz, CD$_3$OD) δ ppm 7.98 (d, 2 H), 7.84 (d, 2 H), 7.70 (m, 2 H), 7.07 (t, 2 H), 6.70 (s, 1 H), 4.84 (s, 2 H), 4.40 (t, 1 H), 3.88 (s, 1 H), 2.50 (m, 2 H), 1.75-2.00 (m, 4 H). MS cald. for C$_{22}$H$_{23}$N$_3$O$_5$S 441, obsd. (ESI$^+$) [(M+H)$^+$] 442.

Examples 10-2a to 10-31a n = 1, 2

The following examples 10-2a to 10-31a were prepared in an analogous manner as described for example 1-1a from the corresponding esters 10-2 to 10-31.

| Example No. | Systematic Name | $^1$H NMR (400 MHz, CD$_3$OD) δ ppm | MS (ESI+, M + H) | Structure |
|---|---|---|---|---|
| 10-2a | [4-(4-Pyridin-3-yl-benzenesulfonylamino)-4,5,6,7-tetrahydro-indazol-1-yl]-acetic acid | 9.29 (s, 1 H), 9.01 (d, 1 H), 8.89 (d, 1 H), 8.23-8.18 (m, 1 H), 8.07 (q, 4 H), 7.51 (s, 1 H), 5.01 (s, 2 H), 4.42 (t, 1 H), 2.65-2.53 (m, 2 H), 1.99-1.88 (m, 1 H), 1.82-1.71 (m, 2 H), 1.70-1.60 (m, 1 H) | 413 | 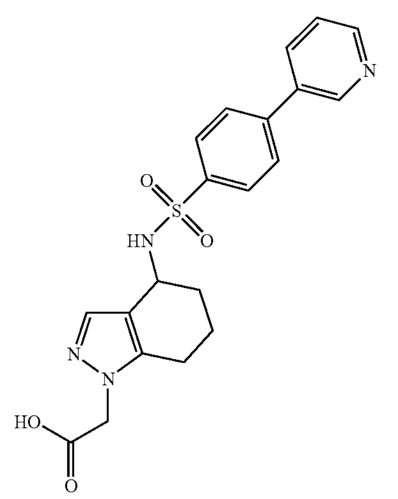 |

-continued

| Example No. | Systematic Name | $^1$H NMR (400 MHz, CD$_3$OD) δ ppm | MS (ESI+, M + H) | Structure |
|---|---|---|---|---|
| 10-3a | [4-(4'-Ethoxy-biphenyl-4-sulfonylamino)-4,5,6,7-tetrahydro-indazol-1-yl]-acetic acid | 8.00-7.94 (m, 2 H), 7.83 (d, J = 1.01 Hz, 2 H), 7.67 (d, J = 1.52 Hz, 2 H), 7.04 (s, 2 H), 6.69 (s, 1 H), 4.77 (s, 2 H), 4.39 (s, 1 H), 4.10 (t, 2 H), 2.67-240 (m, 2 H), 2.03-1.89 (m, 1 H), 1.86-1.67 (m, 3 H), 1.42 (t, 3 H) | 456 | 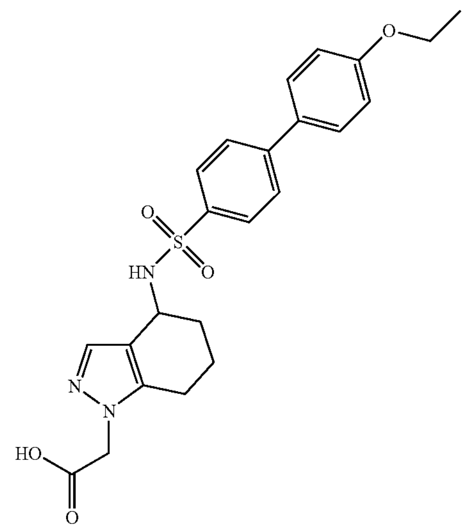 |
| 10-4a | [4-(2'-Chloro-biphenyl-4-sulfonylamino)-4,5,6,7-tetrahydro-indazol-1-yl]-acetic acid | 8.04 (d, 2 H), 7.69 (d, 2 H), 7.57 (m, 1 H), 7.44 (m, 3 H), 6.63 (s, 1 H), 4.72 (s, 2 H), 4.43 (t, 1 H), 2.53 (m., 2 H), 1.97 (m, 1 H), 1.83 (m, 3 H) | 446 | 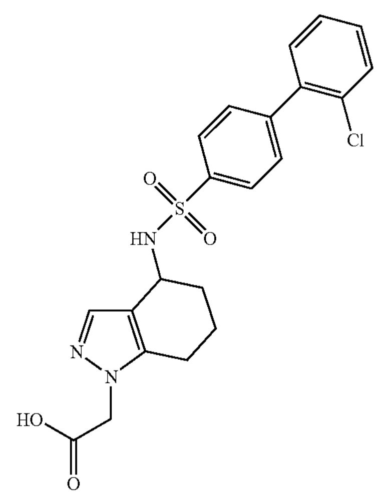 |
| 10-5a | [4-(4'-Methoxy-biphenyl-3-sulfonylamino)-4,5,6,7-tetrahydro-indazol-1-yl]-acetic acid | 8.14 (s, 1 H), 7.89 (t, 2 H), 7.66 (m, 3 H), 7.05 (d, 2 H), 6.61 (s, 1 H), 4.74 (s, 2 H), 4.42 (s, 1 H), 2.50 (m, 2 H), 1.85 (m, 4 H) | 442 | 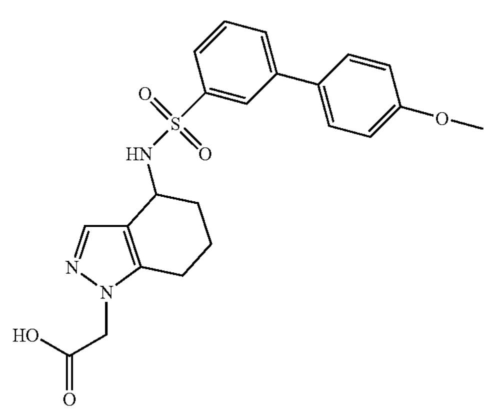 |

-continued

| Example No. | Systematic Name | ¹H NMR (400 MHz, CD₃OD) δ ppm | MS (ESI+, M + H) | Structure |
|---|---|---|---|---|
| 10-6a | [4-(4'-Chloro-biphenyl-4-sulfonylamino)-4,5,6,7-tetrahydro-indazol-1-yl]-acetic acid | 8.04 (d, 2 H), 7.89 (d, 2 H), 7.75 (d, 2 H), 7.53 (d, 2 H), 6.65 (s, 1 H), 4.67 (s, 2 H), 4.41 (t, 1 H), 2.50 (m, 2 H), 2.00-1.75 (m, 4 H) | 446 | 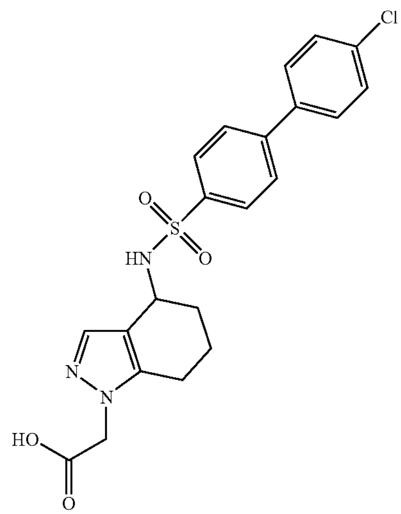 |
| 10-7a | [4-(4'-Fluoro-biphenyl-4-sulfonylamino)-4,5,6,7-tetrahydro-indazol-1-yl]-acetic acid | 8.04 (d, 2 H), 7.88 (d, 2 H), 7.83-7.74 (m, 2 H), 7.31-7.22 (m, 2 H), 6.72 (s, 1 H), 4.80 (s, 2 H), 4.43 (s, 1 H), 2.63-2.44 (m, 2 H), 2.02-1.91 (m, 1 H), 1.89-1.72 (m, 3 H) | 430 | 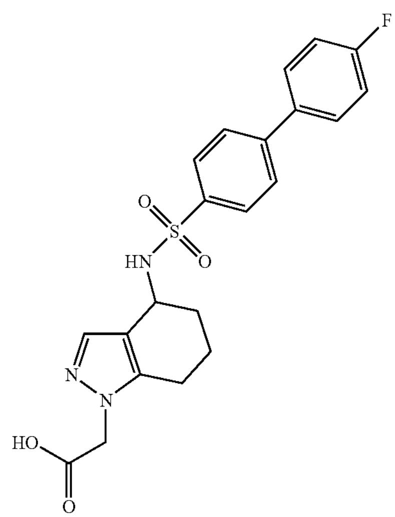 |
| 10-8a | [4-(2-Fluoro-biphenyl-4-sulfonylamino)-4,5,6,7-tetrahydro-indazol-1-yl]-acetic acid | 7.85 (dd, 1 H), 7.79-7.74 (m, 2 H), 7.66-7.62 (m, 2 H), 7.50 (M, 3 H), 6.81 (s, 1 H), 4.80 (s, 2 H), 4.46 (t, 1 H), 2.63-2.46 (m, 2 H), 2.00-1.93 (m, 1 H), 1.90-1.72 (m, 3 H) | 430 | 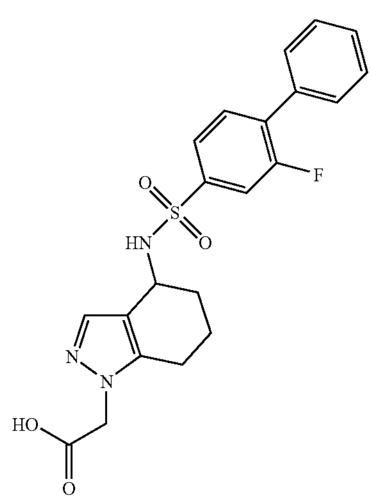 |

-continued

| Example No. | Systematic Name | $^1$H NMR (400 MHz, CD$_3$OD) δ ppm | MS (ESI+, M + H) | Structure |
|---|---|---|---|---|
| 10-9a | [4-(2-Trifluoromethyl-biphenyl-4-sulfonylamino)-4,5,6,7-tetrahydro-indazol-1-yl]-acetic acid | 7.65 (d, 1 H), 7.51-7.46 (m, 3 H), 7.42-7.38 (m, 2 H), 4.80 (s, 2 H), 4.47 (t, 1 H), 2.64-2.47 (m, 2 H), 2.03-1.93 (m, 1 H), 1.90-1.74 (m, 3 H) | 480 | 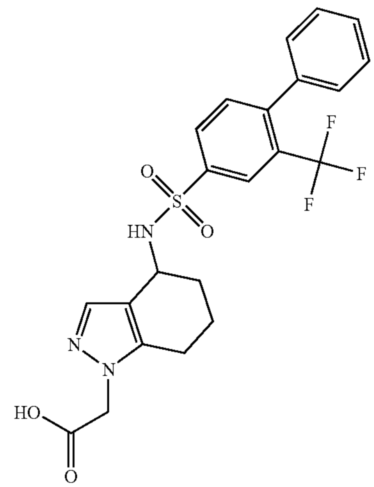 |
| 10-10a | [4-(3'-Methoxy-biphenyl-4-sulfonylamino)-4,5,6,7-tetrahydro-indazol-1-yl]-acetic acid | 8.03 (d, 2 H), 7.89 (d, 2 H), 7.42 (t, 1 H), 7.02 (t, 1 H), 6.70 (s, 1 H), 4.77 (s, 2 H), 4.42 (s, 1 H), 2.50 (m, 2 H), 1.75-2.01 (m, 4 H) | 442 | 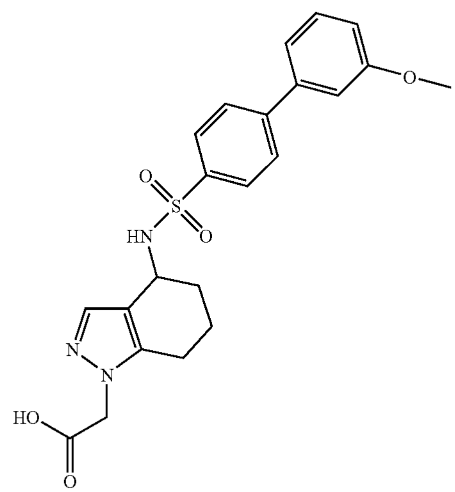 |
| 10-11a | [4-(3'-Cyano-biphenyl-4-sulfonylamino)-4,5,6,7-tetrahydro-indazol-1-yl]-acetic acid | 8.16 (s, 1 H), 8.07 (d, 3 H), 7.94 (d, 2 H), 7.81 (d, 1 H), 7.71 (t, 1 H), 6.53 (s, 1 H), 4.54 (s, 2 H), 4.41 (t, 1 H), 2.61-2.42 (m, 2 H), 2.00-1.91 (m, 1 H), 1.86-1.76 (m, 3 H) | 437 | 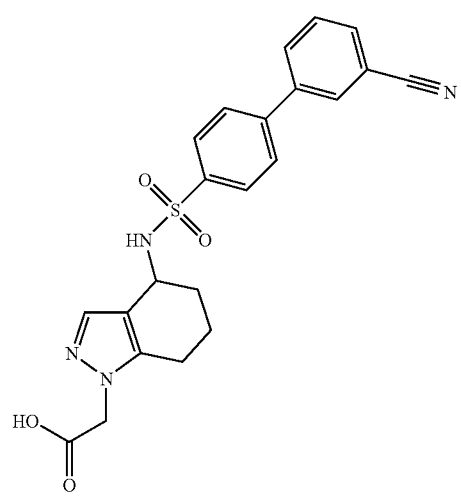 |

-continued

| Example No. | Systematic Name | $^1$H NMR (400 MHz, CD$_3$OD) δ ppm | MS (ESI+, M + H) | Structure |
|---|---|---|---|---|
| 10-12a | [4-(2'-Chloro-biphenyl-3-sulfonylamino)-4,5,6,7-tetrahydro-indazol-1-yl]-acetic acid | 8.02-7.96 (m, 2 H), 7.76-7.68 (m, 2 H), 7.59-7.52 (m, 1 H), 7.42 (s, 3 H), 6.59 (s, 1 H), 4.65 (s, 2 H), 4.44-4.39 (m, 1 H), 2.61-2.44 (m, 2 H), 1.99-1.90 (m, 1 H), 1.87-1.73 (m, 3 H) | 446 | 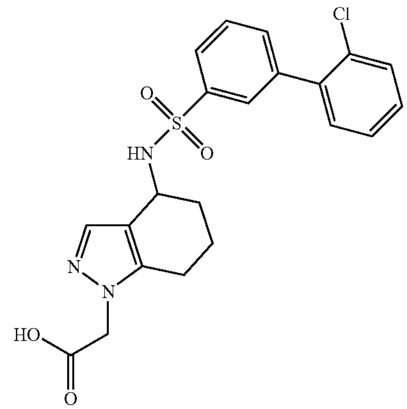 |
| 10-13a | [(R)-4-(3'-Chloro-biphenyl-4-sulfonylamino)-4,5,6,7-tetrahydro-indazol-1-yl]-acetic acid | 8.04 (d, 2 H), 7.90 (d, 2 H), 7.77 (t, 1 H), 7.68 (t, 1 H), 7.49 (m, 2 H), 6.71 (s, 1 H), 4.79 (s, 2 H), 4.43 (d, 1 H), 2.50 (m, 2 H), 1.75-2.00 (m, 4 H) | 446 | 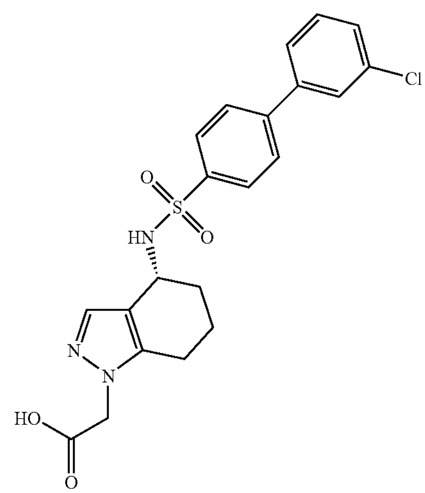 |
| 10-14a | [4-(3'-Trifluoromethoxy-biphenyl-4-sulfonylamino)-4,5,6,7-tetrahydro-indazol-1-yl]-acetic acid | 8.05 (t, 1 H), 8.06-8.02 (m, 2 H), 7.89 (t, 1 H), 7.76-7.73 (m, 1 H), 7.65-7.63 (m, 1 H), 7.60 (d, 1 H), 7.38-7.34 (m, 1 H), 6.83 (s, 1 H), 4.82 (s, 2 H), 4.42 (t, J = 5.05 Hz, 1 H), 2.62-2.45 (m, 2 H), 2.01-1.91 (m, 1 H), 1.86-1.77 (m, 2 H), 1.77-1.69 (m, 1 H) | 496 | 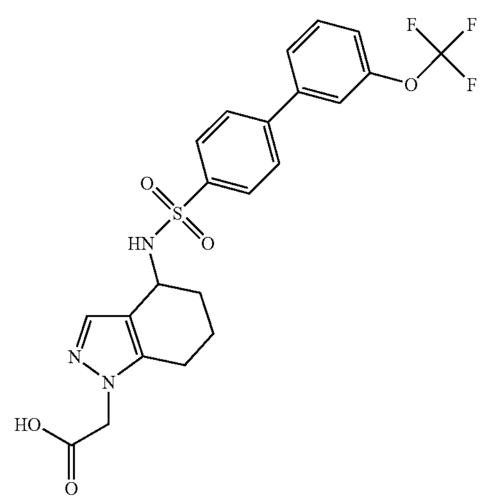 |

| Example No. | Systematic Name | $^1$H NMR (400 MHz, CD$_3$OD) δ ppm | MS (ESI+, M + H) | Structure |
|---|---|---|---|---|
| 10-15a | [4-(3'-Chloro-4'-fluoro-biphenyl-4-sulfonylamino)-4,5,6,7-tetrahydro-indazol-1-yl]-acetic acid | 8.03 (d, J = 8.59 Hz, 2 H), 7.90-7.85 (m, 4 H), 7.71 (ddd, J = 8.59, 4.55, 2.27 Hz, 1 H), 7.39 (t, J = 8.84 Hz, 1 H), 6.56 (s, 1 H), 4.51 (s, 2 H), 4.38 (t, 1 H), 2.60-2.40 (m, 2 H), 1.87-1.73 (m, 4 H) | 464 | 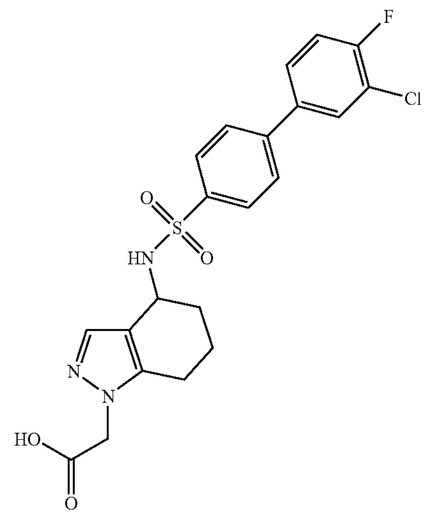 |
| 10-16a | [4-(5-Trifluoromethyl-biphenyl-3-sulfonylamino)-4,5,6,7-tetrahydro-indazol-1-yl]-acetic acid | 8.35 (s, 1 H), 8.14 (d, 2 H), 7.69 (d, 2 H), 7.05 (m, 3 H), 6.90 (s, 1 H), 4.44 (t, 1 H), 2.50 (m, 2 H), 2.00-1.67 (m, 4 H) | 480 | 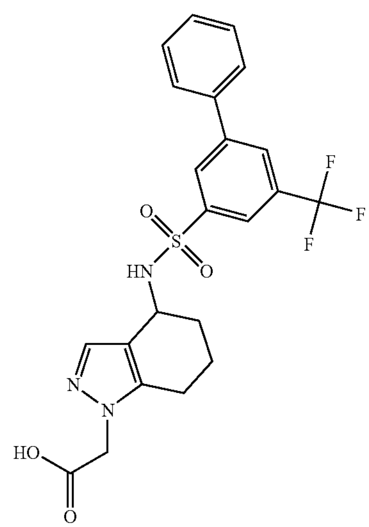 |
| 10-17a | [4-(2'-Trifluoromethyl-biphenyl-4-sulfonylamino)-4,5,6,7-tetrahydro-indazol-1-yl]-acetic acid | 7.96 (d, 2 H), 7.80 (d, 1 H), 7.67 (d, 1 H), 7.59 (t, 1 H), 7.52 (d, 2 H), 7.41 (d, 1 H), 6.69 (s, 1 H), 4.76 (s, 2 H), 4.38 (t, 1 H) 3.72-3.66 (m, 1 H), 2.56-2.43 (m, 2 H), 1.85-1.70 (m, 4 H) | 480 | 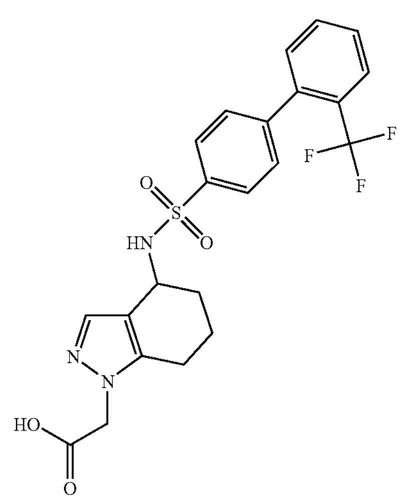 |

| Example No. | Systematic Name | $^1$H NMR (400 MHz, CD$_3$OD) δ ppm | MS (ESI+, M + H) | Structure |
|---|---|---|---|---|
| 10-18a | [4-(3',5'-Dimethyl-biphenyl-4-sulfonylamino)-4,5,6,7-tetrahydro-indazol-1-yl]-acetic acid | 7.97-7.93 (m, 2 H), 7.81-7.78 (m, 2 H), 7.28 (s, 2 H), 7.04 (s, 1 H), 6.62 (s, 1 H), 4.74 (s, 2 H), 4.36 (t, 1 H), 2.56-2.44 (m, 2 H), 2.35 (s, 6 H), 1.96-1.86 (m, 1 H), 1.81-1.68 (m, 3 H) | 440 | 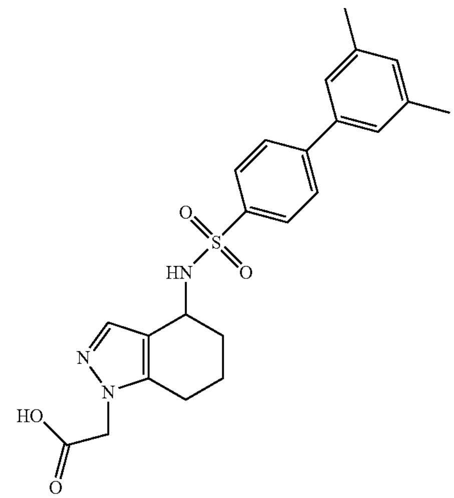 |
| 10-19a | [4-(3'-Hydroxy-biphenyl-4-sulfonylamino)-4,5,6,7-tetrahydro-indazol-1-yl]-acetic acid | 8.00 (d, 2 H), 7.75 (d, 2 H), 7.25 (t, 1 H), 7.10 (t, 2 H), 6.80 (d, 1 H), 6.6 (s, 1 H), 4.75 (s, 2 H), 4.45 (t, 1 H), 2.50 (m, 2 H), 1.75-2.00 (m, 4 H) | 428 | 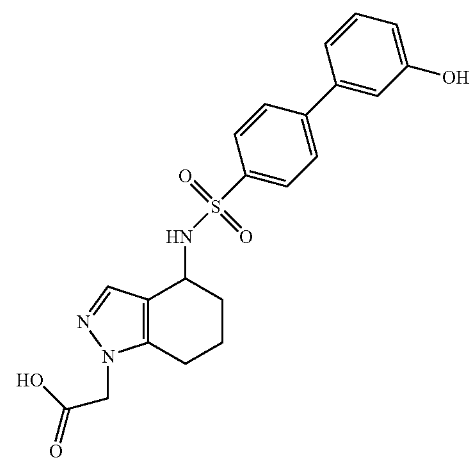 |
| 10-20a | [4-(3'-Ethoxy-biphenyl-4-sulfonylamino)-4,5,6,7-tetrahydro-indazol-1-yl]-acetic acid | 7.95 (d, 2 H), 7.80 (d, 2 H), 7.35 (t, 1 H), 7.20 (t, 2 H), 6.95 (d, 1 H), 6.65 (s, 1 H), 4.75 (s, 2 H), 4.45 (t, 1 H), 4.1 (m, 2 H), 2.50 (m, 2 H), 1.75-2.00 (m, 4 H), 1.4 (t, 3 H) | 456 | 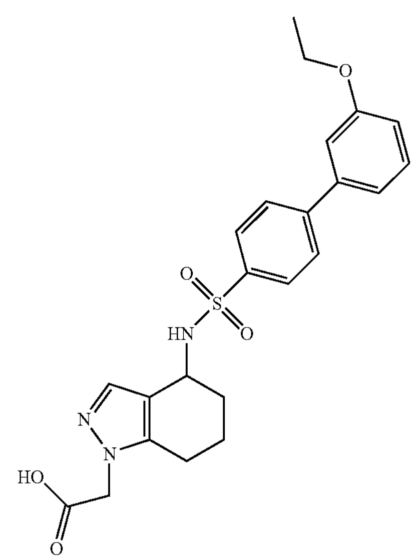 |

| Example No. | Systematic Name | $^1$H NMR (400 MHz, CD$_3$OD) δ ppm | MS (ESI+, M + H) | Structure |
|---|---|---|---|---|
| 10-21a | [4-(3'-Isopropoxy-biphenyl-4-sulfonylamino)-4,5,6,7-tetrahydro-indazol-1-yl]-acetic acid | 8.00 (d, 2 H), 7.75 (d, 2 H), 7.35 (t, 1 H), 7.20 (t, 2 H), 6.90 (t, 1 H), 6.7 (s, 1 H), 4.75 (s, 2 H), 4.60 (m, 1 H), 4.3 (t, 1 H), 2.50 (m, 2 H), 1.75-2.00 (m, 4 H), 1.3 (d, 6 H) | 470 | 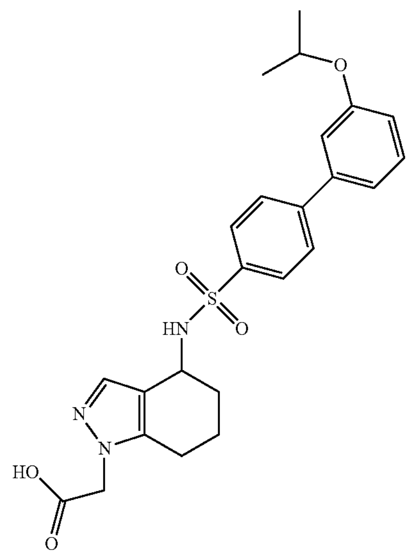 |
| 10-22a | [4-(3'-Acetyl-biphenyl-4-sulfonylamino)-4,5,6,7-tetrahydro-indazol-1-yl]-acetic acid | 8.28 (t, 1 H), 8.05-8.00 (m, 3 H), 7.95 (d, 1 H), 7.91 (d, 2 H), 7.62 (t, 1 H), 6.67 (s, 1 H), 4.74 (s, 2 H), 4.38 (t, 1 H), 2.66 (s, 3 H), 2.54-2.40 (m, 2 H) 1.96-1.85 (m, 1 H), 1.82-1.67 (m, 3 H) | 454 | 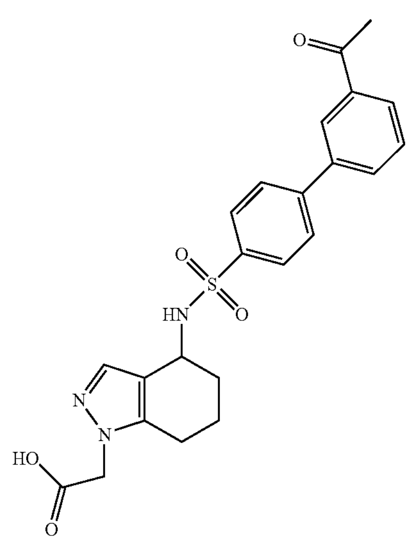 |

-continued

| Example No. | Systematic Name | ¹H NMR (400 MHz, CD₃OD) δ ppm | MS (ESI+, M + H) | Structure |
|---|---|---|---|---|
| 10-23a | [4-(3'-Nitro-biphenyl-4-sulfonylamino)-4,5,6,7-tetrahydro-indazol-1-yl]-acetic acid | 8.56 (t, 1 H), 8.28 (dd, 1 H), 8.13 (d, 1 H), 8.05 (d, 2 H), 7.95 (d, 2 H), 7.74 (t, 1 H), 6.69 (s, 1 H), 4.74 (s, 2 H), 4.39 (t, 1 H), 2.59-2.39 (m, 2 H), 1.99-1.87 (m, 1 H), 1.84-1.68 (m, 3 H) | 457 | 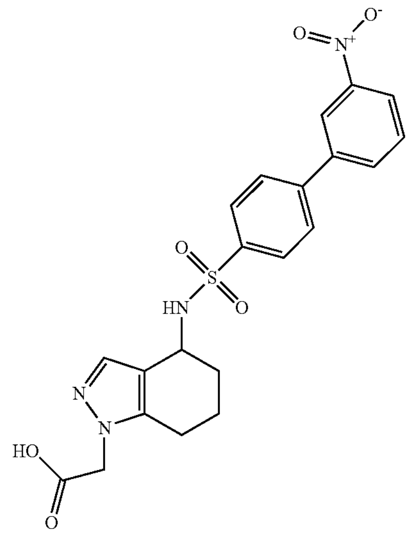 |
| 10-24a | [4-(3',5'-Bis-trifluoromethyl-biphenyl-4-sulfonylamino)-4,5,6,7-tetrahydro-indazol-1-yl]-acetic acid | 8.08-8.04 (m, 2 H), 8.01 (s, 1 H), 7.98-7.95 (m, 2 H), 6.68 (s, 1 H), 4.74 (s, 2 H), 4.40 (t, 1 H), 2.57-2.42 (m, 2 H), 1.96-1.86 (m, 1 H), 1.83-1.68 (m, 3 H) | 548 | 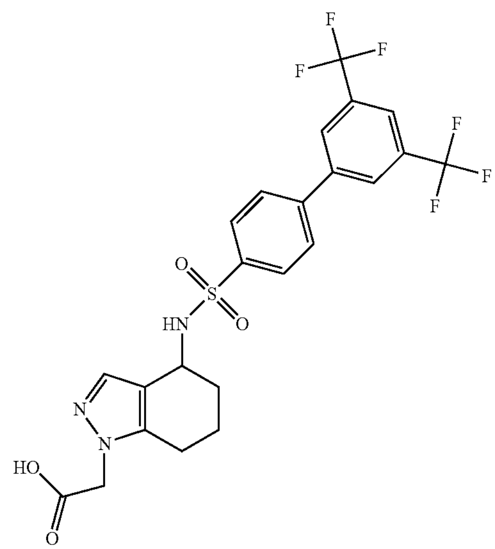 |
| 10-25a | [(R)-4-(3'-Trifluoromethyl-biphenyl-4-sulfonylamino)-4,5,6,7-tetrahydro-indazol-1-yl]-acetic acid | 8.05 (d, 2 H), 8.00 (d, 2 H), 7.95 (d, 2 H), 7.70 (m, 2 H), 6.9 (s, 1 H), 4.85 (s, 2 H), 4.48 (t, 1 H), 2.50 (m, 2 H), 1.75-2.00 (m, 4 H) | 480 | 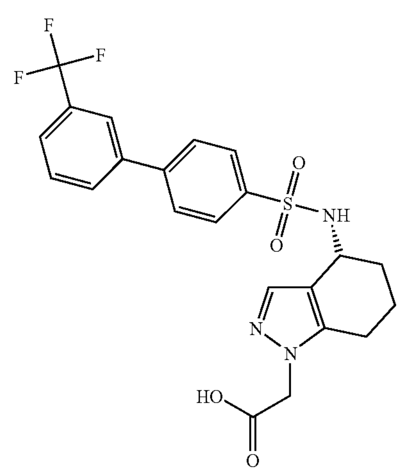 |

| Example No. | Systematic Name | ¹H NMR (400 MHz, CD₃OD) δ ppm | MS (ESI+, M + H) | Structure |
|---|---|---|---|---|
| 10-26a | [(R)-4-(3'-Trimethylsilanyl-biphenyl-4-sulfonylamino)-4,5,6,7-tetrahydro-indazol-1-yl]-acetic acid | 8.00 (d, 2 H), 7.84 (d, 2 H), 7.79 (s, 1 H), 7.65 (m, 1 H), 7.55 (m, 1 H), 7.45 (t, 1 H), 6.7 (s, 1 H), 4.75 (s, 2 H), 4.40 (t, 1 H), 2.50 (m, 2 H), 2.00-1.75 (m, 4 H), 0.30 (s, 9 H) | 484 | 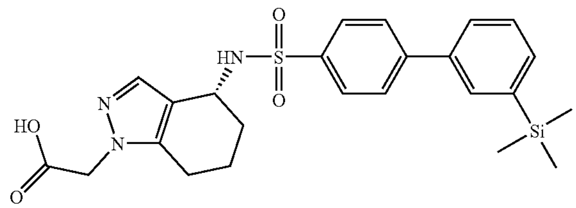 |
| 10-27a | [(R)-4-(3'-Isopropyl-biphenyl-4-sulfonylamino)-4,5,6,7-tetrahydro-indazol-1-yl]-acetic acid | 8.00 (d, 2 H), 7.84 (d, 2 H), 7.57 (s, 1 H), 7.50 (d, 1 H), 7.40 (t, 1 H), 7.30 (d, 1 H), 6.7 (s, 1 H), 4.75 (s, 2 H), 4.40 (t, 1 H), 3.0 (m, 1 H), 2.50 (m, 2 H), 2.00-1.75 (m, 4 H), 1.3 (d, 6 H) | 454 | 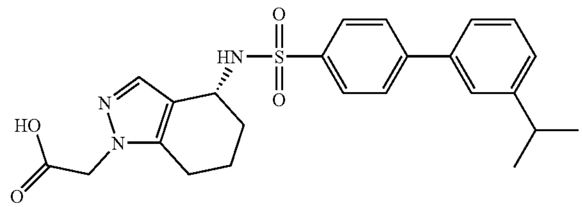 |
| 10-28a | [(R)-4-(3'-Methanesulfonyl-biphenyl-4-sulfonylamino)-4,5,6,7-tetrahydro-indazol-1-yl]-acetic acid | 8.26 (s, 1 H), 8.11-7.89 (m, 6 H), 7.77 (t, 1 H), 6.69 (s, 1 H), 4.71 (s, 2 H), 4.43 (s, 1 H), 3.21 (s, 3 H), 2.66-2.42 (m, 2 H), 2.00-1.92 (m, 1 H), 1.90-1.73 (m, 3 H) | 490 | 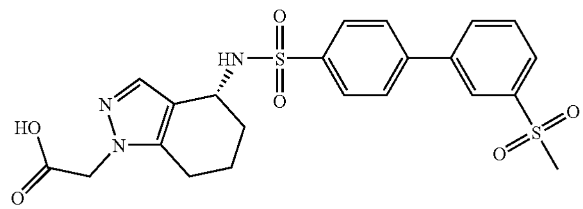 |
| 10-29a | [(R)-4-(3'-Methanesulfinyl-biphenyl-4-sulfonylamino)-4,5,6,7-tetrahydro-indazol-1-yl]-acetic acid | 8.08 (d, 3 H), 7.98 (d, 3 H), 7.83-7.74 (m, 2 H), 6.74 (s, 1 H), 4.78 (s, 2 H), 4.45 (s, 1 H), 2.91 (d, 3 H), 2.67-2.45 (m, 2 H), 2.03-1.93 (m, 1 H), 1.90-1.75 (m, 3 H) | 474 | 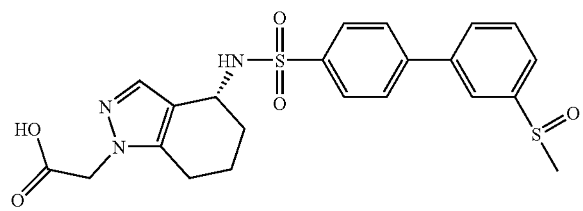 |
| 10-30a | 3-[4-(biphenyl-4-sulfonylamino)-4,5,6,7-tetrahydro-indazol-1-yl]-propionic acid | 7.98 (d, 2 H), 7.85 (d, 2 H), 7.72 (t, 2 H), 7.49 (t, 2 H), 7.41 (m, 1 H), 6.66 (s, 1 H), 4.36 (t, 1 H), 4.16 (t, 2 H), 2.75 (t, 2 H), 2.71-2.52 (m, 2 H), 1.96-1.76 (m, 4 H) | 426 | 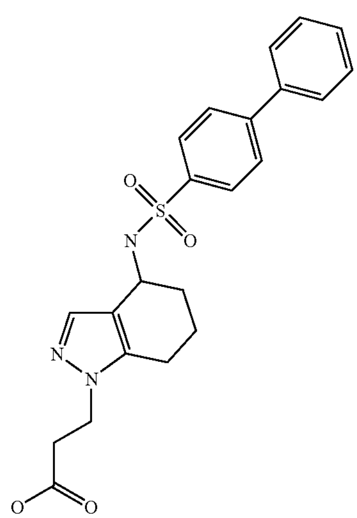 |

| Example No. | Systematic Name | $^1$H NMR (400 MHz, CD$_3$OD) δ ppm | MS (ESI+, M + H) | Structure |
|---|---|---|---|---|
| 10-31a | 3-[(R)-4-(3'-Trifluoromethyl-biphenyl-4-sulfonylamino)-4,5,6,7-tetrahydro-indazol-1-yl]-propionic acid | 8.06-8.01 (m, 4 H), 7.93 (d, 2 H), 7.74 (m, 2 H), 6.67 (s, 1 H), 4.37 (t, 1 H), 4.17 (t, 2 H), 2.86 (t, 2 H), 2.71-2.52 (m, 2 H), 1.99-1.71 (m, 4 H) | 494 | 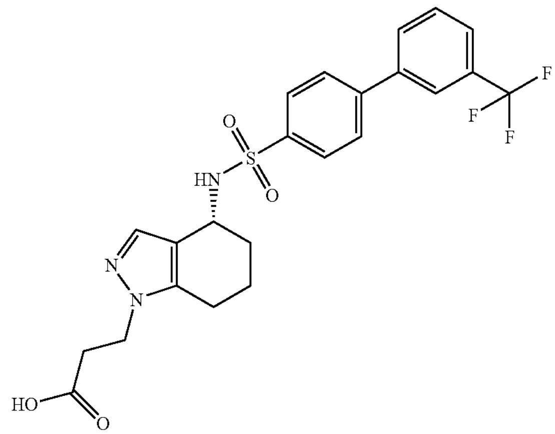 |

Example 11-1

{(R)-4-[Methyl-(3'-trifluoromethyl-biphenyl-4-sulfonyl)-amino]-4,5,6,7-tetrahydro-indazol-1-yl}-acetic acid ethyl ester

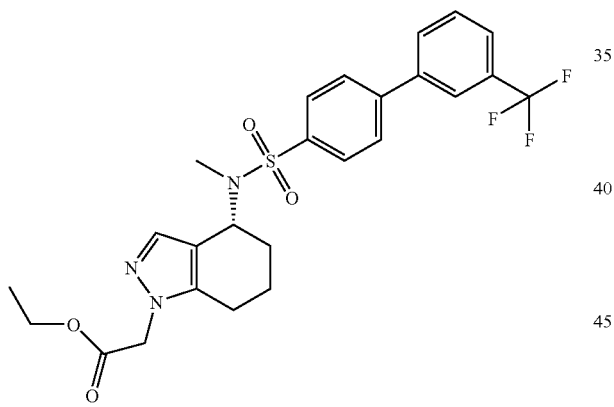

Starting with [(R)-4-(3'-trifluoromethyl-biphenyl-4-sulfonylamino)-4,5,6,7-tetrahydro-indazol-1-yl]-acetic acid ethyl ester (example 10-17) and methyl iodide, and using the method described for example 5-1, 1$^{st}$ step, {(R)-4-[methyl-(3'-trifluoromethyl-biphenyl-4-sulfonyl)-amino]-4,5,6,7-tetrahydro-indazol-1-yl}-acetic acid ethyl ester (7 mg, 40%) was prepared as a white solid. MS cald. for C$_{25}$H$_{26}$F$_3$N$_3$O$_4$S 521, obsd. (ESI$^+$) [(M+H)$^+$] 522.

Example 11-2

The following example 11-2 was prepared in an analogous manner as described for example 11-1 using 3-[(R)-4-(3'-trifluoromethyl-biphenyl-4-sulfonylamino)-4,5,6,7-tetrahydro-indazol-1-yl]-propionic acid methyl ester (example 10-30) and methyl iodide.

| Example No. | Systematic Name | MS (ESI+, M + H) | Structure |
|---|---|---|---|
| 11-2 | 3-{(R)-4-[Methyl-(3'-trifluoromethyl-biphenyl-4-sulfonyl)-amino]-4,5,6,7-tetrahydro-indazol-1-yl}-propionic acid methyl ester | 522 | 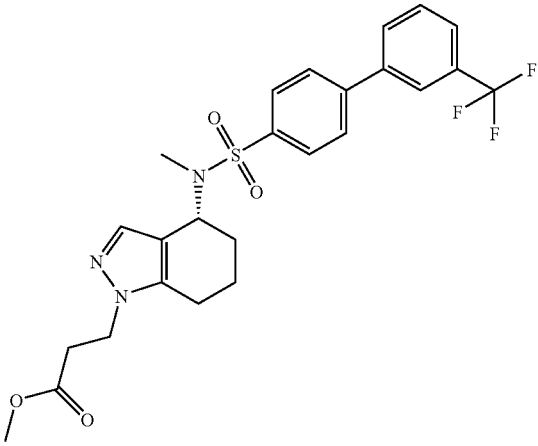 |

Example 11-1a

{(R)-4-[Methyl-(3'-trifluoromethyl-biphenyl-4-sulfonyl)-amino]-4,5,6,7-tetrahydro-indazol-1-yl}-acetic acid

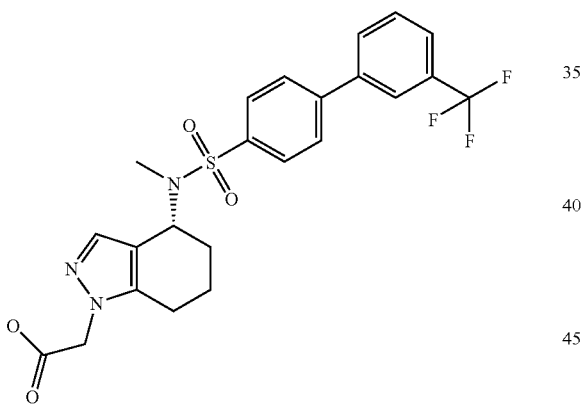

Starting with {(R)-4-[methyl-(3'-trifluoromethyl-biphenyl-4-sulfonyl)-amino]-4,5,6,7-tetrahydro-indazol-1-yl}-acetic acid ethyl ester, and using the method described for example 1-1a, {(R)-4-[methyl-(3'-trifluoro-methyl-biphenyl-4-sulfonyl)-amino]-4,5,6,7-tetrahydro-indazol-1-yl}-acetic acid (7 mg, 40%) was obtained as a white solid. $^1$H NMR (400 MHz, CD$_3$OD) δ ppm 8.07-7.93 (dd, 4 H), 8.02 (d, 2 H), 7.75 (m, 2 H), 6.43 (s, 1 H), 5.12 (q, 1 H), 4.75 (s, 2 H), 2.66 (s, 3 H), 2.66-2.45 (m, 4 H), 2.07-1.57 (m, 4 H). MS cald. for C$_{23}$H$_{22}$F$_3$N$_3$O$_4$S 493, obsd. (ESI$^+$) [(M+H)$^+$] 494.

Example 11-2a

The following examples 11-2a was prepared in an analogous manner as described for example 1-1a from the corresponding ester 11-2.

| Example No. | Systematic Name | ¹H NMR (400 MHz, CD₃OD) δ ppm | MS (ESI⁺, M + H) | Structure |
|---|---|---|---|---|
| 11-2a | 3-{(R)-4-[Methyl-(3'-trifluoromethyl-biphenyl-4-sulfonyl)-amino]-4,5,6,7-tetrahydro-indazol-1-yl}-propionic acid | 8.05-7.92 (m, 6 H), 7.76-7.68 (m, 2 H), 7.02 (s, 1 H), 5.12 (q, 1 H), 4.33 (s, 2 H), 2.86-2.75 (m, 4 H) 2.66 (s, 3 H) 1.85-1.58 (m, 4 H) | 508 | 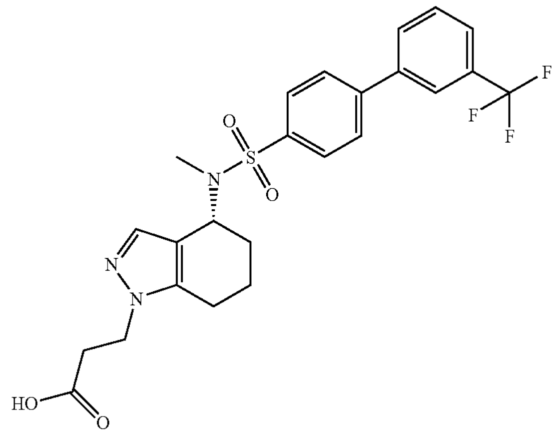 |

Example 12-1

{(R)-4-[(4'-Fluoro-5-trifluoromethyl-biphenyl-3-sulfonyl)-methyl-amino]-4,5,6,7-tetrahydro-indazol-1-yl}-acetic acid ethyl ester

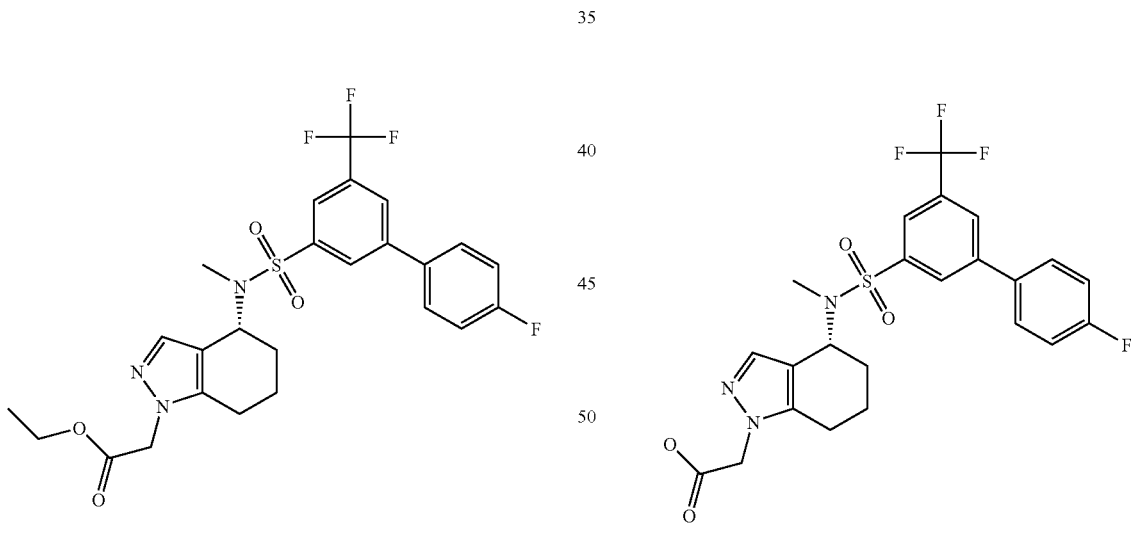

Starting with {(R)-4-[(3-bromo-5-trifluoromethyl-benzenesulfonyl)-methyl-amino]-4,5,6,7-tetrahydro-indazol-1-yl}-acetic acid ethyl ester (prepared by the method analogous to the one described for example 9-1, 1ˢᵗ step) and 4-fluorophenylboronic acid, using a method analogous to the one described for example 10-1, {(R)-4-[(4'-fluoro-5-trifluoromethyl-biphenyl-3-sulfonyl)-methyl-amino]-4,5,6,7-tetrahydro-indazol-1-yl}-acetic acid (5 mg, 42%) was obtained. MS cald. for $C_{25}H_{25}F_4N_3O_4S$ 539, obsd. (ESI⁺) [(M+H)⁺] 540.

Example 12-1a

{(R)-4-[(4'-Fluoro-5-trifluoromethyl-biphenyl-3-sulfonyl)-methyl-amino]-4,5,6,7-tetrahydro-indazol-1-yl}-acetic acid Starting with {(R)-4-[(4'-fluoro-5-trifluoromethyl-biphenyl-3-sulfonyl)-methyl-amino]-4,5,6,7-tetrahydro-indazol-1-yl}-acetic acid ethyl ester, and using the method described for example 1-1a, {(R)-4-[(4'-fluoro-5-trifluoromethyl-biphenyl-3-sulfonyl)-methyl-amino]-4,5,6,7-tetrahydro-indazol-1-yl}-acetic acid (5 mg, 42%) was obtained. ¹H NMR (400 MHz, CD₃OD) δ ppm 8.37 (s, 1 H), 8.24 (s, 1 H), 8.16 (d, 1 H), 7.80 (q, 2 H), 7.32 (t, 2 H), 6.54 (s, 1 H), 5.21 (t, 1 H), 4.82 (s, 2 H), 2.70 (s, 3 H), 2.70-2.51 (m, 2 H), 2.04-1.68 (m, 4 H). MS cald. for $C_{23}H_{21}F_4N_3O_4S$ 511, obsd. (ESI$^+$) [(M+H)$^+$] 512.

Example 13-1

((R)-4-{[3-(4-Chloro-benzenesulfonyl)-5-trifluoromethyl-benzenesulfonyl]-methyl-amino}-4,5,6,7-tetrahydro-indazol-1-yl)-acetic acid ethyl ester

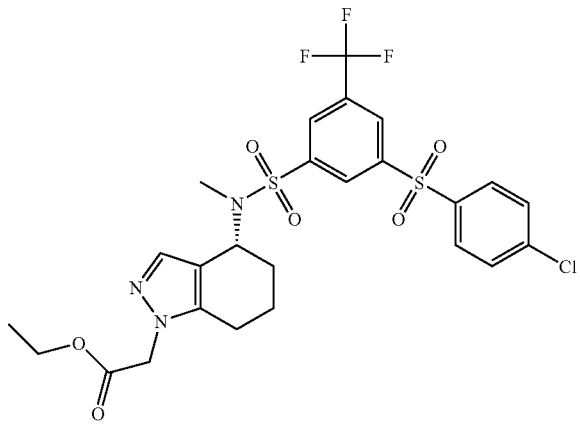

[(R)-4-(3-Fluoro-5-trifluoromethyl-benzenesulfonylamino)-4,5,6,7-tetrahydro-indazol-1-yl]-acetic acid ethyl ester

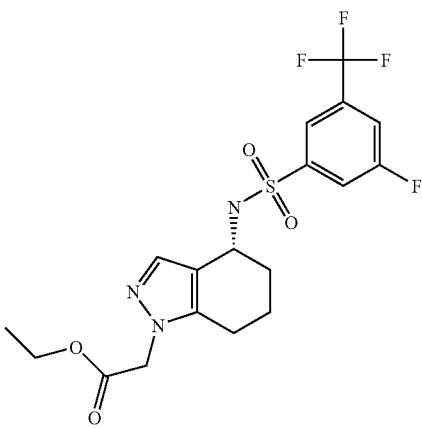

Starting with 3-((R)-4-amino-4,5,6,7-tetrahydro-indazol-1-yl)-acetic acid ethyl ester and 3-fluoro-5-trifluoromethyl-benzenesulfonyl chloride, and using the method described for example 1-1, [(R)-4-(3-fluoro-5-trifluoromethyl-benzenesulfonylamino)-4,5,6,7-tetrahydro-indazol-1-yl]-acetic acid ethyl ester (686 mg, 76.2%) was prepared as a white solid. MS cald. for $C_{18}H_{19}F_4N_3O_4S$ 449, obsd. (ESI$^+$) [(M+H)$^+$] 450.

{(R)-4-[(3-Fluoro-5-trifluoromethyl-benzenesulfonyl)-methyl-amino]-4,5,6,7-tetra-hydro-indazol-1-yl}-acetic acid ethyl ester

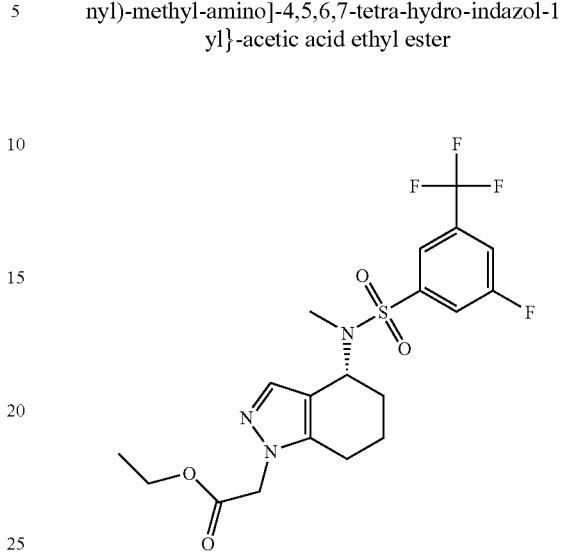

Starting with [(R)-4-(3-fluoro-5-trifluoromethyl-benzenesulfonylamino)-4,5,6,7-tetrahydro-indazol-1-yl]-acetic acid ethyl ester and methyl iodide, and using the method described for example 5-1, {(R)-4-[(3-fluoro-5-trifluoromethyl-benzenesulfonyl)-methyl-amino]-4,5,6,7-tetrahydro-indazol-1-yl}-acetic acid ethyl ester (500 mg, 94%) was prepared as a white solid. MS cald. for $C_{19}H_{21}F_4N_3O_4S$ 463, obsd. (ESI$^+$) [(M+H)$^+$] 464.

((R)-4-{[3-(4-Chloro-benzenesulfanyl)-5-trifluoromethyl-benzenesulfonyl]-methyl amino}-4,5,6,7-tetrahydro-indazol-1-yl)-acetic acid ethyl ester

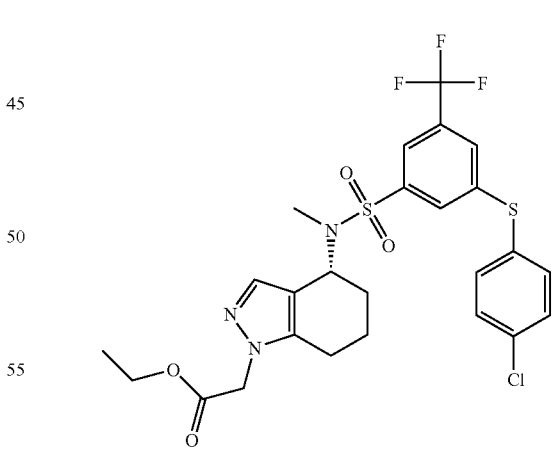

A mixture of [(R)-4-[(3-fluoro-5-trifluoromethyl-benzenesulfonylamino)-4,5,6,7-tetrahydro-indazol-1-yl]-acetic acid ethyl ester (45.0 mg, 0.10 mmol), 4-chloro-benzenethiol (50 μL), potassium carbonate (55.0 mg, 0.40 mmol) and N,N-dimethylformamide (1.0 mL) was heated in a microwave oven at 150° C. for 30 minutes. The resulting mixture was neutralized with 1N hydrochloric acid and extracted with ethyl acetate (20 mL×3). The combined organic layers were washed with brine (20 mL×3), dried over sodium sulfate, and concentrated to afford ((R)-4-{[3-(4-chloro-benzenesulfanyl)-5-trifluoromethyl-benzenesulfonyl]-methyl amino}-4,5,6,7-tetrahydro-indazol-1-yl)-acetic acid ethyl ester (41.9 mg, 71.2%) as a viscous oil, which was used for the next step without any further purification.

((R)-4-{[3-(4-Chloro-benzenesulfonyl)-5-trifluoromethyl-benzenesulfonyl]-methyl amino}-4,5,6,7-tetrahydro-indazol-1-yl)-acetic acid ethyl ester

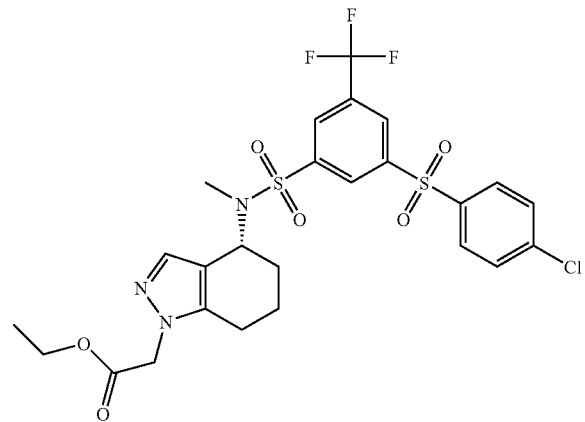

To a solution of ((R)-4-{[3-(4-chloro-benzenesulfanyl)-5-trifluoromethyl-benzenesulfonyl]-methyl amino}-4,5,6,7-tetrahydro-indazol-1-yl)-acetic acid ethyl ester (41.9 mg, 0.07 mmol) in dichloromethane was added 3-chloroperoxybenzoic acid (m-CPBA) (34.7 mg, 0.20 mmol) at 0° C. After being stirred at room temperature for 3 hours, the resulting mixture was concentrated and purified by column chromatography (5% methanol in dichloromethane) to afford ((R)-4-{[3-(4-chloro-phenylsulfonyl)-5-trifluoromethyl-benzenesulfonyl]-methyl amino}-4,5,6,7-tetrahydro-indazol-1-yl)-acetic acid ethyl ester (23.5 mg, 54.6%) as a semisolid. MS cald. for $C_{25}H_{25}ClF_3N_3O_6S_2$ 619, obsd. (ESI$^+$) [(M+H)$^+$] 620.

Examples 13-2 to 13-6

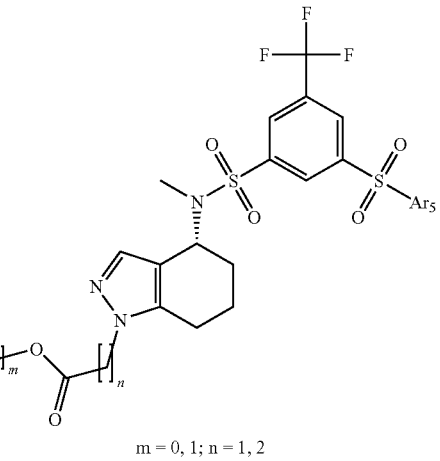

m = 0, 1; n = 1, 2

The following examples 13-2 to 13-6 were prepared in an analogous manner as described for example 13-1 using {(R)-4-[(3-fluoro-5-trifluoromethyl-benzenesulfonyl)-methyl-amino]-4,5,6,7-tetrahydro-indazol-1-yl}-acetic acid ethyl ester or {(R)-4-[(3-fluoro-5-trifluoromethyl-benzenesulfonyl)-methyl-amino]-4,5,6,7-tetrahydro-indazol-1-yl}-propionic acid methyl ester (prepared from 3-((R)-4-amino-4,5,6,7-tetrahydro-indazol-1-yl)-propionic acid and 3-fluoro-5-trifluoromethyl-benzenesulfonyl chloride using the method described for example 13-1, 1$^{st}$ and 2$^{nd}$ steps) and the appropriate commercially available substituted benzenethiols (Ar$_5$SH).

| Example No. | Systematic Name | MS (ESI+, M + H) | Structure |
|---|---|---|---|
| 13-2 | ((R)-4-{Methyl-[3-(toluene-4-sulfonyl)-5-trifluoromethyl-benzenesulfonyl]-amino}-4,5,6,7-tetrahydro-indazol-1-yl)-acetic acid ethyl ester | 600 | 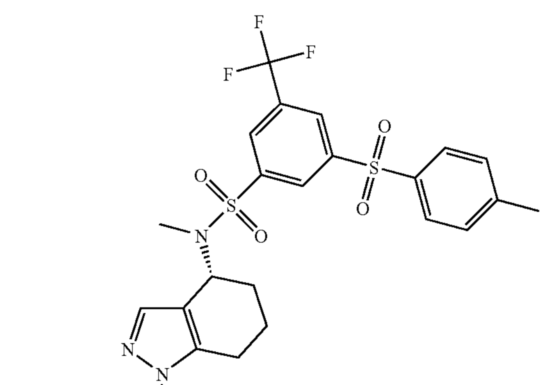 |

-continued

| Example No. | Systematic Name | MS (ESI+, M + H) | Structure |
|---|---|---|---|
| 13-3 | 3-((R)-4-{[3-(4-Fluoro-benzenesulfonyl)-5-trifluoromethyl-benzenesulfonyl]-methyl-amino}-4,5,6,7-tetrahydro-indazol-1-yl)-propionic acid methyl ester | 604 | 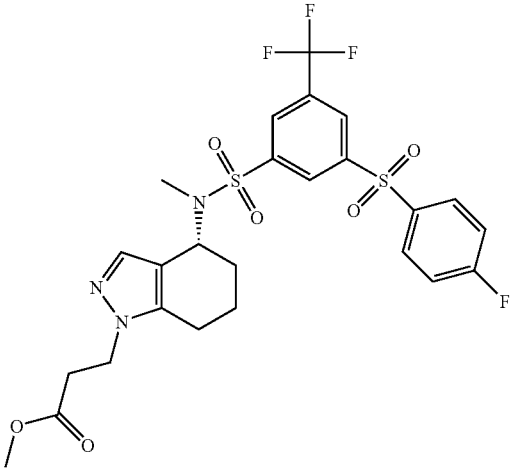 |
| 13-4 | 3-((R)-4-{[3-(4-Chloro-benzenesulfonyl)-5-trifluoromethyl-benzenesulfonyl]-methyl-amino}-4,5,6,7-tetrahydro-indazol-1-yl)-propionic acid methyl ester | 620 | 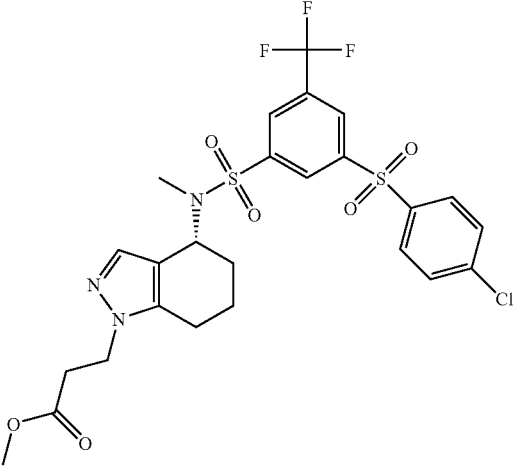 |
| 13-5 | 3-((R)-4-{[3-(4-Methoxy-benzenesulfonyl)-5-trifluoromethyl-benzenesulfonyl]-methyl-amino}-4,5,6,7-tetrahydro-indazol-1-yl)-propionic acid methyl ester | 616 | 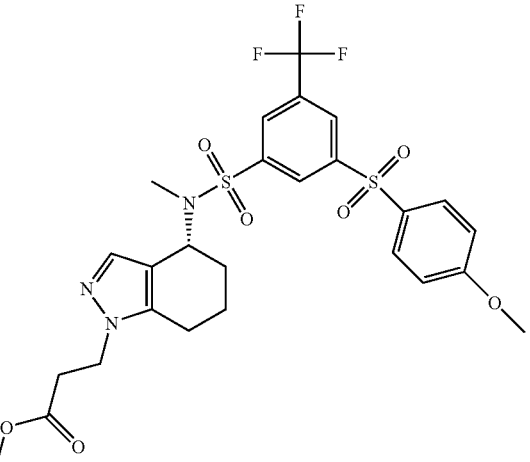 |

| Example No. | Systematic Name | MS (ESI+, M + H) | Structure |
|---|---|---|---|
| 13-6 | 3-((R)-4-{Methyl-[3-(toluene-4-sulfonyl)-5-trifluoromethyl-benzenesulfonyl]-amino}-4,5,6,7-tetrahydro-indazol-1-yl)-propionic acid methyl ester | 600 | 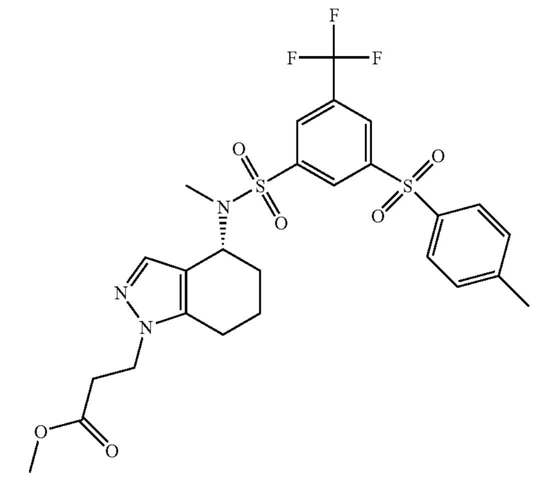 |

Example 13-1a ((R)-4-{[3-(4-Chloro-benzenesulfonyl)-5-trifluoromethyl-benzenesulfonyl]-methyl amino}-4,5,6,7-tetrahydro-indazol-1-yl)-acetic acid Starting from ((R)-4-{[3-(4-chloro-benzenesulfonyl)-5-trifluoromethyl-benzenesulfonyl]-methyl-amino}-4,5,6,7-tetrahydro-indazol-1-yl)-acetic acid ethyl ester, and using the method described for example 1-1a, ((R)-4-{[3-(4-chloro-benzenesulfonyl)-5-trifluoromethyl-benzenesulfonyl]-methyl amino}-4,5,6,7-tetrahydro-indazol-1-yl)-acetic acid (10 mg, 44.4%) was obtained as a white solid. $^1$H NMR (400 MHz, CD$_3$OD) δ ppm 8.62 (s, 1 H), 8.58 (s, 1 H), 8.45 (s, 1 H), 8.07-7.62 (dd, 4 H), 6.31 (s, 1 H), 5.12 (q, 1 H), 4.89 (s, 2 H), 2.63 (s, 3 H), 2.60 (m, 2 H), 1.98-1.58 (m, 4 H). MS cald. for C$_{23}$H$_{21}$ClF$_3$N$_3$O$_6$S$_2$ 591, obsd. (ESI$^+$) [(M+H)$^+$] 592.

Example 13-2a to 13-6a

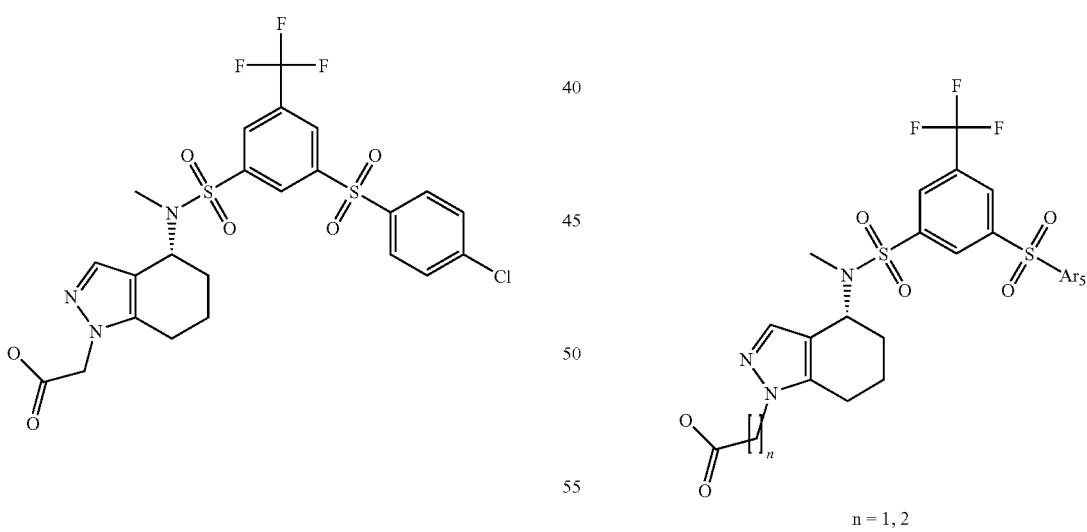

n = 1, 2

The following examples 13-2a to 13-6a were prepared in an analogous manner as described for example 1-1a from the corresponding esters 13-2 to 13-6.

| Example No. | Systematic Name | ¹H NMR (400 MHz, CD₃OD) δ ppm | MS (ESI+, M + H) | Structure |
|---|---|---|---|---|
| 13-2a | ((R)-4-{Methyl-[3-(toluene-4-sulfonyl)-5-trifluoromethyl-benzenesulfonyl]-amino}-4,5,6,7-tetrahydro-indazol-1-yl)-acetic acid | 8.52 (s, 1 H), 8.47 (s, 1 H), 8.37 (s, 1 H), 7.90-7.39 (dd, 4 H), 6.41 (s, 1 H), 5.07 (q, 1 H), 4.69 (s, 2 H), 2.65 (s, 3 H), 2.58 (m, 2 H), 2.38 (s, 3 H), 1.98-1.58 (m, 4 H) | 572 | 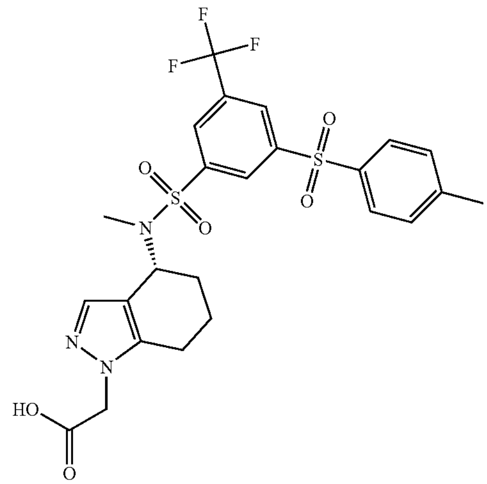 |
| 13-3a | 3-((R)-4-{[3-(4-Fluoro-benzenesulfonyl)-5-trifluoromethyl-benzenesulfonyl]-methyl-amino}-4,5,6,7-tetrahydro-indazol-1-yl)-propionic acid | 8.61 (s, 1 H), 8.58 (s, 1 H), 8.43 (s, 1 H), 8.15 (m, 2 H), 7.38 (t, 2 H), 6.34 (s, 1 H), 5.09 (q, 1 H), 4.23 (s, 2 H), 2.81 (t, 2 H), 2.64 (m, 2 H), 2.58 (s, 3 H), 2.02-1.58 (m, 4 H) | 590 | 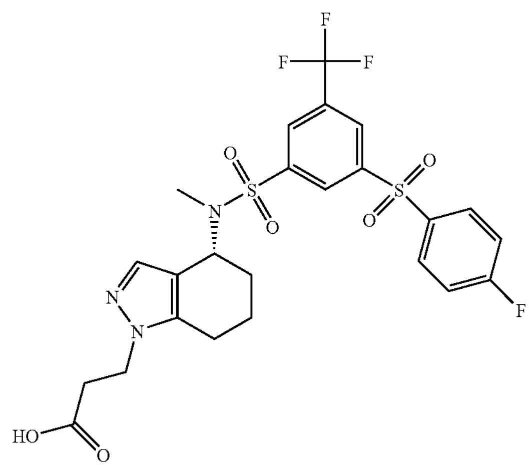 |
| 13-4a | 3-((R)-4-{[3-(4-Chloro-benzenesulfonyl)-5-trifluoromethyl-benzenesulfonyl]-methyl-amino}-4,5,6,7-tetrahydro-indazol-1-yl)-propionic acid | 8.61 (s, 1 H), 8.58 (s, 1 H), 8.44 (s, 1 H), 8.08-7.63 (dd, 4 H), 6.31 (s, 1 H), 5.09 (q, 1 H), 4.23 (s, 2 H), 2.81 (t, 2 H), 2.64 (m, 2 H), 2.57 (s, 3 H), 2.02-1.65 (m, 4 H) | 606 | 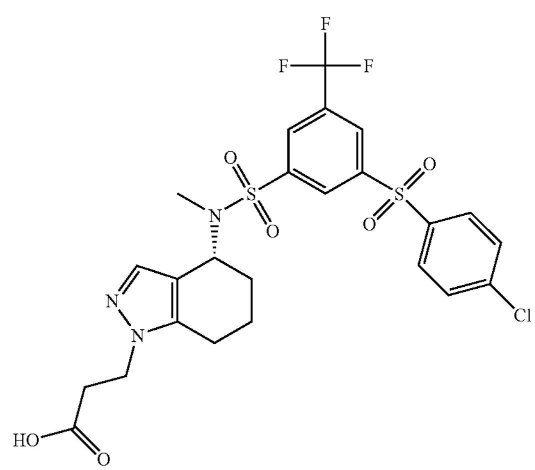 |

-continued

| Example No. | Systematic Name | ¹H NMR (400 MHz, CD₃OD) δ ppm | MS (ESI+, M + H) | Structure |
|---|---|---|---|---|
| 13-5a | 3-((R)-4-{[3-(4-Methoxy-benzenesulfonyl)-5-trifluoromethyl-benzenesulfonyl]-methyl-amino}-4,5,6,7-tetrahydro-indazol-1-yl)-propionic acid | 8.55 (s, 1 H), 8.51 (s, 1 H), 8.39 (s, 1 H), 7.99 (d, J = 8.84 Hz, 2 H), 7.13 (d, J = 8.84 Hz, 2 H), 6.41 (s, 1 H), 5.11-5.04 (m, 1 H), 4.21 (t, J = 6.69 Hz, 2 H), 3.90 (s, 3 H), 2.81 (t, J = 6.69 Hz, 2 H), 2.74-2.52 (m, 5 H), 2.03-1.65 (m, 4 H) | 602 | 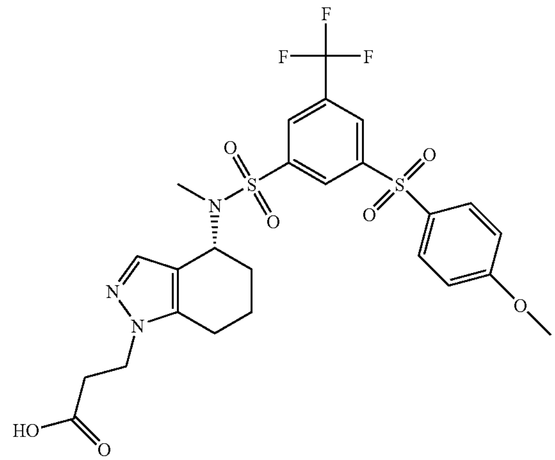 |
| 13-6a | 3-((R)-4-{Methyl-[3-(toluene-4-sulfonyl)-5-trifluoromethyl-benzenesulfonyl]-amino}-4,5,6,7-tetrahydro-indazol-1-yl)-propionic acid | 8.56 (s, 1 H), 8.52 (s, 1 H), 8.40 (s, 1 H), 7.94 (d, J = 8.34 Hz, 2 H), 7.46 (d, J = 8.08 Hz, 2 H), 6.49 (s, 1 H), 5.12-5.04 (m, 1 H), 4.22 (t, J = 6.69 Hz, 2 H), 2.83 (t, 2 H) 2.74-2.58 (m, 5 H), 2.44 (s, 3 H), 2.02-1.94 (m, 1H), 1.79-1.65 (m, 2 H), 1.62-1.55 (m, 1 H) | 586 | 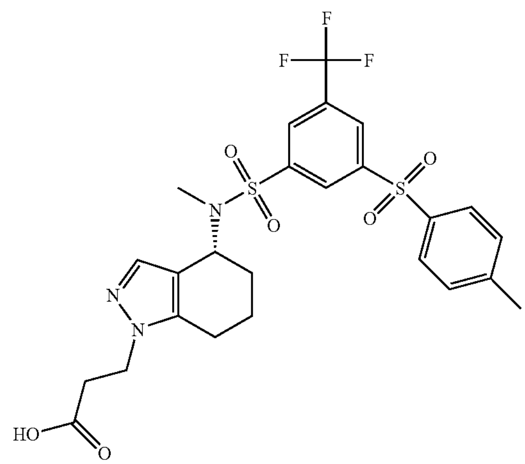 |

Example 14-1

[4-(3-Benzoylamino-benzenesulfonylamino)-4,5,6,7-tetrahydro-indazol-1-yl]-acetic acid ethyl ester

[4-(3-Nitro-benzenesulfonylamino)-4,5,6,7-tetrahydro-indazol-1-yl]-acetic acid ethyl ester

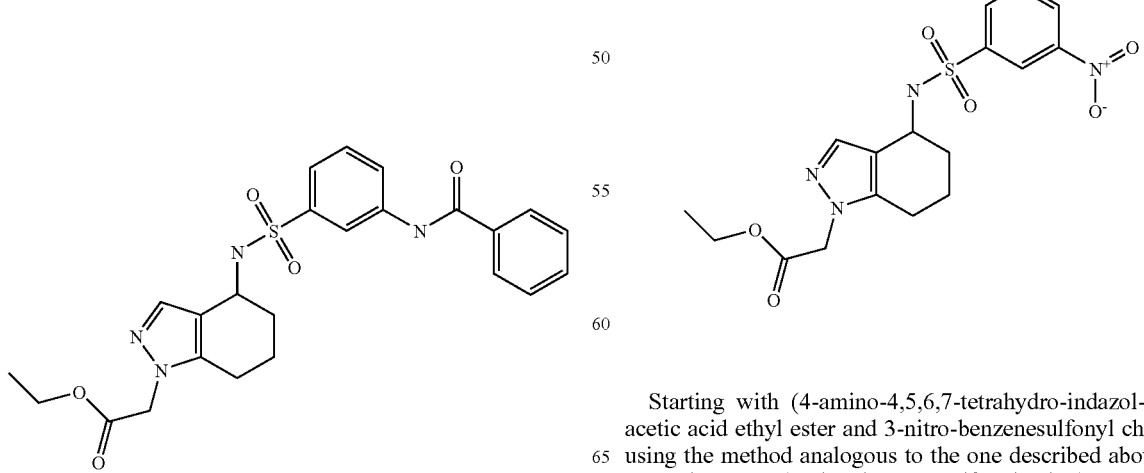

Starting with (4-amino-4,5,6,7-tetrahydro-indazol-1-yl)-acetic acid ethyl ester and 3-nitro-benzenesulfonyl chloride using the method analogous to the one described above for example 1-1, [4-(3-nitro-benzenesulfonylamino)-4,5,6,7-tetrahydro-indazol-1-yl]-acetic acid ethyl ester (519 mg, 63.6%) was obtained as a white solid. MS calcd. for $C_{17}H_{20}N_4O_6S$ 408, obsd. (ESI+) [(M+H)+] 409.

[4-(3-Amino-benzenesulfonylamino)-4,5,6,7-tetrahydro-indazol-1-yl]-acetic acid ethyl ester

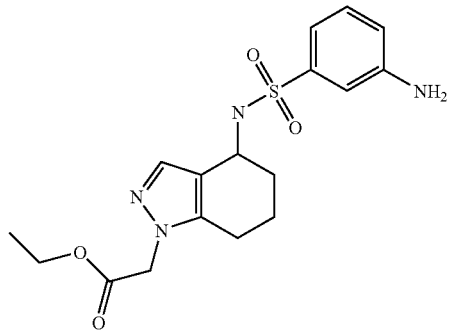

To a solution of [4-(3-nitro-benzenesulfonylamino)-4,5,6,7-tetrahydro-indazol-1-yl]-acetic acid ethyl ester (390 mg, 0.96 mmol) in acetic acid (3 mL) and ethanol (15 mL) was added zinc powder portionwise. After being heated at reflux for 2 hours, the mixture was cooled to room temperature, diluted with dichloromethane (30 mL) and filtered through a glass funnel and concentrated in vacuo. The residue was purified by flash column (gradient elution, 0-5% methanol in dichloromethane) to afford [4-(3-amino-benzenesulfonylamino)-4,5,6,7-tetrahydro-indazol-1-yl]-acetic acid ethyl ester (300 mg, 83%) as a semisolid. MS calcd. for $C_{17}H_{22}N_4O_4S$ 378, obsd. (ESI+) [(M+H)+] 379.

[4-(3-Benzoylamino-benzenesulfonylamino)-4,5,6,7-tetrahydro-indazol-1-yl]-acetic acid ethyl ester

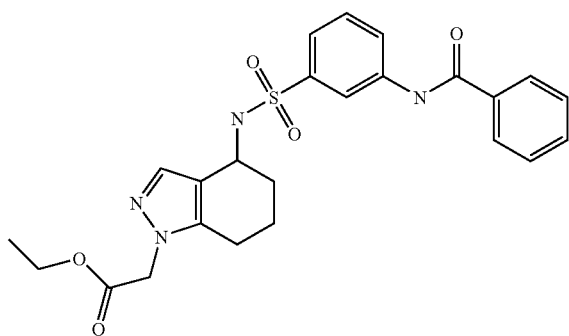

To a solution of [4-(3-amino-benzenesulfonylamino)-4,5,6,7-tetrahydro-indazol-1-yl]-acetic acid ethyl ester (30 mg, 0.079 mmol) and benzoyl chloride (16.4 mg, 0.119 mmol) in tetrahydrofuran (3 mL) was added triethylamine (16 mg, 0.158 mmol) at 0° C. After being stirred at room temperature overnight, the mixture was concentrated in vacuo. The residue was purified by flash column (gradient elution, 0-5% methanol in dichloromethane) to afford [4-(3-benzoylamino-benzenesulfonylamino)-4,5,6,7-tetrahydro-indazol-1-yl]- acetic acid ethyl ester (27.4 mg, 72%) as a white solid. MS calcd. for $C_{24}H_{26}N_4O_5S$ 482, obsd. (ESI+) [(M+H)+] 483.

Example 14-1a

[4-(3-Benzoylamino-benzenesulfonylamino)-4,5,6,7-tetrahydro-indazol-1-yl]-acetic acid

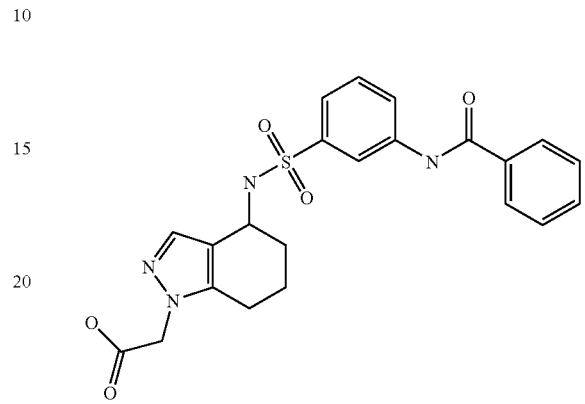

Starting with [4-(3-benzoylamino-benzenesulfonylamino)-4,5,6,7-tetrahydro-indazol-1-yl]-acetic acid ethyl ester using the method analogous to the one described for example 1-1a, [4-(3-benzoylamino-benzenesulfonylamino)-6,7-dihydro-indazol-1-yl]-acetic acid (11.0 mg, 50%) as a white solid. $^1$H NMR (400 MHz, CD$_3$OD) δ ppm 8.48 (s, 1 H), 7.98 (m, 3 H), 7.73-7.52 (m, 5 H), 6.79 (s, 1 H), 4.78 (s, 2 H), 4.42 (s, 1 H), 2.55 (m, 2 H), 2.04-1.77 (m, 4 H). MS calcd. for $C_{22}H_{22}N_4O_5S$ 454, obsd. (ESI+) [(M+H)+] 455.

Example 15-1

[4-(3-Benzenesulfonylamino-benzenesulfonylamino)-4,5,6,7-tetrahydro-indazol-1-yl]-acetic acid ethyl ester

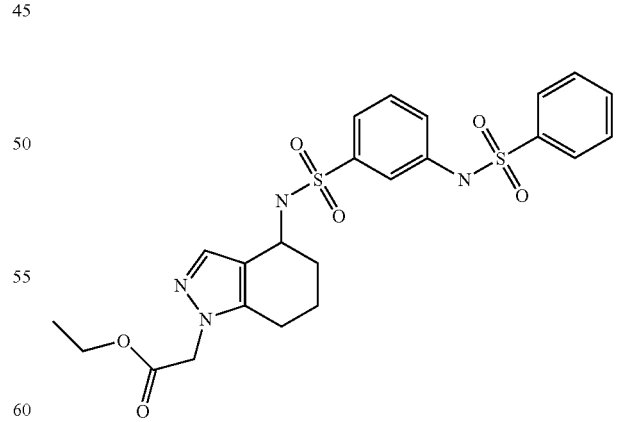

Stating with [4-(3-amino-benzenesulfonylamino)-4,5,6,7-tetrahydro-indazol-1-yl]-acetic acid ethyl ester and benzenesulfonyl chloride, and using the method analogous to the one described for example 14-1, [4-(3-benzenesulfonylamino-benzene-sulfonyl-amino)-4,5,6,7-tetrahydro-indazol-1-yl]- acetic acid ethyl ester (15 mg, 70%) was obtained as a white solid. MS cald. for $C_{23}H_{26}N_4O_6S_2$ 518, obsd. (ESI$^+$) [(M+H)$^+$]:519.

Example 15-1a

[4-(3-Benzenesulfonylamino-benzenesulfonylamino)-4,5,6,7-tetrahydro-indazol-1-yl]-acetic acid

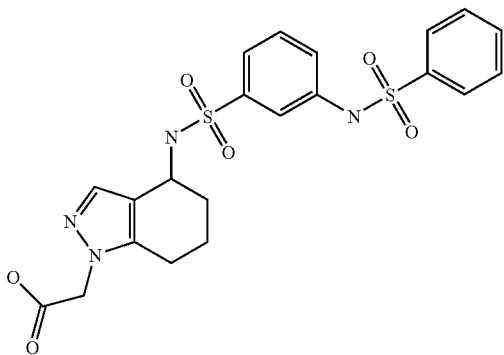

Starting from [4-(3-benzenesulfonylamino-benzenesulfonylamino)-4,5,6,7-dihydro-indazol-1-yl]-acetic acid ethyl ester, and using the method analogous to the one described for example 1-1a, [4-(3-benzenesulfonylamino-benzene-sulfonyl-amino)-4,5,6,7-tetrahydro-indazol-1-yl]-acetic acid (10 mg, 50%) was obtained as a white solid. $^1$H NMR (400 MHz, CD$_3$OD) δ ppm 7.77 (d, 2 H), 7.70 (s, 1 H), 7.58-7.32 (m, 6 H), 6.45 (s, 1 H), 4.78 (s, 2 H), 4.13 (s, 1 H), 2.55 (m, 2 H), 1.87-1.63 (m, 4 H). MS cald. for $C_{21}H_{22}N_4O_6S_2$ 490, obsd. (ESI$^+$) [(M+H)$^+$] 491.

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 µg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA Lonza Inc.), and suspended in PBS containing 10 mM MgCl$_2$ and 0.06% BSA (bovine serum albumin) at $1.5 \times 10^6$ cells/mL.

The binding reactions (0.2 mL) were performed in 96-well plates at room temperature in PBS containing $1.5 \times 10^5$ cells, 10 mM MgCl$_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 µL of Microscint™ 20 scintillation fluid (from PerkinElmer, Inc.) to each well of the filter plates. The radioactivity from non-specific binding was determined by replacing compound with 10 µM of 15(R)-15-methyl PGD$_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The IC$_{50}$ value is defined as the concentration of the tested compound that is required for 50% inhibition of total specific binding. In order to calculate the IC$_{50}$ value, the percent inhibition data were determined for 7 concentrations for each compound. The percent inhibition for a compound at each concentration was calculated according to the following formula, [1-(specific binding in the presence of compound)/(total specific binding)]×100. The IC$_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B-A)/(1+((C/x)^D)))$].

All the compounds of the foregoing examples were tested using the above Human CRTH2 Receptor Binding Assay (examples 1-1 to 8-2). The results of the assay showed that all of these compounds have binding activity exhibiting IC$_{50}$ values ranging from 0.0021 µM to 0.4747 µM. For instance, the following table shows the specific IC$_{50}$ values for these compounds:

| Example No. | Human CRTH2 Binding IC$_{50}$ (µM) |
|---|---|
| Example 1-1a | 0.0277 |
| Example 1-2a | 0.0936 |
| Example 1-3a | 0.1994 |
| Example 1-4a | 0.2439 |
| Example 1-5a | 0.1639 |
| Example 1-6a | 0.4747 |
| Example 2-1a | 0.0072 |
| Example 2-2a | 0.0311 |
| Example 2-3a | 0.0194 |
| Example 2-4a | 0.0103 |
| Example 2-5a | 0.1007 |
| Example 2-6a | 0.0264 |
| Example 2-7a | 0.3930 |
| Example 2-8a | 0.0078 |
| Example 2-9a | 0.0084 |
| Example 2-10a | 0.1961 |
| Example 2-11a | 0.0182 |

| Example No. | Human CRTH2 Binding IC$_{50}$ (µM) |
|---|---|
| Example 2-12a | 0.0303 |
| Example 3-1a | 0.0349 |
| Example 4-1a | 0.1582 |
| Example 5-1a | 0.0146 |
| Example 5-2a | 0.2019 |
| Example 5-3a | 0.0606 |
| Example 5-4a | 0.0359 |
| Example 5-5a | 0.0069 |
| Example 5-6a | 0.0529 |
| Example 5-7a | 0.0530 |
| Example 6-1a | 0.0040 |
| Example 6-2a | 0.0066 |
| Example 6-3a | 0.0265 |
| Example 6-4a | 0.0046 |
| Example 6-5a | 0.0049 |
| Example 6-6a | 0.0068 |
| Example 6-7a | 0.0062 |
| Example 6-8a | 0.0119 |
| Example 6-9a | 0.0071 |
| Example 6-10a | 0.0187 |
| Example 6-11a | 0.0088 |
| Example 6-12a | 0.0084 |
| Example 6-13a | 0.0065 |
| Example 6-14a | 0.0082 |
| Example 7-1a | 0.0121 |
| Example 8-1a | 0.0145 |
| Example 9-1a | 0.0055 |
| Example 9-2a | 0.0122 |
| Example 9-3a | 0.0111 |
| Example 9-4a | 0.0371 |
| Example 9-5a | 0.0082 |
| Example 9-6a | 0.0217 |
| Example 9-7a | 0.0126 |
| Example 9-8a | 0.0914 |
| Example 9-9a | 0.0700 |
| Example 9-10a | 0.0972 |
| Example 9-11a | 0.0072 |
| Example 9-12a | 0.0074 |
| Example 9-13a | 0.0095 |
| Example 9-14a | 0.0044 |
| Example 9-15a | 0.0103 |
| Example 9-16a | 0.0080 |
| Example 9-17a | 0.0129 |
| Example 9-18a | 0.0134 |
| Example 9-19a | 0.0114 |
| Example 9-20a | 0.0102 |
| Example 9-21a | 0.0132 |
| Example 9-22a | 0.0242 |
| Example 9-23a | 0.0067 |
| Example 9-24a | 0.0165 |
| Example 9-25a | 0.0209 |
| Example 9-26a | 0.0237 |
| Example 9-27a | 0.0491 |
| Example 9-28a | 0.0118 |
| Example 9-29a | 0.1507 |
| Example 9-30a | 0.0377 |
| Example 9-31a | 0.0068 |
| Example 9-32a | 0.0076 |
| Example 9-33a | 0.0106 |
| Example 9-34a | 0.0046 |
| Example 9-35a | 0.0171 |
| Example 9-36a | 0.0231 |
| Example 9-37a | 0.0148 |
| Example 9-38a | 0.0080 |
| Example 9-39a | 0.0104 |
| Example 9-40a | 0.0079 |
| Example 9-41a | 0.0075 |
| Example 9-42a | 0.0226 |
| Example 10-1a | 0.2146 |
| Example 10-2a | 0.3710 |
| Example 10-3a | 0.1939 |
| Example 10-4a | 0.2568 |
| Example 10-5a | 0.3688 |
| Example 10-6a | 0.2065 |
| Example 10-7a | 0.3000 |
| Example 10-8a | 0.4121 |
| Example 10-9a | 0.0716 |
| Example 10-10a | 0.3700 |
| Example 10-11a | 0.3206 |
| Example 10-12a | 0.3108 |
| Example 10-13a | 0.1526 |
| Example 10-14a | 0.0581 |
| Example 10-15a | 0.4656 |
| Example 10-16a | 0.0661 |
| Example 10-17a | 0.2619 |
| Example 10-18a | 0.1880 |
| Example 10-19a | 0.2672 |
| Example 10-20a | 0.2716 |
| Example 10-21a | 0.1195 |
| Example 10-22a | 0.1518 |
| Example 10-23a | 0.2384 |
| Example 10-24a | 0.0975 |
| Example 10-25a | 0.0131 |
| Example 10-26a | 0.0021 |
| Example 10-27a | 0.0051 |
| Example 10-28a | 0.0066 |
| Example 10-29a | 0.0275 |
| Example 10-30a | 0.0056 |
| Example 10-31a | 0.0056 |
| Example 11-1a | 0.0073 |
| Example 11-2a | 0.0807 |
| Example 12-1a | 0.1298 |
| Example 13-1a | 0.0029 |
| Example 13-2a | 0.0027 |
| Example 13-3a | 0.0040 |
| Example 13-4a | 0.0025 |
| Example 13-5a | 0.0058 |
| Example 13-6a | 0.0078 |
| Example 14-1a | 0.3556 |
| Example 15-1a | 0.3597 |

Calcium Flux Assay Using Fluorometric Imaging Plate Reader

Cell Culture Conditions:

CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin D$_2$ (DK-PDG$_2$) (ligand) in the Ca$^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to 2.5×10$^5$ cells/mL with complete growth media. Aliquots of 50 µL were dispensed into BD Falcon™ 384 well black/clear microplates (from BD Biosciences, a division of Becton, Dickinson and Company) and the microplates were placed in a 37° C. CO$_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2- hydroxyethyl)-1-piperazineethanesulfonic acid) and 2.5 mM probenecid. Growth media was removed from the cell plates and 25 µL of Hank's Balanced Salt Solution (HBSS) containing 20 mM HEPES, 0.05% BSA and 2.5 mM probenecid was added to each well followed by 25 µL of diluted dye using a Multidrop dispenser. The plates were then incubated for 1 hour at 37° C.

During the incubation, test compound plates were prepared by adding 90 µL of HBSS/20 mM HEPES/0.005% BSA buffer to the 2 µL of serial diluted compounds. To prepare serial diluted compounds, 20 mM stocks of compounds were dissolved in 100% DMSO. The compound dilution plate was set up as follows: well #1 received 5 µL of compound plus 10 µL of DMSO. Wells 2-10 received 10 µL of DMSO. 5 µL was mixed and transferred from well #1 into well #2. 1:3 serial dilutions were continued out 10 steps. 2 µL of diluted compound was transferred into duplicate wells of a 384 well "assay plate" and then 90 µL of buffer was added.

After incubation, both the cell and "assay plate" plates were brought to the fluorometric imaging plate reader (FLIPR®) and 20 µL of the diluted compounds were transferred to the cell plates by the FLIPR®. Plates were then incubated for 1 hour at room temperature. After the 1 hour incubation, plates were returned to the FLIPR® and 20 µL of 4.5× concentrated ligand was added to the cell plates. During the assay, fluorescence readings were taken simultaneously from all 384 wells of the cell plate every 1.5 seconds. Five readings were taken to establish a stable baseline, then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^{\wedge}D)))$].

Representative compounds tested in the binding assay were tested using the above FLIPR® assay. The results of the FLIPR® assay showed that all of the representative compounds tested in this assay have activity exhibiting $IC_{50}$ values ranging from 0.0006 µM to 25.44 µM.

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM DK-PGD$_2$ for 4 hrs at 37° C. in 200 µL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^{\wedge}D)))$].

Representative compounds tested in the binding assay were tested using the foregoing DK-PGD$_2$-induced IL-13 production assay. The results of the DK-PGD$_2$-induced IL-13 production assay showed that all of the representative compounds tested in this assay have activity in inhibiting IL-13 production, exhibiting $IC_{50}$ values ranging from 0.0021 µM to 10 µM.

Thus, the compounds of the present invention possess a specific, substantial and credible utility since the compounds tested show some activity in at least one of the above three assays (i.e., binding at the CRTH2 receptor), and therefore may be useful as antagonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic rhinitis, allergic inflammation, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phoshodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

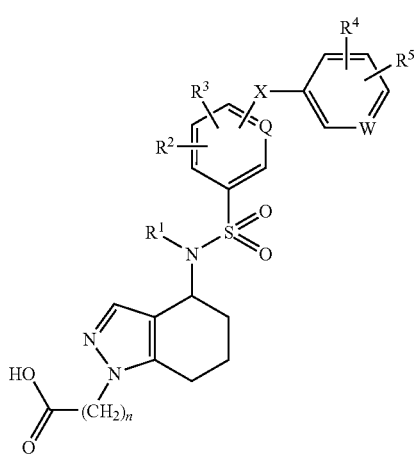

I or a pharmaceutically acceptable salt or ester thereof; wherein:
X is a direct bond, oxygen, or —S(O)$_2$—; and X is bonded to the ring containing Q by substitution of a hydrogen atom of a ring carbon atom;
Q is carbon and W is carbon or nitrogen with the proviso that when W is nitrogen, the nitrogen is unsubstituted;
R$^1$ is hydrogen or methyl;
R$^2$ and R$^3$ are bonded to the ring containing Q by substitution of a hydrogen atom of a ring carbon atom; and R$^2$ and R$^3$, independently of each other, are selected from the group consisting of:
  (1) hydrogen;
  (2) halogen;
  (3) lower alkyl optionally substituted by halogen; and
  (4) lower cycloalkyl optionally substituted by lower alkyl;
R$^4$ and R$^5$ are bonded to the ring containing W by substitution of a hydrogen atom of a ring carbon atom; and R$^4$ and R$^5$, independently of each other, are selected from the group consisting of:
  (1) hydrogen;
  (2) hydroxyl;
  (3) halogen;
  (4) nitro;
  (5) cyano;
  (6) lower alkyl optionally substituted by halogen;
  (7) lower alkoxy optionally substituted by halogen;
  (8) lower cycloalkoxy;
  (9) lower heterocycloalkyloxy;
  (10) lower alkanoyl;
  (11) carbamoyl, lower alkylaminocarbonyl, or lower dialkylaminocarbonyl;
  (12) lower alkylcarbonylamino;
  (13) lower alkylsulfanyl or lower cycloalkylsulfanyl
  (14) lower alkylsulfinyl or lower cycloalkylsulfinyl;
  (15) lower alkylsulfonyl or lower cycloalkylsulfonyl; and
  (16) trimethylsilyl; and
n is 1 or 2.
2. A compound of claim 1 which is an (R)-enantiomer.
3. A compound of claim 1 wherein W is carbon.
4. A compound of claim 1 wherein W is nitrogen.
5. A compound of claim 1 wherein X is a direct bond.
6. A compound of claim 1 wherein X is —S(O)$_2$—.
7. A compound of claim 1 wherein X is oxygen.
8. A compound of claim 1 wherein R$^1$ is hydrogen.
9. A compound of claim 1 wherein R$^1$ is methyl.
10. A compound of claim 1 wherein R$^2$ and R$^3$, independently of each other, are selected from the group consisting of:
  (1) hydrogen;
  (2) halogen; and
  (3) lower alkyl optionally substituted by halogen.
11. A compound of claim 1 wherein R$^2$ and R$^3$, independently of each other, are selected from the group consisting of:
  (1) hydrogen;
  (2) bromo;
  (3) chloro;
  (4) fluoro;
  (5) methyl;
  (6) isopropyl;
  (7) trifluoromethyl; and
  (8) 1-methylcyclopropyl.
12. A compound of claim 1 wherein R$^4$ and R$^5$, independently of each other, are selected from the group consisting of:
  (1) hydrogen;
  (2) halogen;
  (3) cyano;
  (4) lower alkyl optionally substituted by halogen;
  (5) lower alkoxy optionally substituted by halogen; and
  (6) lower alkylsulfonyl or lower cycloalkylsulfonyl.
13. A compound of claim 1 wherein R$^4$ and R$^5$, independently of each other, are selected from the group consisting of:
  (1) hydrogen;
  (2) hydroxyl;
  (3) fluoro or chloro;
  (4) cyano;
  (5) methyl, ethyl, propyl, isopropyl, butyl, sec-butyl, or tert-butyl;
  (6) difluoromethyl or trifluoromethyl;

(7) methoxy, ethoxy, isopropoxy or trifluoromethoxy;
(8) methylcarbonylamino;
(9) carbamoyl;
(10) acetyl;
(11) nitro;
(12) trimethylsilyl;
(13) methylsulfinyl or ethylsulfinyl; and
(14) methylsulfonyl or ethylsulfonyl.

14. A compound of claim 1 wherein X is oxygen attached to the 4 position on the ring containing Q; at least one of $R^2$ or $R^3$ is attached to the 5 position on the ring containing Q; and at least one of $R^4$ or $R^5$ is attached to the 8 or 10 position on the ring containing W.

15. A compound of claim 1 wherein X is —S(O)$_2$— attached to the 3, 4, or 5 position on the ring containing Q; at least one of $R^2$ or $R^3$ is attached to the 5 position on the ring containing Q; and at least one of $R^4$ or $R^5$ is attached to the 10 position on the ring containing W.

16. A compound of claim 1 wherein X is a direct bond attached to the 3, 4, or 5 position on the ring containing Q; at least one of $R^2$ or $R^3$ is attached to the 5 position on the ring containing Q; and at least one of $R^4$ or $R^5$ is attached to the 11 position on the ring containing W.

17. A compound of claim 1 selected from the group consisting of:
- {(R)-4-[4-(2-Chloro-phenoxy)-benzenesulfonylamino]-4,5,6,7-tetrahydro-indazol-1-yl}-acetic acid;
- [(R)-4-(Biphenyl-4-sulfonylamino)-4,5,6,7-tetrahydro-indazol-1-yl]-acetic acid;
- [4-(4-Phenoxy-benzenesulfonylamino)-4,5,6,7-tetrahydro-indazol-1-yl]-acetic acid;
- [4-(3-Phenoxy-benzenesulfonylamino)-4,5,6,7-tetrahydro-indazol-1-yl]-acetic acid;
- 3-[4-(Biphenyl-4-sulfonylamino)-4,5,6,7-tetrahydro-indazol-1-yl]-propionic acid;
- {(R)-4-[3-Chloro-4-(2-chloro-phenoxy)-benzenesulfonylamino]-4,5,6,7-tetrahydro-indazol-1-yl}-acetic acid;
- {4-[4-(3-Chloro-phenoxy)-benzenesulfonylamino]-4,5,6,7-tetrahydro-indazol-1-yl}-acetic acid;
- {4-[4-(4-Chloro-phenoxy)-benzenesulfonylamino]-4,5,6,7-tetrahydro-indazol-1-yl}-acetic acid; and
- [4-(3-Phenoxy-5-trifluoromethyl-benzenesulfonylamino)-4,5,6,7-tetrahydro-indazol-1-yl]-acetic acid;

or a pharmaceutically acceptable salt or ester thereof.

18. A compound of claim 1 selected from the group consisting of:
- {(R)-4-[2-Chloro-4-(2-chloro-phenoxy)-benzenesulfonylamino]-4,5,6,7-tetrahydro-indazol-1-yl}-acetic acid;
- {(R)-4-[2-Chloro-5-fluoro-4-(4-fluoro-phenoxy)-benzenesulfonylamino]-4,5,6,7-tetrahydro-indazol-1-yl}-acetic acid;
- 3-{(R)-4-[3-Chloro-4-(2-chloro-phenoxy)-benzenesulfonylamino]-4,5,6,7-tetrahydro-indazol-1-yl}-propionic acid;
- ((R)-4-{[3-Chloro-4-(2-chloro-phenoxy)-benzenesulfonyl]-methyl-amino}-4,5,6,7-tetrahydro-indazol-1-yl)-acetic acid;
- ((R)-4-{[3-Chloro-4-(3-chloro-phenoxy)-benzenesulfonyl]-methyl-amino}-4,5,6,7-tetrahydro-indazol-1-yl)-acetic acid;
- ((R)-4-{[3-Chloro-4-(4-chloro-phenoxy)-benzenesulfonyl]-methyl-amino}-4,5,6,7-tetrahydro-indazol-1-yl)-acetic acid;
- ((R)-4-{[2-Chloro-4-(4-chloro-phenoxy)-benzenesulfonyl]-methyl-amino}-4,5,6,7-tetrahydro-indazol-1-yl)-acetic acid;
- ((R)-4-{[4-(4-Chloro-phenoxy)-3-trifluoromethyl-benzenesulfonyl]-methyl-amino}-4,5,6,7-tetrahydro-indazol-1-yl)-acetic acid;
- ((R)-4-{[3-Chloro-4-(2,4-dichloro-phenoxy)-benzenesulfonyl]-methyl-amino}-4,5,6,7-tetrahydro-indazol-1-yl)-acetic acid;
- ((R)-4-{[4-(4-tert-Butyl-phenoxy)-3-chloro-benzenesulfonyl]-methyl-amino}-4,5,6,7-tetrahydro-indazol-1-yl)-acetic acid;

or a pharmaceutically acceptable salt or ester thereof.

19. A compound of claim 1 selected from the group consisting of:
- ((R)-4-{[2-Chloro-4-(2,4-dichloro-phenoxy)-benzenesulfonyl]-methyl-amino}-4,5,6,7-tetrahydro-indazol-1-yl)-acetic acid;
- ((R)-4-{[2-Chloro-4-(2-chloro-4-fluoro-phenoxy)-benzenesulfonyl]-methyl-amino}-4,5,6,7-tetrahydro-indazol-1-yl)-acetic acid;
- ((R)-4-{[2-Chloro-4-(2-chloro-phenoxy)-benzenesulfonyl]-methyl-amino}-4,5,6,7-tetrahydro-indazol-1-yl)-acetic acid;
- ((R)-4-{[3-Chloro-4-(4-chloro-2-fluoro-phenoxy)-benzenesulfonyl]-methyl-amino}-4,5,6,7-tetrahydro-indazol-1-yl)-acetic acid;
- ((R)-4-{[4-(4-Chloro-phenoxy)-3-fluoro-benzenesulfonyl]-methyl-amino}-4,5,6,7-tetrahydro-indazol-1-yl)-acetic acid;
- {(R)-4-[(3-Chloro-4-phenoxy-benzenesulfonyl)-methyl-amino]-4,5,6,7-tetrahydro-indazol-1-yl}-acetic acid;
- ((R)-4-{[3-Chloro-4-(4-fluoro-phenoxy)-benzenesulfonyl]-methyl-amino}-4,5,6,7-tetrahydro-indazol-1-yl)-acetic acid;
- {(R)-4-[(3-Chloro-4-p-tolyloxy-benzenesulfonyl)-methyl-amino]-4,5,6,7-tetrahydro-indazol-1-yl}-acetic acid;
- ((R)-4-{[3-Chloro-4-(2-chloro-4-fluoro-phenoxy)-benzenesulfonyl]-methyl-amino}-4,5,6,7-tetrahydro-indazol-1-yl)-acetic acid;
- ((R)-4-{[3-Chloro-4-(4-fluoro-2-methoxy-phenoxy)-benzenesulfonyl]-methyl-amino}-4,5,6,7-tetrahydro-indazol-1-yl)-acetic acid;

or a pharmaceutically acceptable salt or ester thereof.

20. A compound of claim 1 selected from the group consisting of:
- ((R)-4-{[3-Chloro-4-(2-chloro-5-methyl-phenoxy)-benzenesulfonyl]-methyl-amino}-4,5,6,7-tetrahydro-indazol-1-yl)-acetic acid;
- ((R)-4-{[3-Chloro-4-(2,4-dimethyl-phenoxy)-benzenesulfonyl]-methyl-amino}-4,5,6,7-tetrahydro-indazol-1-yl)-acetic acid;
- (((R)-4-{[3-Chloro-4-(4-chloro-2-methoxy-phenoxy)-benzenesulfonyl]-methyl-amino}-4,5,6,7-tetrahydro-indazol-1-yl)-acetic acid;
- (((R)-4-{[3-Chloro-4-(4-chloro-3-fluoro-phenoxy)-benzenesulfonyl]-methyl-amino}-4,5,6,7-tetrahydro-indazol-1-yl)-acetic acid;
- (((R)-4-{[3-Chloro-4-(2,5-difluoro-phenoxy)-benzenesulfonyl]-methyl-amino}-4,5,6,7-tetrahydro-indazol-1-yl)-acetic acid;
- ((R)-4-{[4-(4-Bromo-phenoxy)-3-chloro-benzenesulfonyl]-methyl-amino}-4,5,6,7-tetrahydro-indazol-1-yl)-acetic acid;
- ((R)-4-{[3-Chloro-4-(3-chloro-4-fluoro-phenoxy)-benzenesulfonyl]-methyl-amino}-4,5,6,7-tetrahydro-indazol-1-yl)-acetic acid;

((R)-4-{[3-Chloro-4-(4-methanesulfonyl-phenoxy)-benzenesulfonyl]-methyl-amino}-4,5,6,7-tetrahydro-indazol-1-yl)-acetic acid;
{(R)-4-[(3-Chloro-4-o-tolyloxy-benzenesulfonyl)-methyl-amino]-4,5,6,7-tetrahydro-indazol-1-yl}-acetic acid; and
((R)-4-{[4-(4-Acetylamino-phenoxy)-3-chloro-benzenesulfonyl]-methyl-amino}-4,5,6,7-tetrahydro-indazol-1-yl)-acetic acid;
or a pharmaceutically acceptable salt or ester thereof.

21. A compound of claim 1 selected from the group consisting of:
((R)-4-{[3-Chloro-4-(4-trifluoromethoxy-phenoxy)-benzenesulfonyl]-methyl-amino}-4,5,6,7-tetrahydro-indazol-1-yl)-acetic acid;
((R)-4-{[2-Chloro-5-fluoro-4-(4-fluoro-phenoxy)-benzenesulfonyl]-methyl-amino}-4,5,6,7-tetrahydro-indazol-1-yl)-acetic acid;
((R)-4-{[5-Chloro-2-fluoro-4-(4-fluoro-phenoxy)-benzenesulfonyl]-methyl-amino}-4,5,6,7-tetrahydro-indazol-1-yl)-acetic acid;
((R)-4-{[3-Chloro-4-(4-methoxy-phenoxy)-benzenesulfonyl]-methyl-amino}-4,5,6,7-tetrahydro-indazol-1-yl)-acetic acid;
((R)-4-{[3-Chloro-4-(2,4-difluoro-phenoxy)-benzenesulfonyl]-methyl-amino}-4,5,6,7-tetrahydro-indazol-1-yl)-acetic acid;
((R)-4-{[3-Chloro-4-(2,6-difluoro-phenoxy)-benzenesulfonyl]-methyl-amino}-4,5,6,7-tetrahydro-indazol-1-yl)-acetic acid;
((R)-4-{[3-Chloro-4-(4-cyano-phenoxy)-benzenesulfonyl]-methyl-amino}-4,5,6,7-tetrahydro-indazol-1-yl)-acetic acid;
((R)-4-{[4-(4-Fluoro-phenoxy)-3-methyl-benzenesulfonyl]-methyl-amino}-4,5,6,7-tetrahydro-indazol-1-yl)-acetic acid;
((R)-4-{[4-(4-Carbamoyl-phenoxy)-3-chloro-benzenesulfonyl]-methyl-amino}-4,5,6,7-tetrahydro-indazol-1-yl)-acetic acid; and
((R)-4-{[3-Chloro-4-(2-fluoro-phenoxy)-benzenesulfonyl]-methyl-amino}-4,5,6,7-tetrahydro-indazol-1-yl)-acetic acid;
or a pharmaceutically acceptable salt or ester thereof.

22. A compound of claim 1 selected from the group consisting of:
((R)-4-{[3-Chloro-4-(4-fluoro-2-methyl-phenoxy)-benzenesulfonyl]-methyl-amino}-4,5,6,7-tetrahydro-indazol-1-yl)-acetic acid;
((R)-4-{[3,5-Difluoro-4-(4-fluoro-phenoxy)-benzenesulfonyl]-methyl-amino}-4,5,6,7-tetrahydro-indazol-1-yl)-acetic acid;
((R)-4-{[3-Bromo-4-(4-fluoro-phenoxy)-benzenesulfonyl]-methyl-amino}-4,5,6,7-tetrahydro-indazol-1-yl)-acetic acid;
((R)-4-{[4-(4-Fluoro-phenoxy)-3-trifluoromethyl-benzenesulfonyl]-methyl-amino}-4,5,6,7-tetrahydro-indazol-1-yl)-acetic acid;
((R)-4-{[5-(4-Fluoro-phenoxy)-3-trifluoromethyl-benzenesulfonyl]-methyl-amino}-4,5,6,7-tetrahydro-indazol-1-yl)-acetic acid;
[4-(4'-Methoxy-biphenyl-4-sulfonylamino)-4,5,6,7-tetrahydro-indazol-1-yl]-acetic acid;
[4-(4-Pyridin-3-yl-benzenesulfonylamino)-4,5,6,7-tetrahydro-indazol-1-yl]-acetic acid;
[4-(4'-Ethoxy-biphenyl-4-sulfonylamino)-4,5,6,7-tetrahydro-indazol-1-yl]-acetic acid;
[4-(2'-Chloro-biphenyl-4-sulfonylamino)-4,5,6,7-tetrahydro-indazol-1-yl]-acetic acid; and
[4-(4'-Methoxy-biphenyl-3-sulfonylamino)-4,5,6,7-tetrahydro-indazol-1-yl]-acetic acid;
or a pharmaceutically acceptable salt or ester thereof.

23. A compound of claim 1 selected from the group consisting of:
[4-(4'-Chloro-biphenyl-4-sulfonylamino)-4,5,6,7-tetrahydro-indazol-1-yl]-acetic acid;
[4-(4'-Fluoro-biphenyl-4-sulfonylamino)-4,5,6,7-tetrahydro-indazol-1-yl]-acetic acid;
[4-(2-Fluoro-biphenyl-4-sulfonylamino)-4,5,6,7-tetrahydro-indazol-1-yl]-acetic acid;
[4-(2-Trifluoromethyl-biphenyl-4-sulfonylamino)-4,5,6,7-tetrahydro-indazol-1-yl]-acetic acid;
[4-(3'-Methoxy-biphenyl-4-sulfonylamino)-4,5,6,7-tetrahydro-indazol-1-yl]-acetic acid;
[4-(3'-Cyano-biphenyl-4-sulfonylamino)-4,5,6,7-tetrahydro-indazol-1-yl]-acetic acid;
[4-(2'-Chloro-biphenyl-3-sulfonylamino)-4,5,6,7-tetrahydro-indazol-1-yl]-acetic acid;
[(R)-4-(3'-Chloro-biphenyl-4-sulfonylamino)-4,5,6,7-tetrahydro-indazol-1-yl]-acetic acid;
[4-(3'-Trifluoromethoxy-biphenyl-4-sulfonylamino)-4,5,6,7-tetrahydro-indazol-1-yl]-acetic acid; and
[4-(3'-Chloro-4'-fluoro-biphenyl-4-sulfonylamino)-4,5,6,7-tetrahydro-indazol-1-yl]-acetic acid;
or a pharmaceutically acceptable salt or ester thereof.

24. A compound of claim 1 selected from the group consisting of:
[4-(5-Trifluoromethyl-biphenyl-3-sulfonylamino)-4,5,6,7-tetrahydro-indazol-1-yl]-acetic acid;
[4-(2'-Trifluoromethyl-biphenyl-4-sulfonylamino)-4,5,6,7-tetrahydro-indazol-1-yl]-acetic acid;
[4-(3',5'-Dimethyl-biphenyl-4-sulfonylamino)-4,5,6,7-tetrahydro-indazol-1-yl]-acetic acid;
[4-(3'-Hydroxy-biphenyl-4-sulfonylamino)-4,5,6,7-tetrahydro-indazol-1-yl]-acetic acid;
[4-(3'-Ethoxy-biphenyl-4-sulfonylamino)-4,5,6,7-tetrahydro-indazol-1-yl]-acetic acid;
[4-(3'-Isopropoxy-biphenyl-4-sulfonylamino)-4,5,6,7-tetrahydro-indazol-1-yl]-acetic acid;
[4-(3'-Acetyl-biphenyl-4-sulfonylamino)-4,5,6,7-tetrahydro-indazol-1-yl]-acetic acid;
[4-(3'-Nitro-biphenyl-4-sulfonylamino)-4,5,6,7-tetrahydro-indazol-1-yl]-acetic acid;
[4-(3',5'-Bis-trifluoromethyl-biphenyl-4-sulfonylamino)-4,5,6,7-tetrahydro-indazol-1-yl]-acetic acid; and
[(R)-4-(3'-Trifluoromethyl-biphenyl-4-sulfonylamino)-4,5,6,7-tetrahydro-indazol-1-yl]-acetic acid;
or a pharmaceutically acceptable salt or ester thereof.

25. A compound of claim 1 selected from the group consisting of:
[(R)-4-(3'-Trimethylsilanyl-biphenyl-4-sulfonylamino)-4,5,6,7-tetrahydro-indazol-1-yl]-acetic acid;
[(R)-4-(3'-Isopropyl-biphenyl-4-sulfonylamino)-4,5,6,7-tetrahydro-indazol-1-yl]-acetic acid;
[(R)-4-(3'-Methanesulfonyl-biphenyl-4-sulfonylamino)-4,5,6,7-tetrahydro-indazol-1-yl]-acetic acid;
[(R)-4-(3'-Methanesulfinyl-biphenyl-4-sulfonylamino)-4,5,6,7-tetrahydro-indazol-1-yl]-acetic acid;
(R)-3-[4-(biphenyl-4-sulfonylamino)-4,5,6,7-tetrahydro-indazol-1-yl]-propionic acid;
3-[(R)-4-(3'-Trifluoromethyl-biphenyl-4-sulfonylamino)-4,5,6,7-tetrahydro-indazol-1-yl]-propionic acid;

{(R)-4-[Methyl-(3'-trifluoromethyl-biphenyl-4-sulfonyl)-amino]-4,5,6,7-tetrahydro-indazol-1-yl}-acetic acid; and 3-{(R)-4-[Methyl-(3'-trifluoromethyl-biphenyl-4-sulfonyl)-amino]-4,5,6,7-tetrahydro-indazol-1-yl}-propionic acid;

or a pharmaceutically acceptable salt or ester thereof.

26. A compound of claim 1 selected from the group consisting of:

{(R)-4-[(4'-Fluoro-5-trifluoromethyl-biphenyl-3-sulfonyl)-methyl-amino]-4,5,6,7-tetrahydro-indazol-1-yl}-acetic acid;

((R)-4-{[3-(4-Chloro-phenylsulfonyl)-5-trifluoromethyl-benzenesulfonyl]-methyl amino}-4,5,6,7-tetrahydro-indazol-1-yl)-acetic acid;

((R)-4-{Methyl-[3-(toluene-4-sulfonyl)-5-trifluoromethyl-benzenesulfonyl]-amino}-4,5,6,7-tetrahydro-indazol-1-yl)-acetic acid;

3-((R)-4-{[3-(4-Fluoro-benzenesulfonyl)-5-trifluoromethyl-benzenesulfonyl]-methyl-amino}-4,5,6,7-tetrahydro-indazol-1-yl)-propionic acid;

3-((R)-4-{[3-(4-Chloro-benzenesulfonyl)-5-trifluoromethyl-benzenesulfonyl]-methyl-amino}-4,5,6,7-tetrahydro-indazol-1-yl)-propionic acid;

3-((R)-4-{[3-(4-Methoxy-benzenesulfonyl)-5-trifluoromethyl-benzenesulfonyl]-methyl-amino}-4,5,6,7-tetrahydro-indazol-1-yl)-propionic acid; and 3-((R)-4-{Methyl-[3-(toluene-4-sulfonyl)-5-trifluoromethyl-benzenesulfonyl]-amino}-4,5,6,7-tetrahydro-indazol-1-yl)-propionic acid.

27. A pharmaceutical composition comprising a therapeutically effective amount of a compound according to claim 1 and a pharmaceutically acceptable carrier.

28. A compound selected from the group consisting of:

{4-[3-(5-Methyl-[1,3,4]oxadiazol-2-yl)-benzenesulfonylamino]-4,5,6,7-tetrahydro-indazol-1-yl}-acetic acid;

[4-(3-Benzoylamino-benzenesulfonylamino)-4,5,6,7-tetrahydro-indazol-1-yl]-acetic acid; and

[(R)-4-(3-Benzenesulfonylamino-benzenesulfonylamino)-4,5,6,7-dihydro-indazol-1-yl]-acetic acid;

or a pharmaceutically acceptable salt or ester thereof.

\* \* \* \* \*

UNITED STATES PATENT AND TRADEMARK OFFICE
CERTIFICATE OF CORRECTION

PATENT NO. : 8,138,208 B2
APPLICATION NO. : 12/497807
DATED : March 20, 2012
INVENTOR(S) : Chen et al.

Page 1 of 1

It is certified that error appears in the above-identified patent and that said Letters Patent is hereby corrected as shown below:

Claim 19, column 230, line 40, at the end of the line insert -- and --

Claim 20, column 230, line 53, delete "(((R)" and insert -- ((R) --

Claim 20, column 230, line 56, delete "(((R)" and insert -- ((R) --

Claim 20, column 230, line 59, delete "(((R)" and insert -- ((R) --

Claim 22, column 231, line 59, delete "[5-(4-Fluoro-phenoxy)-3"
and insert -- [3-(4-Fluoro-phenoxy)-5 --

Claim 26, column 234, line 9, delete "acid."
and insert -- acid; or a pharmaceutically acceptable salt or ester thereof. --

Signed and Sealed this
Eighth Day of May, 2012

David J. Kappos
*Director of the United States Patent and Trademark Office*